(12) United States Patent
Weinschenk et al.

(10) Patent No.: US 11,161,880 B2
(45) Date of Patent: *Nov. 2, 2021

(54) IMMUNOTHERAPY AGAINST SEVERAL TUMORS, SUCH AS LUNG CANCER, INCLUDING NSCLC

(71) Applicant: IMMATICS BIOTECHNOLOGIES GMBH, Tuebingen (DE)

(72) Inventors: Toni Weinschenk, Aichwald (DE); Steffen Walter, Reutlingen (DE); Jens Fritsche, Dusslingen (DE); Colette Song, Ostfildern (DE); Harpreet Singh, Munich (DE)

(73) Assignee: IMMATICS BIOTECHNOLOGIES GMBH, Tuebingen (DE)

(*) Notice: Subject to any disclaimer, the term of this patent is extended or adjusted under 35 U.S.C. 154(b) by 0 days.

This patent is subject to a terminal disclaimer.

(21) Appl. No.: 16/599,258

(22) Filed: Oct. 11, 2019

(65) Prior Publication Data

US 2020/0031870 A1 Jan. 30, 2020

Related U.S. Application Data

(63) Continuation of application No. 16/444,693, filed on Jun. 18, 2019, now Pat. No. 10,479,818, which is a continuation of application No. 15/639,165, filed on Jun. 30, 2017, now abandoned, which is a continuation of application No. 14/908,078, filed as application No. PCT/EP2014/066755 on Aug. 4, 2014, now abandoned.

(60) Provisional application No. 61/862,213, filed on Aug. 5, 2013.

(30) Foreign Application Priority Data

Aug. 5, 2013 (GB) .................................... 1313987
Feb. 25, 2014 (GB) .................................... 1403297

(51) Int. Cl.
| | | |
|---|---|---|
| *C07K 7/06* | (2006.01) | |
| *C07K 7/08* | (2006.01) | |
| *C12N 5/0783* | (2010.01) | |
| *C12N 9/64* | (2006.01) | |
| *A61K 38/17* | (2006.01) | |
| *A61K 39/00* | (2006.01) | |

(52) U.S. Cl.
CPC ............ *C07K 7/08* (2013.01); *A61K 38/1709* (2013.01); *A61K 39/0011* (2013.01); *C07K 7/06* (2013.01); *C12N 5/0638* (2013.01); *C12N 9/6491* (2013.01); *C12Y 304/24065* (2013.01)

(58) Field of Classification Search
None
See application file for complete search history.

(56) References Cited

U.S. PATENT DOCUMENTS

| | | |
|---|---|---|
| 7,094,890 B1 | 8/2006 | Crowl et al. |
| 7,807,642 B2 | 10/2010 | Dengjel |
| 7,811,828 B2 | 10/2010 | Lemmel et al. |
| 7,833,969 B2 | 11/2010 | Dengjel |
| 7,833,970 B2 | 11/2010 | Dengjel |
| 8,067,529 B2 | 11/2011 | Rammensee et al. |
| 9,101,585 B2 | 8/2015 | Ritsche et al. |
| 10,196,432 B2 | 2/2019 | Dengjel |
| 10,316,063 B1* | 6/2019 | Weinschenk ............ A61P 35/00 |
| 10,500,259 B2* | 12/2019 | Mahr ..................... C07K 16/30 |
| 2006/0019284 A1 | 1/2006 | Huang et al. |
| 2008/0107668 A1 | 5/2008 | Philip et al. |
| 2008/0206216 A1 | 8/2008 | Dengjel |
| 2011/0033516 A1 | 2/2011 | Markwald |
| 2011/0142865 A1 | 6/2011 | Dengjel |
| 2011/0142919 A1 | 6/2011 | Ramakrishna et al. |
| 2011/0229504 A1 | 9/2011 | Fritsche |

(Continued)

FOREIGN PATENT DOCUMENTS

| | | |
|---|---|---|
| EP | 1760088 A1 | 3/2007 |
| WO | 1999033870 A2 | 7/1999 |

(Continued)

OTHER PUBLICATIONS

BLAST search results for SEQ ID No. 92 (retrieved from https://blast.ncbi.nlm.nih.gov/Blast.cgi on Dec. 2, 20, 14 pages) (Year: 2020).*

(Continued)

*Primary Examiner* — Ronald T Niebauer
(74) *Attorney, Agent, or Firm* — McBee Moore & Vanik IP, LLC

(57) ABSTRACT

A method of treating a patient who has glioblastoma and/or gastric cancer includes administering to said patient a composition containing a population of activated T cells that selectively recognize cells in the patient that aberrantly express a peptide. A pharmaceutical composition contains activated T cells that selectively recognize cells in a patient that aberrantly express a peptide, and a pharmaceutically acceptable carrier, in which the T cells bind to the peptide in a complex with an MHC class I molecule, and the composition is for treating the patient who has glioblastoma and/or gastric cancer. A method of treating a patient who has glioblastoma and/or gastric cancer includes administering to said patient a composition comprising a peptide in the form of a pharmaceutically acceptable salt, thereby inducing a T-cell response to the glioblastoma and/or gastric cancer.

10 Claims, 15 Drawing Sheets

(1 of 15 Drawing Sheet(s) Filed in Color)

Specification includes a Sequence Listing.

(56) References Cited

U.S. PATENT DOCUMENTS

| | | |
|---|---|---|
| 2011/0257890 A1 | 10/2011 | Weinschenk et al. |
| 2012/0027684 A1 | 2/2012 | Singh et al. |
| 2012/0035529 A1 | 2/2012 | Coukos et al. |
| 2012/0156175 A1 | 6/2012 | Lee |
| 2013/0096016 A1 | 4/2013 | Weinschenk et al. |
| 2016/0168200 A1* | 6/2016 | Weinschenk ............ A61K 45/06 514/21.5 |

FOREIGN PATENT DOCUMENTS

| | | | |
|---|---|---|---|
| WO | 03016471 | A2 | 2/2003 |
| WO | 2003102023 | A1 | 12/2003 |
| WO | 2004018633 | A2 | 3/2004 |
| WO | 2005076009 | A2 | 8/2005 |
| WO | 2006037421 | A2 | 4/2006 |
| WO | 2007096142 | A2 | 8/2007 |
| WO | 2008088583 | A2 | 7/2008 |
| WO | 2009036246 | A2 | 3/2009 |
| WO | 2009059011 | A2 | 5/2009 |
| WO | 2009105549 | A2 | 8/2009 |
| WO | 2009111507 | A1 | 9/2009 |
| WO | 2009126271 | A1 | 10/2009 |
| WO | 2009153992 | A1 | 12/2009 |
| WO | 2010045388 | A2 | 4/2010 |
| WO | 2011089921 | A1 | 7/2011 |
| WO | 2011113819 | A2 | 9/2011 |

OTHER PUBLICATIONS

Frank et al. ('Trifluoroacetate in Ocean Waters' Environ. Sci. Technol. v36 2002 pp. 12-15) (Year: 2002).*

Alpdogan et al. ('IL-7 and IL-15: therapeutic cytokines for immunodeficiency' Trends in Immunology v26(1) Jan. 2005, pp. 56-64) (Year: 2005).*

Stowe G. ('Mineral spotlight: chloride' retrieved from https://www.ironmountainhotsprings.com/mineral-spotlight-chloride/#:~:text=Chloride%20is%20one%20of%20the,not%20naturally%20occur%20in%20isolation. on Nov. 30, 2020, 2 pages) (Year: 2020).*

ScienceDirect ('Acetate—an overview' retrieved from https://www.sciencedirect.com/topics/neuroscience/acetate on Nov. 30, 2020, 6 pages) (Year: 2020).*

Schambye HT ('Effect of different buffers on the biocompatibility of CAPD solutions' abstract only retrieved from https://pubmed.ncbi.nlm.nih.gov/8728179/on Nov. 30, 2020, 1 page) (Year: 2020).*

Great Britain Search Report dated Mar. 12, 2014.

International Search Report dated Jan. 13, 2015, issued in PCT/EP2014/066755.

Prades et al., "The human ATP binding cassette gene ABCA13, located on chromosome 7p12.3, encodes a 5058 amino acid protein with an extracellular domain encoded in part by a 4.8-kb conserved exon." Cytogenetic and Genome Research, vol. 98 (2002) 160-168, XP002985952.

Hofmann Hans-Stefan et al., "Matrix metalloproteinase-12 expression correlates with local recurrence and metastatic disease in non-small cell lung cancer patients." Clinical Cancer Research, The American Association for Cancer Research, vol. 11, No. 3 (2005) 1086-1092. XP002443725.

Yu Tian et al., "Periostin and lung diseases: Recent advances and molecular structure modeling." Archives of Biological Sciences. (2010) vol. 62, No. 4: 901-905. XP055158582.

Bin Li, et al., "Upregularion of periostin prevents P53-mediated apoptosis in SGC-7901 gastric cancer cells." Molecular Biology Reports; An International Journal on Molecular and Cellular Biology, vol. 40, No. 2 (2013) 1677-1683. XP035159635.

Laura Morra et al., "Periostin expression and epithelial-mesenchymal transition in cancer: a review and an update," Vichows Archiv, vol. 459, No. 5 (2011) 465-475. XP019970698.

Isabella Tai et al., "Periostin induction in tumor cell line explants and inhibition of in vitro cell growth by anti-periostin antibodies." Carcinogenesis, vol. 26, No. 5 (2005) 908-915. XP008127943.

Mentlein et al., "Expression and role of the cell surface protease seprase/fibroblast activation protein-alpha (FAP-alpha) in astroglial tumors", Biological Chemistry, Mar. 2011, pp. 199-207, vol. 392, No. 3.

Zi et al., "Fibroblast activation protein alpha in tumor microenvironment: Recent progression and implications", Molecular Medicine Reports, May 2015, pp. 3203-3211, vol. 11, No. 5.

National Cancer Institute, "CAR T Cells: Engineering Patients' Immune Cells to Treat Their Cancers", retrieved from https://www.cancer.gov/about-cancer/treatment/research/car-t-cells on Aug. 18, 2017, 9 pages), 2017.

Zhang et al., "CAR-T cell therapy in gastrointestinal tumors and hepatic carcinoma: From bench to bedside", Oncoimmunology, 2016, pp. 1-13, vol. 5, e1251539.

Liao et al.('Clinical implications of fibroblast activation protein-alpha in non-small cell lung cancer after curative resection: a new predictor for prognosis' J Cancer Res Clin on col. v13 2013 pp. 1523-1528) (Year: 2013).

Grunda et al. ('Rationally designed pharmacogenomics treatment using concurrent capecitabine and radiotherapy for glioblastoma; gene expression profiles associated with outcome' Clin Cancer Res v16(10) May 15, 2010, pp. 2890-2898) (Year: 2010).

Babiak et al., "Frequent T cell responses against immunogenic targets in lung cancer patients for targeted immunotherapy" Oncology Reports (2014) vol. 31: 384-390.

Buckanovich et al., "Tumor Vascular Proteins As Biomarkers in Ovarian Cancer" Journal of Clinical Oncology (Mar. 2007) vol. 25, No. 7: 852-861.

Clement et al., "An Expanded Self-Antigen Peptidome Is Carried by the Human Lymph As Compared to the Plasma" PLOS ONE (Mar. 2010) vol. 5, Issue 3: 1-10.

Dehghani et al., "Neurofilament H immunoreaction in oligodendrogliomas as demonstrated by anew polyclonal antibody" AETA Neuropathol (2000) vol. 100: 122-130.

Gautschi et al., "Aurora Kinases as Anticancer Drug Targets" Clin Cancer Res (2008) vol. 14, No. 6: 1639-1648.

Gomez-Ferreria et Sharp, "Cep192 and the generation of the mitotic spindle" Cell Cycle (2008) 7:11: 1507-1510.

Han et al., "Regulation of Dendritic Spines, Spatial Memory, and Embryonic Development by the TANC Family of PSD-95-Interacting Proteins" The Journal of Neuroscience (Nov. 10, 2010) vol. 30, No. 45: 15102-15112.

Hiramoto et al., "Mutations of novel human RAD54 homologue, RAD54B, in primary cancer" Oncogene (1999) vol. 18: 3422-3426.

Kallunki et al., "A Truncated Laminin Chain Homologous to the B2 Chain: Structure, Spatial Expression, and Chromosomal Assignment" The Journal of Cell Biology (Nov. 1992) vol. 119, No. 3: 679-693.

Karagiannis et al., "Proteomic Signatures of the Desmoplastic Invasion Front Reveal Collagen Type XII as a Marker of Myofibroblastic Differentiation During Colorectal Cancer Metastasis" Oncotarget (2012) vol. 3: 267-285.

Kim et al., "Neurofilament Heavy Polypeptide Regulates the Akt-B-Catenin Pathway in Human Esophageal Squamous Cell Carcinoma" PLOS ONE (Feb. 2010) vol. 5, Issue 2: 1-18.

Kosanam et al., "Laminin, gamma 2 (LAMC2): A Promising New Putative Pancreatic Cancer Biomarker Identified by Proteomic Analysis of Pancreatic Adenocarcinoma Tissues" Molecular & Cellular Proteomics (2013) 2820-2832.

Kumar et al., "CEP proteins: the knights of centrosome dynasty" PROTOPLASMA (2013) vol. 250: 965-983.

Kwon et al., "Aberrant up-regulation of LAMB3 and LAMC2 by promoter demethylation in gastric cancer" Biochemical and Biophysical Reasearch Communications (2011) 539-545.

Lees et al., "The structure and organization of the human heavy neurofilament subunit (NF-H) and the gene encoding it" The EMBO Journal (1988) vol. 7, No. 7: 1947-1955.

Maatta et al., "Expression of the laminin gamma2 chain in different histological types of lung carcinoma. A study by immunohistochemistry and in situ hybridization" J Pathol (1999) vol. 188, No. 4: 361-368.

(56) References Cited

OTHER PUBLICATIONS

Manda et al., "Differential Expression of LAMB3 and LAMC2 Genes between Small Cell and Non-Small Cell Lung Carcinoma" Biochemical and Biophysical Reasearch Communications (2000) vol. 215, No. 2: 440-445.

Schneider et al., "Specific immune responses against epitopes derived from Aurora kinase A and B in acute myeloid leukemia" Leukemia and Lymphoma (Jul. 2013) vol. 54, No. 7: 1500-1504.

Zou et al., "Application of cDNA microarrays to generate a molecular taxonomy capable of distinguishing between colon cancer and normal colon" Oncogene (2002) vol. 21: 4855-4862.

Wang et al., "Identification of MXRA5 as a novel biomarker in colorectal cancer" Oncology Letters (2013) vol. 5: 544-548.

Weinschenk et al., "Integrated Functional Genomics Approach for the Design of Patient-individual Antitumor Vaccines" Cancer Research (2002) vol. 62: 5818-5827.

Xiong et al., "Exome sequencing identifies MXRA5 as a novel cancer gene frequently mutated in non-small cell lung carcinoma from Chinese patients" Carcinogenesis (2012) vol. 33, No. 9: 1797-1805.

Yang et al., "Killing tumor cells via their surface B2M or MHC class I molecules" Cancer (Apr. 1, 2010) vol. 116, No. 7: 1638-1645.

\* cited by examiner

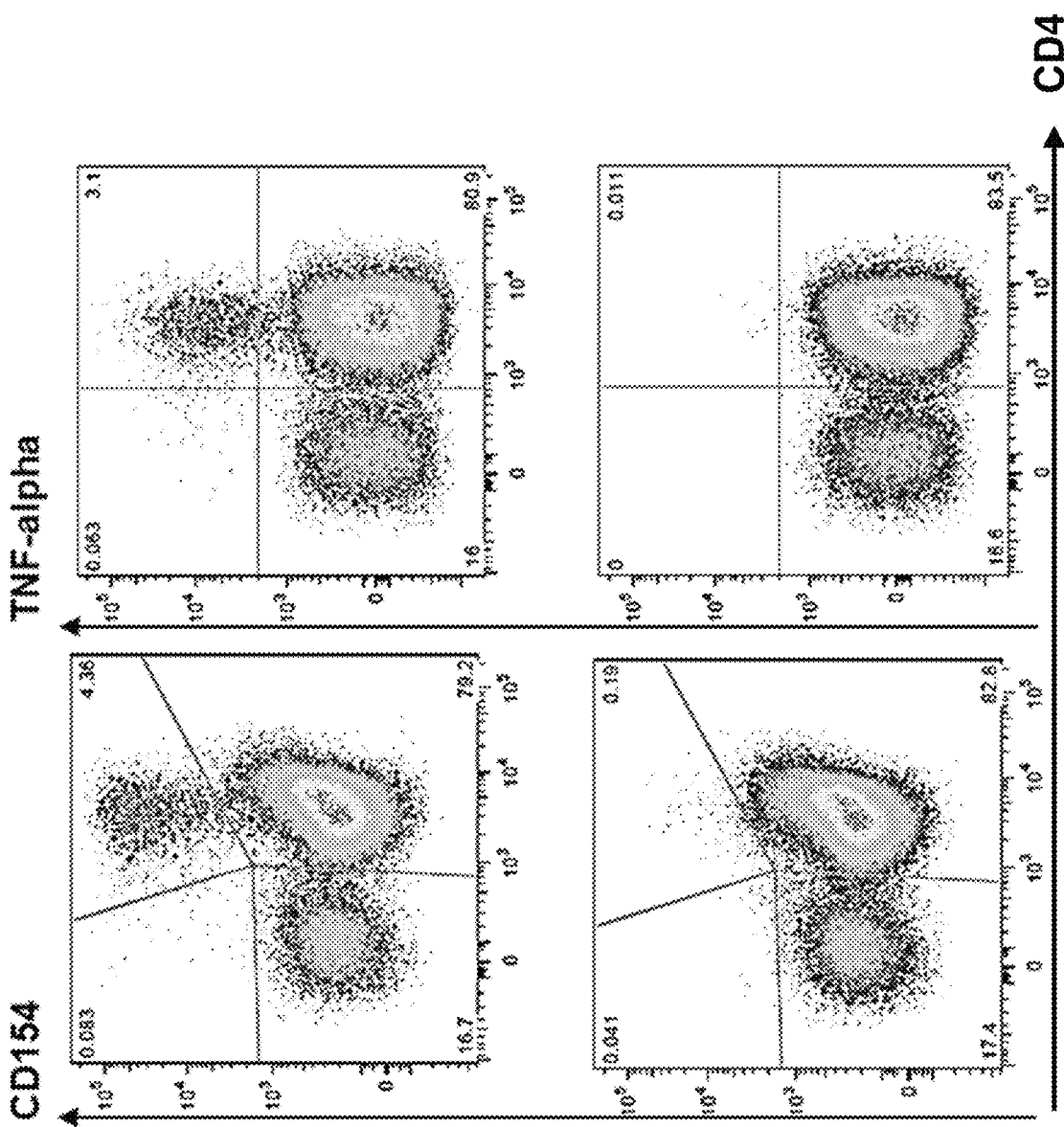

SEQUENCE LISTING

```
<160> NUMBER OF SEQ ID NOS: 92

<210> SEQ ID NO 1
<211> LENGTH: 9
<212> TYPE: PRT
<213> ORGANISM: Homo sapiens

<400> SEQUENCE: 1

Ile Leu Phe Glu Ile Asn Pro Lys Leu
1               5

<210> SEQ ID NO 2
<211> LENGTH: 9
```

```
<212> TYPE: PRT
<213> ORGANISM: Homo sapiens

<400> SEQUENCE: 2

Lys Ile Gln Glu Met Gln His Phe Leu
1               5

<210> SEQ ID NO 3
<211> LENGTH: 9
<212> TYPE: PRT
<213> ORGANISM: Homo sapiens

<400> SEQUENCE: 3

Ala Leu Asp Glu Asn Leu His Gln Leu
1               5

<210> SEQ ID NO 4
<211> LENGTH: 9
<212> TYPE: PRT
<213> ORGANISM: Homo sapiens

<400> SEQUENCE: 4

Asn Leu Ile Glu Lys Ser Ile Tyr Leu
1               5

<210> SEQ ID NO 5
<211> LENGTH: 9
<212> TYPE: PRT
<213> ORGANISM: Homo sapiens

<400> SEQUENCE: 5

Thr Leu Ser Ser Ile Lys Val Glu Val
1               5

<210> SEQ ID NO 6
<211> LENGTH: 9
<212> TYPE: PRT
<213> ORGANISM: Homo sapiens

<400> SEQUENCE: 6

Lys Leu Asp Glu Thr Asn Asn Thr Leu
1               5

<210> SEQ ID NO 7
<211> LENGTH: 9
<212> TYPE: PRT
<213> ORGANISM: Homo sapiens

<400> SEQUENCE: 7

Thr Leu Trp Tyr Arg Ala Pro Glu Val
1               5

<210> SEQ ID NO 8
<211> LENGTH: 9
<212> TYPE: PRT
<213> ORGANISM: Homo sapiens

<400> SEQUENCE: 8

Ser Met Ser Gly Tyr Asp Gln Val Leu
1               5

<210> SEQ ID NO 9
<211> LENGTH: 11
<212> TYPE: PRT
<213> ORGANISM: Homo sapiens
```

```
<400> SEQUENCE: 9

Ala Leu Met Asp Lys Glu Gly Leu Thr Ala Leu
1               5                   10

<210> SEQ ID NO 10
<211> LENGTH: 9
<212> TYPE: PRT
<213> ORGANISM: Homo sapiens

<400> SEQUENCE: 10

Val Leu Ser Val Val Glu Val Thr Leu
1               5

<210> SEQ ID NO 11
<211> LENGTH: 12
<212> TYPE: PRT
<213> ORGANISM: Homo sapiens

<400> SEQUENCE: 11

Val Leu Leu Pro Val Glu Val Ala Thr His Tyr Leu
1               5                   10

<210> SEQ ID NO 12
<211> LENGTH: 9
<212> TYPE: PRT
<213> ORGANISM: Homo sapiens

<400> SEQUENCE: 12

Ser Leu Ile Glu Asp Leu Ile Leu Leu
1               5

<210> SEQ ID NO 13
<211> LENGTH: 9
<212> TYPE: PRT
<213> ORGANISM: Homo sapiens

<400> SEQUENCE: 13

Tyr Leu Ile His Phe Pro Val Ser Val
1               5

<210> SEQ ID NO 14
<211> LENGTH: 9
<212> TYPE: PRT
<213> ORGANISM: Homo sapiens

<400> SEQUENCE: 14

Phe Gln Tyr Asp His Glu Ala Phe Leu
1               5

<210> SEQ ID NO 15
<211> LENGTH: 9
<212> TYPE: PRT
<213> ORGANISM: Homo sapiens

<400> SEQUENCE: 15

Lys Leu Ala Val Ala Leu Leu Ala Ala
1               5

<210> SEQ ID NO 16
<211> LENGTH: 10
<212> TYPE: PRT
<213> ORGANISM: Homo sapiens

<400> SEQUENCE: 16
```

Thr Val Ile Gly Phe Leu Leu Pro Phe Ala
1               5                   10

<210> SEQ ID NO 17
<211> LENGTH: 14
<212> TYPE: PRT
<213> ORGANISM: Homo sapiens

<400> SEQUENCE: 17

Arg Leu Leu Gly Pro Ser Ala Ala Ala Asp Ile Leu Gln Leu
1               5                   10

<210> SEQ ID NO 18
<211> LENGTH: 9
<212> TYPE: PRT
<213> ORGANISM: Homo sapiens

<400> SEQUENCE: 18

Thr Leu Tyr Pro His Thr Ser Gln Val
1               5

<210> SEQ ID NO 19
<211> LENGTH: 9
<212> TYPE: PRT
<213> ORGANISM: Homo sapiens

<400> SEQUENCE: 19

Ala Val Val Glu Phe Leu Thr Ser Val
1               5

<210> SEQ ID NO 20
<211> LENGTH: 9
<212> TYPE: PRT
<213> ORGANISM: Homo sapiens

<400> SEQUENCE: 20

Ala Leu Val Asp His Thr Pro Tyr Leu
1               5

<210> SEQ ID NO 21
<211> LENGTH: 9
<212> TYPE: PRT
<213> ORGANISM: Homo sapiens

<400> SEQUENCE: 21

Ala Ile Leu Asp Thr Leu Tyr Glu Val
1               5

<210> SEQ ID NO 22
<211> LENGTH: 9
<212> TYPE: PRT
<213> ORGANISM: Homo sapiens

<400> SEQUENCE: 22

Phe Leu Ile Pro Ile Tyr His Gln Val
1               5

<210> SEQ ID NO 23
<211> LENGTH: 9
<212> TYPE: PRT
<213> ORGANISM: Homo sapiens

<400> SEQUENCE: 23

Phe Leu His His Leu Glu Ile Glu Leu

<210> SEQ ID NO 24
<211> LENGTH: 9
<212> TYPE: PRT
<213> ORGANISM: Homo sapiens

<400> SEQUENCE: 24

Phe Leu Val Asp Gly Ser Trp Ser Val
1               5

<210> SEQ ID NO 25
<211> LENGTH: 10
<212> TYPE: PRT
<213> ORGANISM: Homo sapiens

<400> SEQUENCE: 25

Gly Leu Tyr Pro Asp Ala Phe Ala Pro Val
1               5                   10

<210> SEQ ID NO 26
<211> LENGTH: 9
<212> TYPE: PRT
<213> ORGANISM: Homo sapiens

<400> SEQUENCE: 26

Lys Leu Phe Gly Glu Lys Thr Tyr Leu
1               5

<210> SEQ ID NO 27
<211> LENGTH: 9
<212> TYPE: PRT
<213> ORGANISM: Homo sapiens

<400> SEQUENCE: 27

Thr Val Ala Glu Val Ile Gln Ser Val
1               5

<210> SEQ ID NO 28
<211> LENGTH: 9
<212> TYPE: PRT
<213> ORGANISM: Homo sapiens

<400> SEQUENCE: 28

Ser Ile Ser Asp Val Ile Ala Gln Val
1               5

<210> SEQ ID NO 29
<211> LENGTH: 11
<212> TYPE: PRT
<213> ORGANISM: Homo sapiens

<400> SEQUENCE: 29

Arg Leu Glu Glu Asp Asp Gly Asp Val Ala Met
1               5                   10

<210> SEQ ID NO 30
<211> LENGTH: 9
<212> TYPE: PRT
<213> ORGANISM: Homo sapiens

<400> SEQUENCE: 30

Lys Ile Tyr Asn Glu Phe Ile Ser Val
1               5

<210> SEQ ID NO 31
<211> LENGTH: 9
<212> TYPE: PRT
<213> ORGANISM: Homo sapiens

<400> SEQUENCE: 31

Ala Ile Asp Gly Asn Asn His Glu Val
1               5

<210> SEQ ID NO 32
<211> LENGTH: 9
<212> TYPE: PRT
<213> ORGANISM: Homo sapiens

<400> SEQUENCE: 32

Lys Leu Ser Trp Asp Leu Ile Tyr Leu
1               5

<210> SEQ ID NO 33
<211> LENGTH: 9
<212> TYPE: PRT
<213> ORGANISM: Homo sapiens

<400> SEQUENCE: 33

Ala Leu Leu Arg Thr Val Val Ser Val
1               5

<210> SEQ ID NO 34
<211> LENGTH: 9
<212> TYPE: PRT
<213> ORGANISM: Homo sapiens

<400> SEQUENCE: 34

Ala Leu Gly Ala Gly Ile Glu Arg Met
1               5

<210> SEQ ID NO 35
<211> LENGTH: 9
<212> TYPE: PRT
<213> ORGANISM: Homo sapiens

<400> SEQUENCE: 35

Val Leu Phe Pro Asn Leu Lys Thr Val
1               5

<210> SEQ ID NO 36
<211> LENGTH: 9
<212> TYPE: PRT
<213> ORGANISM: Homo sapiens

<400> SEQUENCE: 36

Thr Leu Val Ala Ile Val Val Gly Val
1               5

<210> SEQ ID NO 37
<211> LENGTH: 9
<212> TYPE: PRT
<213> ORGANISM: Homo sapiens

<400> SEQUENCE: 37

Val Leu Ala Pro Leu Phe Val Tyr Leu
1               5

<210> SEQ ID NO 38

```
<211> LENGTH: 9
<212> TYPE: PRT
<213> ORGANISM: Homo sapiens

<400> SEQUENCE: 38

Ser Leu His Phe Leu Ile Leu Tyr Val
1               5

<210> SEQ ID NO 39
<211> LENGTH: 9
<212> TYPE: PRT
<213> ORGANISM: Homo sapiens

<400> SEQUENCE: 39

Arg Leu Leu Asp Ser Val Ser Arg Leu
1               5

<210> SEQ ID NO 40
<211> LENGTH: 9
<212> TYPE: PRT
<213> ORGANISM: Homo sapiens

<400> SEQUENCE: 40

Gly Leu Thr Asp Asn Ile His Leu Val
1               5

<210> SEQ ID NO 41
<211> LENGTH: 12
<212> TYPE: PRT
<213> ORGANISM: Homo sapiens

<400> SEQUENCE: 41

Ser Ile Leu Thr Ile Glu Asp Gly Ile Phe Glu Val
1               5                   10

<210> SEQ ID NO 42
<211> LENGTH: 9
<212> TYPE: PRT
<213> ORGANISM: Homo sapiens

<400> SEQUENCE: 42

Ser Leu Trp Gly Gly Asp Val Val Leu
1               5

<210> SEQ ID NO 43
<211> LENGTH: 10
<212> TYPE: PRT
<213> ORGANISM: Homo sapiens

<400> SEQUENCE: 43

Ala Leu Phe Pro His Leu Leu Gln Pro Val
1               5                   10

<210> SEQ ID NO 44
<211> LENGTH: 9
<212> TYPE: PRT
<213> ORGANISM: Homo sapiens

<400> SEQUENCE: 44

Asn Leu Leu Ala Glu Ile His Gly Val
1               5

<210> SEQ ID NO 45
<211> LENGTH: 10
<212> TYPE: PRT
```

-continued

```
<213> ORGANISM: Homo sapiens

<400> SEQUENCE: 45

Ala Ile Met Gly Phe Ile Gly Phe Phe Val
1               5                   10

<210> SEQ ID NO 46
<211> LENGTH: 9
<212> TYPE: PRT
<213> ORGANISM: Homo sapiens

<400> SEQUENCE: 46

Thr Leu Thr Asn Ile Ile His Asn Leu
1               5

<210> SEQ ID NO 47
<211> LENGTH: 9
<212> TYPE: PRT
<213> ORGANISM: Homo sapiens

<400> SEQUENCE: 47

Gly Val Leu Glu Asn Ile Phe Gly Val
1               5

<210> SEQ ID NO 48
<211> LENGTH: 9
<212> TYPE: PRT
<213> ORGANISM: Homo sapiens

<400> SEQUENCE: 48

Gly Leu Ile Glu Ile Ile Ser Asn Ala
1               5

<210> SEQ ID NO 49
<211> LENGTH: 9
<212> TYPE: PRT
<213> ORGANISM: Homo sapiens

<400> SEQUENCE: 49

Arg Leu Leu Ala Ala Glu Asn Phe Leu
1               5

<210> SEQ ID NO 50
<211> LENGTH: 11
<212> TYPE: PRT
<213> ORGANISM: Homo sapiens

<400> SEQUENCE: 50

Ser Leu Leu Pro Val Asp Ile Arg Gln Tyr Leu
1               5                   10

<210> SEQ ID NO 51
<211> LENGTH: 9
<212> TYPE: PRT
<213> ORGANISM: Homo sapiens

<400> SEQUENCE: 51

Tyr Leu Ala Pro Phe Leu Arg Asn Val
1               5

<210> SEQ ID NO 52
<211> LENGTH: 9
<212> TYPE: PRT
<213> ORGANISM: Homo sapiens
```

```
<400> SEQUENCE: 52

Ala Leu Leu Glu Arg Gly Tyr Ser Leu
1               5

<210> SEQ ID NO 53
<211> LENGTH: 9
<212> TYPE: PRT
<213> ORGANISM: Homo sapiens

<400> SEQUENCE: 53

Tyr Leu Pro His Ala Pro Pro Phe Ala
1               5

<210> SEQ ID NO 54
<211> LENGTH: 10
<212> TYPE: PRT
<213> ORGANISM: Homo sapiens

<400> SEQUENCE: 54

Lys Leu Val Glu Phe Asp Phe Leu Gly Ala
1               5                   10

<210> SEQ ID NO 55
<211> LENGTH: 9
<212> TYPE: PRT
<213> ORGANISM: Homo sapiens

<400> SEQUENCE: 55

Ser Leu Ala Asp Phe Met Gln Glu Val
1               5

<210> SEQ ID NO 56
<211> LENGTH: 9
<212> TYPE: PRT
<213> ORGANISM: Homo sapiens

<400> SEQUENCE: 56

Ser Leu Tyr Lys Gly Leu Leu Ser Val
1               5

<210> SEQ ID NO 57
<211> LENGTH: 11
<212> TYPE: PRT
<213> ORGANISM: Homo sapiens

<400> SEQUENCE: 57

Gly Leu Ala Glu Asp Ile Asp Lys Gly Glu Val
1               5                   10

<210> SEQ ID NO 58
<211> LENGTH: 9
<212> TYPE: PRT
<213> ORGANISM: Homo sapiens

<400> SEQUENCE: 58

Ser Leu Ile Asp Ala Asp Pro Tyr Leu
1               5

<210> SEQ ID NO 59
<211> LENGTH: 9
<212> TYPE: PRT
<213> ORGANISM: Homo sapiens

<400> SEQUENCE: 59
```

Ile Leu Val Ser Trp Leu Pro Arg Leu
1               5

<210> SEQ ID NO 60
<211> LENGTH: 9
<212> TYPE: PRT
<213> ORGANISM: Homo sapiens

<400> SEQUENCE: 60

Val Val Asp Lys Thr Leu Leu Leu Val
1               5

<210> SEQ ID NO 61
<211> LENGTH: 9
<212> TYPE: PRT
<213> ORGANISM: Homo sapiens

<400> SEQUENCE: 61

Thr Leu Ile Ser Arg Leu Pro Ala Val
1               5

<210> SEQ ID NO 62
<211> LENGTH: 10
<212> TYPE: PRT
<213> ORGANISM: Homo sapiens

<400> SEQUENCE: 62

Ile Leu Phe Pro Asp Ile Ile Ala Arg Ala
1               5                   10

<210> SEQ ID NO 63
<211> LENGTH: 11
<212> TYPE: PRT
<213> ORGANISM: Homo sapiens

<400> SEQUENCE: 63

Ser Leu Ala Gly Asp Val Ala Leu Gln Gln Leu
1               5                   10

<210> SEQ ID NO 64
<211> LENGTH: 9
<212> TYPE: PRT
<213> ORGANISM: Homo sapiens

<400> SEQUENCE: 64

Ala Met Leu Ala Val Leu His Thr Val
1               5

<210> SEQ ID NO 65
<211> LENGTH: 9
<212> TYPE: PRT
<213> ORGANISM: Homo sapiens

<400> SEQUENCE: 65

Lys Val Leu Glu Ile Leu His Arg Val
1               5

<210> SEQ ID NO 66
<211> LENGTH: 9
<212> TYPE: PRT
<213> ORGANISM: Homo sapiens

<400> SEQUENCE: 66

Lys Ile Gln Glu Ile Leu Thr Gln Val
1               5

```
<210> SEQ ID NO 67
<211> LENGTH: 9
<212> TYPE: PRT
<213> ORGANISM: Homo sapiens

<400> SEQUENCE: 67

Ile Leu Gln Asp Arg Leu Asn Gln Val
1               5

<210> SEQ ID NO 68
<211> LENGTH: 9
<212> TYPE: PRT
<213> ORGANISM: Homo sapiens

<400> SEQUENCE: 68

Tyr Val Tyr Gln Asn Asn Ile Tyr Leu
1               5

<210> SEQ ID NO 69
<211> LENGTH: 9
<212> TYPE: PRT
<213> ORGANISM: Homo sapiens

<400> SEQUENCE: 69

Ala Met Ser Ser Lys Phe Phe Leu Val
1               5

<210> SEQ ID NO 70
<211> LENGTH: 9
<212> TYPE: PRT
<213> ORGANISM: Homo sapiens

<400> SEQUENCE: 70

Lys Ile Leu Glu Asp Val Val Gly Val
1               5

<210> SEQ ID NO 71
<211> LENGTH: 9
<212> TYPE: PRT
<213> ORGANISM: Homo sapiens

<400> SEQUENCE: 71

Lys Leu Leu Glu Tyr Ile Glu Glu Ile
1               5

<210> SEQ ID NO 72
<211> LENGTH: 9
<212> TYPE: PRT
<213> ORGANISM: Homo sapiens

<400> SEQUENCE: 72

Lys Leu Leu Thr Glu Val His Ala Ala
1               5

<210> SEQ ID NO 73
<211> LENGTH: 9
<212> TYPE: PRT
<213> ORGANISM: Homo sapiens

<400> SEQUENCE: 73

Phe Leu Leu Asp Gly Ser Ala Asn Val
1               5
```

```
<210> SEQ ID NO 74
<211> LENGTH: 11
<212> TYPE: PRT
<213> ORGANISM: Homo sapiens

<400> SEQUENCE: 74

Ser Leu Leu Ala Gln Asn Thr Ser Trp Leu Leu
1               5                   10

<210> SEQ ID NO 75
<211> LENGTH: 9
<212> TYPE: PRT
<213> ORGANISM: Homo sapiens

<400> SEQUENCE: 75

Ala Leu Tyr Asp Ser Val Ile Leu Leu
1               5

<210> SEQ ID NO 76
<211> LENGTH: 18
<212> TYPE: PRT
<213> ORGANISM: Homo sapiens

<400> SEQUENCE: 76

Ile Asn Asn Tyr Thr Pro Asp Met Asn Arg Glu Asp Val Asp Tyr Ala
1               5                   10                  15

Ile Arg

<210> SEQ ID NO 77
<211> LENGTH: 17
<212> TYPE: PRT
<213> ORGANISM: Homo sapiens

<400> SEQUENCE: 77

Thr Asn Gly Val Ile His Val Val Asp Lys Leu Leu Tyr Pro Ala Asp
1               5                   10                  15

Thr

<210> SEQ ID NO 78
<211> LENGTH: 10
<212> TYPE: PRT
<213> ORGANISM: Homo sapiens

<400> SEQUENCE: 78

Ser Leu Tyr Asp Asn Gln Ile Thr Thr Val
1               5                   10

<210> SEQ ID NO 79
<211> LENGTH: 10
<212> TYPE: PRT
<213> ORGANISM: Homo sapiens

<400> SEQUENCE: 79

Ser Leu Ala Pro Ala Gly Val Ile Arg Val
1               5                   10

<210> SEQ ID NO 80
<211> LENGTH: 12
<212> TYPE: PRT
<213> ORGANISM: Homo sapiens

<400> SEQUENCE: 80

Ser Leu Phe Gly Asn Ser Gly Ile Leu Glu Asn Val
1               5                   10
```

```
<210> SEQ ID NO 81
<211> LENGTH: 9
<212> TYPE: PRT
<213> ORGANISM: Homo sapiens

<400> SEQUENCE: 81

Ala Leu Tyr Gly Arg Leu Glu Val Val
1               5

<210> SEQ ID NO 82
<211> LENGTH: 9
<212> TYPE: PRT
<213> ORGANISM: Homo sapiens

<400> SEQUENCE: 82

Ala Leu Trp Glu Lys Asn Thr His Leu
1               5

<210> SEQ ID NO 83
<211> LENGTH: 10
<212> TYPE: PRT
<213> ORGANISM: Homo sapiens

<400> SEQUENCE: 83

Ala Leu Ala Asn Gln Lys Leu Tyr Ser Val
1               5                   10

<210> SEQ ID NO 84
<211> LENGTH: 10
<212> TYPE: PRT
<213> ORGANISM: Homo sapiens

<400> SEQUENCE: 84

Ile Leu Met Gly Thr Glu Leu Thr Gln Val
1               5                   10

<210> SEQ ID NO 85
<211> LENGTH: 9
<212> TYPE: PRT
<213> ORGANISM: Homo sapiens

<400> SEQUENCE: 85

Lys Ile Val Asp Phe Ser Tyr Ser Val
1               5

<210> SEQ ID NO 86
<211> LENGTH: 11
<212> TYPE: PRT
<213> ORGANISM: Homo sapiens

<400> SEQUENCE: 86

Ala Met Ala Thr Glu Ser Ile Leu His Phe Ala
1               5                   10

<210> SEQ ID NO 87
<211> LENGTH: 11
<212> TYPE: PRT
<213> ORGANISM: Homo sapiens

<400> SEQUENCE: 87

Arg Val Leu Pro Pro Ser Ala Leu Gln Ser Val
1               5                   10
```

```
<210> SEQ ID NO 88
<211> LENGTH: 11
<212> TYPE: PRT
<213> ORGANISM: Homo sapiens

<400> SEQUENCE: 88

Ser Leu Leu Glu Ser Asn Lys Asp Leu Leu Leu
1               5                   10

<210> SEQ ID NO 89
<211> LENGTH: 9
<212> TYPE: PRT
<213> ORGANISM: Homo sapiens

<400> SEQUENCE: 89

Ala Leu Ala Ser Val Ile Lys Glu Leu
1               5

<210> SEQ ID NO 90
<211> LENGTH: 10
<212> TYPE: PRT
<213> ORGANISM: Homo sapiens

<400> SEQUENCE: 90

Ser Leu Val Ala Val Glu Leu Glu Lys Val
1               5                   10

<210> SEQ ID NO 91
<211> LENGTH: 9
<212> TYPE: PRT
<213> ORGANISM: Homo sapiens

<400> SEQUENCE: 91

Ala Met Phe Glu Asn Phe Val Ser Val
1               5

<210> SEQ ID NO 92
<211> LENGTH: 9
<212> TYPE: PRT
<213> ORGANISM: Homo sapiens

<400> SEQUENCE: 92

His Leu Leu Glu Asp Ile Ala His Val
1               5
```

IMMUNOTHERAPY AGAINST SEVERAL TUMORS, SUCH AS LUNG CANCER, INCLUDING NSCLC

CROSS REFERENCE TO RELATED APPLICATIONS

This is a continuation application of U.S. application Ser. No. 16/444,693, filed on Jun. 18, 2019, which is a continuation application of U.S. application Ser. No. 15/639,165, filed on Jun. 30, 2017, which is a continuation application of U.S. application Ser. No. 14/908,078, filed on Jan. 27, 2016, which is a national phase of International Application No. PCT/EP2014/066755, filed on Aug. 4, 2014, which claims priority to U.S. Provisional Application No. 61/862,213, filed on Aug. 5, 2013, GB Application No. 1403297.3, filed on Feb. 25, 2014, and GB Application No. 1313987.8, filed on Aug. 5, 2013. Each of these applications is incorporated by reference in its entirety.

REFERENCE TO SEQUENCE LISTING SUBMITTED AS A COMPLIANT ASCII TEXT FILE (.TXT)

Pursuant to the EFS-Web legal framework and 37 CFR §§ 1.821-825 (see MPEP § 2332.03(a)), a Sequence Listing in the form of an ASCII-compliant text file (entitled "2912919-032015_Sequence_Listing_ST25.txt" created on Oct. 10, 2019, and 14,782 bytes in size) is submitted concurrently with the instant application, and the entire contents of the Sequence Listing are incorporated herein by reference.

FIELD OF THE INVENTION

The present invention relates to peptides, nucleic acids and cells for use in immunotherapeutic methods. In particular, the present invention relates to the immunotherapy of cancer. The present invention furthermore relates to tumor-associated cytotoxic T cell (CTL) peptide epitopes, alone or in combination with other tumor-associated peptides that serve as active pharmaceutical ingredients of vaccine compositions that stimulate anti-tumor immune responses. The present invention relates to 67 novel peptide sequences and their variants derived from HLA class I and HLA class II molecules of human tumor cells that can be used in vaccine compositions for eliciting anti-tumor immune responses.

BACKGROUND OF THE INVENTION

Lung cancer accounts for the most cancer-related deaths in both men and women. Worldwide, lung cancer is the most common cancer in terms of both incidence and mortality. In 2008, there were 1.61 million new cases, and 1.38 million deaths due to lung cancer. The highest rates are in Europe and North America.

Since 1987, more women have died each year from lung cancer than from breast cancer. Death rates have continued to decline significantly in men from 1991-2003 by about 1.9% per year. Female lung cancer death rates are approaching a plateau after continuously increasing for several decades. These trends in lung cancer mortality reflect the decrease in smoking rates over the past 30 years.

An estimated 230,000 new cases of lung cancer and 160,000 deaths due to lung cancer are expected in 2013 in the USA according to the national cancer institute (NCI).

Lung cancer is classified clinically as small cell (13%, SCLC) or non-small cell (87%, NSCLC) for the purposes of treatment. Prognosis is generally poor. Of all people with lung cancer, 15% survive for five years after diagnosis. Stage is often advanced at the time of diagnosis. At presentation, 30-40% of cases of NSCLC are stage IV, and 60% of SCLC are stage IV.

Treatment options are determined by the type (small cell or non-small cell) and stage of cancer and include surgery, radiation therapy, chemotherapy, and targeted biological therapies such as bevacizumab (AVASTIN®) and erlotinib (TARCEVA®). For localized cancers, surgery is usually the treatment of choice. Recent studies indicate that survival with early-stage, non-small cell lung cancer is improved by chemotherapy following surgery. Because the disease has usually spread by the time it is discovered, radiation therapy and chemotherapy are often used, sometimes in combination with surgery. Chemotherapy alone or combined with radiation is the usual treatment of choice for small cell lung cancer; on this regimen, a large percentage of patients experience remission, which is long lasting in some cases.

The 1-year relative survival for lung cancer has slightly increased from 37% in 1975-1979 to 42% in 2002, largely due to improvements in surgical techniques and combined therapies. However, the 5-year survival rate for all stages combined is only 16%. The survival rate is 49% for cases detected when the disease is still localized; however, only 16% of lung cancers are diagnosed at this early stage.

Despite the above, there remains a need for new efficacious and safe treatment option for cancers such as lung cancer, in particular non-small-cell lung cancer (NSCLC), gastric cancers and brain tumors of different phenotypes which improve the well-being of the patients by not using excessive chemotherapeutic agents or other agents that may lead to severe side effects.

The present invention employs peptides that stimulate the immune system of the patient and act as anti-tumor-agents in a non-invasive fashion.

SUMMARY OF THE INVENTION

In a first aspect of the present invention, the present invention relates to a peptide comprising an amino acid sequence selected from the group of SEQ ID No. 1 to SEQ ID No. 65, and SEQ ID No. 76 to SEQ ID No. 84, and SEQ ID No. 92 or a variant sequence thereof which is at least 80%, preferably at least 90%, homologous (preferably at least 80% or at least 90% identical) to SEQ ID No. 1 to SEQ ID No. 65, and SEQ ID No. 76 to SEQ ID No. 84, and SEQ ID No. 92, wherein said variant induces T cells cross-reacting with said peptide, or a pharmaceutical acceptable salt thereof, wherein said peptide is not a full-length polypeptide.

The present invention further relates to a peptide of the present invention comprising a sequence that is selected from the group of SEQ ID No. 1 to SEQ ID No. 65, and SEQ ID No. 76 to, and SEQ ID No. 84, and SEQ ID No. 92 or a variant thereof, which is at least 80%, preferably at least 90%, homologous (preferably at least 80% or at least 90% identical) to SEQ ID No. 1 to SEQ ID No. 65, and SEQ ID No. 76 to SEQ ID No. 84, and SEQ ID No. 92, wherein said peptide or variant thereof has an overall length for SEQ ID No. 1 to SEQ ID No. 65 and SEQ ID 78 to SEQ ID No. 84 and SEQ ID No. 92 of between 8 and 100, preferably between 8 and 30, and most preferred of between 8 and 14 amino acids, and for SEQ ID No. 76 and 77 of between 12 and 100, preferably between 12 and 30, and most preferred of between 12 to 18 amino acids.

The following tables show the peptides according to the present invention, their respective SEQ ID NO, and the prospective source proteins for these peptides. All peptides in Tables 1a, 1b and 1c bind to the HLA A*02 allele, peptides in Table Id bind to HLA-DR alleles. The peptides in table 1c are further useful in the diagnosis and/or treatment of gastric cancer and or glioblastoma.

The class II peptides in table Id are further useful in the diagnosis and/or treatment of gastric cancer and other cancers over-expressing or over-presenting MMP12 or POSTN.

Thus, the present invention relates in particular to a peptide of the present invention comprising a sequence according to SEQ ID No. 76 or a variant thereof, which is at least 80%, preferably at least 90%, homologous (preferably at least 80% or at least 90% identical) to SEQ ID No. 76, wherein said peptide or variant thereof has an overall length of between 12 and 100, preferably between 12 and 30, and most preferred of between 12 to 18 amino acids. The present invention relates in particular to a peptide of the present invention consisting of the sequence according to SEQ ID No. 76.

Also, the present invention relates in particular to a peptide of the present invention comprising a sequence according to SEQ ID No. 77 or a variant thereof, which is at least 80%, preferably at least 90%, homologous (preferably at least 80% or at least 90% identical) to SEQ ID No. 77, wherein said peptide or variant thereof has an overall length of between 12 and 100, preferably between 12 and 30, and most preferred of between 12 to 18 amino acids. The present invention relates in particular to a peptide of the present invention consisting of the sequence according to SEQ ID No. 77.

TABLE 1a

Peptides of the present invention

| SEQ ID NO: | Peptide Code | Sequence | Source Protein(s) |
|---|---|---|---|
| 1 | ABCA13-001 | ILFEINPKL | ABCA13 |
| 2 | MMP12-003 | KIQEMQHFL | MMP12 |
| 3 | ABCA13-002 | ALDENLHQL | ABCA13 |
| 4 | DST-001 | NLIEKSIYL | DST |
| 5 | MXRA5-001 | TLSSIKVEV | MXRA5 |
| 6 | DST-002 | KLDETNNTL | DST |
| 7 | CDK4-001 | TLWYRAPEV | CDK4/CDK6 |
| 8 | HNRNPH-001 | SMSGYDQVL | HNRNPH1, HNRNPH2 |
| 9 | TANC2-001 | ALMDKEGLTAL | TANC2 |
| 10 | RNF213-001 | VLSVVEVTL | RNF213 |
| 11 | SLC34A2-001 | VLLPVEVATHYL | SLC34A2 |
| 12 | SMYD3-001 | SLIEDLILL | SMYD3 |
| 13 | AKR-001 | YLIHFPVSV | AKR1C1, AKR1C2 |
| 14 | RCN1-001 | FQYDHEAFL | RCN1, RCN3 |
| 15 | IL8-001 | KLAVALLAA | IL8 |
| 16 | P2RY6-001 | TVIGFLLPFA | P2RY6 |
| 17 | HUWE1-001 | RLLGPSAAADILQL | HUWE1 |
| 18 | VCAN-001 | TLYPHTSQV | VCAN |
| 19 | DROSHA-001 | AVVEFLTSV | DROSHA |
| 20 | VCAN-002 | ALVDHTPYL | VCAN |
| 21 | PLEKHA8-001 | AILDTLYEV | PLEKHA8 |
| 22 | ACACA-001 | FLIPIYHQV | ACACA |
| 23 | ITGA11-001 | FLHHLEIEL | ITGA11 |
| 24 | COL12A1-002 | FLVDGSWSV | COL12A1 |
| 25 | ELANE-001 | GLYPDAFAPV | ELANE |
| 26 | SERPINB3-001 | KLFGEKTYL | SERPINB3 |
| 27 | KIF26B-001 | TVAEVIQSV | KIF26B |
| 28 | ANKH-001 | SISDVIAQV | ANKH |
| 29 | NXF1-001 | RLEEDDGDVAM | NXF1 |
| 30 | RGS4-001 | KIYNEFISV | RGS4 |
| 31 | GFPT2-001 | AIDGNNHEV | GFPT2 |
| 32 | CERC-001 | KLSWDLIYL | CERCAM |
| 33 | GALNT2-001 | ALLRTVVSV | GALNT2 |
| 34 | HNRNPM-001 | ALGAGIERM | HNRNPM |
| 35 | BNC1-001 | VLFPNLKTV | BNC1 |
| 36 | FKBP10-001 | TLVAIVVGV | FKBP10 |
| 37 | FZD-001 | VLAPLFVYL | FZD1, FZD2, FZD7 |
| 38 | ATP-001 | SLHFLILYV | ATP2A1, ATP2A2 |
| 39 | LAMC2-001 | RLLDSVSRL | LAMC2 |
| 40 | MXRA5-002 | GLTDNIHLV | MXRA5 |
| 41 | HSP-002 | SILTIEDGIFEV | HSPA2, HSPA8 |
| 42 | VPS13B-001 | SLWGGDVVL | VPS13B |
| 43 | CSE1-001 | ALFPHLLQPV | CSE1L |
| 44 | DPYSL4-001 | NLLAEIHGV | DPYSL4 |
| 45 | SEC61G-001 | AIMGFIGFFV | SEC61G |
| 46 | ORMDL1-002 | TLTNIIHNL | ORMDL1 |
| 47 | PCNXL3-001 | GVLENIFGV | PCNXL3 |
| 48 | SNRNP20-001 | GLIEIISNA | SNRNP200 |

TABLE 1b

Additional peptides of the present invention

| SEQ ID NO: | Peptide Code | Sequence | Source Protein(s) |
|---|---|---|---|
| 49 | SAMSN1-001 | RLLJAAENFL | SAMSN1 |
| 50 | STAT2-001 | SLLPVDIRQYL | STAT2 |
| 51 | CNOT1-001 | YLAPFLRNV | CNOT1 |
| 52 | SHMT2-001 | ALLERGYSL | SHMT2 |
| 53 | JUNB-001 | YLPHAPPFA | JUNB |
| 54 | TACC3-001 | KLVEFDFLGA | TACC3 |
| 55 | CNOT1-002 | SLADFMQEV | CNOT1 |
| 56 | RAD54B-001 | SLYKGLLSV | RAD54B |
| 57 | EEF-002 | GLAEDIDKGEV | EEF2 |
| 58 | CCNA2-001 | SLIDADPYL | CCNA2 |
| 59 | NET1-001 | ILVSWLPRL | NET1 |
| 60 | C11orf24-001 | VVDKTLLLV | C11orf24 |
| 61 | RCC1-001 | TLISRLPAV | RCC1 |
| 62 | MAGEF1-001 | ILFPDIIARA | MAGEF1 |
| 63 | NCAPD2-001 | SLAGDVALQQL | NCAPD2 |
| 64 | C12orf44-001 | AMLAVLHTV | C12orf44 |
| 65 | HERC4-001 | KVLEILHRV | HERC4 |

TABLE 1c

Additional peptides that are also over-expressed in glioblastoma and/or gastric cancer

| SEQ ID NO: | Peptide Code | Sequence | Source Protein(s) |
|---|---|---|---|
| 66 | IGF2BP3-001 | KIQEILTQV | IGF2BP3 |
| 67 | CDC6-001 | ILQDRLNQV | CDC6 |
| 68 | FAP-003 | YVYQNNIYL | FAP |
| 69 | WNT5A-001 | AMSSKFFLV | WNT5A |
| 70 | TPX2-001 | KILEDVVGV | TPX2 |
| 71 | HMMR-001 | KLLEYIEEI | HMMR |
| 72 | ADAM8-001 | KLLTEVHAA | ADAM8 |
| 73 | COL6A3-002 | FLLDGSANV | COL6A3 |
| 74 | THY1-001 | SLLAQNTSWLL | THY1 |
| 75 | DIO2-001 | ALYDSVILL | DIO2 |

TABLE 1d

MHC class II peptides of the invention

| SEQ ID NO: | Peptide Code | Sequence | Source Protein(s) |
|---|---|---|---|
| 76 | MMP12-002 | INNYTPDMNREDVDYAIR | MMP12 |
| 77 | POSTN-002 | TNGVIHVVDKLLYPADT | POSTN |

TABLE 1e

Further preferred peptides of the present invention with an additional abundance in other cancers

| SEQ ID NO: | Peptide Code | Sequence | Source Protein(s) |
|---|---|---|---|
| 78 | SLI-001 | SLYDNQITTV | SLIT1, SLIT2 |
| 79 | TLX3-001 | SLAPAGVIRV | TLX3 |
| 80 | CEP192-001 | SLFGNSGILENV | CEP192 |
| 81 | ANKS1A-001 | ALYGRLEVV | ANKS1A |
| 82 | CEP250-002 | ALWEKNTHL | CEP250 |
| 83 | MDN1-001 | ALANQKLYSV | MDN1 |
| 84 | OLFM1-001 | ILMGTELTQV | OLFM1 |
| 92 | NEFH-001 | HLLEDIAHV | NEFH |

TABLE 1f

Further peptides of the present invention with an additional abundance in other cancers

| SEQ ID NO: | Peptide Code | Sequence | Source Protein(s) |
|---|---|---|---|
| 85 | BUB1B-001 | KIVDFSYSV | BUB1B |
| 86 | PI4KA-001 | AMATESILHFA | PI4KA |
| 87 | AURKB-001 | RVLPPSALQSV | AURKB |
| 88 | SLC3A2-001 | SLLESNKDLLL | SLC3A2 |
| 89 | IFT81-001 | ALASVIKEL | IFT81 |
| 90 | COG4-001 | SLVAVELEKV | COG4 |
| 91 | NCBP1-001 | AMFENFVSV | NCBP1 |

The present invention furthermore relates to the peptides according to the present invention that have the ability to bind to a molecule of the human major histocompatibility complex (MHC) class-I or -II.

The present invention further relates to the peptides according to the present invention wherein said peptides consist or consist essentially of an amino acid sequence according to SEQ ID No. 1 to SEQ ID No. 65, and SEQ ID No. 76 to SEQ ID No. 84, and SEQ ID No. 92.

The present invention further relates to the peptides according to the present invention, wherein said peptide is modified and/or includes non-peptide bonds.

The present invention further relates to the peptides according to the present invention, wherein said peptide is part of a fusion protein, in particular fused to the N-terminal amino acids of the HLA-DR antigen-associated invariant chain (Ii), or fused to (or into the sequence of) an antibody, such as, for example, an antibody that is specific for dendritic cells.

The present invention further relates to a nucleic acid, encoding the peptides according to the present invention.

The present invention further relates to the nucleic acid according to the present invention that is DNA, cDNA, PNA, RNA or combinations thereof.

The present invention further relates to an expression vector capable of expressing a nucleic acid according to the present invention.

The present invention further relates to a peptide according to the present invention, a nucleic acid according to the present invention or an expression vector according to the present invention for use in medicine.

The present invention further relates to antibodies according to the present invention, and methods of making them.

The present invention further relates to T-cell receptors (TCR), in particular soluble TCR (sTCRs), according to the present invention, and methods of making them.

The present invention further relates to a host cell comprising a nucleic acid according to the present invention or an expression vector as described before.

The present invention further relates to the host cell according to the present invention that is an antigen presenting cell.

The present invention further relates to the host cell according to the present invention wherein the antigen presenting cell is a dendritic cell.

The present invention further relates to a method of producing a peptide according to the present invention, the method comprising culturing the host cell according to the present invention, and isolating the peptide from the host cell or its culture medium.

The present invention further relates to an in vitro method for producing activated cytotoxic T lymphocytes (CTL), the method comprising contacting in vitro CTL with antigen loaded human class I or II MHC molecules expressed on the surface of a suitable antigen-presenting cell for a period of time sufficient to activate said CTL in an antigen specific manner, wherein said antigen is any peptide according to the present invention.

The present invention further relates to the method according to the present invention, wherein the antigen is loaded onto class I or II MHC molecules expressed on the surface of a suitable antigen-presenting cell by contacting a sufficient amount of the antigen with an antigen-presenting cell.

The present invention further relates to the method according to the present invention, wherein the antigen-presenting cell comprises an expression vector capable of expressing said peptide containing SEQ ID No. 1 to SEQ ID No. 92, preferably containing SEQ ID No. 1 to SEQ ID No. 65 and SEQ ID No. 76 to SEQ ID No. 84, and SEQ ID No. 92, or said variant amino acid sequence.

The present invention further relates to activated cytotoxic T lymphocytes (CTL), produced by the method according to the present invention, which selectively recognize a cell which aberrantly expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of cytotoxic T lymphocytes (CTL) as according to the present invention.

The present invention further relates to the use of any peptide described, a nucleic acid according to the present invention, an expression vector according to the present invention, a cell according to the present invention, or an activated cytotoxic T lymphocyte according to the present invention as a medicament or in the manufacture of a medicament.

The present invention further relates to a use according to the present invention, wherein said medicament is a vaccine.

The present invention further relates to a use according to the present invention, wherein the medicament is active against cancer.

The present invention further relates to a use according to the present invention, wherein said cancer cells are lung cancer cells, gastric, gastrointestinal, colorectal, pancreatic or renal cancer cells, and glioblastoma cells.

The present invention further relates to particular marker proteins and biomarkers based on the peptides according to the present invention that can be used in the diagnosis and/or prognosis of lung, gastric, gastrointestinal, colorectal, pancreatic or renal cancer, and glioblastoma.

Further, the present invention relates to the use of these novel targets for cancer treatment.

Stimulation of an immune response is dependent upon the presence of antigens recognised as foreign by the host immune system. The discovery of the existence of tumor associated antigens has raised the possibility of using a host's immune system to intervene in tumor growth. Various mechanisms of harnessing both the humoral and cellular arms of the immune system are currently being explored for cancer immunotherapy.

Specific elements of the cellular immune response are capable of specifically recognising and destroying tumor cells. The isolation of cytotoxic T-cells (CTL) from tumor-infiltrating cell populations or from peripheral blood suggests that such cells play an important role in natural immune defences against cancer. CD8-positive T-cells in particular, which recognise Class I molecules of the major histocompatibility complex (MHC)-bearing peptides of usually 8 to 10 amino acid residues derived from proteins or defect ribosomal products (DRIPS) located in the cytosol, play an important role in this response. The MHC-molecules of the human are also designated as human leukocyte-antigens (HLA).

There are two classes of MHC-molecules: MHC class I molecules that can be found on most cells having a nucleus. MHC molecules are composed of an alpha heavy chain and beta-2-microglobulin (MHC class I receptors) or an alpha and a beta chain (MHC class II receptors), respectively. Their three-dimensional conformation results in a binding groove, which is used for non-covalent interaction with peptides. MHC class I present peptides that result from proteolytic cleavage of predominantly endogenous proteins, DRIPs and larger peptides. MHC class II molecules can be found predominantly on professional antigen presenting cells (APCs), and primarily present peptides of exogenous or transmembrane proteins that are taken up by APCs during the course of endocytosis, and are subsequently processed. Complexes of peptide and MHC class I molecules are recognized by CD8-positive cytotoxic T-lymphocytes bearing the appropriate TCR (T-cell receptor), whereas complexes of peptide and MHC class II molecules are recognized by CD4-positive-helper-T cells bearing the appropriate TCR. It is well known that the TCR, the peptide and the MHC are thereby present in a stoichiometric amount of 1:1:1.

CD4-positive helper T cells play an important role in inducing and sustaining effective responses by CD8-positive cytotoxic T-cell. The identification of CD4-positive T-cell epitopes derived from tumor associated antigens (TAA) is of great importance for the development of pharmaceutical products for triggering anti-tumor immune responses (Kobayashi et al., 2002; Qin et al., 2003; Gnjatic et al., 2003). At the tumor site, T helper cells, support a CTL friendly cytokine milieu (Mortara et al., 2006) and attract effector cells, e.g. CTLs, NK cells, macrophages, granulocytes (Hwang et al., 2007).

In the absence of inflammation, expression of MHC class II molecules is mainly restricted to cells of the immune system, especially professional antigen-presenting cells (APC), e.g., monocytes, monocyte-derived cells, macrophages, dendritic cells. In cancer patients, cells of the tumor have surprisingly been found to express MHC class II molecules (Dengjel et al., 2006).

It was shown in mammalian animal models, e.g., mice, that even in the absence of CTL effector cells (i.e., CD8-positive T lymphocytes), CD4-positive T cells are sufficient for inhibiting manifestation of tumors via inhibition of angiogenesis by secretion of interferon-gamma (IFNγ).

Additionally, it was shown that CD4-positive T cells recognizing peptides from tumor-associated antigens presented by HLA class II molecules can counteract tumor progression via the induction of antibody (Ab) responses.

In contrast to tumor-associated peptides binding to HLA class I molecules, only a small number of class II ligands of tumor associated antigens (TAA) have been described to date.

Since the constitutive expression of HLA class II molecules is usually limited to cells of the immune system, the possibility of isolating class II peptides directly from primary tumors was not considered possible. However, Dengjel et al. were successful in identifying a number of MHC Class II epitopes directly from tumors (WO 2007/028574, EP 1 760 088 B1; (Dengjel et al., 2006).

The antigens that are recognized by the tumor specific cytotoxic T lymphocytes, that is, their epitopes, can be molecules derived from all protein classes, such as enzymes, receptors, transcription factors, etc. which are expressed and, as compared to unaltered cells of the same origin, up-regulated in cells of the respective tumor.

Since both types of response, CD8 and CD4 dependent, contribute jointly and synergistically to the anti-tumor effect, the identification and characterization of tumor-associated antigens recognized by either CD8+ CTLs (ligand: MHC class I molecule+peptide epitope) or by CD4-positive T-helper cells (ligand: MHC class II molecule+peptide epitope) is important in the development of tumor vaccines.

The present invention also relates to two new and very useful MHC class II peptides (according to SEQ ID NOs 76 and 77). These peptides are particularly useful in the diagnosis and/or treatment of gastric cancer, NSCLC and other cancers over-expressing and/or over-presenting MMP12 and POSTN respectively.

The present invention also relates to so-called length variants of the inventive MHC class II peptides according to SEQ ID NO 76 or 77. As mentioned above, the peptide according to SEQ ID NO 76 consists of the amino acid sequence INNYTPDMNREDVDYAIR (MMP12-peptide), and the peptide according to SEQ ID NO 77 consists of the amino acid sequence TNGVIHVVDKLLYPADT (POSTN-002-peptide). The length variants are generally N- and/or C-terminally extended (between 1 and 5, preferably 1 to 10 amino acids) or N- and/or C-terminally shortened (between 1 and 5 amino acids) peptides, which still can bind to MHC, and elicit a cellular immune response as described herein. As is known in the state of the art, peptides binding to class II proteins are not constrained in size and can vary from 11 to 30 amino acids in length. The peptide binding groove in the MHC class II molecules is open at both ends, which enables binding of peptides with relatively longer length. Though the "core" nine residues long segment contributes the most to the recognition of the peptide, the flanking regions are also important for the specificity of the peptide to the class II allele (see, for example, Meydan C, et al., Prediction of peptides binding to MHC class I and II alleles by temporal motif mining. BMC Bioinformatics. 2013; 14 Suppl 2: S13. Epub 2013 Jan. 21). Using the many software tools as available (e.g. as described above), the person of skill in the art will be able to identify the binding motif, and thus identify the possibilities for extensions and/or deletions of the MHC class II peptides according to SEQ ID NO 76 or 77, in order to create length variants.

For a peptide to trigger (elicit) a cellular immune response, it must bind to an MHC-molecule. This process is dependent on the allele of the MHC-molecule and specific polymorphisms of the amino acid sequence of the peptide. MHC-class-I-binding peptides are usually 8-12 amino acid residues in length and usually contain two conserved residues ("anchors") in their sequence that interact with the corresponding binding groove of the MHC-molecule. In this way each MHC allele has a "binding motif" determining which peptides can bind specifically to the binding groove.

In the MHC class I dependent immune reaction, peptides not only have to be able to bind to certain MHC class I molecules being expressed by tumor cells, they also have to be recognized by T cells bearing specific T cell receptors (TCR).

The antigens that are recognized by the tumor specific cytotoxic T lymphocytes, that is, their epitopes, can be molecules derived from all protein classes, such as enzymes, receptors, transcription factors, etc. which are expressed and, as compared to unaltered cells of the same origin, up-regulated in cells of the respective tumor.

The current classification of tumor associated antigens comprises the following major groups:

a) Cancer-testis antigens: The first TAAs ever identified that can be recognized by T cells belong to this class, which was originally called cancer-testis (CT) antigens because of the expression of its members in histologically different human tumors and, among normal tissues, only in spermatocytes/spermatogonia of testis and, occasionally, in placenta. Since the cells of testis do not express class I and II HLA molecules, these antigens cannot be recognized by T cells in normal tissues and can therefore be considered as immunologically tumor-specific. Well-known examples for CT antigens are the MAGE family members or NY-ESO-1.

b) Differentiation antigens: These TAAs are shared between tumors and the normal tissue from which the tumor arose; most are found in melanomas and normal melanocytes. Many of these melanocyte lineage-related proteins are involved in the biosynthesis of melanin and are therefore not tumor specific but nevertheless are widely used for cancer immunotherapy. Examples include, but are not limited to, tyrosinase and Melan-A/MART-1 for melanoma or PSA for prostate cancer.

c) Overexpressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T-cell recognition, while their overexpression in tumor cells can trigger an anticancer response by breaking previously established tolerance. Prominent examples for this class of TAAs are Her-2/neu, Survivin, Telomerase or WT1.

d) Tumor specific antigens: These unique TAAs arise from mutations of normal genes (such as β-catenin, CDK4, etc.). Some of these molecular changes are associated with neoplastic transformation and/or progression. Tumor specific antigens are generally able to induce strong immune responses without bearing the risk for autoimmune reactions against normal tissues. On the other hand, these TAAs are in most cases only relevant to the exact tumor on which they were identified and are usually not shared between many individual tumors.

e) TAAs arising from abnormal post-translational modifications: Such TAAs may arise from proteins which are neither specific nor overexpressed in tumors but nevertheless become tumor associated by posttranslational processes primarily active in tumors. Examples for this class arise from altered glycosylation patterns leading to novel epitopes in tumors as for MUC1 or events like protein splicing during degradation which may or may not be tumor specific.

f) Oncoviral proteins: These TAAs are viral proteins that may play a critical role in the oncogenic process and, because they are foreign (not of human origin), they can evoke a T-cell response. Examples of such proteins are the human papilloma type 16 virus proteins, E6 and E7, which are expressed in cervical carcinoma.

For proteins to be recognized by cytotoxic T-lymphocytes as tumor-specific or -associated antigens, and to be used in a therapy, particular prerequisites must be fulfilled. The antigen should be expressed mainly by tumor cells and not or in comparably small amounts by normal healthy tissues or in another preferred embodiment the peptide should be over-presented by tumor cells as compared to normal healthy tissues. It is furthermore desirable, that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to a function e.g. in cell cycle control or suppression of apoptosis. Additionally, downstream targets of the proteins directly causative for a transformation may be upregulated und thus may be indirectly tumor-associated. Such indirect tumor-associated antigens may also be targets of a vaccination approach (Singh-Jasuja et al., 2004). In both cases it is essential that epitopes are present in the amino acid sequence of the antigen, since such a peptide ("immunogenic peptide") that is derived from a tumor associated antigen should lead to an in vitro or in vivo T-cell-response.

Basically, any peptide able to bind a MHC molecule may function as a T-cell epitope. A prerequisite for the induction of an in vitro or in vivo T-cell-response is the presence of a T cell with a corresponding TCR and the absence of immunological tolerance for this particular epitope.

Therefore, TAAs are a starting point for the development of a tumor vaccine. The methods for identifying and characterizing the TAAs are based on the use of CTL that can be isolated from patients or healthy subjects, or they are based on the generation of differential transcription profiles or differential peptide expression patterns between tumors and normal tissues.

However, the identification of genes over-expressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T cell with a corresponding TCR has to be present and immunological tolerance for this particular epitope needs to be absent or minimal. In a very preferred embodiment of the invention it is therefore important to select only those over- or selectively presented peptides against which a functional and/or a proliferating T cell can be found. Such a functional T cell is defined as a T cell, which upon stimulation with a specific antigen can be clonally expanded and is able to execute effector functions ("effector T cell").

In case of TCRs and antibodies according to the invention the immunogenicity of the underlying peptides is secondary. For TCRs and antibodies according to the invention the presentation is the determining factor.

T-helper cells play an important role in orchestrating the effector function of CTLs in anti-tumor immunity. T-helper cell epitopes that trigger a T-helper cell response of the TH1 type support effector functions of CD8-positive killer T cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate anti-tumor immune responses.

Uses against further cancers are disclosed in the following description of the proteins of the peptides according to the invention.

ATP-Binding Cassette, Sub-Family A (ABC1), Member 13 (ABCA13)

In human, the ATP-binding cassette (ABC) family of transmembrane transporters has at least 48 genes and 7 gene subfamilies. The predicted ABCA13 protein consists of 5,058 amino acid residues making it the largest ABC protein described to date (Prades et al., 2002). Knight et al. determined that ABCA13 protein is expressed in mouse and human hippocampus and cortex, both regions relevant to schizophrenia and bipolar disorder (Knight et al., 2009). The ABCA13 gene maps to chromosome 7p12.3, a region that contains an inherited disorder affecting the pancreas (Shwachman-Diamond syndrome) as well as a locus involved in T-cell tumor invasion and metastasis (INM7), and therefore is a positional candidate for these pathologies (Prades et al., 2002).

Matrix Metallopeptidase 12 (Macrophage Elastase) (MMP12)

MMP12, also known as human metalloelastase (HME) or macrophage metalloelastase (MME) is a zinc endopeptidase recognized for its ability to degrade elastin. Apart from that, it has a broad substrate range, extending to other matrix proteins such as collagens, fibronectin, laminin, proteoglycans, and non-matrix proteins such as alpha-1-antitrypsin. In asthma, emphysema and chronic obstructive pulmonary disease (COPD), MMP12 may contribute to alveolar destruction and airway remodeling (Cataldo et al., 2003; Wallace et al., 2008). MMP12 has been implicated in macrophage migration, and as it can generate angiostatin from plasminogen, it contributes to inhibition of angiogenesis (Chakraborti et al., 2003; Chandler et al., 1996; Sang, 1998). Like other metalloproteinases, MMP12 is involved in physiological processes like embryogenesis, wound healing and the menstrual cycle (Chakraborti et al., 2003; Labied et al., 2009), but also in pathological processes of tissue destruction.

Although data are based on low numbers of patients in several cases, there is ample evidence in literature that MMP12 is frequently over-expressed in cancer (Denys et al., 2004; Hagemann et al., 2001; Ma et al., 2009; Vazquez-Ortiz et al., 2005; Ye et al., 2008). However, data are controversial with respect to the impact of MMP12 over-expression on clinical parameters and prognosis. While it may be involved in matrix dissolution and, thus, metastasis, it can also inhibit tumor growth through production of angiostatin, which negatively impacts angiogenesis (Gorrin-Rivas et al., 2000; Gorrin Rivas et al., 1998; Kim et al., 2004).

For lung cancer, consequences of MMP12 expression are controversial. MMP12 overexpression in epithelial cells has been reported in inflammation-triggered lung remodeling. MMP12 up-regulation may play a role in emphysema-to-lung cancer transition (Qu et al., 2009). Animal studies suggest that MMP12 expression by stroma or macrophages suppresses growth of lung tumors (Acuff et al., 2006; Houghton et al., 2006). However, there are also reports that MMP12 over-expression in lung tumors correlates with recurrence, metastatic disease and shorter relapse-free survival after resection (Cho et al., 2004; Hofmann et al., 2005).

Dystonin (DST)

DST (BPAG1-e) encodes a member of the plakin protein family of adhesion junction plaque proteins. BPAG1-e is expressed in epithelial tissue, anchoring keratin-containing intermediate filaments to hemidesmosomes (HDs). HDs are multiprotein adhesion complexes that promote epithelial stromal attachment in stratified and complex epithelia. Modulation of their function is of crucial importance in a variety of biological processes, such as differentiation and migration of keratinocytes during wound healing and carcinoma invasion, in which cells become detached from the substrate and acquire a motile phenotype (Litjens et al., 2006).

Malignant melanoma is one of the most aggressive types of tumor. BPAG1 is expressed in human melanoma cell lines (A375 and G361) and normal human melanocytes. The levels of anti-BPAG1 auto-antibodies in the sera of melanoma patients were significantly higher than in the sera of healthy volunteers (p<0.01). Anti-BPAG1 auto-antibodies may be a promising marker for the diagnosis of melanoma (Shimbo et al., 2010). DST was associated with breast cancer invasion (Schuetz et al., 2006). The BPAG1 gene is likely to be involved in the proliferation, apoptosis, invasion and metastasis of nasopharyngeal carcinoma NPC (Fang et al., 2005).

Matrix-Remodeling Associated 5 (MXRA5)

MXRA5, also known as adlican, encodes an adhesion proteoglycan and belongs to a group of genes involved in ECM remodeling and cell-cell adhesion (Rodningen et al., 2008). Although the function of MXRA5 in cancer is unknown, somatic mutations in MXRA5 have been identified in tumors obtained from a variety of tissues such as skin, brain, lung, and ovary. RT-PCR was performed on adlican (MXRA5) confirmed microarray findings of overexpression in colon cancers compared to normal colon tissue (13 colorectal tumors and 13 normal tissues) (Zou et al., 2002). In a recent study, matrix-remodeling associated 5 was the second most frequently mutated gene in NSCLC (first is TP53) (Xiong et al., 2012).

Cyclin-Dependent Kinase 4 (CDK4)/Cyclin-Dependent Kinase 6 (CDK6)

CDK4 is a member of the Ser/Thr protein kinase family. It is a catalytic subunit of the protein kinase complex that is important for cell cycle G1 phase progression. The activity of this kinase is restricted to the G1-to S phase transition during the cell cycle and its expression is primarily controlled at the transcriptional level (Xiao et al., 2007). CDK4 and CDK6 enzymes and their regulators, e.g., cyclins, play critical roles in embryogenesis, homeostasis, and cancerogenesis (Graf et al., 2010).

In lung cancer tissues the expression level of CDK4 protein was significantly increased compared to normal tissues (P<0.001). Patients with higher CDK4 expression had a markedly shorter overall survival time than patients with low CDK4 expression. Multivariate analysis suggested the level of CDK4 expression was an independent prognostic indicator (P<0.001) for the survival of patients with lung cancer. Furthermore, suppressing CDK4 expression also significantly elevated the expression of cell cycle regulator p21 (Wu et al., 2011a). In lung cells that express an endogenous K-Ras oncogene, ablation of Cdk4, but not Cdk2 or Cdk6, induces an immediate senescence response. No such response occurs in lungs expressing a single Cdk4 allele or in other K-Ras-expressing tissues. Targeting Cdk4 alleles in advanced tumors detectable by computed tomography scanning also induces senescence and prevents tumor progression (Puyol et al., 2010).

Heterogeneous Nuclear Ribonucleoprotein H1 (H) (HNRNPH1)/Heterogeneous Nuclear Ribonucleoprotein H2 (H') (HNRNPH2)

These genes belong to the subfamily of ubiquitously expressed heterogeneous nuclear ribonucleoproteins (hnRNPs). The hnRNPs are RNA binding proteins and they complex with heterogeneous nuclear RNA (hnRNA). These proteins are associated with pre-mRNAs in the nucleus and appear to influence pre-mRNA processing and other aspects of mRNA metabolism and transport.

hnRNPH activity appears to be involved in the pathogenesis and progression of malignant gliomas as the center of a splicing oncogenic switch, which might reflect reactivation of stem cell patterns and mediates multiple key aspects of aggressive tumor behavior, including evasion from apoptosis and invasiveness (Lefave et al., 2011). Small interfering RNA-mediated knockdown of hnRNP H or A-Raf resulted in MST2-dependent apoptosis. In contrast, enforced expression of either hnRNP H or A-Raf partially counteracted apoptosis induced by etoposide (Rauch et al., 2010). Up-regulation of hnRNP H/H' is found in a few tissues that normally express low cytoplasmic levels of hnRNP H/H', for example, adenocarcinoma of the pancreas, hepatocellular carcinoma and gastric carcinoma (Honore et al., 2004).

Tetratricopeptide Repeat, Ankyrin Repeat and Coiled-Coil Containing 2 (TANC2)

TANC family comprises TANC1 and TANC2, which was identified in 2005 (Han et al., 2010). TANC family proteins are involved in the regulation of dendritic spines, spatial learning, and embryonic development, as TANC1-deficiency in mice reduces spine density in the hippocampus and impaired spatial learning, whereas TANC2-deficiency causes embryonic lethality. In contrast, overexpression of TANC1 and TANC2 in cultured neurons enhances the density of dendritic spines and excitatory synapses. TANC1 and 2 proteins are mainly expressed in the brain, in which a significant proportion of protein is located in small-vesicle membranes (Han et al., 2010).

Ring Finger Protein 213 (RNF213)

RNF213 encodes a protein containing a C3HC4-type RING finger domain, which is a specialized type of Zn-finger that binds two atoms of zinc and is thought to be involved in mediating protein-protein interactions.

A research group provided evidence suggesting, for the first time, the involvement of RNF213 in genetic susceptibility to moyamoya disease (Liu et al., 2011b). Another study has shown that the RNF213 gene was related to moymoya disease susceptibility in the Han Chinese population (Wu et al., 2012).

Solute Carrier Family 34 (Sodium Phosphate), Member 2 (SLC34A2)

SLC34A2 is a pH-sensitive sodium-dependent phosphate transporter. Upregulation of SLC34A2 gene expression in well-differentiated tumors may reflect cell differentiation processes during ovarian cancerogenesis and could serve as potential marker for ovarian cancer diagnosis and prognosis (Shyian et al., 2011). RT-PCR confirmed increased expression of SLC34A2 in papillary thyroid cancer (Kim et al., 2010b). There was also a significantly increased gene expression of SLC34A2 among breast cancer tissues compared with normal tissues (Chen et al., 2010a).

SET and MYND Domain Containing 3 (SMYD3)

It was previously reported that upregulation of SMYD3, a histone H3 lysine-4-specific methyltransferase, plays a key role in the proliferation of colorectal carcinoma (CRC) and hepatocellular carcinoma (HCC). In another study, they reveal that SMYD3 expression is also elevated in the great majority of breast cancer tissues. Similarly to CRC and HCC, silencing of SMYD3 by small interfering RNA to this gene resulted in the inhibited growth of breast cancer cells, suggesting that increased SMYD3 expression is also essential for the proliferation of breast cancer cells (Hamamoto et al., 2006). Knockdown of SMYD3 by RNA interference down-regulates c-Met expression and inhibits cells migration and invasion induced by HGF (Zou et al., 2009). SMYD3 plays crucial roles in HeLa cell proliferation and migration/invasion, and it may be a useful therapeutic target in human cervical carcinomas (Wang et al., 2008b).

Aldo-Keto Reductase Family 1, Member C1 (AKR1C1)/ Aldo-Keto Reductase Family 1, Member C2 (AKR1C2)

AKR1C1 and AKR1C2 differ in only seven amino-acid residues (Le et al., 2010). AKR1C1 and AKR1C2 regulate the activity of androgens, estrogens, and progesterone, and the occupancy and transactivation of the corresponding receptors (Penning et al., 2000; Steckelbroeck et al., 2004). The AKR1C enzymes, except AKR1C4 which is liver specific, are expressed in different normal and diseased tissues and have thus been related to several diseases, such as lung, breast, prostate, endometrial cancer, myeloid leukemia, and others (Brozic et al., 2011; Byrns et al., 2011). Sensitivity to cisplatin appeared to be associated with AKR1C levels in epithelial lung cancer cell lines (Chen et al., 2010b) and in NSCLC patients (Kuang et al., 2012; Stewart, 2010). Thus, overexpression of AKR1C is an indicator of poor prognosis and chemo-resistance in human non-small lung cancer (NSCLC) (Wang et al., 2007). Overexpression of AKR1C2 is also associated with disease progression in prostatic cancer (Huang et al., 2010). Depletion of AKR1C2 expression with RNAi inhibits turmorigenesis in vivo and in vitro, which strongly suggests that AKR1C2 siRNA might play a critical role in blocking hepatocarcinogenesis (Dong-Dong, 2007).

Reticulocalbin 1, EF-Hand Calcium Binding Domain (RCN1)/Reticulocalbin 3, EF-Hand Calcium Binding Domain (RCN3)

Reticulocalbin 1 is a calcium-binding protein located in the lumen of the ER. Immunohistochemical examination demonstrated a broad distribution of RCN in various organs of fetuses and adults, predominantly in the endocrine and exocrine organs. Overexpression of RCN may play a role in tumorigenesis, tumor invasion, and drug resistance (Fukuda et al., 2007). Reticulocalbin 1 (RCN1) is a cell surface-associated protein on both endothelial (EC) and prostate cancer (PCa) cell lines. RCN1 expression on the cell surface was upregulated by tumor necrosis factor alpha treatment of bone-marrow endothelial cells (Cooper et al., 2008). RCN1 is up-regulated in colorectal carcinoma (CRC) and was localized in cancer cells or in stromal cells near the cancer cells. It could be a novel candidate for CRC marker (Watanabe et al., 2008). RCN3 is a member of the CREC (Cab45/reticulocalbin/ERC45/calumenin) family of multiple EF-hand Ca2+-binding proteins localized to the secretory pathway (Tsuji et al., 2006). In oligodendrogliomas RCN3 is suggested as a potentially important candidate gene. Though little is known about the function of RCN3 (Drucker et al., 2009).

Interleukin 8 (IL8)

IL8 is a chemokine of the CXC family that is one of the major mediators of the inflammatory response. This chemokine is secreted by several cell types. It functions as a chemoattractant, and is also a potent angiogenic factor. The CXC (ELR+) chemokines like IL8 induce angiogenesis and may be important in cancers that have an angiogenic phenotype such as NSCLC (Arenberg et al., 1997). Recently it was found that tumor derived IL8 acted as an attractant for circulating tumor cells to return to the original tumor (breast cancer, colon cancer, and melanoma tumors), leading to a more aggressive tumor phenotype (Kim et al., 2009). IL-8 levels are associated with lung cancer risk several years before diagnosis. Combination of IL-8 and CRP are more robust biomarkers in predicting subsequent lung cancer (Pine et al., 2011). Activating mutations of KRAS or EGFR upregulate IL-8 expression in NSCLC; IL-8 is highly expressed in NSCLCs from males, smokers, elderly patients, NSCLCs with pleural involvement, and KRAS-mutated adenocarcinomas; and IL-8 plays a role in cell growth and migration in oncogenic KRAS-driven NSCLC (Sunaga et al., 2012).

Pyrimidinergic Receptor P2Y, G-Protein Coupled, 6 (P2RY6)

P2RY6 belongs to the family of G-protein coupled receptors. This family has several receptor subtypes with different pharmacological selectivity, which overlaps in some cases, for various adenosine and uridine nucleotides. The P2Y6 subtype is expressed at particularly high levels in the placenta, suggesting that P2Y6 plays an important role in placental function. However, the cellular localization of P2Y6 within the placenta is unknown. P2Y6 may play an important role in trophoblastic development, differentiation, and neoplasia (Somers et al., 1999). An important role for the pyrimidine-activated P2Y receptor in the inflammatory response of lung epithelia was indicated (Schafer et al., 2003).

HECT, UBA and WWE Domain Containing 1, E3 Ubiquitin Protein Ligase (HUWE1) HUWE1 encodes a member of the HECT E3 ubiquitin ligase family. The HECT domain lies in the C-terminus and contains the active-site cysteine which forms an intermediate ubiquitin-thioester bond.

ARF-BP1 (HUWE1) is a critical mediator of both the p53-independent and p53-dependent tumor suppressor functions of ARF. As such, ARF-BP1 may serve as a potential target for therapeutic intervention in tumors regardless of p53 status (Chen et al., 2005a). Inactivation of ARF-BP1 stabilized p53 and induced apoptosis (Chen et al., 2006). HUWE1 (HectH9) is overexpressed in multiple human tumors and is essential for proliferation of a subset of tumor cells (Adhikary et al., 2005; Zhang et al., 2011a). In breast cancer HUWE1 correlated significantly with relevant prognostic factors, and with clinical outcome (Confalonieri et al., 2009).

Versican (VCAN)

VCAN is a member of the aggrecan/versican proteoglycan family. VCAN is known to associate with a number of molecules in the extracellular matrix including hyaluronan, tenascin, fibulin-1, fibronectin, CD44 and L-selectin, fibrillin, integrin, and link protein (Zheng et al., 2004). VCAN is expressed in a variety of tissues. It is highly expressed in the early stages of tissue development, and its expression decreases after tissue maturation. Its expression is also elevated during wound repair and tumor growth (Ghosh et al., 2010). Knockdown in human lung adenocarcinoma (A549) cells of VCAN by RNA interference significantly inhibited tumor growth in vivo but not in vitro (Creighton et al., 2005). VCAN is a direct target of p53. High expression of VCAN has also been found in the peritumoral stromal tissue of early stage prostate cancers, and of breast cancers, and it is associated with an aggressive tumor behavior (Yoon et al., 2002).

Drosha, Ribonuclease Type III (DROSHA)

Drosha is a Class 2 RNase III enzyme responsible for initiating the processing of microRNA (miRNA), or short RNA molecules naturally expressed by the cell that regulate a wide variety of other genes by interacting with the RNA-induced silencing complex (RISC) to induce cleavage of complementary messenger RNA (mRNA) as part of the RNAi pathway. A microRNA molecule is synthesized as a long RNA primary transcript known as a pri-miRNA, which is cleaved by Drosha to produce a characteristic stem-loop structure of about 70 base pairs long, known as a pre-miRNA (Lee et al., 2003). Drosha exists as part of a protein complex called the Microprocessor complex, which also contains the double-stranded RNA binding protein Pasha (also called DGCR8) (Denli et al., 2004), which is essential for Drosha activity and is capable of binding single-stranded fragments of the pri-miRNA that are required for proper processing (Han et al., 2006). Human Drosha was cloned in 2000, when it was identified as a nuclear dsRNA ribonuclease involved in the processing of ribosomal RNA precursors (Wu et al., 2000). Drosha was the first human RNase III enzyme identified and cloned. The other two human enzymes that participate in the processing and activity of miRNA are the Dicer and Argonaute proteins. Both Drosha and Pasha are localized to the cell nucleus, where processing of pri-miRNA to pre-miRNA occurs. This latter molecule is then further processed by the RNase Dicer into mature miRNAs in the cell cytoplasm (Lee et al., 2003). Drosha and other miRNA processing enzymes may be important in cancer prognosis (Slack and Weidhaas, 2008).

Pleckstrin Homology Domain Containing, Family a (Phosphoinositide Binding Specific) Member 8 (PLEKHA8)

The gene for phosphatidylinositol-4-phosphate adaptor-2 (FAPP2=PLEKHA8) encodes a cytoplasmic lipid transferase with a plekstrin homology domain that has been implicated in vesicle maturation and transport from trans-Golgi to the plasma membrane (Cao et al., 2009). The introduction of ribozymes targeting the FAPP2 gene in colon carcinoma cells induced their apoptosis in the presence of Fas agonistic antibody. Also, FAPP2 siRNA transfected glioma and breast tumor cells showed significant increases in apoptosis (Tritz et al., 2009). Later studies have highlighted a role for FAPP2 as lipid transfer protein involved in glycosphingolipid metabolism at the Golgi complex (D'Angelo et al., 2012). Phosphoinositol 4-phosphate adaptor protein-2 (FAPP2) plays a key role in glycosphingolipid (GSL) production using its C-terminal domain to transport newly synthesized glucosylceramide away from the cytosol-facing glucosylceramide synthase in the cis-Golgi for further anabolic processing (Kamlekar et al., 2013).

Acetyl-CoA Carboxylase Alpha (ACACA)

ACACA is a biotin-containing enzyme which catalyzes the carboxylation of acetyl-CoA to malonyl-CoA, the rate-limiting step in fatty acid synthesis (Tong and Harwood, Jr., 2006). ACACA up-regulation has been recognized in multiple human cancers, promoting lipogenesis to meet the need of cancer cells for rapid growth and proliferation. Therefore, ACACA might be effective as a potent target for cancer intervention, and the inhibitors developed for the treatment of metabolic diseases would be potential therapeutic agents for cancer therapy (Wang et al., 2010a). Two studies have shown that silencing of ACACA by RNA interference causes growth inhibition and induces cell death almost to the same extent as observed after silencing of FASN gene expression (Brusselmans et al., 2005; Chajes et al., 2006). TOFA (5-tetradecyloxy-2-furoic acid), an allosteric inhibitor of ACACA, is cytotoxic to lung cancer cells NCI-H460 and colon carcinoma cells HCT-8 and HCT-15 and induce apoptosis (Wang et al., 2009a). Another highly potent inhibitor of ACACA, soraphen A, blocks lipogenesis and enhances fatty acid oxidation in prostate cancer cells. Cancer cells stop proliferating and ultimately die (Beckers et al., 2007). These findings suggest that apart from malonyl-CoA accumulation, inhibition of lipogenesis per se may cause cancer cell death and that ACACA may be a target for antineoplastic therapy after all (Brusselmans et al., 2005).

Integrin, alpha 11 (ITGA11)

Integrins play crucial roles in diverse cellular and developmental processes, including cell growth, differentiation, and survival, as well as carcinogenesis, cancer cell invasion, and metastases. Integrin alpha11 (ITGA11/alpha11) is localized to stromal fibroblasts and commonly overexpressed in non-small-cell lung carcinoma (NSCLC). The alpha11 mRNA was overexpressed in both lung adenocarcinoma and squamous cell carcinoma (Wang et al., 2002). It has been reported that alpha11 plays an important role in the ability of fibroblasts to promote the growth of NSCLC cells in vivo, and such activity is partially mediated by its regulation of IGF2 expression (Zhu et al., 2007). For NSCLC patients' clinicopathological characteristics, the overexpression of hMTH1, SPD, HABP 2, ITGA11, COL11A1, and CK-19 was significantly correlated with the pathological stage ($p<0.05$). In addition, the overexpression of hMTH1, SPD, ITGA11, and COL11A1 was correlated with lymph node metastasis and poor prognosis (Chong et al., 2006).

Collagen, Type XII, Alpha 1 (COL12A1)

The COL12A1 gene encodes the alpha chain of type XII collagen, a member of the FACIT (fibril-associated collagens with interrupted triple helices) collagen family. Type XII collagen is a homotrimer found in association with type I collagen, an association that is thought to modify the interactions between collagen I fibrils and the surrounding matrix (Oh et al., 1992). COL12A1 may be involved in basement membrane regulation providing specific molecular bridges between fibrils and other matrix components (Thierry et al., 2004). COL12A1 is expressed in heart, placenta, lung, skeletal muscle and pancreas (Dharmavaram et al., 1998), in a variety of connective tissues including articular and epiphyseal cartilage (Gregory et al., 2001; Walchli et al., 1994; Watt et al., 1992). COL12A1 was down-regulated in tumors with high microsatellite instability when compared to the stable group with low or null microsatellite instability (Ortega et al., 2010).

Elastase, Neutrophil Expressed (ELANE)

Neutrophil elastase (or leukocyte elastase) also known as ELA2 (elastase 2, neutrophil) is a serine proteinase in the same family as chymotrypsin and has broad substrate specificity. Secreted by neutrophils during inflammation, it destroys bacteria and host tissue (Belaaouaj et al., 2000). Human neutrophil elastase (ELANE), a main actor in the development of chronic obstructive pulmonary diseases, has been recently involved in non-small cell lung cancer progression. It can act at several levels (i) intracellularly, clearing for instance the adaptor molecule insulin receptor substrate-1 (IRS-1) (ii) at the cell surface, hydrolyzing receptors as CD40 (iii) in the extracellular space, generating elastin fragments i.e. morphoelastokines which potently stimulate cancer cell invasiveness and angiogenesis (Moroy et al., 2012). Neutrophil elastase directly induced tumor cell proliferation in both human and mouse lung adenocarcinomas by gaining access to an endosomal compartment within tumor cells, where it degraded insulin receptor substrate-1 (IRS-1) (Houghton et al., 2010).

Serpin Peptidase Inhibitor, Clade B (Ovalbumin), Member 3 (SERPINB3)

Squamous cellular carcinoma antigen (SCCA), also called SERPINB3, is a member of the high molecular weight family of serine protease inhibitors (serpins) (Suminami et al., 1991). High levels have been reported in cancer of the head and neck tissue and other epithelial cancers (Torre, 1998). SCCA has been reported to be overexpressed in tumoral compared to peritumoral tissue, suggesting a role as a potential marker for histological detection of HCC (Pontisso et al., 2004). Serpin B3/B4, particularly Serpin B4, appears to play an important role in aberrant epithelial proliferation. Evaluation of Serpin B3/B4 could have prognostic value in predicting disease progression, especially in patients with increased susceptibility to lung cancer (Calabrese et al., 2012). On one hand, SCCA1 (SERPINB3) inhibits cell death induced by lysosomal injury while, on the other hand, it sensitizes cells to ER stress by activating caspase-8 independently of the death receptor apoptotic pathway (Ullman et al., 2011). Some findings indicate that SERPINB3 plays an important role in the induction of epidermal barrier disruption. SERPINB3 may be a critical determinant of barrier function in the epidermis (Katagiri et al., 2010).

Kinesin Family Member 26B (KIF26B)

A kinesin is a protein belonging to a class of motor proteins found in eukaryotic cells. Kinesins move along microtubule filaments, and are powered by the hydrolysis of ATP (thus kinesins are ATPases). Kif26b, a kinesin family gene, is a downstream target of Sall1 (Nishinakamura et al., 2011). Kif26b is essential for kidney development because it regulates the adhesion of mesenchymal cells in contact with ureteric buds. Overexpression of Kif26b in vitro caused increased cell adhesion through interactions with non-muscle myosin (Terabayashi et al., 2012; Uchiyama et al., 2010).

Ankylosis, Progressive Homolog (Mouse) (ANKH)

ANKH (human homolog of progressive ankylosis) regulates the transport of inorganic pyrophosphate (PPi) through the cell membrane (Wang et al., 2008a). Some data suggest that ANKH expression and function in vitro and in vivo are repressed in hypoxic environments and that the effect is regulated by HIF-1 (Zaka et al., 2009). Human ANKH gene is expressed in vivo in a tissue-specific manner, with highest levels of mRNA expression found in brain, heart, and skeletal muscle (Guo et al., 2001). Mutations in the ANKH gene have been associated with autosomal dominant craniometaphyseal dysplasia (Kornak et al., 2010). ANKH was significantly upregulated in cervical cancer cell lines with amplifications as compared to cell lines without amplifications (Kloth et al., 2007). Genomic amplification of regions on chromosome arm 5p has been observed frequently in small cell lung cancer (SCLC), implying the presence of multiple oncogenes on this arm. Coe et al. described the identification of microdeletions that have escaped detection by conventional screens and the identification TRIO and ANKH as novel putative oncogenes (Coe et al., 2005).

Nuclear RNA Export Factor 1 (NXF1)

In human cells, the mRNA export factor NXF1 resides in the nucleoplasm and at nuclear pore complexes (Zhang et al., 2011b). The transport of mRNA from the site of transcription in the nucleus to the site of translation in the cytoplasm is an essential process in eukaryotic gene expression. In human cells, the mRNA export factor NXF1 (also known as TAP) escorts mRNA transcripts out of the nucleus by simultaneously binding mRNA, mRNA adaptor proteins, and phenylalanine-glycine (FG) repeats of the nuclear pore complex (Kelly and Corbett, 2009). NXF1 is unique among nuclear transport factors, as it is a multidomain protein that bears no structural or mechanistic resemblance to the karyopherin proteins that transport protein cargos, tRNAs, and microRNAs through the NPC. mRNA export by NXF1 is a process that occurs independent of the GTPase Ran (Gruter et al., 1998). Nuclear export of mRNPs is mediated by transport factors such as NXF1 that bind mRNPs and mediate their translocation through the central channel of nuclear pores (NPC) using transient interactions with FG-nucleoporins (Wickramasinghe et al., 2010). mRNAs can be transported by either bulk export pathways involving NXF1/TAP or more specialized pathways involving chromosome region maintenance 1 (CRM1) (Siddiqui and Borden, 2012).

Regulator of G-Protein Signaling 4 (RGS4)

RGS4 acts as a GTPase accelerating protein to modulate μ- and δ-opioid receptor (MOR and DOR, respectively) signaling. Opioid agonist-induced reduction in RGS4 occurs via the ubiquitin-proteasome pathway and may contribute to the maintenance of cell homeostasis in the morphine-dependent state (Wang and Traynor, 2011). RGS4 plays an important role in regulating beta-cell function (Ruiz, I et al., 2010). Xie et al. suggested RGS4 as a novel suppressor of breast cancer migration and invasion, important steps of metastatic cascades (Xie et al., 2009). RGS4 was overexpressed in thyroid carcinoma. The effective down-regulation of its expression levels in thyroid cancer cells significantly attenuated viability of thyroid cancer cells, indicating the significant role of RGS4 in thyroid carcinogenesis (Nikolova et al., 2008). RGS4 was differentially expressed in a human pancreatic tumor cell line and found to be a possible marker gene for local tumor invasion and liver metastases in pancreatic carcinoma (Niedergethmann et al., 2007). RGS4 overexpression delayed and altered lung epithelial cell tubulation by selectively inhibiting G protein-mediated p38 MAPK activation, and, consequently, by reducing epithelial cell proliferation, migration, and expression of vascular endothelial growth factor (VEGF) (Albig and Schiemann, 2005).

Glutamine-Fructose-6-Phosphate Transaminase 2 (GFPT2)

GFPT2 is involved in neurite outgrowth, early neuronal cell development, neuropeptide signaling/synthesis and neuronal receptor (Tondreau et al., 2008). Genetic variants in GFPT2 are associated with type 2 diabetes and diabetic nephropathy (Zhang et al., 2004). Furthermore, the association of SNPs in GFPT2 suggests that the gene involved in modulation of oxidative pathway could be major contributor to diabetic chronic renal insufficiency (Prasad et al., 2010). DNA methylation of the GFPT2 gene was validated in primary acute lymphoblastic leukemia (ALL) samples. Patients with methylation of multiple CpG islands had a worse overall survival (Kuang et al., 2008). GFPT2 plays a role in glutamine metabolism and was observed to be more highly expressed in mesenchymal cell lines. Glutamine metabolism may play an important role in tumor progression and inhibitors of cellular metabolic pathways may be a form of epigenetic therapy (Simpson et al., 2012).

Cerebral Endothelial Cell Adhesion Molecule (CERCAM)

CERCAM is localized at the surface of endothelial cells (Starzyk et al., 2000) and mapped on chromosome 9q34.11, a candidate region on 9q, identified as linked to familial idiopathic scoliosis (Miller et al., 2012). The CEECAM1 gene is widely transcribed in the nervous system and in several secretory tissues such as salivary glands, pancreas, liver and placenta (Schegg et al., 2009). The CERCAM protein is structurally similar to the ColGalT enzymes GLT25D1 and GLT25D2. But although its function is still not known, it seems to be is functionally different from the related GLT25D1 protein, and the protein does not function as a glycosyltransferase like GLT25D1 and GLT25D2 proteins (Perrin-Tricaud et al., 2011).

UDP-N-Acetyl-Alpha-D-Galactosamine: Polypeptide N-Acetylgalactosaminyl-Transferase 2 (GalNAc-T2) (GALNT2)

GALNT2, catalyze the first step in mucin-type O-glycosylation of peptides in the Golgi apparatus. These enzymes transfer N-acetylgalactosamine (GalNAc) from UDP-GalNAc to the hydroxyl group of serine or threonine in target proteins (Peng et al., 2010). GALNT2 was expressed constitutively and at low levels in most or all human adenocarcinoma cell lines from pancreas, colon, stomach, and breast examined (Sutherlin et al., 1997). Studies have shown that O-glycans and GALNT genes play critical roles in a variety of biological functions and human disease development. Risk of epithelial ovarian cancer (Terry et al., 2010) and coronary artery disease (Willer et al., 2008) have been associated with single nucleotide polymorphisms of GALNT2.

Aberrant glycosylation of cell surface glycoprotein due to specific alterations of glycosyltransferase activity is usually associated with invasion and metastasis of cancer. GALNT2 is involved in tumor migration and invasion in gastric carcinomas (Hua et al., 2012), in hepatocellular carcinoma (HCC) (Wu et al., 201 b) and in human malignant glioma (Liu et al., 2011a).

Heterogeneous Nuclear Ribonucleoprotein M (HNRNPM)

The HNRNPM gene belongs to the subfamily of ubiquitously expressed heterogeneous nuclear ribonucleoproteins (hnRNPs). HNRNPM is an abundant component of human hnRNP complexes that can influence pre-mRNA splicing by regulating its own pre-mRNA splicing (Hase et al., 2006) or by affecting the regulation of alternative splicing of fibroblast growth factor receptor 2 (Hovhannisyan and Carstens, 2007). Proteomic analyses of in vitro purified spliceosomes detected HNRNPM in the pre-spliceosomal H-complex and throughout the spliceosome assembly (Rappsilber et al., 2002; Wahl et al., 2009). HNRNPM is involved in the spliceosome machinery through its interaction with the CDC5L/PLRG1 spliceosomal subcomplex (Lleres et al., 2010). In human cancer cells, some results show that, cytoplasmic retention of IMP-3 and HNRNPM leads to significant drop in proliferation. A nuclear IMP-3-HNRNPM complex is important for the efficient synthesis of CCND1, D3 and G1 and for the proliferation of human cancer cells (Rivera et al., 2013).

Basonuclin 1 (BNC1)

Basonuclin is a zinc-finger protein with a highly restricted tissue distribution (Tseng, 1998). Thus far, basonuclin has been detected mainly in the basal keratinocytes of stratified squamous epithelia (skin, oral epithelium, esophagus, vagina, and cornea) and in the gametogenic cells of the testis and ovary (Tseng and Green, 1994; Weiner and Green, 1998). There is now considerable evidence that basonuclin is a cell-type-specific transcription factor for rRNA genes (rDNA). The zinc fingers of basonuclin interact with three evolutionarily conserved sites within the rDNA promoter (Iuchi and Green, 1999; Tseng et al., 1999). Epigenetic regulation by CpG methylation has an important role in tumorigenesis as well as in the response to cancer therapy. BNC1 was hypomethylated in radioresistant H1299 human non-small cell lung cancer (NSCLC) cell lines. Suppression of BNC1 mRNA expression in H1299 cells also reduced the resistance of these cells to ionizing radiation (Kim et al., 2010a). Aberrant DNA methylation of BNC1 was also detected in chronic lymphocytic leukemia (CLL) samples (Tong et al., 2010). In Renal Cell Carcinoma (RCC), methylation of BNC1 was associated with a poorer prognosis independent of tumor size, stage or grade (Morris et al., 2010).

FK506 Binding Protein 10, 65 kDa (FKBP10)

FK506-binding protein 10 (FKBP10) belongs to the FKBP-type peptidyl-prolyl cis/trans isomerase family. It is located in endoplasmic reticulum and acts as molecular chaperones (Ishikawa et al., 2008; Patterson et al., 2000). It is highly expressed in lung development and can be reactivated in a coordinated manner with extracellular matrix proteins after lung injury (Patterson et al., 2005).

Frizzled Family Receptor 1 (FZD1), Frizzled Family Receptor 2 (FZD2), Frizzled Family Receptor 7 (FZD7)

The genes FZD2, FZD1 and FZD7 are all from the 'frizzled' gene family; members of this gene family encode 7-transmembrane domain proteins that are receptors for Wnt signaling proteins.

The expression of the FZD2 gene appears to be developmentally regulated, with high levels of expression in fetal kidney and lung and in adult colon and ovary (Sagara et al., 1998; Zhao et al., 1995).

The FZD1 protein contains a signal peptide, a cysteine-rich domain in the N-terminal extracellular region, 7 transmembrane domains, and a C-terminal PDZ domain-binding motif. The FZD1 transcript is expressed in various tissues, including lung as well as heart, kidney, pancreas, prostate, and ovary (Sagara et al., 1998). The expression of frizzled 1 and 2 receptors was found to be up-regulated in breast cancer (Milovanovic et al., 2004).

The FZD7 protein contains an N-terminal signal sequence, 10 cysteine residues typical of the cysteine-rich extracellular domain of Fz family members, 7 putative transmembrane domains, and an intracellular C-terminal tail with a PDZ domain-binding motif. FZD7 gene expression may downregulate APC function and enhance beta-catenin-mediated signals in poorly differentiated human esophageal carcinomas (Sagara et al., 1998; Tanaka et al., 1998).

ATPase, Ca++ Transporting, Cardiac Muscle, Fast Twitch 1 (ATP2A1), ATPase, Ca++ Transporting, Cardiac Muscle, Fast Twitch 2 (ATP2A2)

Both genes (ATP2A1 and ATP2A2) encode SERCA Ca(2+)-ATPases. Sarcoplasmic reticulum (SR)1/ER calcium ATPases (SERCAs) are calcium pumps that couple ATP hydrolysis with calcium transport across the SR/ER membrane (MacLennan et al., 1997). SERCAs are encoded by three homologous genes: SERCA1 (ATP2A1), SERCA2 (ATP2A2), and SERCA3 (Wu et al., 1995). Some evidence has emerged to show that SERCA may also have a direct impact on the processes of apoptosis, differentiation, and cell proliferation (Chami et al., 2000; Ma et al., 1999; Sakuntabhai et al., 1999).

Mutations in ATP2A1, encoding SERCA1, cause some autosomal recessive forms of Brody disease, characterized by increasing impairment of muscular relaxation during exercise (Odermatt et al., 1996).

ATP2A2 is an ATPase associated with Darier's disease, a rare, autosomal dominant hereditary skin disorder characterized by abnormal keratinization and acantholysis (Huo et al., 2010). Germline alterations of ATP2A2 may predispose to lung and colon cancer and an impaired ATP2A2 gene might be involved in carcinogenesis (Korosec et al., 2006). In a Small Cell Lung Cancer (H1339) and an Adeno Carcinoma Lung Cancer (HCC) cell line the ER Ca2+-content was reduced compared to normal human bronchial epithelial. The reduced Ca2+-content correlated with a reduced expression of SERCA 2 pumping calcium into the ER (Bergner et al., 2009). ATP2A2 could be potential prognostic markers for colorectal cancer CRC patients. It was detected in circulating tumor cells (CTCs), and the postoperative relapse was significantly correlated with gene overexpression (Huang et al., 2012).

Laminin, Gamma 2 (LAMC2)

Laminins, a family of extracellular matrix glycoproteins, are the major noncollagenous constituent of basement membranes. They have been implicated in a wide variety of biological processes including cell adhesion, differentiation, migration, signaling, neurite outgrowth and metastasis. The LAMC2 gene encodes the laminin-5 γ2 chain, which is part of laminin-5, one of the major components of the basement membrane zone. LAMC2 was frequently up-regulation by promoter demethylation in gastric cancer (Kwon et al., 2011). LAMC2 was found to be overexpressed in angiotropic melanoma areas vs. avascular melanoma areas (Lugassy et al., 2009). LAMC2 is a biomarker of bladder cancer metastasis, and its expression level was associated with tumor grade (Smith et al., 2009b). LAMB3 and LAMC2 genes were co-expressed in 21 of 32 non-SCLC cell lines (66%) but only in one of 13 SCLC cell lines (8%). Coexpression of the LAMB3 and LAMC2 genes was also observed in all 4 cases of primary non-SCLC cells examined but not in the corresponding non-cancerous lung cells (Manda et al., 2000).

Heat Shock 70 kDa Protein 2 (HSPA2), Heat Shock 70 kDa Protein 8 (HSPA8)

HSPA2 has been identified as a potential cancer-promoting protein expressed at abnormal levels in a subset of human cancers, such as breast cancer (Mestiri et al., 2001), cervical cancer (Garg et al., 2010a), bladder urothelial cancer (Garg et al., 2010b), nasopharyngeal carcinoma (Jalbout et al., 2003) and malignant tumors (Chouchane et al., 1997). Some level of the HSPA2 gene activity was also observed in cell lines derived from several human cancers (Scieglinska et al., 2008), while silencing of the HSPA2 gene in cancer cells led to growth arrest and decrease in tumorigenic potential (Rohde et al., 2005; Xia et al., 2008). Furthermore, polymorphism in the HSPA2 gene is associated with an increase in the risk of developing lung cancer (Wang et al., 2010b). Overexpression of HSPA2 is correlated with increased cell proliferation, poor differentiation and lymph node metastases in human breast cancer, cervical cancer and bladder urothelial cancer (Garg et al., 2010a; Garg et al., 2010b; Mestiri et al., 2001).

The HSPA8 gene encodes a member of the heat shock protein 70 family Hsc70, which contains both heat-inducible and constitutively expressed members. HSPA8 binds to nascent polypeptides to facilitate correct protein folding (Beckmann et al., 1990). Hsc70 function as molecular chaperones, assisting in protein synthesis, folding, assembly, trafficking between cellular compartments, and degradation (Bukau and Horwich, 1998; Hartl and Hayer-Hartl, 2002). Hsc70 is expressed in non-malignant mammary cells as well as breast cancer cells (Kao et al., 2003; Vargas-Roig et al., 1998) and the overexpression of Hsp/hsc70 in chemoresistant cancer cells (Ciocca et al., 1992; Lazaris et al., 1997) has prompted studies about possible clinical markers of these proteins (Ciocca and Calderwood, 2005). There is a potential role of this secreted hsc70 chaperone in cell proliferation that might account for the higher tumor growth of cancer cells overexpressing cathepsin D (Nirde et al., 2010). Furthermore Ruisin et al. reported an association between a polymorphism of this gene and lung cancer risk (Rusin et al., 2004).

Vacuolar Protein Sorting 13 Homolog B (Yeast) (VPS13B)

VPS13B was identified as a peripheral membrane protein localized to the Golgi complex, where it overlaps with the cis-Golgi matrix protein GM130. Consistent with its subcellular localization, VPS13B depletion using RNAi causes fragmentation of the Golgi ribbon into ministacks (Seifert et al., 2011). Kolehmainen et al. (2003) identified the COH1 gene, also known as VPS13B, within the Cohen syndrome critical region on chromosome 8q22 (Kolehmainen et al., 2003). Loss-of-function mutations in the gene VPS13B lead to autosomal recessive Cohen syndrome (Seifert et al., 2011). Mutations of VPS13B and other genes were described in gastric and colorectal cancers with microsatellite instability (An et al., 2012).

CSE1 Chromosome Segregation 1-Like (Yeast) (CSE1L)

The cellular apoptosis susceptibility (CSE1L) gene has been demonstrated to regulate multiple cellular mechanisms including the mitotic spindle check point as well as proliferation and apoptosis. CSE1L is located in both the cytoplasm and the nuclei of cells. Nuclear CSE1L regulates the transcriptional activity of the p53 protein, a major tumor suppressor protein (Rao et al., 2011; Tanaka et al., 2007). Cytoplasmic CSE1L is associated with microtubules; this association has been shown to stimulate the extension of invadopodia and to enhance the migration of tumor cells (Tai et al., 2010). CSE1L is highly expressed in most cancers, such as benign and malignant cutaneous melanocytic lesions (Boni et al., 1999), endometrial carcinoma (Peiro et al., 2001), ovarian carcinoma (Brustmann, 2004), breast cancer (Behrens et al., 2001), urinary bladder urothelial carcinomas (Chang et al., 2012), and its expression has been shown to correlate with cancer progression. Silencing of CSE1L may be a potential therapeutic approach for colon cancer (Zhu et al., 2013).

Dihydropyrimidinase-Like 4 (DPYSL4)

Dihydropyrimidinase-related protein 4 (DPYSL4) is a known regulator of hippocampal neuron development. DPYSL4 is involved in growth regulation, polarization and differentiation of dental epithelial cells during tooth germ morphogenesis (Yasukawa et al., 2013). Some studies showed DPYSL4's role in attenuating neurite outgrowth possibility through inhibiting microtubule polymerization, and also revealed its novel association with vimentin during nuclear condensation prior to neuronal death (Aylsworth et al., 2009). The p53 tumor suppressor gene, which is frequently mutated in a wide variety of tumors, plays an important role in maintaining genomic integrity. Both mRNA and protein expressions of DPYSL4 were specifically induced by anticancer agents in p53-proficient cells. DPYSL4 is an apoptosis-inducible factor controlled by p53 in response to DNA damage (Kimura et al., 2011).

Sec61 Gamma Subunit (SEC61G)

SEC61γ, a heterotrimeric protein channel comprising the subunits SEC61α, β, and γ, is a member of the SEC61 translocon (Greenfield and High, 1999). The SEC61 complex forms a transmembrane pore for the translocation of nascent polypeptides into the ER lumen, as well as the integration of transmembrane proteins into the ER bilayer (Osborne et al., 2005). SEC61γ is required for tumor cell survival, and for the cellular response to endoplasmic reticulum stress. Furthermore it is highly overexpressed in malignant cells and near absent in normal cells (Lu et al., 2009). Knocking down SEC61γ expression resulted in apoptosis and abrogation of EGFR/AKT survival signaling (Lu et al., 2009) as well as to growth inhibition of the tumor cells (Neidert et al., 2012).

ORM1-Like 1 (*S. cerevisiae*) (ORMDL1)

The human genes (ORMDL1, ORMDL2 and ORMDL3) are expressed ubiquitously in adult and fetal tissues. They encode transmembrane proteins anchored in the endoplasmic reticulum which are likely involved in protein folding in the ER. By genomic sequence analysis, Hjelmqvist et al. (2002) mapped the ORMDL1 gene to chromosome 2q32.2 (Hjelmqvist et al., 2002). ORMDL proteins are the primary regulators of ceramide biosynthesis in mammalian cells (Siow and Wattenberg, 2012). ORMDL1 is specifically down-regulated in association with presenilin 1 (PS1) mutations (Araki et al., 2008).

Pecanex-like 3 (*Drosophila*) (PCNXL3)

Pecanex-like protein 3 (PCNXL3) is a multi-pass membrane protein; it belongs to the pecanex family.

The PCNXL3 gene was mapped to the chromosomal region 11q12.1-q13. Three novel human tumor-associated translocation breakpoints were located in the chromosome 11q13 region between the markers D11S4933 and D11S546. Thus PCNXL3 might be a 11q13-associated disease gene (van et al., 2000).

Small Nuclear Ribonucleoprotein 200 kDa (U5) (SNRNP200)

Pre-mRNA splicing is catalyzed by the spliceosome, a complex of specialized RNA and protein subunits that removes introns from a transcribed pre-mRNA segment. The spliceosome consists of small nuclear RNA proteins (snRNPs) U1, U2, U4, U5 and U6, together with approximately 80 conserved proteins. SNRNP200 is a gene required for unwinding of the U4/U6 duplex, a step essential for catalytic activation of the spliceosome (Maeder et al., 2009). SNRNP200 expression was detected in heart, brain, placenta, lung, liver, skeletal muscle, kidney, and pancreas (Zhao et al., 2009). Mutations in SNRNP200 have recently been discovered to be associated with autosomal dominant retinitis pigmentosa (adRP) (Benaglio et al., 2011; Liu et al., 2012).

SAM Domain, SH3 Domain and Nuclear Localization Signals 1 (SAMSN1)

SAMSN1 is a member of a novel gene family of putative adaptors and scaffold proteins containing SH3 and SAM (sterile alpha motif) domains. SAMSN1 is expressed in hematopoietic tissues, muscle, heart, brain, lung, pancreas, endothelial cells and myelomas. Endogenous SAMSN1 expression was shown to be up-regulated in primary B cells upon differentiation and proliferation-inducing stimuli, and transduction experiments suggest a stimulatory role for SAMSN1 in B cell differentiation to plasma cells (Brandt et al., 2010). Cell lines and primary cells from acute myeloid leukemia and multiple myeloma patients express SAMSN1 (Claudio et al., 2001). SAMSN1 was down-regulated in the large cell lung carcinoma cell line Calu-6 (Yamada et al., 2008). SAMSN1 was differentially expressed in ulcerative colitis-associated cancer (Watanabe et al., 2011).

Signal Transducer and Activator of Transcription 2, 113 kDa (STAT2)

STAT2 as a novel contributor to colorectal and skin carcinogenesis that may act to increase the gene expression and secretion of pro-inflammatory mediators, which in turn activate the oncogenic STAT3 signaling pathway (Gamero et al., 2010). STAT2 is a critical mediator in the activation of type I IFN-induced apoptosis. More importantly, defects in the expression or nuclear localization of STAT2 could lessen the efficacy of type I IFN immunotherapy (Romero-Weaver et al., 2010). Lower expression of STAT2 in low grade astrocytomas were detected when comparing with high grade astrocytomas. The results showed existing relationship between STAT and PPARgamma signaling in glial tumors and further support expected important role of STATs in regulation of growth and differentiation in these tumors (Ehrmann et al., 2008).

CCR4-NOT Transcription Complex, Subunit 1 (CNOT1)

The human CCR4-NOT deadenylase complex consists of at least nine enzymatic and non-enzymatic subunits. CNOT1 has an important role in exhibiting enzymatic activity of the CCR4-NOT complex, and thus is critical in control of mRNA deadenylation and mRNA decay. CNOT1 depletion structurally and functionally deteriorates the CCR4-NOT-complex and induces stabilization of mRNAs, which results in the increment of translation causing ER stress-mediated apoptosis. Ito et al. conclude that CNOT1 contributes to cell viability by securing the activity of the CCR4-NOT deadenylase (Ito et al., 2011). siRNA-mediated depletion of endogenous CNOT1 or other Ccr4-Not subunits in breast cancer cells results in deregulation of ERalpha target genes (increased induction of ERa target genes TTF 1 and c-Myc). These findings define a function for the human Ccr4-Not complex as a transcriptional repressor of nuclear receptor signaling that is relevant for the understanding of molecular pathways involved in cancer (Winkler et al., 2006).

Serine Hydroxymethyltransferase 2 (Mitochondrial) (SHMT2)

The SHMT2 gene encodes the mitochondrial form of a pyridoxal phosphate-dependent enzyme that catalyzes the reversible reaction of serine and tetrahydrofolate to glycine and 5,10-methylene tetrahydrofolate. The encoded product is primarily responsible for glycine synthesis. In a polygenic disease such as lung cancer, gene-gene interactions are expected to play an important role in determining the phenotypic variability of the diseases. Interactions between MTHFR677, MTHFR1298, and SHMT polymorphisms may have a significant impact on genetic instability in lung cancer patients. It was shown that with regard to cytogenetic alterations lymphocytes from lung cancer patients exposed to the tobacco-specific carcinogen 4-(methylnitrosamino)-1-(3-pyridyl)-1-butanone [NNK] had considerably increased frequency of cytogenetic damage in presence of MTHFR 677, MTHFR 1298, and SHMT allelic variants (Piskac-Collier et al., 2011). Pharmacogenomic studies on the role of polymorphism of the SHMT gene in the efficacy of 5-FU and FOLFIRI protocols of colorectal cancer patients revealed a significant effect resulting in altered overall survival as well (Timar et al., 2006).

Jun B Proto-Oncogene (JUNB)

JunB is a member of the AP-1 (activator protein-1) family of dimeric transcription factors. The transcription factor AP-1 is involved in cellular proliferation, transformation and death (Shaulian and Karin, 2002). JunB might be regulated through an NF-6B pathway and up-regulation of JunB induced by HGF might play an important role in the regulation of cell proliferation and cell invasion through MMP-9 expression (Lee and Kim, 2012). JunB seems to play an oncogenic role in lymphomas, particularly in Hodgkin's lymphomas (Shaulian, 2010). JunB is an essential upstream regulator of p16 and contributes to maintain cell senescence that blocks malignant transformation of TAC. JunB thus apparently plays an important role in controlling prostate carcinogenesis (Konishi et al., 2008). JunB promotes tumor invasiveness and enhances angiogenesis in VHL-defective ccRCCs (Kanno et al., 2012).

Transforming, Acidic Coiled-Coil Containing Protein 3 (TACC3)

TACC3 exists in a complex with ch-TOG (colonic and hepatic tumor over-expressed gene) and clathrin that cross-links microtubules in kinetochore fibres. TACC3 is expressed in certain proliferative tissues including testis, lung, spleen, bone marrow, thymus and peripheral blood leukocytes. TACC3 expression is altered in some human tumor types. In cells, TACC3 is localized to both centrosomes and spindle microtubules but not at astral microtubules (Hood and Royle, 2011). TACC3 expression was correlated with p53 expression, and patient whose tumors highly expressed TACC3 and p53 had a significantly poorer prognosis than patients whose tumors had low-level expression for both immunostainings (P=0.006). It is suggested that increase in TACC3 may impart a proliferative advantage to NSCLC and contribute to tumor progression, and that TACC3 expression is a strong prognostic indicator of clinical outcome in NSCLC (Jung et al., 2006). Tacc3 may be a negative regulator of the Notch signalling pathway (Bargo et al., 2010).

RAD54 Homolog B (S. cerevisiae) (RAD54B)

DNA repair and recombination protein RAD54B is a protein that in humans is encoded by the RAD54B gene. RAD54 binds to double-stranded DNA, and displays ATPase activity in the presence of DNA. The human RAD54B protein is a paralog of the RAD54 protein, which plays important roles in homologous recombination. Homologous recombination (HR) is essential for the accurate repair of DNA double-strand breaks (DSBs) (Sarai et al., 2008). Knockdown of RAD54B, a gene known to be somatically mutated in cancer, causes chromosome instability (CIN) in mammalian cells (McManus et al., 2009). RAD54B elevated gene expression is significantly associated with shorter time-to-progression and poor OS in GBM patients (Grunda et al., 2010).

Eukaryotic Translation Elongation Factor 2 (EEF2)

EEF2 encodes a member of the GTP-binding translation elongation factor family. This protein is an essential factor for protein synthesis. It promotes the GTP-dependent translocation of the nascent protein chain from the A-site to the P-site of the ribosome. EEF2 was highly expressed in lung adenocarcinoma (LADC), but not in the neighboring non-tumor lung tissue. It is suggested that eEF2 is an anti-apoptotic marker in LADC, because patients with high eEF2 expression had a significantly higher incidence of early tumor recurrence, and a significantly worse prognosis. Silencing of eEF2 expression increased mitochondrial elongation, cellular autophagy and cisplatin sensitivity. Moreover, eEF2 was SUMOylated in LADC cells, and eEF2 SUMOylation correlated with drug resistance (Chen et al., 2011a). EEF2 is an attractive target for cancer therapy because inhibiting EEF2 causes the rapid arrest of protein synthesis, inducing apoptosis and leading ultimately to cell death. siRNA-induced silencing of EEF2 resulted in specific cytotoxicity of tumor cells (Chen et al., 2011b; Wullner et al., 2008).

Cyclin A2 (CCNA2)

CCNA2 belongs to the highly conserved cyclin family. Cyclins function as regulators of CDK kinases. Different cyclins exhibit distinct expression and degradation patterns which contribute to the temporal coordination of each mitotic event (Deshpande et al., 2005). Human cyclin A2 is a key regulator of S phase progression and entry into mitosis. CCNA2 binds and activates CDC2 or CDK2 kinases, and thus promotes both cell cycle G1/S and G2/M transitions (Honda et al., 2012). Mutations, amplifications and overexpression of this gene, which alters cell cycle progression, are observed frequently in a variety of tumors and may contribute to tumorigenesis (Cooper et al., 2009; Kars et al., 2011; Kim et al., 2011; Tompkins et al., 2011). Furthermore, it is described that CCNA2 expression is associated with a poor prognosis in several types of cancer (Yasmeen et al., 2003) and that elevated expression of cyclin A correlated to shorter survival periods (Dobashi et al., 1998).

Neuroepithelial Cell Transforming 1 (NET1) 41

NET1 is part of the family of Rho guanine nucleotide exchange factors. Members of this family activate Rho proteins by catalyzing the exchange of GDP for GTP. The protein encoded by NET1 interacts with RhoA within the cell nucleus and may play a role in repairing DNA damage after ionizing radiation.

The NET1 gene, but not opioid receptors, is expressed in breast adenocarcinoma cells and may facilitate their migration (Ecimovic et al., 2011). NET1 is up-regulated in gastric cancer (GC) tissue and drives the invasive phenotype of this disease (Srougi and Burridge, 2011). NET1 plays an important role in GC cell migration and invasion, key aspects of GC progression (Bennett et al., 2011). The higher expressions of RhoC and NET1 in human prostate cancers after short-term endocrine therapy suggest that RhoC and NET1 may become therapeutic targets during endocrine therapy (Kawata et al., 2012).

Chromosome 11 Open Reading Frame 24 (C11orf24)

C11orf24 was identified by Twells et al (2001). The C11orf24 gene has no known similarity to other genes, and its function is unknown. Northern blot analysis detected high expression of a 1.9-kb transcript in heart, placenta, liver, pancreas, and colon. Lower levels were detected in brain, lung, skeletal muscle, kidney, spleen, prostate, testis, ovary, and small intestine, and very low levels were detected in thymus and leukocytes (Twells et al., 2001). The 449 amino acid long protein C11orf24 is located on the chromosomal region 11q13. This region is described as a multi-cancer susceptibility region (Gudmundsson et al., 2009; Purdue et al., 2011).

Regulator of Chromosome Condensation 1 (RCC1)

Regulator of chromosome condensation 1 (RCC1) is the guanine nucleotide exchange factor for Ran GTPase. Localised generation of Ran-GTP by RCC1 on chromatin is critical for nucleocytoplasmic transport, mitotic spindle assembly and nuclear envelope formation (Hitakomate et al., 2010). Some data suggested that chromosomal binding of the mitotic regulators such as RCC1, Mad2 and survivin is essential for mitotic progression (Ho et al., 2008). Wong et al. have found that the nuclear RanGTP level is diminished during the early stages of apoptosis, which correlates with immobilization of RCC1 on the chromosomes. Therefore, they propose that RCC1 reads the histone code created by caspase-activated Mst1 to initiate apoptosis by reducing the level of RanGTP in the nucleus (Wong et al., 2009).

Melanoma Antigen Family F, 1 (MAGEF1)

Most known members of the MAGE (melanoma-associated antigen) superfamily are expressed in tumors, testis and fetal tissues, which has been described as a cancer/testis expression, pattern (MAGE subgroup I). Peptides of MAGE subgroup I have been successfully used in peptide and DC vaccination (Nestle et al., 1998; Marchand et al., 1999; Marchand et al., 1999; Marchand et al., 1995; Thurner et al., 1999). In contrast, some MAGE genes (MAGE subgroup II), such as MAGEF1, are expressed ubiquitously in all adult and fetal tissues tested and also in many tumor types including ovarian, breast, cervical, melanoma and leukemia (Nestle et al., 1998; Marchand et al., 1999; Marchand et al., 1999; Marchand et al., 1995; Thurner et al., 1999). Nevertheless, overexpression of MAGEF1 could be detected in NSCLC (Tsai et al., 2007) and in 79% of a cohort of Taiwanese colorectal cancer patients (Chung et al., 2010).

Non-SMC Condensin I Complex, Subunit D2 (NCAPD2)

Condensins are heteropentameric complexes that were first identified as structural components of mitotic chromosomes. NCAPD2 is an essential component of the human condensin complex required for mitotic chromosome condensation. NCAPD2 depletion affects chromosome alignment in metaphase and delays entry into anaphase (Watrin and Legagneux, 2005). Recent linkage and association studies have implicated the chromosome 12p13 locus as possibly harboring genetic variants predisposed to Alzheimer's disease (AD). Single marker association revealed the two SNPs in NCAPD2 (rs7311174 and rs2072374) as showing nominal significant p values (p=0.0491 and 0.0116, respectively). These genetic analyses provide evidence that the chromosome 12p13 locus is associated with AD in Chinese (Li et al., 2009).

Chromosome 12 Open Reading Frame 44 (C12orf44)

By searching databases for orthologs of a *Drosophila* Atg13-interacting protein, Mercer et al. (2009) identified human ATG101, also known as C12orf44 (Mercer et al., 2009). The ATG101 gene was mapped to chromosome 12q113.13. The deduced 218 amino acid protein was predicted to be a cytosolic hydrophilic protein (Hosokawa et al., 2009). Macroautophagy is a catabolic process for lysosome-mediated degradation of cytoplasmic proteins, organelles, and macromolecules. ATG proteins, such as ATG101, are required for formation of autophagosomes, double-membrane vesicles that surround and sequester cytoplasmic cargo prior to fusion with lysosomes. ATG101 (C12orf44) is essential for autophagy (Mercer et al., 2009).

HECT and RLD Domain Containing E3 Ubiquitin Protein Ligase 4 (HERC4)

HERC4 belongs to the HERC family of ubiquitin ligases, all of which contain a HECT domain and at least 1 RCC1 (MIM 179710)-like domain (RLD). The 350-amino acid HECT domain is predicted to catalyze the formation of a thioester with ubiquitin before transferring it to a substrate, and the RLD is predicted to act as a guanine nucleotide exchange factor for small G proteins (Hochrainer et al., 2005). E3 ubiquitin ligase Herc4, though ubiquitously expressed in all tissues, is most highly expressed in the testis, specifically during spermiogenesis. Herc4 ligase is required for proper maturation and removal of the cytoplasmic droplet for the spermatozoon to become fully functional (Rodriguez and Stewart, 2007).

Insulin-Like Growth Factor 2 mRNA Binding Protein 3 (IGF2BP3)

IGF2BP3 is a member of the insulin-like growth factor-II mRNA-binding protein family, implicated in mRNA localization, turnover and translational control. The protein contains several KH (K-homologous) domains, which are important in RNA binding and are known to be involved in RNA synthesis and metabolism. Expression occurs mainly during embryonic development and has been described for some tumors. Thus, IGF2BP3 is considered to be an onco-foetal protein (Liao et al., 2005). IGF2BP3 may promote tumor cell proliferation by enhancing IGF-II protein synthesis and by inducing cell adhesion and invasion through stabilization of CD44 mRNA (Findeis-Hosey and Xu, 2012). Moreover, IGF2BP3 expression has been studied in many human neoplasms with growing evidence that it mediates migration, invasion, cell survival and tumor metastasis (Jeng et al., 2009; Kabbarah et al., 2010; Li et al., 2011; Liao et al., 2011; Lu et al., 2011; Hwang et al., 2012; Samanta et al., 2012) and it might also be implicated in angiogenesis (Suvasini et al., 2011; Chen et al., 2012). In lung adenocarcinomas, a higher frequency of IGF2BP3 expression can be detected in moderately or poorly differentiated adenocarcinomas, which may be associated with an aggressive biological behavior (Findeis-Hosey et al., 2010; Beljan et al., 2012; Findeis-Hosey and Xu, 2012).

Cell Division Cycle 6 Homolog (*S. cerevisiae*) (CDC6)

CDC6 protein functions as a regulator at the early steps of DNA replication. It localizes in cell nucleus during cell cycle G1, but translocates to the cytoplasm at the start of S phase. Further, CDC6 is supposed to regulate replication-checkpoint activation through the interaction with ATR in higher eukaryotic cells (Yoshida et al., 2010). CDC6 is essential for DNA replication and its deregulation is involved in carcinogenesis. It was found that CDC6 down-regulation by RNA interference (RNAi) prevented cell proliferation and promoted apoptosis (Lau et al., 2006). Overexpression of CDC6 was found in several cancers. Among the cancer types overexpressing CDC6 are gastric cancer (Tsukamoto et al., 2008), brain tumors (Ohta et al., 2001), oral squamous cell carcinoma (Feng et al., 2008), cervical carcinoma (Wang et al., 2009b) and malignant mesothelioma (Romagnoli et al., 2009).

Fibroblast Activation Protein, Alpha (FAP)

Fibroblast activation protein (FAP) is a type II integral membrane glycoprotein belonging to the serine protease family. The putative serine protease activity of FAP alpha and its in vivo induction pattern may indicate a role for this molecule in the control of fibroblast growth or epithelial-mesenchymal interactions during development, tissue repair, and epithelial carcinogenesis (Scanlan et al., 1994). Most normal adult tissues and benign epithelial tumors show little or no detectable FAP expression. However, FAP expression is detected in the stroma of over 90% of malignant breast, colorectal, lung, skin and pancreatic tumors, fibroblasts of healing wounds, soft tissue sarcomas, and some fetal mesenchymal cells. FAP has a potential role in cancer growth and metastasis through cell adhesion and migration processes, as well as rapid degradation of ECM components. Thus, it is present on tumor cells invading the ECM, and endothelial cells involved in angiogenesis, but is not expressed in inactive cells of the same type (Dolznig et al., 2005; Kennedy et al., 2009; Rettig et al., 1993; Rettig et al., 1994; Scanlan et al., 1994; Zhang et al., 2010a).

Wingless-Type MMTV Integration Site Family, Member 5A (WNT5A)

In general, Wnt5a regulates a variety of cellular functions, such as proliferation, differentiation, migration, adhesion and polarity (Kikuchi et al., 2012). It is expressed in undifferentiated human embryonic stem cells (Katoh, 2008). WNT5A is classified as a non-transforming WNT family member whose role in carcinogenesis is still ambiguous. It exhibits tumor suppressor activities in some cancers (thyroid, brain, breast and colorectum), but is aberrantly up-regulated in cancers of lung, stomach and prostate (Li et al., 2010). Oncogenic WNT5A activates canonical WNT signaling in cancer stem cells for self-renewal, and non-canonical WNT signaling at the tumor-stromal interface for invasion and metastasis (Katoh and Katoh, 2007). Expression of WNT5A has been described for a variety of tumor entities. For example, abnormal protein expression of Wnt5a was observed in 28% of prostate cancer where it promotes aggressiveness (Yamamoto et al., 2010). Furthermore, WNT5A over-expression is described to be associated with poor prognosis and/or increasing tumor grade in ovarian cancer (Badiglian et al., 2009), melanoma (Da Forno et al., 2008; Weeraratna et al., 2002), GBM (Yu et al., 2007), lung cancer (Huang et al., 2005) and pancreatic cancer (Ripka et al., 2007). In HCC, it seems that the canonical Wnt signaling pathway contributes to tumor initiation and the noncanonical signaling to tumor progression (Yuzugullu et al., 2009).

TPX2, Microtubule-Associated, Homolog (*Xenopus laevis*) (TPX2)

TPX2 is a spindle assembly factor. It is required for normal assembly of mitotic spindles and of microtubules during apoptosis. TPX2 is required for chromatin and/or kinetochore dependent microtubule nucleation (Bird and Hyman, 2008; Moss et al., 2009). Newly synthesized TPX2 is required for nearly all Aurora A activation and for full p53 synthesis and phosphorylation in vivo during oocyte maturation (Pascreau et al., 2009). TPX2 is a cell cycle-associated protein which is overexpressed in many tumor types, such as meningiomas (Stuart et al., 2010), squamous cell carcinoma of the larynx (SCCL) (Cordes et al., 2010), oral squamous cell carcinomas (SCC) (Shigeishi et al., 2009), hepatocellular carcinomas (HCC) (Satow et al., 2010), pancreatic tumor (Warner et al., 2009), ovarian cancer (Ramakrishna et al., 2010), squamous cell carcinoma of the lung (Lin et al., 2006; Ma et al., 2006). It is frequently co-overexpressed with Aurora-A giving rise to a novel functional unit with oncogenic properties (Asteriti et al., 2010). TPX2 expression is a prognostic indicator in lung cancer (Kadara et al., 2009).

Hyaluronan-Mediated Motility Receptor (RHAMM) (HMMR)

The receptor for hyaluronan-mediated motility RHAMM (HMMR) exerts different functions in the cell as well as on the cell membrane. RHAMM can be exported to the cell surface where it binds hyaluronic acid (HA) and interacts with the HA receptor CD44. Processes like cell motility, wound healing and invasion are modulated by RHAMM (Sohr and Engeland, 2008). RHAMM (receptor for HYA-mediating motility) is one of the receptors for hyaluronan (HYA) (Gares and Pilarski, 2000). Also cancer cells exhibit binding sites (CD44, RHAMM, etc.) for HYA and HYA protects cancer cells against immune cell attack. Serum HYA is often increased in metastatic patients (Delpech et al., 1997). In addition, HYA-interaction with RHAMM (HMMR) and CD44 on cancer cells has been proposed to be important in promoting tumor progression and dissemination (Li et al., 2000b). Furthermore, RHAMM is overexpressed in several cancer tissues (Tzankov et al., 2011); (Kramer et al., 2010); (Twarock et al., 2010); (Shigeishi et al., 2009); (Zlobec et al., 2008); (Li et al., 2000a)).

ADAM Metallopeptidase Domain 8 (ADAM8)

ADAM8 is a member of the ADAM (a disintegrin and metalloprotease domain) family. Many ADAM species, including ADAM8, are expressed in human malignant tumors, where they are involved in the regulation of growth factor activities and integrin functions, leading to promotion of cell growth and invasion (Mochizuki and Okada, 2007). The expression of ADAM8 was positively correlated to EGFR. Both were mainly expressed in the cytoplasm and on the cell membrane (Wu et al., 2008). ADAM8 was abundantly expressed in the great majority of lung cancers examined. Exogenous expression of ADAM8 increased the migratory activity of mammalian cells, an indication that ADAM8 may play a significant role in progression of lung cancer (Ishikawa et al., 2004). ADAM8 has been associated with poor prognosis of lung cancer (Hernandez et al., 2010). ADAM8 over-expression was associated with shorter patient survival and it was a good predictor of distant metastases in RCC (Roemer et al., 2004b; Roemer et al., 2004a). In addition, expression levels and the protease activities of ADAM8 correlated with invasive activity of glioma cells, indicating that ADAM8 may play a significant role in tumor invasion in brain cancer (Wildeboer et al., 2006).

Collagen Alpha-3(VI) Chain Protein (COL6A3)

COL6A3 encodes the alpha-3 chain, one of the three alpha chains of type VI collagen. The protein domains have been shown to bind extracellular matrix proteins, an interaction that explains the importance of this collagen in organizing matrix components.

Remodeling of the extracellular matrix through overexpression of collagen VI contributes to cisplatin resistance in ovarian cancer cells. The presence of collagen VI correlated with tumor grade, an ovarian cancer prognostic factor (Sherman-Baust et al., 2003). COL6A3 is overexpressed in colorectal tumor (Smith et al., 2009a), salivary gland carcinoma (Leivo et al., 2005) and differentially expressed in gastric cancer (Yang et al., 2007). COL6A3 was identified as one of seven genes with tumor-specific splice variants. The validated tumor-specific splicing alterations were highly consistent, enabling clear separation of normal and cancer samples and in some cases even of different tumor stages (Thorsen et al., 2008).

Thy-1 Cell Surface Antigen (THY1)

Thy-1 (CD90) is a 25-37 kDa glycosylphosphatidylinositol (GPI)-anchored glycol-protein expressed on many cell types, including T cells, thymocytes, neurons, endothelial cells, and fibroblasts. Activation of Thy-1 can promote T cell activation. Thy-1 also affects numerous non-immunologic biological processes, including cellular adhesion, neurite outgrowth, tumor growth, tumor suppression, migration, wound healing and cell death. Thy-1 is an important regulator of cell-cell and cell-matrix interactions, with important roles in nerve regeneration, metastasis, inflammation, and fibrosis (Rege and Hagood, 2006b; Rege and Hagood, 2006a). Furthermore, Thy-1 appears to be a marker of adult but not embryonic angiogenesis. The up-regulation of Thy-1 by cytokines but not growth factors indicates the importance of inflammation in the pathogenesis of adult angiogenesis (Lee et al., 1998). There is a significant overexpression of Thy-1 located in the lung cancer cell nucleus as compared to the normal tissue or benign tumor cells of lung, and it is one of the factors related to the prognosis of NSCLC patients. Thus, Thy-1 may be a novel latent malignant marker in the lung cancer pathology (Chen et al., 2005b). Thy-1 can be considered as a surrogate marker for various kind of stem cells (mesenchymal stem cells, hepatic stem cells ("oval cells") (Masson et al., 2006), keratinocyte stem cells (Nakamura et al., 2006) and hematopoietic stem cells (Yamazaki et al., 2009).

Deiodinase, Iodothyronine, Type II (DIO2)

The protein encoded by the DIO2 gene belongs to the iodothyronine deiodinase family. It is highly expressed in the thyroid, and may contribute significantly to the relative increase in thyroidal T3 production in patients with Graves' disease and thyroid adenomas (Meyer et al., 2008); (de Souza Meyer et al., 2005)). The gene expression patterns are significantly different between upward and downward progressing types of nasopharygeal carcinoma (NPC). The expression of DIO2 gene is higher in the downward progressing type (downward=distant metastasis) than in upward progressing type (local growth and invasion of the base of skull), which may be closely related to the metastasis potential of NPC (Liang et al., 2008). DIO2 mRNA as well as DIO2 activity is expressed in brain tumors (Murakami et al., 2000). D2 activity in lung is present and similar in peripheral lung and lung cancer tissue (Wawrzynska et al., 2003).

Periostin, Osteoblast Specific Factor (POSTN)

POSTN, a gene encoding a protein with similarity to the fasciclin family and involved in cell survival and angiogenesis, has emerged as a promising marker for tumor progression in various types of human cancers (Ruan et al., 2009).

High expression of periostin protein or mRNA was detected in most solid tumors including breast (Zhang et al., 2010b), colon (Kikuchi et al., 2008), head and neck (Kudo et al., 2006), pancreatic (Kanno et al., 2008), papillary thyroid (Puppin et al., 2008), prostate (Tischler et al., 2010), ovarian (Choi et al., 2010), lung (Takanami et al., 2008) and liver (Utispan et al., 2010) carcinoma, as well as oesophageal squamous cell carcinoma (Kwon et al., 2009). Periostin is abnormally highly expressed in lung cancer and is correlated with angiogenesis, invasion and metastasis (Takanami et al., 2008). Silencing of periostin in A549 non-small cell lung cancer (NSCLC) cells inhibits tumor cell growth and decrease cell invasion (Wu et al., 2013).

SLIT1 (Slit Homolog 1 (Drosophila)), SLIT2 (Slit Homolog 2 (Drosophila))

SLITs (SLIT1, SLIT2, and SLIT3) are a family of secreted proteins that mediate positional interactions between cells and their environment during development by signaling through ROBO receptors (Hinck, 2004). SLIT/ROBO signaling, however, is not restricted to development, and loss of these cues likely plays an important role during tumor progression. Slits and Robos are considered candidate tumor suppressor genes because their promoters are frequently hypermethylated in epithelial cancers (Narayan et al., 2006; Schmid et al., 2007; Latil et al., 2003). In ~50% of sampled human breast tumors, SLIT2 or SLIT3 gene expression is silenced (Sharma et al., 2007). Hypermethylation of SLIT2 was frequently detected in NSCLCs and associated with various clinical features (Suzuki et al., 2013).

TLX3 (T-Cell Leukemia Homeobox 3)

TLX3 (also known as RNX or HOX11L2) belongs to a family of orphan homeobox genes that encode DNA-binding nuclear transcription factors. Members of the HOX11 gene family are characterized by a threonine-47 replacing cytosine in the highly conserved homeodomain (Dear et al., 1993). TLX3 is uniquely expressed in the developing medulla oblongata and is required for proper formation of first-order relay visceral sensory neurons and of most of the (nor) adrenergic centers in the brainstem, especially involved in the physiologic control of cardiovascular and respiratory systems (Qian et al., 2001). Expression of TLX3 has also been detected in leukaemia samples from 20% of children and 13% of adults affected with T-cell acute lymphocytic leukaemia (Cave et al., 2004), although this gene has never been involved in normal T-cell differentiation (Ferrando et al., 2004).

CEP192 (Centrosomal Protein 192 kDa)

Centrosomes play an important role in various cellular processes, including spindle formation and chromosome segregation. CEP192 is a centrosome protein that plays a critical role in centrosome biogenesis and function in mammals, *Drosophila* and *C. elegans* (Gomez-Ferreria et al., 2012). It stimulates the formation of the scaffolding upon which gamma tubulin ring complexes and other proteins involved in microtubule nucleation and spindle assembly become functional during mitosis (Gomez-Ferreria et al., 2007).

ANKS1A (Ankyrin Repeat and Sterile Alpha Motif Domain Containing 1A)

Ankyrin repeat and SAM domain-containing protein 1A is a protein that in humans is encoded by the ANKS1A gene (Nagase et al., 1996). ANKS1A has been first described as a target and signal transmitter of receptor tyrosine kinases like EGFR and PDGFR (Pandey et al., 2002) and more recently as an interaction partner of the receptor tyrosine kinase EphA8 (Shin et al., 2007). In a recent study, single-nucleotide polymorphisms (SNPs) were genotyped in 348 advanced NSCLC patients. They identified 17 top candidate SNPs related to prognosis. SNPs were located in the genomic region of the ANKS1A gene (Lee et al., 2013).

CEP250 (Centrosomal Protein 250 kDa)

The CEP250 gene encodes a core centrosomal protein required for centriole-centriole cohesion during interphase of the cell cycle (Mayor et al., 2002). By radiation hybrid analysis, Fry et al. (1998) mapped the CEP250 gene to the centromeric region of chromosome 20, at approximately 20q11.2 (Fry et al., 1998). Mayor et al. (2002) found that overexpression of CEP250 in a human osteosarcoma cell line resulted in formation of large centrosome-associated structures. CEP250 overexpression did not interfere with centrosome separation or cell division, however, indicating that cell cycle-regulated activity dissociates CEP250 from centrosomes (Mayor et al., 2002).

MDN1 (MDN1, Midasin Homolog (Yeast))

MDN1, midasin homolog (yeast) is a protein that in humans is encoded by the MDN1 gene. Midasin is present as a single-copy gene encoding a well-conserved protein of approximately 600 kDa in all eukaryotes for which data are available. In humans, the gene maps to 6q115 and encodes a predicted protein of 5596 residues (632 kDa) (Garbarino and Gibbons, 2002). Recently, MDN1 was found to be mutated in breast cancers of the luminal B subtype. MDN1 may play a role in the development and hormone resistance of this aggressive subtype (Cornen et al., 2014).

OLFM1 (Olfactomedin 1)

OLFM1, also called Noelin-1, is a secreted glycoprotein belonging to a family of olfactomedin domain-containing proteins and plays an important role in regulating the production of neural crest cells by the neural tube (Barembaum et al., 2000). Olfactomedin was originally identified as the major component of the mucus layer that surrounds the chemosensory dendrites of olfactory neurons (Kulkarni et al., 2000). Expression of olfactomedin 1 protein was significantly higher in lung adenocarcinoma than in lung cancer of other histologic types and normal lung tissues (Wu et al., 2010). Furthermore, OLFM1 is deregulated in the endometrial cancer, Ewing's sarcoma, and neuroblastoma (Wong et al., 2007; Allander et al., 2002; Khan et al., 2001).

BUB1B (Budding Uninhibited by Benzimidazoles 1 Homolog Beta (Yeast))

BUB1B, also named BubR1, is a core mitotic checkpoint component that binds to and inhibits the Cdc20-activated anaphase-promoting complex (APC/CCdc20), a ubiquitin E3 ligase that initiates anaphase by orchestrating separase-mediated cleavage of cohesion rings that hold sister chromatids together (Baker et al., 2004). BubR1 not only contributes to proper chromosome segregation through mitotic checkpoint activation but also by regulation of chromosome-spindle attachments (Malureanu et al., 2009; Lampson and Kapoor, 2005). Impaired spindle checkpoint function has been found in many forms of cancer. Mutations in BubR1 have been associated with mosaic variegated aneuploidy (MVA), a rare human syndrome characterized by aneuploidization, tumor predisposition, and several progeroid traits, including short lifespan, growth and mental retardation, cataracts, and facial dysmorphisms (Matsuura et al., 2006).

PI4KA (Phosphatidylinositol 4-Kinase, Catalytic, Alpha)

Four different phosphatidylinositol 4-kinases (PI4Ks) are expressed in human cells. These isoenzymes (PI4KA, PI4KB, PI4K2A and PI4K2B) catalyze the phosphorylation of phosphatidylinositol (PtdIns) in the cytoplasmic face of cellular membranes, leading to the production of phosphatidylinositol 4-phosphate (PtdIns4P) (Minogue and Waugh, 2012). PI4KA is mainly found in the endoplasmic reticulum (ER). Its activity seems to regulate both the formation of ER exit sites (Blumental-Perry et al., 2006) and the concentration of PtdIns4P in the plasma membrane (Balla et al., 2008). A research group has found that PI4KA mRNA was more abundant in HCC than normal healthy tissues. This up-regulation correlated significantly with both poor differentiation and the active proliferation rate in HCC. Therefore PI4KA could be used as a new molecular marker to improve established prognostic models for HCC (Ilboudo et al., 2014).

AURKB (Aurora Kinase B)

Aurora B kinase is a protein that functions in the attachment of the mitotic spindle to the centromere (Kim et al., 2011). AURKB localizes to microtubules near kinetochores (Kunitoku et al., 2003). Aurora kinases are over-expressed in a variety of tumor cell lines, suggesting that these kinases might play a role in tumorigenesis, and have already become potential targets for cancer diagnosis and therapy (Fu et al., 2007). Recently a gene signature of five genes (TOP2A, AURKB, BRRN1, CDK1 and FUS) that are closely associated with the outcomes in patients with NSCLC was identified. The results suggested that genes involved in chromosome condensation, like AURKB, are likely related with stem-like properties and might predict survival in lung adenocarcinoma (Perumal et al., 2012).

SLC3A2 (Solute Carrier Family 3 (Activators of Dibasic and Neutral Amino Acid Transport), Member 2)

SLC3A2 comprises the light subunit of the large neutral amino acid transporter (LAT1) that is also known as CD98 (cluster of differentiation 98) (Lemaitre et al., 2005). The CD98 heterodimer consists of a type II single-pass transmembrane heavy chain (CD98hc, also known as 4F2 antigen heavy chain or FRP-1; encoded by the genes SLC3A2 and Slc3a2 for human and mouse, respectively) of ~80-85 kDa that is disulfide-linked with a multi-pass light chain of ~40 kDa (Deves and Boyd, 2000). CD98hc functions in amplifying integrin signalling and in the transport of amino acids; both of these functions can contribute to cell survival and proliferation (Cantor and Ginsberg, 2012). Many tumors express CD98hc (SLC3A2), and its expression correlates with poor prognosis in B cell lymphomas. Furthermore, nearly all studies that have examined the expression of CD98hc or CD98 light chains in solid tumors show that their expression is correlated with progressive or metastatic tumors (Kaira et al., 2009).

IFT81 (Intraflagellar Transport 81 Homolog (*Chlamydomonas*))

Intraflagellar transport (IFT) of ciliary precursors such as tubulin from the cytoplasm to the ciliary tip is involved in the construction of the cilium, a hairlike organelle found on most eukaryotic cells. Knockdown of IFT81 and rescue experiments with point mutants showed that tubulin binding by IFT81 was required for ciliogenesis in human cells (Bhogaraju et al., 2013). Together with IFT74/72, IFT81 forms a core complex to build IFT particles which are required for cilium formation (Lucker et al., 2005).

COG4 (Component of Oligomeric Golgi Complex 4)

The COG complex consists of eight subunits named COG1-8 (Ungar et al., 2002; Whyte and Munro, 2001) grouped into two sub-complexes: COG1-4 (Lobe A) and COG5-8 (Lobe B) (Ungar et al., 2005). The COG complex functions in the tethering of vesicles recycling resident Golgi proteins (such as glycosylation enzymes) (Pokrovskaya et al., 2011). The COG4 gene maps to chromosome 16q22.1 (Reynders et al., 2009). Ungar et al. (2002) concluded that COG4 is critical for the structure and function of the Golgi apparatus and can influence intracellular membrane trafficking (Ungar et al., 2002).

NCBP1 (Nuclear Cap Binding Protein Subunit 1, 80 kDa)

Nuclear cap-binding protein complex is a RNA-binding protein which binds to the 5' cap of RNA polymerase II. Kataoka et al. (1994) described the cloning of a gene that encodes an 80-kD nuclear cap-binding protein (NCBP1) found in HeLa cell nuclear extracts that may be involved in mRNA splicing and RNA export (Kataoka et al., 1994). By hybridizing to genomic DNA from a somatic cell hybrid panel, Chadwick et al. (1996) mapped the NCBP1 gene to 9q34.1 (Chadwick et al., 1996).

NEFH (Neurofilament, Heavy Polypeptide)

The NEFH encoding neurofilament heavy chain is one of the major components of the neuronal cytoskeleton neurofilaments. The neurofilament heavy polypeptide (NEFH, 200 kD) gene resides at chromosomal band 22q12.2 and was proposed as a DNA marker for presymptomatic diagnosis in neurofibromatosis type 2 (NF2) families. Loss or down-regulation of NEFH has been mostly reported in human autonomic nerve tumors or central neurocytomas (Mena et al., 2001; Segal et al., 1994). In addition, absent or diminished NEFH expression in human prostate cancer (Schleicher et al., 1997), clear-cell epithelioid tumor (Tanaka et al., 2000), and small cell lung carcinoma (Bobos et al., 2006) has been observed. Interestingly, over-expression of NEFH disrupted normal cell structure and function, and induced cell death (Szebenyi et al., 2002).

DETAILED DESCRIPTION OF THE INVENTION

As used herein and except as noted otherwise all terms are defined as given below.

The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11, 12, 13 or 14 and in case of MHC class II peptides they can be as long as 15, 16, 17, 18, 19 or 20 amino acids in length.

Further the term "peptide" shall include salts of a series of amino acid residues, connected one to the other typically by peptide bonds between the alpha-amino and carbonyl groups of the adjacent amino acids. Preferably the salts are pharmaceutical acceptable salts.

The term "peptide" shall include "oligopeptide". The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 15 amino acids in length.

The term "the peptides of the present invention" shall include the peptides consisting of or comprising a peptide as defined above according to SEQ ID No. 1 to SEQ ID No. 92.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus is an "immunogen" within the present invention), if it is capable of inducing an immune response. In the case of the present invention, immunogenicity is more specifically defined as the ability to induce a T-cell response. Thus, an "immunogen" would be a molecule that is capable of inducing an immune response, and in the case of the present invention, a molecule capable of inducing a T-cell response. In another aspect, the immunogen can be the peptide, the complex of the peptide with MHC, oligopeptide, and/or protein that is used to raise specific antibodies or TCRs against it.

A class I T cell "epitope" requires a short peptide that is bound to a class I MHC receptor, forming a ternary complex (MHC class I alpha chain, beta-2-microglobulin, and peptide) that can be recognized by a T cell bearing a matching T-cell receptor binding to the MHC/peptide complex with appropriate affinity. Peptides binding to MHC class I molecules are typically 8-14 amino acids in length, and most typically 9 amino acids in length.

In humans there are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-B*07 are examples of different MHC class I alleles that can be expressed from these loci.

TABLE 2

Expression frequencies F of HLA*A02 and the most frequent HLA-DR serotypes. Frequencies are deduced from haplotype frequencies $G_f$ within the American population adapted from Mori et al. (Mori et al., 1997) employing the Hardy-Weinberg formula $F = 1 - (1 - G_f)^2$. Combinations of A*02 with certain HLA-DR alleles might be enriched or less frequent than expected from their single frequencies due to linkage disequilibrium. For details refer to Chanock et al. (Chanock et al., 2004).

| HLA Allele | Expression frequencies of HLA*02 and HLA-DR serotypes within North American subpopulations | | | |
|---|---|---|---|---|
| | Caucasian American | African American | Asian American | Latin American |
| A*02 | 49.1% | 34.1% | 43.2% | 48.3% |
| DR1 | 19.4% | 13.2% | 6.8% | 15.3% |
| DR2 | 28.2% | 29.8% | 33.8% | 21.2% |
| DR3 | 20.6% | 24.8% | 9.2% | 15.2% |
| DR4 | 30.7% | 11.1% | 28.6% | 36.8% |
| DR5 | 23.3% | 31.1% | 30.0% | 20.0% |
| DR6 | 26.7% | 33.7% | 25.1% | 31.1% |
| DR7 | 24.8% | 19.2% | 13.4% | 20.2% |
| DR8 | 5.7% | 12.1% | 12.7% | 18.6% |
| DR9 | 2.1% | 5.8% | 18.6% | 2.1% |

Therefore, for therapeutic and diagnostic purposes a peptide that binds with appropriate affinity to several different HLA class II receptors is highly desirable. A peptide binding to several different HLA class II molecules is called a promiscuous binder.

As used herein, reference to a DNA sequence includes both single stranded and double stranded DNA. Thus, the specific sequence, unless the context indicates otherwise, refers to the single strand DNA of such sequence, the duplex of such sequence with its complement (double stranded DNA) and the complement of such sequence. The term "coding region" refers to that portion of a gene which either naturally or normally codes for the expression product of that gene in its natural genomic environment, i.e., the region coding in vivo for the native expression product of the gene.

The coding region can be from a non-mutated ("normal"), mutated or altered gene, or can even be from a DNA sequence, or gene, wholly synthesized in the laboratory using methods well known to those of skill in the art of DNA synthesis.

The term "nucleotide sequence" refers to a heteropolymer of deoxyribonucleotides.

The nucleotide sequence coding for a particular peptide, oligopeptide, or polypeptide may be naturally occurring or they may be synthetically constructed. Generally, DNA segments encoding the peptides, polypeptides, and proteins of this invention are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

As used herein the term "a nucleotide coding (or encoding) for a peptide" refers to a nucleotide sequence coding for the peptide including artificial (man-made) start and stop codons compatible for the biological system the sequence is going to be expressed by.

The term "expression product" means the polypeptide or protein that is the natural translation product of the gene and any nucleic acid sequence coding equivalents resulting from genetic code degeneracy and thus coding for the same amino acid(s).

The term "fragment", when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal non-translated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that can be paired with one strand of DNA and provides a free 3'-OH end at which a DNA polymerase starts synthesis of a deoxyribonucleotide chain.

The term "promoter" means a region of DNA involved in binding of RNA polymerase to initiate transcription.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, a claimed polypeptide which has a purity of preferably 99.999%, or at least 99.99% or 99.9%; and even desirably 99% by weight or greater is expressly contemplated.

The nucleic acids and polypeptide expression products disclosed according to the present invention, as well as expression vectors containing such nucleic acids and/or such polypeptides, may be in "enriched form". As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form.

The term "active fragment" means a fragment that generates an immune response (i.e., has immunogenic activity) when administered, alone or optionally with a suitable adjuvant, to an animal, such as a mammal, for example, a rabbit or a mouse, and also including a human, such immune response taking the form of stimulating a T-cell response within the recipient animal, such as a human. Alternatively, the "active fragment" may also be used to induce a T-cell response in vitro.

As used herein, the terms "portion", "segment" and "fragment," when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, these terms refer to the products produced by treatment of said polynucleotides with any of the endonucleases.

In accordance with the present invention, the term "percent identity" or "percent identical", when referring to a sequence, means that a sequence is compared to a claimed or described sequence after alignment of the sequence to be compared (the "Compared Sequence") with the described or claimed sequence (the "Reference Sequence"). The Percent Identity is then determined according to the following formula:

$$\text{Percent Identity} = 100[1-(C/R)]$$

wherein C is the number of differences between the Reference Sequence and the Compared Sequence over the length of alignment between the Reference Sequence and the Compared Sequence, wherein
(i) each base or amino acid in the Reference Sequence that does not have a corresponding aligned base or amino acid in the Compared Sequence and
(ii) each gap in the Reference Sequence and
(iii) each aligned base or amino acid in the Reference Sequence that is different from an aligned base or amino acid in the Compared Sequence, constitutes a difference and
(iiii) the alignment has to start at position 1 of the aligned sequences;
and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the Percent Identity as calculated above is about equal to or greater than a specified minimum Percent Identity then the Compared Sequence has the specified minimum Percent Identity to the Reference Sequence even though alignments may exist in which the herein above calculated Percent Identity is less than the specified Percent Identity.

The original (unmodified) peptides as disclosed herein can be modified by the substitution of one or more residues at different, possibly selective, sites within the peptide chain, if not otherwise stated.

Preferably those substitutions are located at the end of the amino acid chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

Less conservative substitutions might involve the replacement of one amino acid by another that has similar characteristics but is somewhat different in size, such as replacement of an alanine by an isoleucine residue. Highly non-conservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, amino acids possessing non-standard R groups (i.e., R groups other than those found in the common 20 amino acids of natural proteins) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than 4 positions within the peptide would simultaneously be substituted.

The peptides of the invention can be elongated by up to four amino acids, that is 1, 2, 3 or 4 amino acids can be added to either end in any combination between 4:0 and 0:4.

Combinations of the elongations according to the invention can be depicted from table 3:

| C-terminus | N-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

| N-terminus | C-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

The amino acids for the elongation can be the peptides of the original sequence of the protein or any other amino acid. The elongation can be used to enhance the stability or solubility of the peptides.

The term "T-cell response" means the specific proliferation and activation of effector functions induced by a peptide in vitro or in vivo. For MHC class I restricted CTLs, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or perforins induced by peptide, or degranulation.

Preferably, when the CTLs specific for a peptide of SEQ ID No. 1 to SEQ ID No. 92 are tested against the substituted peptides, the peptide concentration at which the substituted peptides achieve half the maximal increase in lysis relative to background is no more than about 1 mM, preferably no more than about 1 µM, more preferably no more than about 1 nM, and still more preferably no more than about 100 pM, and most preferably no more than about 10 pM. It is also preferred that the substituted peptide be recognized by CTLs from more than one individual, at least two, and more preferably three individuals.

Thus, the epitopes of the present invention may be identical to naturally occurring tumor-associated or tumor-specific epitopes or may include epitopes that differ by no more than 4 residues from the reference peptide, as long as they have substantially identical antigenic activity.

Stimulation of an immune response is dependent upon the presence of antigens recognized as foreign by the host immune system. The discovery of the existence of tumor associated antigens has now raised the possibility of using a host's immune system to intervene in tumor growth. Various mechanisms of harnessing both the humoral and cellular arms of the immune system are currently explored for cancer immunotherapy.

Specific elements of the cellular immune response are capable of specifically recognizing and destroying tumor cells. The isolation of cytotoxic T-cells (CTL) from tumor-infiltrating cell populations or from peripheral blood suggests that such cells play an important role in natural immune defences against cancer. CD8-positive T-cells in particular, which recognize class I molecules of the major histocompatibility complex (MHC)-bearing peptides of usually 8 to 12 residues derived from proteins or defect ribosomal products (DRIPS) located in the cytosols, play an important role in this response. The MHC-molecules of the human are also designated as human leukocyte-antigens (HLA).

MHC class I molecules can be found on most cells having a nucleus which present peptides that result from proteolytic cleavage of mainly endogenous, cytosolic or nuclear proteins, DRIPS, and larger peptides. However, peptides derived from endosomal compartments or exogenous sources are also frequently found on MHC class I molecules. This non-classical way of class I presentation is referred to as cross-presentation in literature.

Since both types of response, CD8 and CD4 dependent, contribute jointly and synergistically to the anti-tumor effect, the identification and characterization of tumor-associated antigens recognized by either CD8-positive CTLs (MHC class I molecule) or by CD4-positive CTLs (MHC class II molecule) is important in the development of tumor vaccines. It is therefore an object of the present invention, to provide compositions of peptides that contain peptides binding to MHC complexes of either class.

Considering the severe side-effects and expense associated with treating cancer better prognosis and diagnostic methods are desperately needed. Therefore, there is a need to identify other factors representing biomarkers for cancer in general and lung cancer in particular. Furthermore, there is a need to identify factors that can be used in the treatment of cancer in general and lung cancer in particular.

The present invention provides peptides that are useful in treating cancers/tumors, preferably lung cancers, even more preferably non-small cell lung carcinoma (NSCLC) that over- or exclusively present the peptides of the invention. These peptides were shown by mass spectrometry to be naturally presented by HLA molecules on primary human lung cancer samples (see example 1, and FIGS. 1A through 1D).

The source gene/protein (also designated "full-length protein" or "underlying protein") from which the peptides are derived were shown to be highly overexpressed in non-small cell lung carcinoma, and for SEQ IDs No. 66 to 75 gastric cancer and glioblastoma compared with normal tissues (see example 2, and FIGS. 2A and 2B for NSCLC) demonstrating a high degree of tumor association of the source genes. Moreover, the peptides themselves are strongly over-presented on tumor tissue but not on normal tissues (see example 3 and FIGS. 3A through 3C).

HLA-bound peptides can be recognized by the immune system, specifically T lymphocytes/T cells. T cells can destroy the cells presenting the recognized HLA/peptide complex, e.g. lung cancer cells presenting the derived peptides.

The peptides of the present invention have been shown to be capable of stimulating T cell responses and/or are over-presented and thus can be used for the production of antibodies and/or TCRs, in particular sTCRs, according to the present invention (see example 4 and FIG. 4). Furthermore, the peptides when complexed with the respective MHC can be used for the production of antibodies and/or TCRs, in particular sTCRs, according to the present invention, as well. Respective methods are well known to the person of skill, and can be found in the respective literature as well. Thus, the peptides of the present invention are useful for generating an immune response in a patient by which tumor cells can be destroyed. An immune response in a patient can be induced by direct administration of the described peptides or suitable precursor substances (e.g. elongated peptides, proteins, or nucleic acids encoding these peptides) to the patient, ideally in combination with an agent enhancing the immunogenicity (i.e. an adjuvant). The immune response originating from such a therapeutic vaccination can be expected to be highly specific against tumor cells because the target peptides of the present invention are not presented on normal tissues in comparable copy numbers, preventing the risk of undesired autoimmune reactions against normal cells in the patient.

The pharmaceutical compositions comprise the peptides either in the free form or in the form of a pharmaceutically acceptable salt. As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —$NH_2$ group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like.

In an especially preferred embodiment, the pharmaceutical compositions comprise the peptides as salts of acetic acid (acetates), trifluoro acetates or hydrochloric acid (chlorides).

In addition to being useful for treating cancer, the peptides of the present invention are also useful as diagnostics. Since the peptides were generated from lung cancer cells and since it was determined that these peptides are not or at lower levels present in normal tissues, these peptides can be used to diagnose the presence of a cancer.

The presence of claimed peptides on tissue biopsies can assist a pathologist in diagnosis of cancer. Detection of certain peptides by means of antibodies, mass spectrometry or other methods known in the art can tell the pathologist that the tissue is malignant or inflamed or generally diseased. Presence of groups of peptides can enable classification or sub-classification of diseased tissues.

The detection of peptides on diseased tissue specimen can enable the decision about the benefit of therapies involving the immune system, especially if T-lymphocytes are known or expected to be involved in the mechanism of action. Loss of MHC expression is a well described mechanism by which infected of malignant cells escape immuno-surveillance. Thus, presence of peptides shows that this mechanism is not exploited by the analyzed cells.

The peptides of the present invention might be used to analyze lymphocyte responses against those peptides such as T cell responses or antibody responses against the peptide or the peptide complexed to MHC molecules. These lymphocyte responses can be used as prognostic markers for decision on further therapy steps. These responses can also be used as surrogate markers in immunotherapy approaches aiming to induce lymphocyte responses by different means, e.g. vaccination of protein, nucleic acids, autologous materials, adoptive transfer of lymphocytes. In gene therapy settings, lymphocyte responses against peptides can be considered in the assessment of side effects. Monitoring of lymphocyte responses might also be a valuable tool for follow-up examinations of transplantation therapies, e.g. for the detection of graft versus host and host versus graft diseases.

The peptides of the present invention can be used to generate and develop specific antibodies against MHC/peptide complexes. These can be used for therapy, targeting toxins or radioactive substances to the diseased tissue. Another use of these antibodies can be targeting radionuclides to the diseased tissue for imaging purposes such as PET. This use can help to detect small metastases or to determine the size and precise localization of diseased tissues.

Therefore it is a further aspect of the invention to provide a method for producing a recombinant antibody specifically binding to a human major histocompatibility complex (MHC) class I or II being complexed with a HLA-restricted antigen, the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically binding to said human major histocompatibility complex (MHC) class I or II being complexed with said HLA-restricted antigen.

It is a further aspect of the invention to provide an antibody that specifically binds to a human major histocompatibility complex (MHC) class I or II being complexed with a HLA-restricted antigen, wherein the antibody preferably is a polyclonal antibody, monoclonal antibody, bi-specific antibody and/or a chimeric antibody.

Yet another aspect of the present invention then relates to a method of producing said antibody specifically binding to a human major histocompatibility complex (MHC) class I or II being complexed with a HLA-restricted antigen, the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically bindable to said human major histocompatibility complex (MHC) class I or II being complexed with said HLA-restricted antigen. Respective methods for producing such antibodies and single chain class I major histocompatibility complexes, as well as other tools for the production of these antibodies are disclosed in WO 03/068201, WO 2004/084798, WO 01/72768, WO 03/070752, and Cohen C J, Denkberg G, Lev A, Epel M, Reiter Y. Recombinant antibodies with MHC-restricted, peptide-specific, T-cell receptor-like specificity: new tools to study antigen presentation and TCR-peptide-MHC interactions. J Mol Recognit. 2003 September-October; 16(5):324-32.; Denkberg G, Lev A, Eisenbach L, Benhar I, Reiter Y. Selective targeting of melanoma and APCs using a recombinant antibody with TCR-like specificity directed toward a melanoma differentiation antigen. J Immunol. 2003 Sep. 1; 171(5):2197-207; and Cohen C J, Sarig O, Yamano Y, Tomaru U, Jacobson S, Reiter Y. Direct phenotypic analysis of human MHC class I antigen presentation: visualization, quantitation, and in situ detection of human viral epitopes using peptide-specific, MHC-restricted human recombinant antibodies. J Immunol. 2003 Apr. 15; 170(8):4349-61, which for the purposes of the present invention are all explicitly incorporated by reference in their entireties.

Preferably, the antibody is binding with a binding affinity of below 20 nanomolar, preferably of below 10 nanomolar, to the complex, which is regarded as "specific" in the context of the present invention.

It is a further aspect of the invention to provide a method for producing a soluble T-cell receptor recognizing a specific peptide-MHC complex. Such soluble T-cell receptors can be generated from specific T-cell clones, and their affinity can be increased by mutagenesis targeting the complementarity-determining regions. For the purpose of T-cell receptor selection, phage display can be used (US 2010/0113300, Liddy N, Bossi G, Adams K J, Lissina A, Mahon T M, Hassan N J, et al. Monoclonal TCR-redirected tumor cell killing. Nat Med 2012 June; 18(6):980-987). For the purpose of stabilization of T-cell receptors during phage display and in case of practical use as drug, alpha and beta chain can be linked e.g. by non-native disulfide bonds, other covalent bonds (single-chain T-cell receptor), or by dimerization domains (see Boulter J M, Glick M, Todorov P T, Baston E, Sami M, Rizkallah P, et al. Stable, soluble T-cell receptor molecules for crystallization and therapeutics. Protein Eng 2003 September; 16(9):707-711.; Card K F, Price-Schiavi S A, Liu B, Thomson E, Nieves E, Belmont H, et al. A soluble single-chain T-cell receptor IL-2 fusion protein retains MHC-restricted peptide specificity and IL-2 bioactivity. Cancer Immunol Immunother 2004 April; 53(4):345-357; and Willcox B E, Gao G F, Wyer J R, O'Callaghan C A, Boulter J M, Jones E Y, et al. Production of soluble alphabeta T-cell receptor heterodimers suitable for biophysical analysis of ligand binding. Protein Sci 1999 November; 8 (11): 2418-2423). The T-cell receptor can be linked to toxins, drugs, cytokines (see US 2013/0115191), domains recruiting effector cells such as an anti-CD3 domain, etc., in order to execute particular functions on target cells. Moreover, it could be expressed in T cells used for adoptive transfer.

Further information can be found in WO 2004/033685A1 and WO 2004/074322A1. A combination of sTCRs is described in WO 2012/056407A1. Further methods for the production are disclosed in WO 2013/057586A1.

In addition, they can be used to verify a pathologist's diagnosis of a cancer based on a biopsied sample.

To select over-presented peptides, a presentation profile is calculated showing the median sample presentation as well as replicate variation. The profile juxtaposes samples of the tumor entity of interest to a baseline of normal tissue samples. Each of these profiles can then be consolidated into an over-presentation score by calculating the p-value of a Linear Mixed-Effects Model (J. Pinheiro, D. Bates, S. DebRoy, Sarkar D., R Core team. nlme: Linear and Nonlinear Mixed Effects Models. 2008) adjusting for multiple testing by False Discovery Rate (Y. Benjamini and Y. Hochberg. Controlling the False Discovery Rate: A Practical and Powerful Approach to Multiple Testing. Journal of the Royal Statistical Society. Series B (Methodological), Vol. 57 (No. 1):289-300, 1995).

For the identification and relative quantitation of HLA ligands by mass spectrometry, HLA molecules from shock-frozen tissue samples were purified and HLA-associated peptides were isolated. The isolated peptides were separated and sequences were identified by online nano-electrospray-ionization (nanoESI) liquid chromatography-mass spectrometry (LC-MS) experiments. The resulting peptide sequences were verified by comparison of the fragmentation pattern of natural TUMAPs recorded from NSCLC samples with the fragmentation patterns of corresponding synthetic reference peptides of identical sequences. Since the peptides were directly identified as ligands of HLA molecules of primary tumors, these results provide direct evidence for the natural processing and presentation of the identified peptides on primary tumor tissue obtained from NSCLC patients.

The proprietary discovery pipeline XPRESIDENT® v2.1 (see, for example, US 2013-0096016 which is hereby incorporated in its entirety) allows the identification and selection of relevant over-presented peptide vaccine candidates based on direct relative quantitation of HLA-restricted peptide levels on cancer tissues in comparison to several different non-cancerous tissues and organs. This was achieved by the development of label-free differential quantitation using the acquired LC-MS data processed by a proprietary data analysis pipeline, combining algorithms for sequence identification, spectral clustering, ion counting, retention time alignment, charge state deconvolution and normalization.

Presentation levels including error estimates for each peptide and sample were established. Peptides exclusively presented on tumor tissue and peptides over-presented in tumor versus non-cancerous tissues and organs have been identified.

HLA-peptide complexes from 50 shock-frozen NSCLC tumor tissue samples were purified and HLA-associated peptides were isolated and analysed by LC-MS.

All TUMAPs contained in the application at hand were identified with this approach on primary NSCLC tumor samples confirming their presentation on primary NSCLC.

TUMAPs identified on multiple NSCLC tumor and normal tissues were quantified using ion-counting of label-free LC-MS data. The method assumes that LC-MS signal areas of a peptide correlate with its abundance in the sample. All quantitative signals of a peptide in various LC-MS experiments were normalized based on central tendency, averaged per sample and merged into a bar plot, called presentation profile. The presentation profile consolidates different analysis methods like protein database search, spectral clustering, charge state deconvolution (decharging) and retention time alignment and normalization.

The present invention therefore relates to a peptide comprising a sequence that is selected from the group consisting of SEQ ID No. 1 to SEQ ID No. 65, and SEQ ID No. 76 to SEQ ID No. 84, and SEQ ID No. 92 or a variant thereof which is at least 90% homologous (preferably identical) to SEQ ID No. 1 to SEQ ID No. 65, and SEQ ID No. 76 to SEQ ID No. 84 and SEQ ID No. 92 or a variant thereof that induces T cells cross-reacting with said peptide, wherein said peptide is not a full-length polypeptide.

The present invention further relates to a peptide comprising a sequence that is selected from the group consisting of SEQ ID No. 1 to SEQ ID No. 65 and SEQ IDs No. 76 to SEQ ID No. 84, and SEQ ID No. 92 or a variant thereof which is at least 90% homologous (preferably identical) to SEQ ID No. 1 to SEQ ID No. 65, and SEQ ID No. 76 to SEQ ID No. 84, wherein said peptide or variant has an overall length of between 8 and 100, preferably between 8 and 30, and most preferred between 8 and 14 amino acids.

The present invention further relates to the peptides according to the invention that have the ability to bind to a molecule of the human major histocompatibility complex (MHC) class-I or -II.

The present invention further relates to the peptides according to the invention wherein the peptide consists or consists essentially of an amino acid sequence according to SEQ ID No. 1 to SEQ ID No. 65, and SEQ ID No. 76 to SEQ ID No. 84, and SEQ ID No. 92.

The present invention further relates to the peptides according to the invention, wherein the peptide is modified and/or includes non-peptide bonds.

The present invention further relates to the peptides according to the invention, wherein the peptide is a fusion protein, in particular comprising N-terminal amino acids of the HLA-DR antigen-associated invariant chain (Ii), or wherein the peptide is fused to (or into) an antibody, such as, for example, an antibody that is specific for dendritic cells.

The present invention further relates to a nucleic acid, encoding the peptides according to the invention, provided that the peptide is not the full human protein.

The present invention further relates to the nucleic acid according to the invention that is DNA, cDNA, PNA, RNA or combinations thereof.

The present invention further relates to an expression vector capable of expressing a nucleic acid according to the invention.

The present invention further relates to a peptide according to the invention, a nucleic acid according to the invention or an expression vector according to the invention for use in medicine.

The present invention further relates to a host cell comprising a nucleic acid according to the invention or an expression vector according to the invention.

The present invention further relates to the host cell according to the invention that is an antigen presenting cell.

The present invention further relates to the host cell according to the invention wherein the antigen presenting cell is a dendritic cell.

The present invention further relates to a method of producing a peptide according to the invention, the method comprising culturing the host cell described and isolating the peptide from the host cell or its culture medium.

The present invention further relates to an in vitro method for producing activated cytotoxic T lymphocytes (CTL), the method comprising contacting in vitro CTL with antigen loaded human class I or II MHC molecules expressed on the surface of a suitable antigen-presenting cell for a period of time sufficient to activate said CTL in an antigen specific manner, wherein said antigen is any peptide according to the invention.

The present invention further relates to the method as described, wherein said antigen is loaded onto class I or II MHC molecules expressed on the surface of a suitable antigen-presenting cell by contacting a sufficient amount of the antigen with an antigen-presenting cell.

The present invention further relates to the method according to the invention, wherein the antigen-presenting cell comprises an expression vector capable of expressing said peptide containing SEQ ID No. 1 to SEQ ID No. 65, and SEQ ID No. 76 to SEQ ID No. 84, and SEQ ID No. 92 or said variant amino acid sequence.

The present invention further relates to activated cytotoxic T lymphocytes (CTL), produced by the method according to the invention, which selectively recognise a cell which aberrantly expresses a polypeptide comprising an amino acid sequence described.

The present invention further relates to a method of killing target cells in a patient which target cells aberrantly express a polypeptide comprising any amino acid sequence according to the invention, the method comprising administering to the patient an effective number of cytotoxic T lymphocytes (CTL) according to the invention.

The present invention further relates to the use of any peptide according to the invention, a nucleic acid according to the invention, an expression vector according to the invention, a cell according to the invention, or an activated cytotoxic T lymphocyte according to the invention as a medicament or in the manufacture of a medicament.

The present invention further relates to a use according to the invention, wherein the medicament is a vaccine.

The present invention further relates to a use according to the invention, wherein the medicament is active against cancer.

The present invention further relates to a use according to the invention, wherein said cancer cells are lung cancer cells, gastric, gastrointestinal, colorectal, pancreatic or renal.

The present invention further relates to particular marker proteins and biomarkers that can be used in the prognosis of lung cancer.

Further, the present invention relates to the use of the novel targets as described in accordance with the present invention for cancer treatment.

The term "antibody" or "antibodies" is used herein in a broad sense and includes both polyclonal and monoclonal antibodies. In addition to intact or "full" immunoglobulin molecules, also included in the term "antibodies" are fragments or polymers of those immunoglobulin molecules and humanized versions of immunoglobulin molecules, so long as they exhibit any of the desired properties (e.g., specific binding of an lung cancer marker polypeptide, delivery of a toxin to an lung cancer cell expressing a lung cancer marker gene at an increased level, and/or inhibiting the activity of a lung cancer marker polypeptide) according to the invention.

Whenever possible, the antibodies of the invention may be purchased from commercial sources. The antibodies of the invention may also be generated using well-known methods. The skilled artisan will understand that either full length lung cancer marker polypeptides or fragments thereof may be used to generate the antibodies of the invention. A polypeptide to be used for generating an antibody of the invention may be partially or fully purified from a natural source, or may be produced using recombinant DNA techniques.

For example, a cDNA encoding a ABCA13, MMP12, DST, MXRA5, CDK4, HNRNPH, TANC2, 1RNF213, SMYD3 and SLC34A2, or any other polypeptide of SEQ ID No. 1 to SEQ ID No. 65, and SEQ ID No. 76 to SEQ ID No. 84 and SEQ ID No. 92 polypeptide, or a fragment thereof, can be expressed in prokaryotic cells (e.g., bacteria) or eukaryotic cells (e.g., yeast, insect, or mammalian cells), after which the recombinant protein can be purified and used to generate a monoclonal or polyclonal antibody preparation that specifically bind the lung cancer marker polypeptide used to generate the antibody according to the invention.

One of skill in the art will realize that the generation of two or more different sets of monoclonal or polyclonal antibodies maximizes the likelihood of obtaining an antibody with the specificity and affinity required for its intended use (e.g., ELISA, immunohistochemistry, in vivo imaging, immunotoxin therapy). The antibodies are tested for their desired activity by known methods, in accordance with the purpose for which the antibodies are to be used (e.g., ELISA, immunohistochemistry, immunotherapy, etc.; for further guidance on the generation and testing of antibodies, see, e.g., Harlow and Lane, Antibodies: A Laboratory Manual, Cold Spring Harbor Laboratory Press, Cold Spring Harbor, N.Y., 1988, new $2^{nd}$ edition 2013). For example, the antibodies may be tested in ELISA assays, Western blots, immunohistochemical staining of formalin-fixed lung cancers or frozen tissue sections. After their initial in vitro characterization, antibodies intended for therapeutic or in vivo diagnostic use are tested according to known clinical testing methods.

The term "monoclonal antibody" as used herein refers to an antibody obtained from a substantially homogeneous population of antibodies, i.e.; the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity (U.S. Pat. No. 4,816,567, which is hereby incorporated by reference in its entirety).

Monoclonal antibodies of the invention may be prepared using hybridoma methods. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fe fragment. Pepsin treatment yields a fragment that has two antigen combining sites and is still capable of cross-linking antigen.

The antibody fragments, whether attached to other sequences or not, can also include insertions, deletions, substitutions, or other selected modifications of particular regions or specific amino acids residues, provided the activity of the fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody fragment.

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region gene in chimeric and germ-line mutant mice results in complete inhibition of endogenous antibody production. Transfer of the human germ-line immunoglobulin gene array in such germ-line mutant mice will result in the production of human antibodies upon antigen challenge. Human antibodies can also be produced in phage display libraries.

Antibodies of the invention are preferably administered to a subject in a pharmaceutically acceptable carrier. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intratumoral or peritumoral routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. A typical daily dosage of the antibody used alone might range from about 1 (μg/kg to up to 100 mg/kg of body weight or more per day, depending on the factors mentioned above. Following administration of an antibody for treating lung cancer, the efficacy of the therapeutic antibody can be assessed in various ways well known to the skilled practitioner. For instance, the size, number, and/or distribution of lung cancer in a subject receiving treatment may be monitored using standard tumor imaging techniques. A therapeutically-administered antibody that arrests tumor growth, results in tumor shrinkage, and/or prevents the development of new tumors, compared to the disease course that would occurs in the absence of antibody administration, is an efficacious antibody for treatment of lung cancer.

Because the lung tumor markers ABCA13, MMP12 of the invention are highly expressed in lung cancer cells and are expressed at extremely low levels in normal cells, inhibition of ABCA13 and MMP12 expression or polypeptide activity may be integrated into any therapeutic strategy for treating or preventing NSCLC.

The principle of antisense therapy is based on the hypothesis that sequence-specific suppression of gene expression (via transcription or translation) may be achieved by intracellular hybridization between genomic DNA or mRNA and a complementary antisense species. The formation of such a hybrid nucleic acid duplex interferes with transcription of the target tumor antigen-encoding genomic DNA, or processing/transport/translation and/or stability of the target tumor antigen mRNA.

Antisense nucleic acids can be delivered by a variety of approaches. For example, antisense oligonucleotides or antisense RNA can be directly administered (e.g., by intravenous injection) to a subject in a form that allows uptake into tumor cells. Alternatively, viral or plasmid vectors that encode antisense RNA (or RNA fragments) can be introduced into cells in vivo. Antisense effects can also be induced by sense sequences; however, the extent of phenotypic changes is highly variable. Phenotypic changes induced by effective antisense therapy are assessed according to changes in, e.g., target mRNA levels, target protein levels, and/or target protein activity levels.

In a specific example, inhibition of lung tumor marker function by antisense gene therapy may be accomplished by direct administration of antisense lung tumor marker RNA to a subject. The antisense tumor marker RNA may be produced and isolated by any standard technique, but is most readily produced by in vitro transcription using an antisense tumor marker cDNA under the control of a high efficiency promoter (e.g., the T7 promoter). Administration of antisense tumor marker RNA to cells can be carried out by any of the methods for direct nucleic acid administration described below.

An alternative strategy for inhibiting ABCA13, and MMP12 function using gene therapy involves intracellular expression of an anti-ABCA13, MMP12 antibody or a portion of an anti-ABCA13, MMP12 antibody. For example, the gene (or gene fragment) encoding a monoclonal antibody that specifically binds to an ABCA13, MMP12 polypeptide and inhibits its biological activity is placed under the transcriptional control of a specific (e.g., tissue- or tumor-specific) gene regulatory sequence, within a nucleic acid expression vector. The vector is then administered to the subject such that it is taken up by lung cancer cells or other cells, which then secrete the anti-ABCA13, MMP12 antibody and thereby block biological activity of the ABCA13, MMP12 polypeptide. Preferably, the ABCA13, MMP12 polypeptides are present at the extracellular surface of gastric cancer cells.

In the methods described above, which include the administration and uptake of exogenous DNA into the cells of a subject (i.e., gene transduction or transfection), the nucleic acids of the present invention can be in the form of naked DNA or the nucleic acids can be in a vector for delivering the nucleic acids to the cells for inhibition of gastric tumor marker protein expression. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPOFECTAMINE (GIBCO-25 BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system that can package a recombinant retroviral genome. The recombinant retrovirus can then be used to infect and thereby deliver to the infected cells antisense nucleic acid that inhibits expression of ABCA13, MMP12. The exact method of introducing the altered nucleic acid into mammalian cells is, of course, not limited to the use of retroviral vectors. Other techniques are widely available for this procedure including the use of adenoviral vectors, adeno-associated viral (AAV) vectors, lentiviral vectors, pseudotyped retroviral vectors. Physical transduction techniques can also be used, such as liposome delivery and receptor-mediated and other endocytosis mechanisms. This invention can be used in conjunction with any of these or other commonly used gene transfer methods.

The antibodies may also be used for in vivo diagnostic assays. Generally, the antibody is labeled with a radionucleotide (such as $^{111}$In, $^{99}$Tc, $^{14}$C, $^{131}$I, $^{3}$H, $^{32}$P or $^{35}$S) so that the tumor can be localized using immunoscintiography. In one embodiment, antibodies or fragments thereof bind to the extracellular domains of two or more ABCA13, MMP12 targets and the affinity value (Kd) is less than 1×10 µM.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the ABCA13, MMP12 proteins express in situ.

The present invention thus provides a peptide comprising a sequence that is selected from the group of consisting of SEQ ID No. 1 to SEQ ID No. 65, and SEQ ID No. 76 to SEQ ID No. 84, and SEQ ID No. 92 or a variant thereof which is 90% homologous to SEQ ID No. 1 to SEQ ID No. 65, and SEQ ID No. 76 to SEQ ID No. 84, and SEQ ID No. 92 or a variant thereof that will induce T cells cross-reacting with said peptide.

The peptides of the invention have the ability to bind to a molecule of the human major histocompatibility complex (MHC) class-I and/or class II.

In the present invention, the term "homologous" refers to the degree of identity (see Percent Identity above) between sequences of two amino acid sequences, i.e. peptide or polypeptide sequences. The aforementioned "homology" is determined by comparing two sequences aligned under optimal conditions over the sequences to be compared. Such a sequence homology can be calculated by creating an alignment using, for example, the ClustalW algorithm. Commonly available sequence analysis software, more specifically, Vector NTI, GENETYX or other analysis tools are provided by public databases.

A person skilled in the art will be able to assess, whether T cells induced by a variant of a specific peptide will be able to cross-react with the peptide itself (Fong et al., 2001); (Zaremba et al., 1997; Colombetti et al., 2006; Appay et al., 2006).

By a "variant" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence in consisting of SEQ ID No. 1 to SEQ ID No. 65, and SEQ ID No. 76 to SEQ ID No. 84, and SEQ ID No. 92. For example, a peptide may be modified so that it at least maintains, if not improves, the ability to interact with and bind to the binding groove of a suitable MHC molecule, such as HLA-A*02 or -DR, and in that way it at least maintains, if not improves, the ability to bind to the TCR of activated CTL.

These CTL can subsequently cross-react with cells and kill cells that express a polypeptide that contains the natural amino acid sequence of the cognate peptide as defined in the aspects of the invention. As can be derived from the scientific literature (Rammensee et al., 1997) and databases (Rammensee et al., 1999), certain positions of HLA binding peptides are typically anchor residues forming a core sequence fitting to the binding motif of the HLA receptor, which is defined by polar, electrophysical, hydrophobic and spatial properties of the polypeptide chains constituting the binding groove. Thus one skilled in the art would be able to modify the amino acid sequences set forth in SEQ ID No. 1 to SEQ ID No. 65 and SEQ ID No. 76 to SEQ ID No. 84, and SEQ ID No. 92, by maintaining the known anchor residues, and would be able to determine whether such variants maintain the ability to bind MHC class I or II molecules. The variants of the present invention retain the ability to bind to the TCR of activated CTL, which can subsequently cross-react with- and kill cells that express a polypeptide containing the natural amino acid sequence of the cognate peptide as defined in the aspects of the invention.

Those amino acid residues that do not substantially contribute to interactions with the T-cell receptor can be modified by replacement with another amino acid whose incorporation does not substantially affect T-cell reactivity and does not eliminate binding to the relevant MHC. Thus, apart from the proviso given, the peptide of the invention may be any peptide (by which term the inventors include oligopeptide or polypeptide), which includes the amino acid sequences or a portion or variant thereof as given.

TABLE 4

Variants and motif of the peptides according to SEQ ID NO: 1, 2, 4, 5 and 7

| | | Position | | | | | | | | |
|---|---|---|---|---|---|---|---|---|---|---|
| | | 1 | 2 | 3 | 4 | 5 | 6 | 7 | 8 | 9 |
| ABCA13-001 SEQ ID No. | Peptide Code Variants | I | L | F | E | I | N | P | K | L |
| | | | | | | | | | | V |
| | | | | | | | | | | I |
| | | | | | | | | | | A |
| | | | M | | | | | | | V |
| | | | M | | | | | | | I |
| | | | M | | | | | | | |
| | | | M | | | | | | | A |
| | | | A | | | | | | | V |
| | | | A | | | | | | | I |
| | | | A | | | | | | | |
| | | | A | | | | | | | A |
| | | | V | | | | | | | V |
| | | | V | | | | | | | I |
| | | | V | | | | | | | |
| | | | V | | | | | | | A |
| | | | T | | | | | | | V |
| | | | T | | | | | | | I |
| | | | T | | | | | | | |
| | | | T | | | | | | | A |
| | | | Q | | | | | | | V |
| | | | Q | | | | | | | I |
| | | | Q | | | | | | | |
| | | | Q | | | | | | | A |
| MMP12-003 SEQ ID No. | Peptide Code Variants | K | I | Q | E | M | Q | H | F | L |
| | | | L | | | | | | | V |
| | | | L | | | | | | | I |
| | | | L | | | | | | | |
| | | | L | | | | | | | A |
| | | | M | | | | | | | V |
| | | | M | | | | | | | I |
| | | | M | | | | | | | |
| | | | M | | | | | | | A |
| | | | A | | | | | | | V |
| | | | A | | | | | | | I |
| | | | A | | | | | | | |
| | | | A | | | | | | | A |
| | | | V | | | | | | | V |
| | | | V | | | | | | | I |
| | | | V | | | | | | | |
| | | | V | | | | | | | A |
| | | | T | | | | | | | V |
| | | | T | | | | | | | I |
| | | | T | | | | | | | |
| | | | T | | | | | | | A |
| | | | Q | | | | | | | V |
| | | | Q | | | | | | | I |
| | | | Q | | | | | | | |
| DST-001 SEQ ID No. | Peptide Code Variants | N | L | I | E | K | S | I | Y | L |
| | | | | | | | | | | V |
| | | | | | | | | | | I |
| | | | | | | | | | | A |
| | | | M | | | | | | | V |
| | | | M | | | | | | | I |
| | | | M | | | | | | | |
| | | | M | | | | | | | A |
| | | | A | | | | | | | V |
| | | | A | | | | | | | I |
| | | | A | | | | | | | |
| | | | A | | | | | | | A |
| | | | V | | | | | | | V |
| | | | V | | | | | | | I |
| | | | V | | | | | | | |
| | | | V | | | | | | | A |
| | | | T | | | | | | | V |
| | | | T | | | | | | | I |
| | | | T | | | | | | | |
| | | | T | | | | | | | A |
| | | | Q | | | | | | | V |
| | | | Q | | | | | | | I |
| | | | Q | | | | | | | |
| | | | Q | | | | | | | A |
| MXRA5-001 SEQ ID No. | Peptide Code Variants | T | L | S | S | I | K | V | E | V |
| | | | | | | | | | | I |
| | | | | | | | | | | L |
| | | | | | | | | | | A |
| | | | M | | | | | | | V |
| | | | M | | | | | | | I |
| | | | M | | | | | | | L |
| | | | M | | | | | | | A |
| | | | A | | | | | | | V |
| | | | A | | | | | | | I |
| | | | A | | | | | | | L |
| | | | A | | | | | | | A |
| | | | V | | | | | | | V |
| | | | V | | | | | | | I |
| | | | V | | | | | | | L |
| | | | V | | | | | | | A |
| | | | T | | | | | | | V |
| | | | T | | | | | | | I |
| | | | T | | | | | | | L |
| | | | T | | | | | | | A |
| | | | Q | | | | | | | V |
| | | | Q | | | | | | | I |
| | | | Q | | | | | | | L |
| | | | Q | | | | | | | A |
| CDK4-001 SEQ ID No. | Peptide Code Variants | T | L | W | Y | R | A | P | E | V |
| | | | | | | | | | | I |
| | | | | | | | | | | L |
| | | | | | | | | | | A |
| | | | M | | | | | | | V |
| | | | M | | | | | | | I |
| | | | M | | | | | | | L |
| | | | M | | | | | | | A |
| | | | A | | | | | | | V |
| | | | A | | | | | | | I |
| | | | A | | | | | | | L |
| | | | A | | | | | | | A |
| | | | V | | | | | | | V |
| | | | V | | | | | | | I |
| | | | V | | | | | | | L |
| | | | V | | | | | | | A |
| | | | T | | | | | | | V |
| | | | T | | | | | | | I |
| | | | T | | | | | | | L |
| | | | T | | | | | | | A |
| | | | Q | | | | | | | V |
| | | | Q | | | | | | | I |
| | | | Q | | | | | | | L |
| | | | Q | | | | | | | A |

Longer peptides may also be suitable. It is also possible, that MHC class I epitopes, although usually between 8-11 amino acids long, are generated by peptide processing from longer peptides or proteins that include the actual epitope. It is preferred that the residues that flank the actual epitope are residues that do not substantially affect proteolytic cleavage necessary to expose the actual epitope during processing.

Accordingly, the present invention also provides peptides and variants of MHC class I epitopes wherein the peptide or variant has an overall length of between 8 and 100, preferably between 8 and 30, and most preferred between 8 and 14, namely 8, 9, 10, 11, 12, 13, 14 amino acids, in case of the class II binding peptides the length can also be 15, 16, 17, 18, 19, 20, 21 or 33 amino acids.

Of course, the peptide or variant according to the present invention will have the ability to bind to a molecule of the human major histocompatibility complex (MHC) class I. Binding of a peptide or a variant to a MHC complex may be tested by methods known in the art.

In a particularly preferred embodiment of the invention the peptide consists or consists essentially of an amino acid sequence according to SEQ ID No. 1 to SEQ ID No. 65, and SEQ ID No. 76 to SEQ ID No. 84, and SEQ ID No. 92.

"Consisting essentially of" shall mean that a peptide according to the present invention, in addition to the sequence according to any of SEQ ID No. 1 to SEQ ID No. 65, and SEQ ID No. 76 to SEQ ID No. 84, and SEQ ID No. 92 or a variant thereof contains additional N- and/or C-terminally located stretches of amino acids that are not necessarily forming part of the peptide that functions as an epitope for MHC molecules epitope.

Nevertheless, these stretches can be important to provide an efficient introduction of the peptide according to the present invention into the cells. In one embodiment of the present invention, the peptide is a fusion protein which comprises, for example, the 80 N-terminal amino acids of the HLA-DR antigen-associated invariant chain (p33, in the following "Ii") as derived from the NCBI, GenBank Accession number X00497. In other fusions, the peptides of the present invention can be fused to an antibody as described herein, or a functional part thereof, in particular into a sequence of an antibody, so as to be specifically targeted by said antibody, or, for example, to or into an antibody that is specific for dendritic cells.

In addition, the peptide or variant may be modified further to improve stability and/or binding to MHC molecules in order to elicit a stronger immune response. Methods for such an optimization of a peptide sequence are well known in the art and include, for example, the introduction of reverse peptide bonds or non-peptide bonds.

In a reverse peptide bond amino acid residues are not joined by peptide (—CO—NH—) linkages but the peptide bond is reversed. Such retro-inverso peptidomimetics may be made using methods known in the art, for example such as those described in Meziere et al (1997) J. Immunol. 159, 3230-3237, incorporated herein by reference. This approach involves making pseudopeptides containing changes involving the backbone, and not the orientation of side chains. Meziere et al (1997) show that for MHC binding and T helper cell responses, these pseudopeptides are useful. Retro-inverse peptides, which contain NH—CO bonds instead of CO—NH peptide bonds, are much more resistant to proteolysis.

A non-peptide bond is, for example, —CH$_2$—NH, —CH$_2$S—, —CH$_2$CH$_2$—, —CH=CH—, —COCH$_2$—, —CH(OH)CH$_2$—, and —CH$_2$SO—. U.S. Pat. No. 4,897,445 provides a method for the solid phase synthesis of non-peptide bonds (—CH$_2$—NH) in polypeptide chains which involves polypeptides synthesized by standard procedures and the non-peptide bond synthesized by reacting an amino aldehyde and an amino acid in the presence of NaCNBH$_3$.

Peptides comprising the sequences described above may be synthesized with additional chemical groups present at their amino and/or carboxy termini, to enhance the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenyl-methoxy-carbonyl group may be placed at the peptides' amino termini. Additionally, the hydrophobic group, t-butyloxycarbonyl, or an amido group may be added to the peptides' carboxy termini.

Further, the peptides of the invention may be synthesized to alter their steric configuration. For example, the D-isomer of one or more of the amino acid residues of the peptide may be used, rather than the usual L-isomer. Still further, at least one of the amino acid residues of the peptides of the invention may be substituted by one of the well-known non-naturally occurring amino acid residues. Alterations such as these may serve to increase the stability, bioavailability and/or binding action of the peptides of the invention.

Similarly, a peptide or variant of the invention may be modified chemically by reacting specific amino acids either before or after synthesis of the peptide. Examples for such modifications are well known in the art and are summarized e.g. in R. Lundblad, Chemical Reagents for Protein Modification, 3rd ed. CRC Press, 2005, which is incorporated herein by reference. Chemical modification of amino acids includes but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley and Sons NY 1995-2000) for more extensive methodology relating to chemical modification of proteins.

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginine residues. Cysteine can be modified without concomitant modification of other nucleophilic sites such as lysine and histidine. As a result, a large number of reagents are available for the modification of cysteine. The websites of companies such as Sigma-Aldrich (http://www.sigma-aldrich.com) provide information on specific reagents.

Selective reduction of disulfide bonds in proteins is also common. Disulfide bonds can be formed and oxidized during the heat treatment of biopharmaceuticals.

Woodward's Reagent K may be used to modify specific glutamic acid residues. N-(3-(dimethylamino)propyl)-N'-ethylcarbodiimide can be used to form intra-molecular crosslinks between a lysine residue and a glutamic acid residue.

For example, diethylpyrocarbonate is a reagent for the modification of histidyl residues in proteins. Histidine can also be modified using 4-hydroxy-2-nonenal.

The reaction of lysine residues and other α-amino groups is, for example, useful in binding of peptides to surfaces or the cross-linking of proteins/peptides. Lysine is the site of attachment of poly(ethylene)glycol and the major site of modification in the glycosylation of proteins.

Methionine residues in proteins can be modified with e.g. iodoacetamide, bromoethylamine, and chloramine T.

Tetranitromethane and N-acetylimidazole can be used for the modification of tyrosyl residues. Cross-linking via the formation of dityrosine can be accomplished with hydrogen peroxide/copper ions.

Recent studies on the modification of tryptophan have used N-bromosuccinimide, 2-hydroxy-5-nitrobenzyl bromide or 3-bromo-3-methyl-2-(2-nitrophenylmercapto)-3H-indole (BPNS-skatole).

Successful modification of therapeutic proteins and peptides with PEG is often associated with an extension of circulatory half-life while cross-linking of proteins with glutaraldehyde, polyethyleneglycol diacrylate and formaldehyde is used for the preparation of hydrogels. Chemical modification of allergens for immunotherapy is often achieved by carbamylation with potassium cyanate.

A peptide or variant, wherein the peptide is modified or includes non-peptide bonds is a preferred embodiment of the invention. Generally, peptides and variants (at least those containing peptide linkages between amino acid residues) may be synthesized by the Fmoc-polyamide mode of solid-phase peptide synthesis as disclosed by Lu et al (1981) and references therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N, N-dicyclohexyl-carbodiimide/1hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used include ethandithiol, phenol, anisole and water, the exact choice depending on the constituent amino acids of the peptide being synthesized. Also a combination of solid phase and solution phase methodologies for the synthesis of peptides is possible (see, for example (Bruckdorfer et al., 2004) and the references as cited therein).

Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from e.g. Calbiochem-Novabiochem (UK) Ltd, Nottingham NG7 2QJ, UK.

Purification may be performed by any one, or a combination of, techniques such as re-crystallization, size exclusion chromatography, ion-exchange chromatography, hydrophobic interaction chromatography and (usually) reverse-phase high performance liquid chromatography using e.g. acetonitril/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

A further aspect of the invention provides a nucleic acid (for example a polynucleotide) encoding a peptide or peptide variant of the invention. The polynucleotide may be, for example, DNA, cDNA, PNA, RNA or combinations thereof, either single- and/or double-stranded, or native or stabilized forms of polynucleotides, such as, for example, polynucleotides with a phosphorothioate backbone and it may or may not contain introns so long as it codes for the peptide. Of course, only peptides that contain naturally occurring amino acid residues joined by naturally occurring peptide bonds are encodable by a polynucleotide. A still further aspect of the invention provides an expression vector capable of expressing a polypeptide according to the invention.

A variety of methods have been developed to link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc. New Haven, Conn., USA.

A desirable method of modifying the DNA encoding the polypeptide of the invention employs the polymerase chain reaction as disclosed by (Saiki et al., 1988)). This method may be used for introducing the DNA into a suitable vector, for example by engineering in suitable restriction sites, or it may be used to modify the DNA in other useful ways as is known in the art. If viral vectors are used, pox- or adenovirus vectors are preferred.

The DNA (or in the case of retroviral vectors, RNA) may then be expressed in a suitable host to produce a polypeptide comprising the peptide or variant of the invention. Thus, the DNA encoding the peptide or variant of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. Nos. 4,440,859, 4,530,901, 4,582,800, 4,677,063, 4,678,751, 4,704,362, 4,710,463, 4,757,006, 4,766,075, and 4,810,648.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus* spec.), plant cells, animal cells and insect cells. Preferably, the system can be mammalian cells such as CHO cells available from the ATCC Cell Biology Collection.

A typical mammalian cell vector plasmid for constitutive expression comprises the CMV or SV40 promoter with a suitable poly A tail and a resistance marker, such as neomycin. One example is pSVL available from Pharmacia, Piscataway, N.J., USA. An example of an inducible mammalian expression vector is pMSG, also available from Pharmacia. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). CMV promoter-based vectors (for example from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potent cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the b-lactamase gene for ampicillin resistance selection in bacteria, hGH polyA, and the f1 origin. Vectors containing the preprotrypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

In another embodiment two or more peptides or peptide variants of the invention are encoded and thus expressed in a successive order (similar to "beads on a string" constructs). In doing so, the peptides or peptide variants may be linked or fused together by stretches of linker amino acids, such as for example LLLLLL, or may be linked without any additional peptide(s) between them.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors. An overview regarding the choice of suitable host cells for expression can be found in, for example, the textbook of Paulina Balbas and Argelia Lorence "Methods in Molecular Biology Recombinant Gene Expression, Reviews and Protocols," Part One, Second Edition, ISBN 978-1-58829-262-9, and other literature known to the person of skill.

Transformation of appropriate cell hosts with a DNA construct of the present invention is accomplished by well-known methods that typically depend on the type of vector used. With regard to transformation of prokaryotic host cells, see, for example, Cohen et al (1972) Proc. Natl. Acad. Sci. USA 69, 2110, and Sambrook et al (1989) Molecular Cloning, A Laboratory Manual, Cold Spring Harbor Laboratory, Cold Spring Harbor, N.Y. Transformation of yeast cells is described in Sherman et al (1986) Methods In Yeast Genetics, A Laboratory Manual, Cold Spring Harbor, N.Y. The method of Beggs (1978) Nature 275, 104-109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well-known techniques such as PCR. Alternatively, the presence of the protein in the supernatant can be detected using antibodies.

It will be appreciated that certain host cells of the invention are useful in the preparation of the peptides of the invention, for example bacterial, yeast and insect cells. However, other host cells may be useful in certain therapeutic methods. For example, antigen-presenting cells, such as dendritic cells, may usefully be used to express the peptides of the invention such that they may be loaded into appropriate MHC molecules. Thus, the current invention provides a host cell comprising a nucleic acid or an expression vector according to the invention.

In a preferred embodiment the host cell is an antigen presenting cell, in particular a dendritic cell or antigen presenting cell. APCs loaded with a recombinant fusion protein containing prostatic acid phosphatase (PAP) are currently under investigation for the treatment of prostate cancer (Sipuleucel-T) (Small et al., 2006; Rini et al., 2006).

A further aspect of the invention provides a method of producing a peptide or its variant, the method comprising culturing a host cell and isolating the peptide from the host cell or its culture medium.

In another embodiment the peptide, the nucleic acid or the expression vector of the invention are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. Doses of e.g. between 50 μg and 1.5 mg, preferably 125 μg to 500 μg, of peptide or DNA may be given and will depend on the respective peptide or DNA. Dosages of this range were successfully used in previous trials (Walter et al Nature Medicine 18, 1254-1261 (2012)).

Another aspect of the present invention includes an in vitro method for producing activated T cells, the method comprising contacting in vitro T cells with antigen loaded human MHC molecules expressed on the surface of a suitable antigen-presenting cell for a period of time sufficient to activate the T cell in an antigen specific manner, wherein the antigen is a peptide according to the invention. Preferably a sufficient amount of the antigen is used with an antigen-presenting cell. Preferably the mammalian cell lacks or has a reduced level or function of the TAP peptide transporter. Suitable cells that lack the TAP peptide transporter include T2, RMA-S and Drosophila cells. TAP is the transporter associated with antigen processing.

The human peptide loading deficient cell line T2 is available from the American Type Culture Collection, 12301 Parklawn Drive, Rockville, Md. 20852, USA under Catalogue No CRL 1992; the Drosophila cell line Schneider line 2 is available from the ATCC under Catalogue No CRL 19863; the mouse RMA-S cell line is described in Karre et al 1985.

Preferably, the host cell before transfection expresses substantially no MHC class I molecules. It is also preferred that the stimulator cell expresses a molecule important for providing a co-stimulatory signal for T-cells such as any of B7.1, B7.2, ICAM-1 and LFA 3. The nucleic acid sequences of numerous MHC class I molecules and of the co-stimulator molecules are publicly available from the GenBank and EMBL databases.

In case of a MHC class I epitope being used as an antigen, the T cells are CD8-positive CTLs.

If an antigen-presenting cell is transfected to express such an epitope, preferably the cell comprises an expression vector capable of expressing a peptide containing SEQ ID No. 1 to SEQ ID No. 65, and SEQ ID No. 76 to SEQ ID No. 84, and SEQ ID No. 92, or a variant amino acid sequence thereof.

A number of other methods may be used for generating CTL in vitro. For example, the methods described in Peoples et al (1995) and Kawakami et al (1992) use autologous tumor-infiltrating lymphocytes in the generation of CTL. Plebanski et al (1995) makes use of autologous peripheral blood lymphocytes (PLBs) in the preparation of CTL. Jochmus et al (1997) describes the production of autologous CTL by pulsing dendritic cells with peptide or polypeptide, or via infection with recombinant virus. Hill et al (1995) and Jerome et al (1993) make use of B cells in the production of autologous CTL. In addition, macrophages pulsed with peptide or polypeptide, or infected with recombinant virus, may be used in the preparation of autologous CTL. S. Walter et al. 2003 describe the in vitro priming of T cells by using artificial antigen presenting cells (aAPCs), which is also a suitable way for generating T cells against the peptide of choice. In this study, aAPCs were generated by the coupling of preformed MHC:peptide complexes to the surface of polystyrene particles (microbeads) by biotin:streptavidin biochemistry. This system permits the exact control of the MHC density on aAPCs, which allows to selectively elicit high- or low-avidity antigen-specific T cell responses with high efficiency from blood samples. Apart from MHC:peptide complexes, aAPCs should carry other proteins with co-stimulatory activity like anti-CD28 antibodies coupled to their surface. Furthermore such aAPC-based systems often require the addition of appropriate soluble factors, e. g. cytokines like interleukin-12.

Allogeneic cells may also be used in the preparation of T cells and a method is described in detail in WO 97/26328, incorporated herein by reference. For example, in addition to Drosophila cells and T2 cells, other cells may be used to present antigens such as CHO cells, baculovirus-infected insect cells, bacteria, yeast, vaccinia-infected target cells. In addition plant viruses may be used (see, for example, Porta et al (1994)) which describes the development of cowpea mosaic virus as a high-yielding system for the presentation of foreign peptides.

The activated T cells that are directed against the peptides of the invention are useful in therapy. Thus, a further aspect of the invention provides activated T cells obtainable by the foregoing methods of the invention.

Activated T cells, which are produced by the above method, will selectively recognize a cell that aberrantly expresses a polypeptide that comprises an amino acid sequence of SEQ ID No. 1 to SEQ ID No. 92, preferably a sequence of SEQ ID No. 1 to SEQ ID No. 65, and SEQ ID No. 76 to SEQ ID No. 84, and SEQ ID No. 92.

Preferably, the T cell recognizes the cell by interacting through its TCR with the HLA/peptide-complex (for example, binding). The T cells are useful in a method of killing target cells in a patient whose target cells aberrantly express a polypeptide comprising an amino acid sequence of the invention wherein the patient is administered an effective number of the activated T cells. The T cells that are administered to the patient may be derived from the patient and activated as described above (i.e. they are autologous T cells). Alternatively, the T cells are not from the patient but are from another individual. Of course, it is preferred if the individual is a healthy individual. By "healthy individual" the inventors mean that the individual is generally in good health, preferably has a competent immune system and, more preferably, is not suffering from any disease that can be readily tested for, and detected.

In vivo, the target cells for the CD8-positive T cells according to the present invention can be cells of the tumor (which sometimes express MHC class II) and/or stromal cells surrounding the tumor (tumor cells) (which sometimes also express MHC class II; (Dengjel et al., 2006)).

The T cells of the present invention may be used as active ingredients of a therapeutic composition. Thus, the invention also provides a method of killing target cells in a patient whose target cells aberrantly express a polypeptide comprising an amino acid sequence of the invention, the method comprising administering to the patient an effective number of T cells as defined above.

By "aberrantly expressed" the inventors also mean that the polypeptide is over-expressed compared to normal levels of expression or that the gene is silent in the tissue from which the tumor is derived but in the tumor it is expressed. By "over-expressed" the inventors mean that the polypeptide is present at a level at least 1.2-fold of that present in normal tissue; preferably at least 2-fold, and more preferably at least 5-fold or 10-fold the level present in normal tissue.

T cells may be obtained by methods known in the art, e.g. those described above.

Protocols for this so-called adoptive transfer of T cells are well known in the art. Reviews can be found in (Gattinoni et al., 2006) and (Morgan et al., 2006).

Any molecule of the invention, i.e. the peptide, nucleic acid, antibody, expression vector, cell, activated CTL, T-cell receptor or the nucleic acid encoding it is useful for the treatment of disorders, characterized by cells escaping an immune response. Therefore any molecule of the present invention may be used as medicament or in the manufacture of a medicament. The molecule may be used by itself or combined with other molecule(s) of the invention or (a) known molecule(s).

Preferably, the medicament of the present invention is a vaccine. It may be administered directly into the patient, into the affected organ or systemically i.d., i.m., s.c., i.p. and i.v., or applied ex vivo to cells derived from the patient or a human cell line which are subsequently administered to the patient, or used in vitro to select a subpopulation of immune cells derived from the patient, which are then re-administered to the patient. If the nucleic acid is administered to cells in vitro, it may be useful for the cells to be transfected so as to co-express immune-stimulating cytokines, such as interleukin-2. The peptide may be substantially pure, or combined with an immune-stimulating adjuvant (see below) or used in combination with immune-stimulatory cytokines, or be administered with a suitable delivery system, for example liposomes. The peptide may also be conjugated to a suitable carrier such as keyhole limpet haemocyanin (KLH) or mannan (see WO 95/18145 and Longenecker, 1993). The peptide may also be tagged, may be a fusion protein, or may be a hybrid molecule. The peptides whose sequence is given in the present invention are expected to stimulate CD4 or CD8 T cells. However, stimulation of CD8 CTLs is more efficient in the presence of help provided by CD4 T-helper cells. Thus, for MHC Class I epitopes that stimulate CD8 CTL the fusion partner or sections of a hybrid molecule suitably provide epitopes which stimulate CD4-positive T cells. CD4- and CD8-stimulating epitopes are well known in the art and include those identified in the present invention.

In one aspect, the vaccine comprises at least one peptide having the amino acid sequence set forth SEQ ID No. 1 to SEQ ID No. 92 and at least one additional peptide, preferably two to 50, more preferably two to 25, even more preferably two to 20 and most preferably two, three, four, five, six, seven, eight, nine, ten, eleven, twelve, thirteen, fourteen, fifteen, sixteen, seventeen or eighteen peptides. The peptide(s) may be derived from one or more specific TAAs and may bind to MHC class I molecules.

In another aspect, the vaccine comprises at least one peptide having the amino acid sequence set forth SEQ ID No. 1 to SEQ ID No. 65 and SEQ ID No. 76 to SEQ ID No. 84, and SEQ ID No. 92, and at least one additional peptide, preferably two to 50, more preferably two to 25, even more preferably two to 20 and most preferably two, three, four, five, six, seven, eight, nine, ten, eleven, twelve, thirteen, fourteen, fifteen, sixteen, seventeen or eighteen peptides. The peptide(s) may be derived from one or more specific TAAs and may bind to MHC class I molecules.

The polynucleotide may be substantially pure, or contained in a suitable vector or delivery system. The nucleic acid may be DNA, cDNA, PNA, RNA or a combination thereof. Methods for designing and introducing such a nucleic acid are well known in the art. An overview is provided by e.g. (Pascolo et al., 2005). Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun," may also be used. The peptide or peptides encoded by the nucleic acid may be a fusion protein, for example with an epitope that stimulates T cells for the respective opposite CDR as noted above.

The medicament of the invention may also include one or more adjuvants. Adjuvants are substances that non-specifically enhance or potentiate the immune response (e.g., immune responses mediated by CTLs and helper-T (TH) cells to an antigen, and would thus be considered useful in the medicament of the present invention. Suitable adjuvants include, but are not limited to, 1018 ISS, aluminium salts, AMPLIVAX®, AS 15, BCG, CP-870,893, CpG7909, CyaA, dSLIM, flagellin or TLR5 ligands derived from flagellin, FLT3 ligand, GM-CSF, IC30, IC31, Imiquimod (AL-DARA®), resiquimod, ImuFact IMP321, Interleukins as IL-2, IL-13, IL-21, Interferon-alpha or -beta, or pegylated derivatives thereof, IS Patch, ISS, ISCOMATRIX, ISCOMs, JuvImmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, poly(lactid co-glycolid) [PLG]-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Allison and Krummel, 1995; Allison and Krummel, 1995). Also cytokines may be used. Several cytokines have been directly linked to influencing dendritic cell migration to lymphoid tissues (e.g., TNF-), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha. IFN-beta) (Gabrilovich, 1996).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of TH1 cells and strong cytotoxic T-lymphocyte (CTL) generation, even in the absence of CD4 T cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg, 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera), dsRNA analogues such as Poly(I:C) and derivates thereof (e.g. AmpliGen®, Hiltonol®, poly-(ICLC), poly(IC-R), poly(I:C12U), non-CpG bacterial DNA or RNA as well as immunoactive small molecules and antibodies such as cyclophosphamide, sunitinib, Bevacizumab®, celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4, other antibodies targeting key structures of the immune system (e.g. anti-CD40, anti-TGFbeta, anti-TNFalpha receptor) and SC58175, which may act therapeutically and/or as an adjuvant. The amounts and concentrations of adjuvants and additives useful in the context of the present invention can readily be determined by the skilled artisan without undue experimentation.

Preferred adjuvants are imiquimod, resiquimod, GM-CSF, cyclophosphamide, sunitinib, bevacizumab, interferon-alpha, CpG oligonucleotides and derivates, poly-(I:C) and derivates, RNA, sildenafil, and particulate formulations with PLG or virosomes.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod, resiquimod, and interferon-alpha.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, immiquimod and resiquimod.

In a preferred embodiment of the pharmaceutical composition according to the invention, the adjuvant is cyclophosphamide, imiquimod or resiquimod.

Even more preferred adjuvants are Montanide IMS 1312, Montanide ISA 206, Montanide ISA 50V, Montanide ISA-51, poly-ICLC (Hiltonol®) and anti-CD40 mAB or combinations thereof This composition is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavours, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients, $3^{rd}$ Ed., 2000, American Pharmaceutical Association and pharmaceutical press. The composition can be used for a prevention, prophylaxis and/or therapy of adenomateous or cancerous diseases. Exemplary formulations can be found in, for example, EP2113253.

Nevertheless depending on the number and the physico-chemical characteristics of the peptides of the invention further research is needed to provide formulations for specific combinations of peptides, especially combinations with more than 20 peptides that are stable for more than 12 to 18 months.

The present invention provides a medicament that useful in treating cancer, in particular non-small cell lung carcinoma, gastric cancer, renal cell carcinoma, colon cancer, adenocarcinoma, prostate cancer, benign neoplasm and malignant melanoma.

The present invention is further directed at a kit comprising:
(a) a container containing a pharmaceutical composition as described above, in solution or in lyophilized form;
(b) optionally a second container containing a diluent or reconstituting solution for the lyophilized formulation; and
(c) optionally, instructions for (i) use of the solution or (ii) reconstitution and/or use of the lyophilized formulation.

The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. Preferably the kit and/or container contain/s instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous administration.

The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 µg) and preferably not more than 3 mg/mL/peptide (=1500

μg). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, an anti-angiogenesis agent or inhibitor, a apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The present formulation is one that is suitable for administration of the peptides by any acceptable route such as oral (enteral), nasal, ophthal, subcutaneous, intradermal, intramuscular, intravenous or transdermal. Preferably the administration is s.c., and most preferably i.d. Administration may be by infusion pump.

Since the peptides of the invention were isolated from NSCLC, the medicament of the invention is preferably used to treat NSCLC. In a preferred embodiment, since the peptides of the invention derived from ABCA13 and MMP12 were isolated from NSCLC, the medicament of the invention is preferably used to treat NSCLC.

The peptides with the SEQ ID Nos. 78 to 92 were also isolated from Merkel cell carcinoma, and thus can be used to treat Merkel cell carcinoma.

The present invention will now be described in the following examples that describe preferred embodiments thereof, nevertheless, without being limited thereto. For the purposes of the present invention, all references as cited herein are incorporated by reference in their entireties.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A) Exemplary mass spectrum from ABCA13-001 demonstrating its presentation on primary tumor sample NSCLC898. NanoESI-LCMS was performed on a peptide pool eluted from the NSCLC sample 898. The mass chromatogram for m/z 543.8318±0.001 Da, z=2 shows a peptide peak at the retention time 86.36 min. FIG. 1B) The detected peak in the mass chromatogram at 86.36 min revealed a signal of m/z 543.8318 in the MS spectrum. FIG. 1C) A collisionally induced decay mass spectrum from the selected precursor m/z 543.8318 recorded in the nanoESI-LCMS experiment at the given retention time confirmed the presence of ABCA13-001 in the NSCLC898 tumor sample. FIG. 1D) The fragmentation pattern of the synthetic ABCA13-001 reference peptide was recorded and compared to the generated natural TUMAP fragmentation pattern shown in FIG. 1C for sequence verification.

FIG. 2B) MMP12 (Probeset ID: 204580_at)

FIG. 3A) ABCA13-001

FIG. 3B) DST-001

FIG. 3C) MXRA5-001

EXAMPLES

Example 1

Figure 1A:
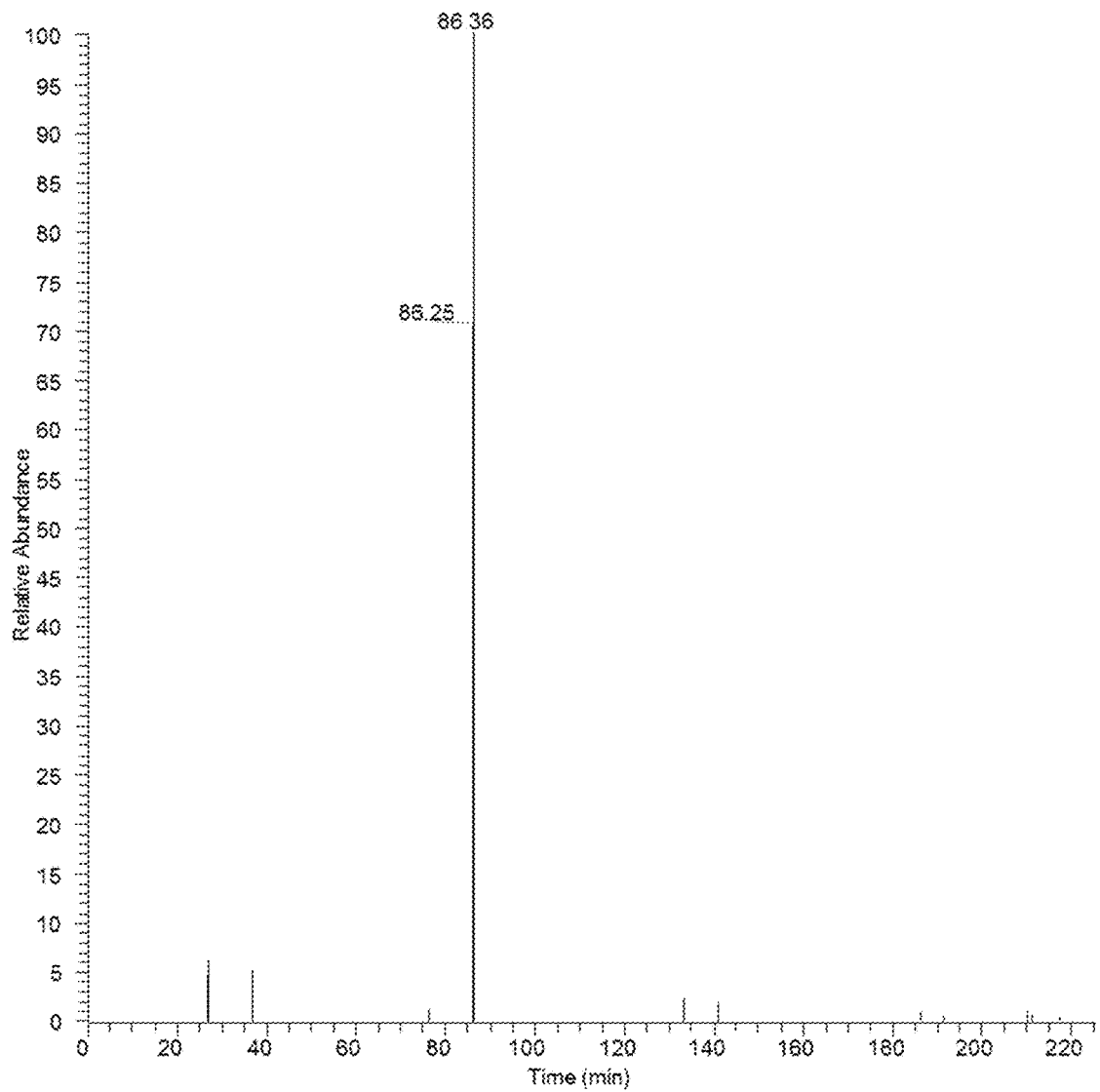
FIGS. 1A through 1D.
Figure 1B:
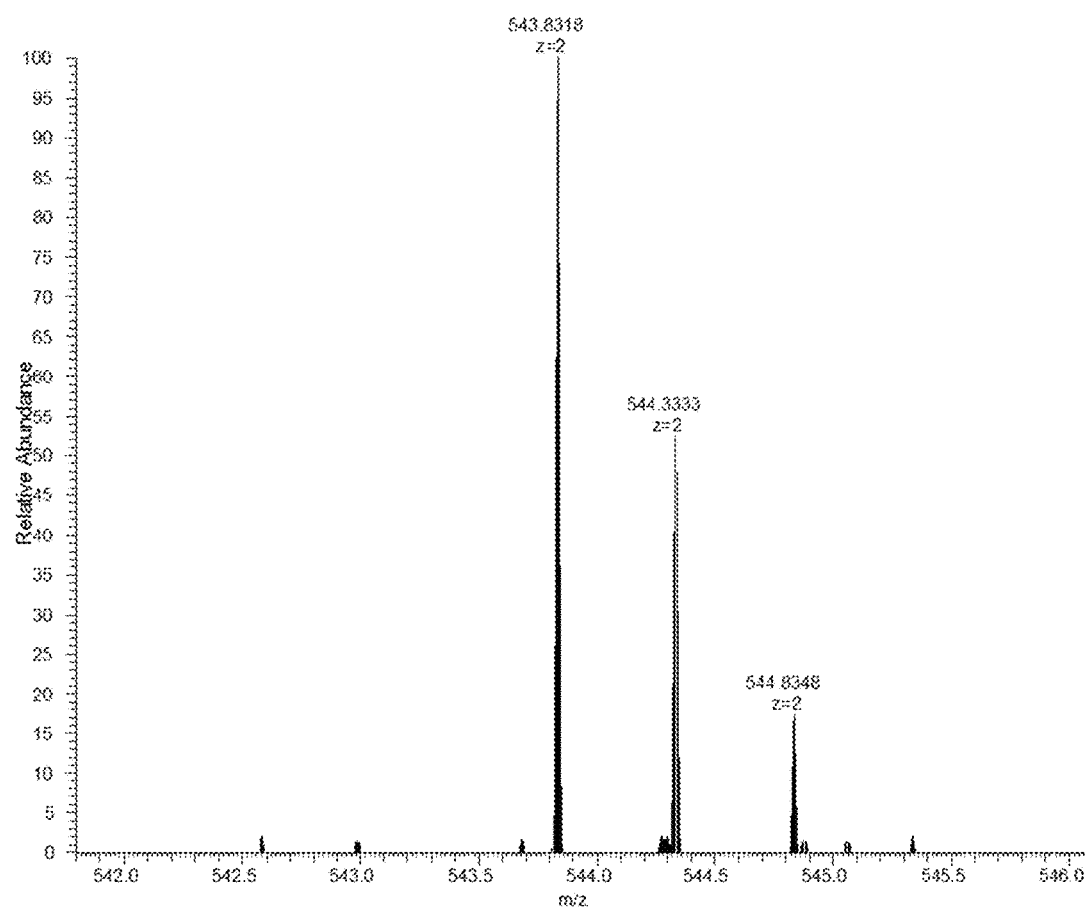
Figure 1C:
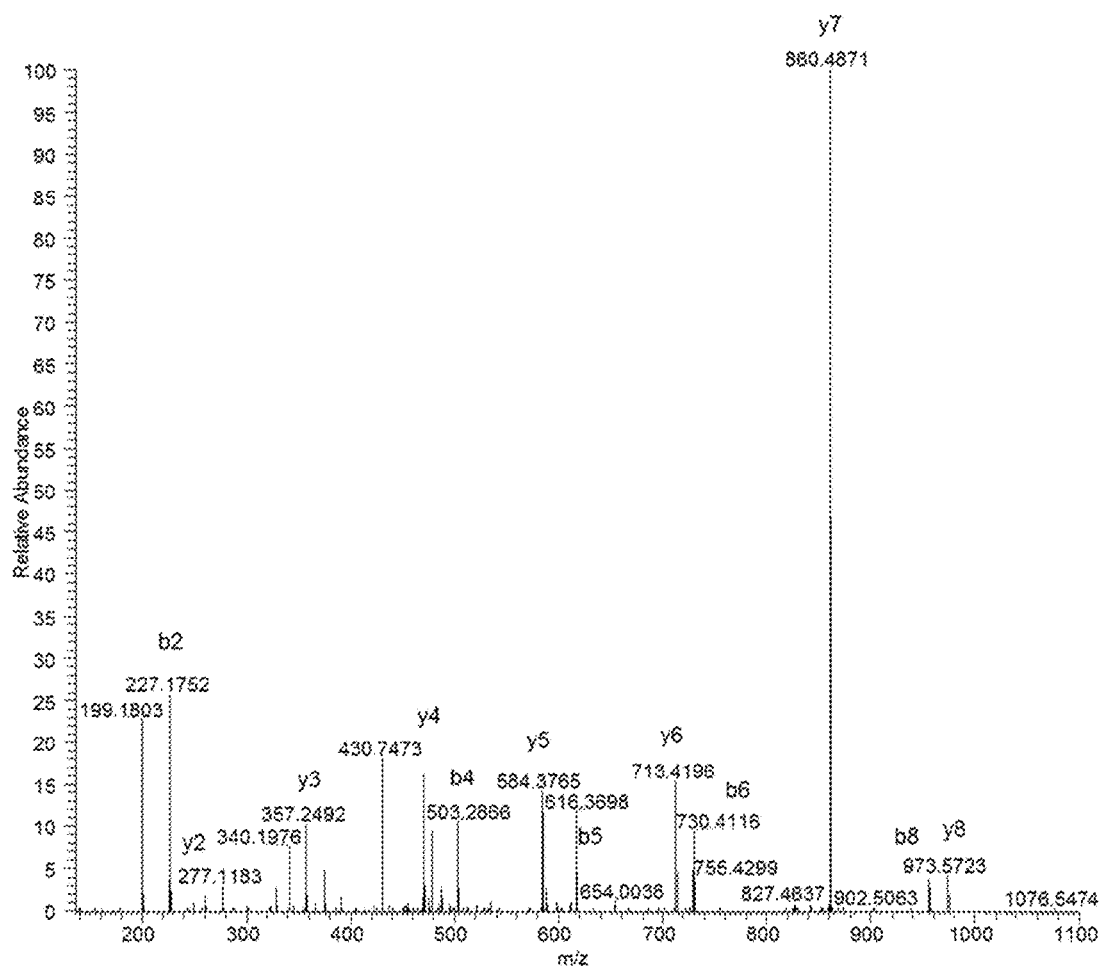
Figure 1D:
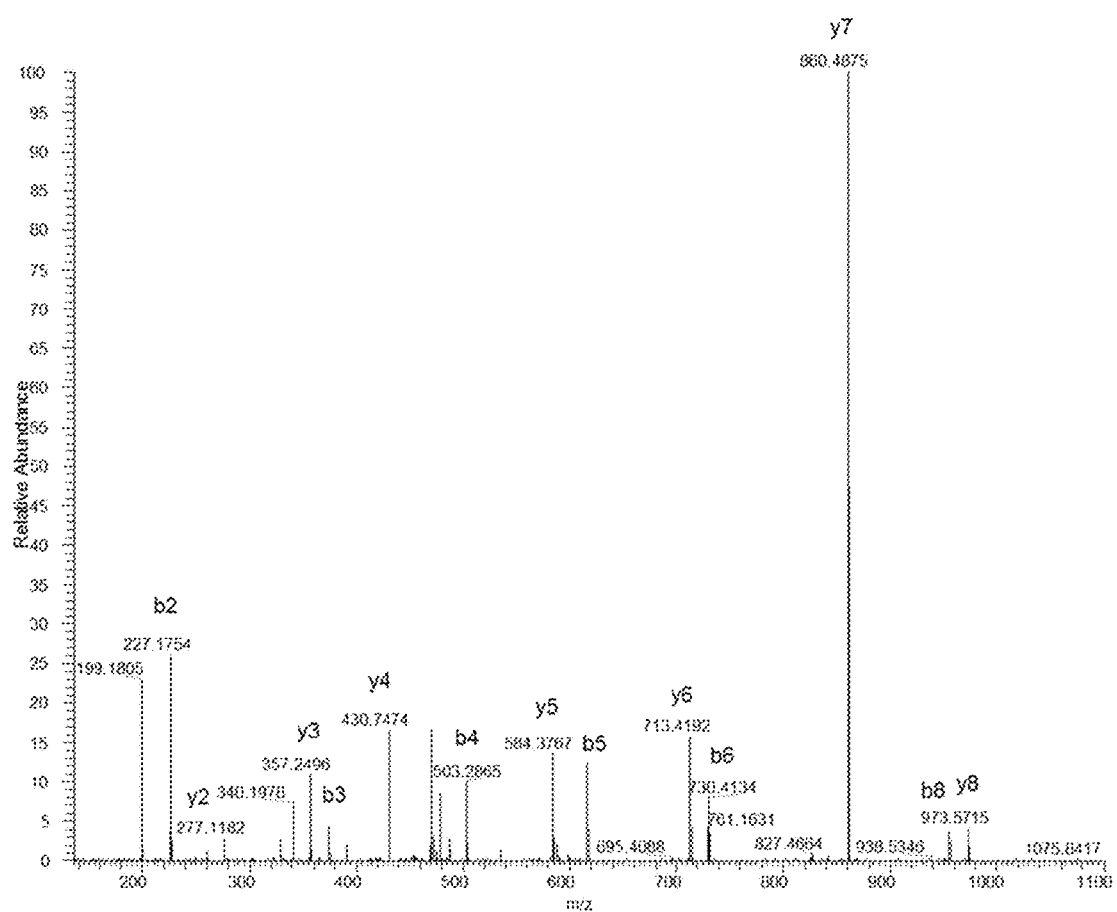

Identification and Quantitation of Tumor Associated Peptides Presented on the Cell Surface Tissue Samples Patients' tumor tissues were provided by University of Heidelberg, Heidelberg, Germany. Written informed consents of all patients had been given before surgery. Tissues were shock-frozen in liquid nitrogen immediately after surgery and stored until isolation of TUMAPs at −80° C.

Isolation of HLA peptides from tissue samples HLA peptide pools from shock-frozen tissue samples were obtained by immune precipitation from solid tissues according to a slightly modified protocol (Falk, K., 1991; Seeger, F. H. T., 1999) using the HLA-A*02-specific antibody BB7.2, the HLA-A, -B, -C-specific antibody W6/32, CNBr-activated sepharose, acid treatment, and ultrafiltration.

Methods

The HLA peptide pools as obtained were separated according to their hydrophobicity by reversed-phase chromatography (Acquity UPLC system, Waters) and the eluting peptides were analyzed in an LTQ-Orbitrap hybrid mass spectrometer (ThermoElectron) equipped with an ESI source. Peptide pools were loaded directly onto the analytical fused-silica micro-capillary column (75 µm i.d.×250 mm) packed with 1.7 µm C18 reversed-phase material (Waters) applying a flow rate of 400 nL per minute. Subsequently, the peptides were separated using a two-step 180 minute-binary gradient from 10% to 33% B at a flow rate of 300 nL per minute. The gradient was composed of Solvent A (0.1% formic acid in water) and solvent B (0.1% formic acid in acetonitrile). A gold coated glass capillary (PicoTip, New Objective) was used for introduction into the nanoESI source. The LTQ-Orbitrap mass spectrometer was operated in the data-dependent mode using a TOP5 strategy. In brief, a scan cycle was initiated with a full scan of high mass accuracy in the orbitrap (R=30 000), which was followed by MS/MS scans also in the orbitrap (R=7500) on the 5 most abundant precursor ions with dynamic exclusion of previously selected ions. Tandem mass spectra were interpreted by SEQUEST and additional manual control. The identified peptide sequence was assured by comparison of the generated natural peptide fragmentation pattern with the fragmentation pattern of a synthetic sequence-identical reference peptide. FIGS. 1A through 1D show an exemplary spectrum obtained from tumor tissue for the MHC class I associated peptide ABCA13-001 and its elution profile on the UPLC system.

Label-free relative LC-MS quantitation was performed by ion counting i.e. by extraction and analysis of LC-MS features (Mueller et al. 2007a). The method assumes that the peptide's LC-MS signal area correlates with its abundance in the sample. Extracted features were further processed by charge state deconvolution and retention time alignment (Mueller et al. 2007b; Sturm et al. 2008). Finally, all LC-MS features were cross-referenced with the sequence identification results to combine quantitative data of different samples and tissues to peptide presentation profiles. The quantitative data were normalized in a two-tier fashion according to central tendency to account for variation within technical and biological replicates. Thus each identified peptide can be associated with quantitative data allowing relative quantification between samples and tissues. In addition, all quantitative data acquired for peptide candidates was inspected manually to assure data consistency and to verify the accuracy of the automated analysis. For each peptide a presentation profile was calculated showing the mean sample presentation as well as replicate variations. The profile juxtaposes NSCLC samples to a baseline of normal tissue samples.

Figure 3A:
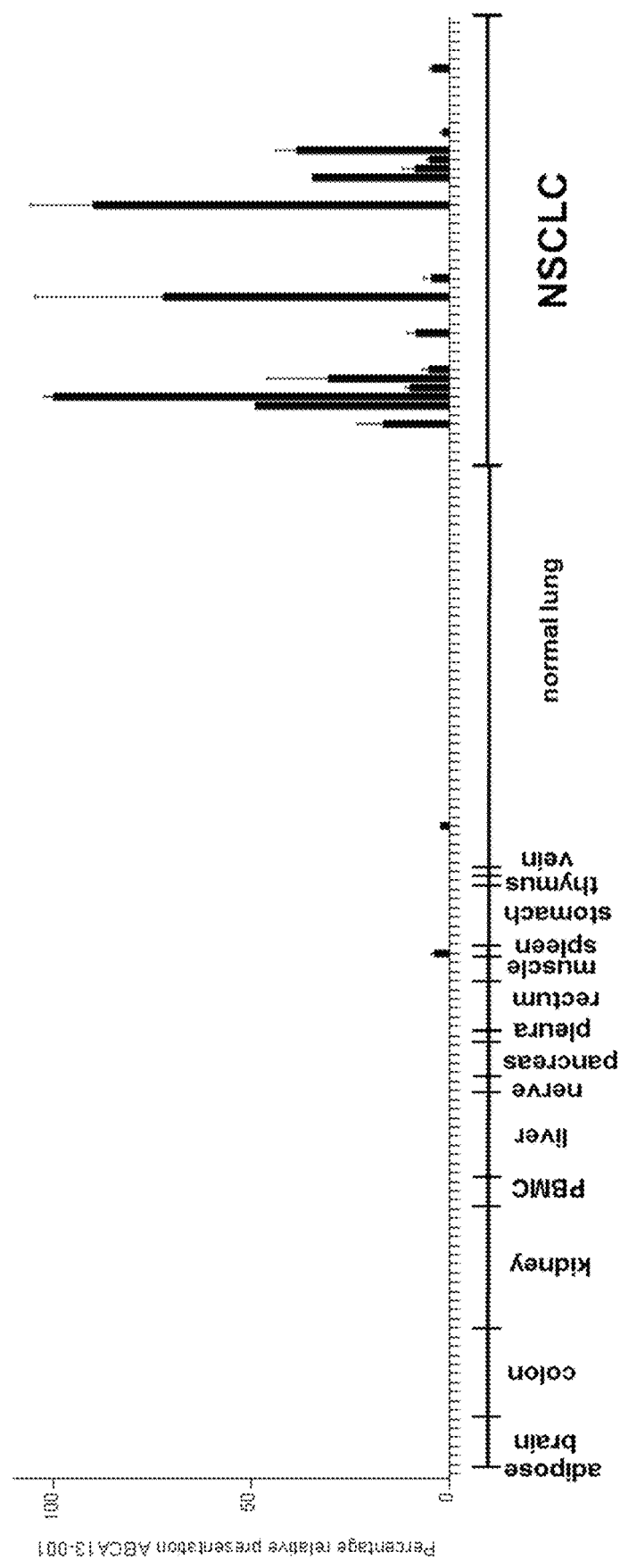
FIGS. 3A through 3C: Presentation profiles for selected HLA class I peptides. A presentation profile was calculated for each peptide showing the mean sample presentation as well as replicate variations. The profile juxtaposes samples of the tumor entity of interest to a baseline of normal tissue samples.
Figure 3B:
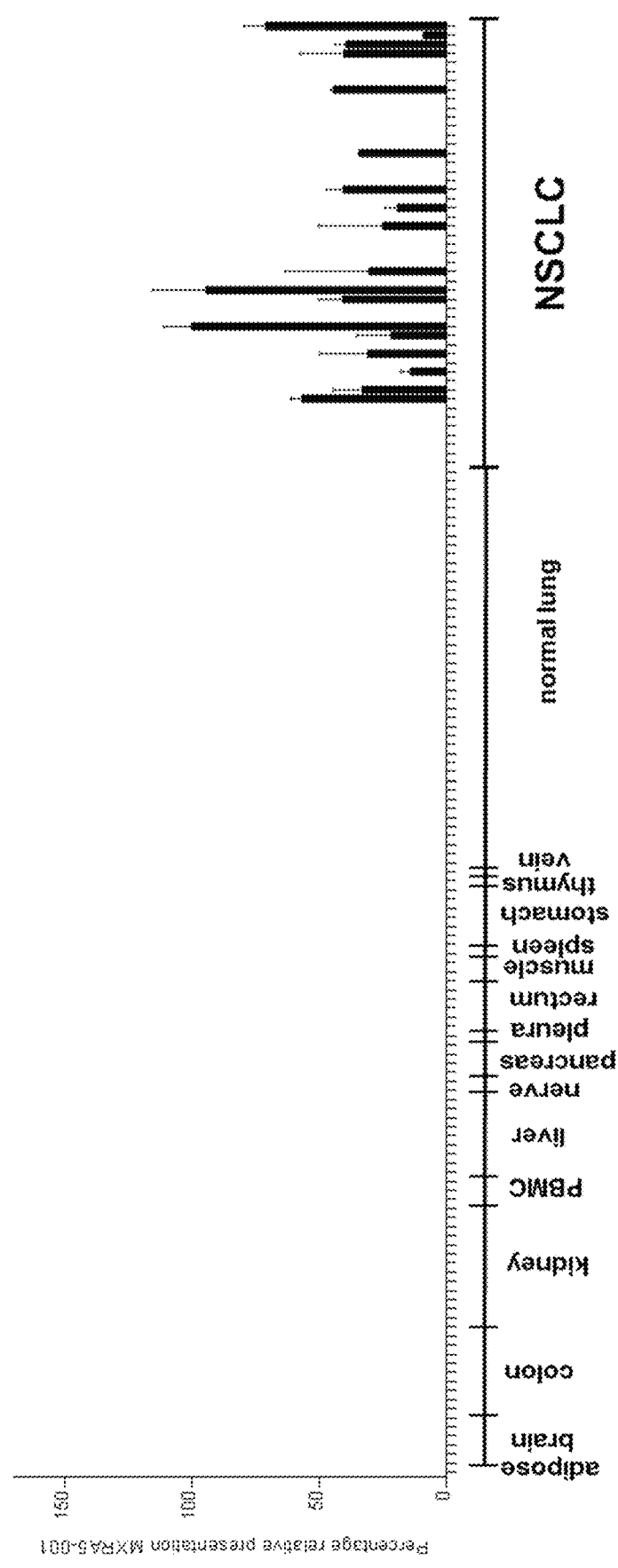
Figure 3C:
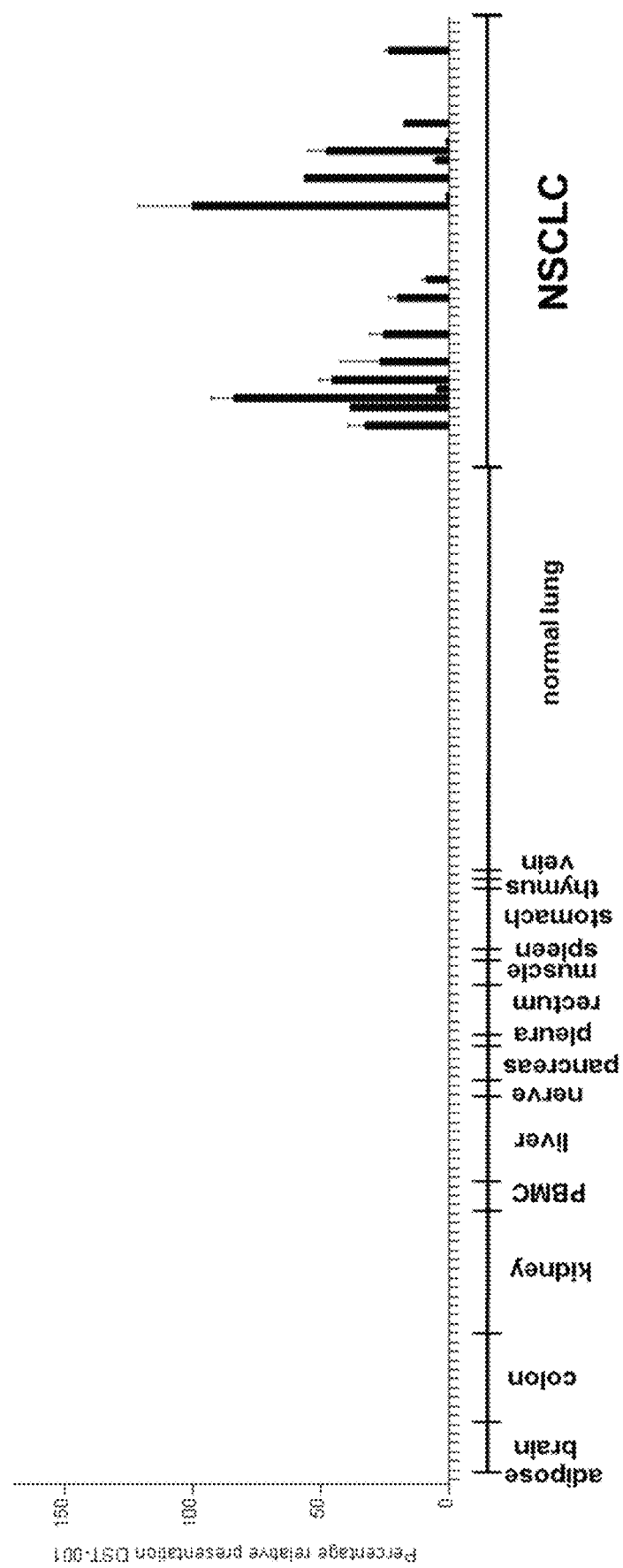

Presentation profiles of exemplary over-presented peptides are shown in FIGS. 3A through 3C.

Example 2

Expression Profiling of Genes Encoding the Peptides of the Invention

Not all peptides identified as being presented on the surface of tumor cells by MHC molecules are suitable for immunotherapy, because the majority of these peptides are derived from normal cellular proteins expressed by many cell types. Only few of these peptides are tumor-associated and likely able to induce T cells with a high specificity of recognition for the tumor from which they were derived. In order to identify such peptides and minimize the risk for autoimmunity induced by vaccination the inventors focused on those peptides that are derived from proteins that are over-expressed on tumor cells compared to the majority of normal tissues.

The ideal peptide will be derived from a protein that is unique to the tumor and not present in any other tissue. To identify peptides that are derived from genes with an expression profile similar to the ideal one the identified peptides were assigned to the proteins and genes, respectively, from which they were derived and expression profiles of these genes were generated.

RNA Sources and Preparation

Surgically removed tissue specimens were provided by University of Heidelberg, Heidelberg, Germany (see Example 1) after written informed consent had been obtained from each patient. Tumor tissue specimens were snap-frozen in liquid nitrogen immediately after surgery and later homogenized with mortar and pestle under liquid nitrogen. Total RNA was prepared from these samples using TRI Reagent (Ambion, Darmstadt, Germany) followed by a cleanup with RNeasy (QIAGEN, Hilden, Germany); both methods were performed according to the manufacturer's protocol.

Total RNA from healthy human tissues was obtained commercially (Ambion, Huntingdon, UK; Clontech, Heidelberg, Germany; Stratagene, Amsterdam, Netherlands; BioChain, Hayward, Calif., USA). The RNA from several individuals (between 2 and 123 individuals) was mixed such that RNA from each individual was equally weighted.

Quality and quantity of all RNA samples were assessed on an Agilent 2100 Bioanalyzer (Agilent, Waldbronn, Germany) using the RNA 6000 Pico LabChip Kit (Agilent).

Microarray Experiments

Gene expression analysis of all tumor and normal tissue RNA samples was performed by Affymetrix Human Genome (HG) U133A or HG-U133 Plus 2.0 oligonucleotide microarrays (Affymetrix, Santa Clara, Calif., USA). All steps were carried out according to the Affymetrix manual. Briefly, double-stranded cDNA was synthesized from 5-8 µg of total RNA, using SuperScript RTII (Invitrogen) and the oligo-dT-T7 primer (MWG Biotech, Ebersberg, Germany) as described in the manual. In vitro transcription was performed with the BioArray High Yield RNA Transcript Labelling Kit (ENZO Diagnostics, Inc., Farmingdale, N.Y., USA) for the U133A arrays or with the GeneChip IVT Labelling Kit (Affymetrix) for the U133 Plus 2.0 arrays, followed by cRNA fragmentation, hybridization, and staining with streptavidin-phycoerythrin and biotinylated anti-streptavidin antibody (Molecular Probes, Leiden, Netherlands). Images were scanned with the Agilent 2500A GeneArray Scanner (U133A) or the Affymetrix Gene-Chip Scanner 3000 (U133 Plus 2.0), and data were analyzed with the GCOS software (Affymetrix), using default settings for all parameters. For normalisation, 100 housekeeping genes provided by Affymetrix were used. Relative expression values were calculated from the signal log ratios given by the software and the normal kidney sample was arbitrarily set to 1.0.

Figure 2A:
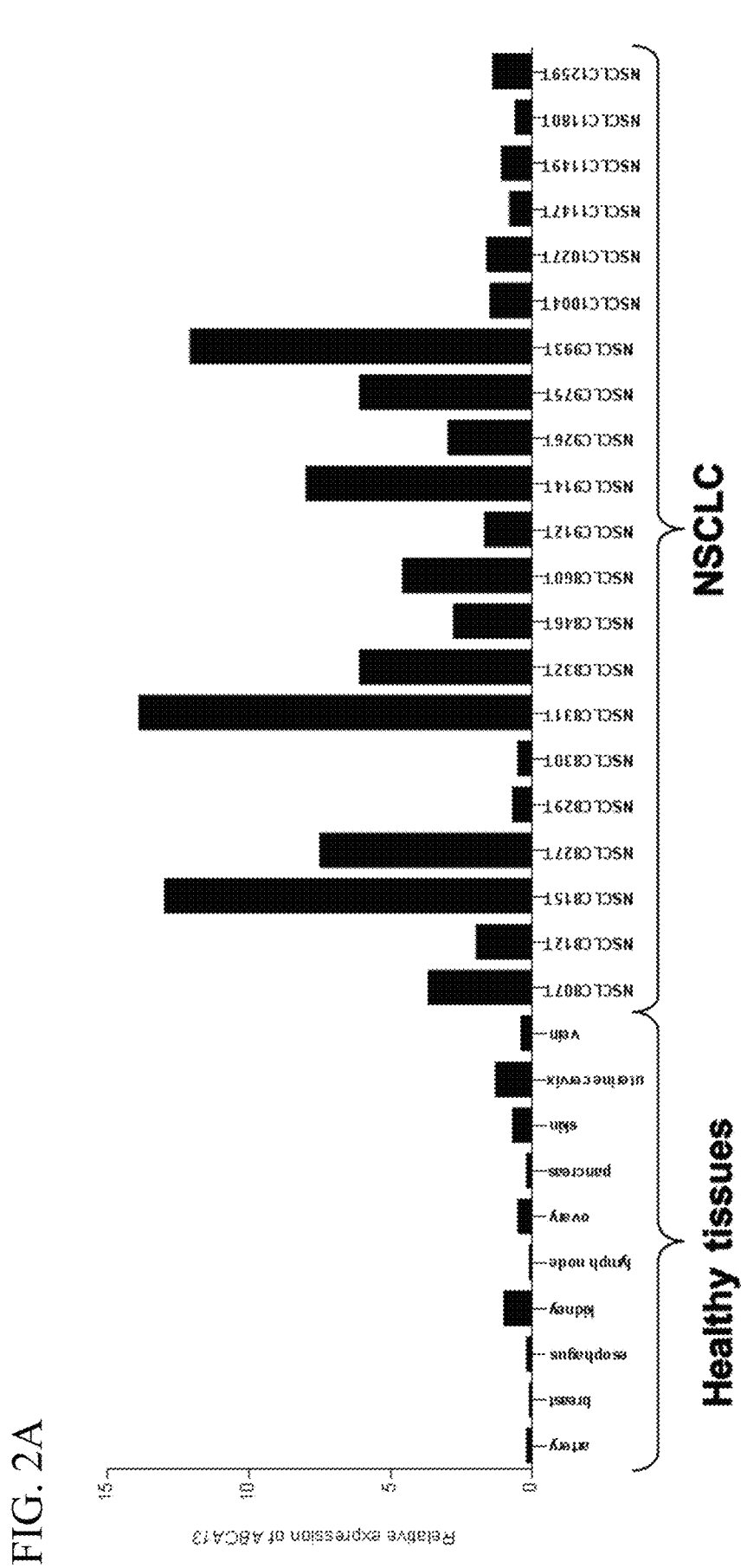
FIGS. 2A and 2B: Expression profiles of mRNA of selected proteins in normal tissues and in 21 lung cancer samples FIG. 2A) ABCA13 (Probeset ID: 1553605_a_at)
Figure 2B:
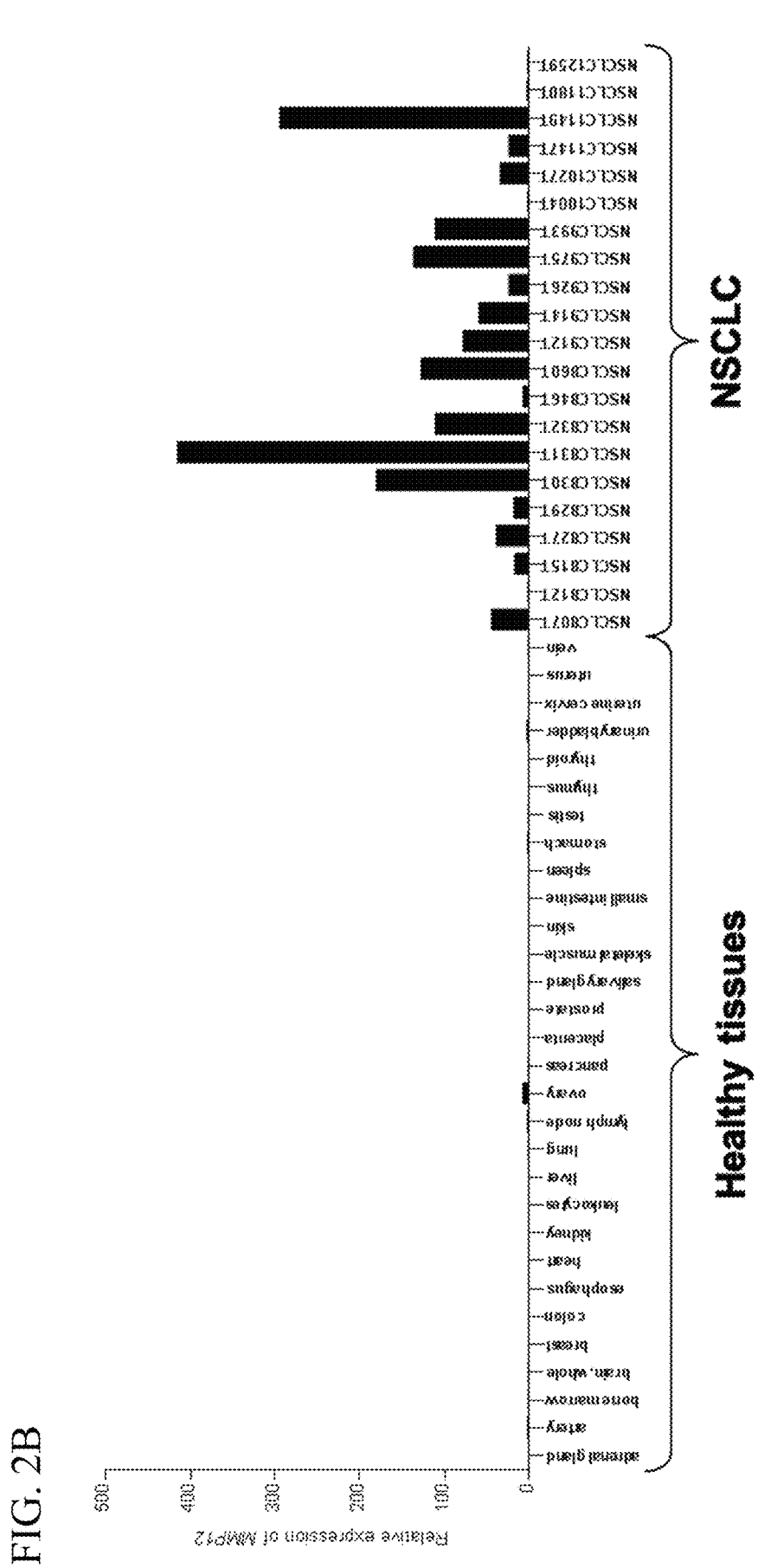

Exemplary expression profiles of source genes of the present invention that are highly over-expressed or exclusively expressed in non-small-cell lung carcinoma are shown in FIGS. 2A and 2B.

Example 4

In Vitro Immunogenicity for NSCLC MHC Class I Presented Peptides

In order to obtain information regarding the immunogenicity of the TUMAPs of the present invention, we performed investigations using an in vitro T-cell priming assay based on repeated stimulations of CD8+ T cells with artificial antigen presenting cells (aAPCs) loaded with peptide/MHC complexes and anti-CD28 antibody. This way we could show immunogenicity for 9 HLA-A*0201 restricted TUMAPs of the invention so far, demonstrating that these peptides are T-cell epitopes against which CD8+ precursor T cells exist in humans (Table 4).

In Vitro Priming of CD8+ T Cells

In order to perform in vitro stimulations by artificial antigen presenting cells loaded with peptide-MHC complex (pMHC) and anti-CD28 antibody, we first isolated CD8+ T cells from fresh HLA-A*02 leukapheresis products via positive selection using CD8 microbeads (Miltenyi Biotec, Bergisch-Gladbach, Germany) of healthy donors obtained from the Transfusion Medicine Tuebingen, Germany, after informed consent.

Isolated CD8+ lymphocytes or PBMCs were incubated until use in T-cell medium (TCM) consisting of RPMI-Glutamax (Invitrogen, Karlsruhe, Germany) supplemented with 10% heat inactivated human AB serum (PAN-Biotech, Aidenbach, Germany), 100 U/ml Penicillin/100 g/ml Streptomycin (Cambrex, Cologne, Germany), 1 mM sodium pyruvate (CC Pro, Oberdorla, Germany), 20 µg/ml Gentamycin (Cambrex). 2.5 ng/ml IL-7 (PromoCell, Heidelberg, Germany) and 10 U/ml IL-2 (Novartis Pharma, Niirnberg, Germany) were also added to the TCM at this step. Generation of pMHC/anti-CD28 coated beads, T-cell stimulations and readout was performed in a highly defined in vitro system using four different pMHC molecules per stimulation condition and 8 different pMHC molecules per readout condition.

All pMHC complexes used for aAPC loading and cytometric readout were derived from UV-induced MHC ligand exchange (Rodenko et al., 2006) with minor modifications. In order to determine the amount of pMHC monomer obtained by exchange we performed streptavidin-based sandwich ELISAs according to (Rodenko et al., 2006).

The purified co-stimulatory mouse IgG2a anti human CD28 Ab 9.3 (Jung et al., 1987) was chemically biotinylated using Sulfo-N-hydroxysuccinimidobiotin as recommended by the manufacturer (Perbio, Bonn, Germany). Beads used were 5.6 m diameter streptavidin coated polystyrene particles (Bangs Laboratories, Illinois, USA).

pMHC used for positive and negative control stimulations were A*0201/MLA-001 (peptide ELAGIGILTV from modified Melan-A/MART-1) and A*0201/DDX5-001 (YLLPAIVHI from DDX5), respectively.

800.000 beads/200 µl were coated in the presence of 4×12.5 ng different biotin-pMHC, washed and 600 ng biotin anti-CD28 were added subsequently in a volume of 200 µl. Stimulations were initiated in 96-well plates by co-incubating $1 \times 10^6$ CD8+ T cells with $2 \times 10^5$ washed coated beads in 200 µl TCM supplemented with 5 ng/ml IL-12 (PromoCell) for 3-4 days at 37° C. Half of the medium was then exchanged by fresh TCM supplemented with 80 U/ml IL-2 and incubating was continued for 3-4 days at 37° C. This stimulation cycle was performed for a total of three times. For the pMHC multimer readout using 8 different pMHC molecules per condition, a two-dimensional combinatorial coding approach was used as previously described (Andersen et al., 2012) with minor modifications encompassing coupling to 5 different fluorochromes. Finally, multimeric analyses were performed by staining the cells with Live/dead near IR dye (Invitrogen, Karlsruhe, Germany), CD8-FITC antibody clone SK1 (BD, Heidelberg, Germany) and fluorescent pMHC multimers. For analysis, a BD LSRII SORP cytometer equipped with appropriate lasers and filters was used. Peptide specific cells were calculated as percentage of total CD8+ cells. Evaluation of multimeric analysis was done using the FlowJo software (Tree Star, Oregon, USA). In vitro priming of specific multimer+ CD8+ lymphocytes was detected by by comparing to negative control stimulations. Immunogenicity for a given antigen was detected if at least one evaluable in vitro stimulated well of one healthy donor was found to contain a specific CD8+ T-cell line after in vitro stimulation (i.e. this well contained at least 1% of specific multimer+among CD8+ T-cells and the percentage of specific multimer+ cells was at least 10× the median of the negative control stimulations).

In Vitro Immunogenicity for NSCLC Peptides

Figure 4:
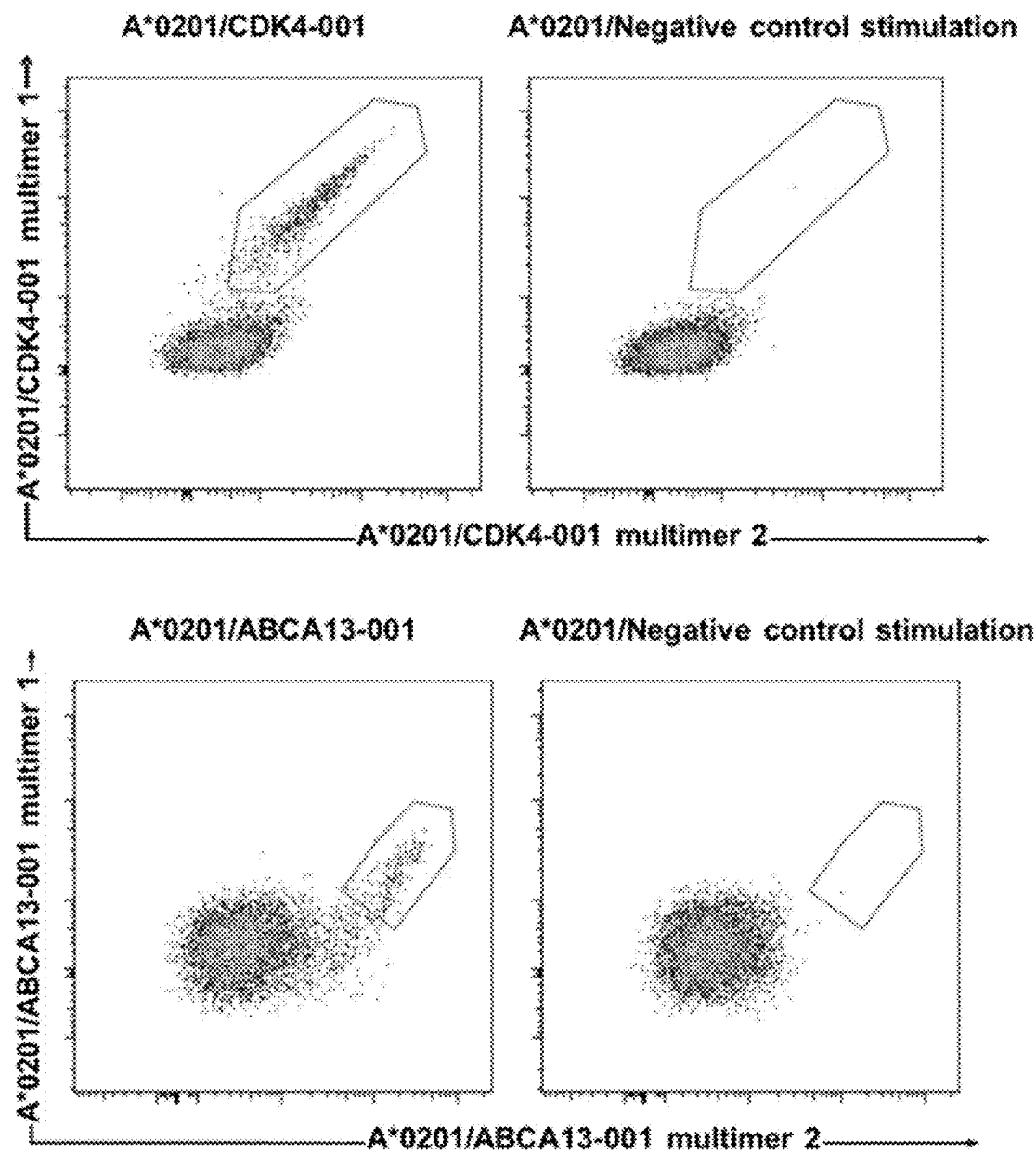
FIG. 4: Exemplary results of peptide-specific in vitro immunogenicity of class I TUMAPs. Specific CD8+ T cells were stained with HLA multimers linked to two different fluorochromes. Dot plots show the MHC multimer-double-positive populations for the stimulating peptide (left panels) and the respective negative control stimulation (right panels).

For tested HLA class I peptides, in vitro immunogenicity could be demonstrated by generation of peptide specific T-cell lines. Exemplary flow cytometry results after TUMAP-specific multimer staining for two peptides of the invention are shown in FIG. 4 together with corresponding negative controls. Results for 25 peptides from the invention are summarized in Table 5.

TABLE 5

In vitro immunogenicity of HLA class I peptides of the invention Exemplary results of in vitro immunogenicity experiments conducted by the applicant for the peptides of the invention. <20% = +; 20%-49% = ++; 50%-70% = +++; and >70% = ++++

| SEQ ID NO: | Wells | Donors |
|---|---|---|
| 1 | + | ++ |
| 2 | + | ++ |
| 3 | + | ++ |
| 4 | + | ++ |
| 7 | ++ | ++++ |
| 8 | + | ++ |
| 9 | + | + |
| 10 | + | ++ |
| 11 | ++ | ++++ (100%) |
| 15 | ++ | ++ |
| 16 | + | ++ |
| 19 | + | ++ |
| 18 | + | +++ |
| 21 | ++ | ++ |
| 22 | + | +++ |
| 24 | + | ++ |
| 30 | + | ++ |
| 31 | + | +++ |
| 32 | + | +++ |
| 33 | + | +++ |
| 35 | + | ++ |
| 37 | + | ++++ (100%) |
| 38 | + | ++ |
| 39 | + | ++ |
| 40 | + | ++ |
| 42 | ++ | ++++ (100%) |

TABLE 5-continued

In vitro immunogenicity of HLA class I peptides of the invention
Exemplary results of in vitro immunogenicity experiments conducted
by the applicant for the peptides of the invention. <20% = +;
20%-49% = ++; 50%-70% = +++; and >70% = ++++

| SEQ ID NO: | Wells | Donors |
|---|---|---|
| 43 | + | +++ |
| 44 | + | ++ |
| 45 | + | + |
| 46 | + | +++ |
| 47 | + | ++ |
| 48 | + | + |
| 52 | + | + |
| 53 | ++ | ++ |
| 54 | + | ++ |
| 55 | + | ++ |
| 56 | ++ | ++++ (100%) |
| 62 | ++ | ++++ |
| 57 | + | ++ |
| 59 | + | +++ |
| 60 | +++ | ++++ (100%) |
| 61 | + | +++ |
| 63 | + | ++ |
| 64 | + | +++ |
| 65 | ++ | +++ |
| 66 | + | +++ |
| 67 | + | ++ |
| 68 | + | + |
| 69 | ++ | +++ |
| 70 | + | +++ |
| 71 | + | +++ |
| 72 | + | +++ |
| 73 | + | ++ |
| 74 | + | +++ |
| 75 | + | ++ |
| 78 | ++ | ++ |
| 79 | + | ++++ |
| 80 | + | ++ |
| 81 | + | ++ |
| 85 | ++ | ++++ |
| 86 | + | ++ |
| 87 | + | +++ |
| 88 | + | ++ |
| 92 | + | ++ |

Example 5

Syntheses of Peptides

All peptides were synthesized using standard and well-established solid phase peptide synthesis using the Fmoc-strategy. After purification by preparative RP-HPLC, ion-exchange procedure was performed to incorporate physiological compatible counter ions (for example trifluoro-acetate, acetate, ammonium or chloride).

Identity and purity of each individual peptide have been determined by mass spectrometry and analytical RP-HPLC. After ion-exchange procedure the peptides were obtained as white to off-white lyophilizates in purities of 90% to 99.7%.

All TUMAPs are preferably administered as trifluoro-acetate salts or acetate salts, other salt-forms are also possible. For the measurements of example 4, trifluoro-acetate salts of the peptides were used.

Example 6

UV-Ligand Exchange

Candidate peptides for the vaccines according to the present invention were further tested for immunogenicity by in vitro priming assays. The individual peptide-MHC complexes required for these assays were produced by UV-ligand exchange, where a UV-sensitive peptide is cleaved upon UV-irradiation, and exchanged with the peptide of interest as analyzed. Only peptide candidates that can effectively bind and stabilize the peptide-receptive MHC molecules prevent dissociation of the MHC complexes. To determine the yield of the exchange reaction, an ELISA was performed based on the detection of the light chain (β2m) of stabilized MHC complexes. The assay was performed as generally described in Rodenko et al. (Rodenko B, Toebes M, Hadrup S R, van Esch W J, Molenaar A M, Schumacher T N, Ovaa H. Generation of peptide-MHC class I complexes through UV-mediated ligand exchange. Nat Protoc. 2006; 1(3): 1120-32.). 96 well MAXISorp plates (NUNC) were coated over night with 2 ug/ml streptavidin in PBS at room temperature, washed 4× and blocked for 30 min at 37° C. in 2% BSA containing blocking buffer. Refolded HLA-A*0201/MLA-001 monomers served as standards, covering the range of 8-500 ng/ml. Peptide-MHC monomers of the UV-exchange reaction were diluted 100 fold in blocking buffer. Samples were incubated for 1 h at 37° C., washed four times, incubated with 2 ug/ml HRP conjugated anti-β2m for 1 h at 37° C., washed again and detected with TMB solution that is stopped with $NH_2SO_4$. Absorption was measured at 450 nm.

TABLE 6

UV-Ligand exchange

| SEQ ID NO. | Peptide name | Average exchange yield in % | Exchange yield |
|---|---|---|---|
| 81 | ANKS1A-001 | 78 | ++++ |
| 87 | AURKB-001 | 54 | +++ |
| 85 | BUB1B-001 | 59 | +++ |
| 48 | SNRNP20-001 | 54 | +++ |
| 80 | CEP192-001 | 56 | +++ |
| 90 | COG4-001 | 57 | +++ |
| 89 | IFT81-001 | 57 | +++ |
| 83 | MDN1-001 | 67 | +++ |
| 82 | CEP250-002 | 70 | +++ |
| 91 | NCBP1-001 | 65 | +++ |
| 92 | NEFH-001 | 50 | ++ |
| 84 | OLFM1-001 | 48 | ++ |
| 86 | PI4KA-001 | 51 | +++ |
| 11 | SLC3A2-001 | 56 | +++ |
| 78 | SLI-001 | 47 | ++ |
| 79 | TLX3-001 | 70 | +++ |
| 2 | MMP12-003 | 57 | +++ |
| 68 | FAP-003 | 31 | ++ |
| 66 | IGF2BP3-001 | 46 | ++ |
| 4 | DST-001 | 50 | ++ |
| 5 | MXRA5-001 | 57 | +++ |
| 31 | GFPT2-001 | 43 | ++ |
| 1 | ABCA13-001 | 93 | ++++ |
| 6 | DST-002 | 59 | +++ |
| 40 | MXRA5-002 | 56 | +++ |
| 49 | SAMSN1-001 | 47 | ++ |
| 8 | HNRNPH-001 | 26 | ++ |
| 69 | WNT5A-001 | 37 | ++ |
| 15 | IL8-001 | 41 | ++ |
| 50 | STAT2-001 | 69 | +++ |
| 72 | ADAM8-001 | 67 | +++ |
| 73 | COL6A3-002 | 81 | ++++ |
| 18 | VCAN-001 | 41 | ++ |
| 12 | SMYD3-001 | 50 | ++ |
| 3 | ABCA13-002 | 36 | ++ |
| 35 | BNC1-001 | 43 | ++ |
| 7 | CDK4-001 | 45 | ++ |
| 19 | DROSHA-001 | 68 | +++ |
| 33 | GALNT2-001 | 73 | ++++ |
| 13 | AKR-001 | 13 | + |
| 39 | LAMC2-001 | 61 | +++ |
| 56 | RAD54B-001 | 48 | ++ |
| 24 | COL12A1-002 | 55 | +++ |
| 43 | CSE1-001 | 55 | +++ |
| 45 | SEC61G-001 | 18 | + |

TABLE 6-continued

UV-Ligand exchange

| SEQ ID NO. | Peptide name | Average exchange yield in % | Exchange yield |
|---|---|---|---|
| 47 | PCNXL3-001 | 87 | ++++ |
| 9 | TANC2-001 | 71 | ++++ |
| 70 | TPX2-001 | 56 | +++ |
| 17 | HUWE1-001 | 45 | ++ |
| 54 | TACC3-001 | 54 | +++ |
| 32 | CERC-001 | 62 | +++ |
| 26 | SERPINB3-001 | 47 | ++ |
| 58 | CCNA2-001 | 54 | +++ |
| 44 | DPYSL4-001 | 77 | ++++ |
| 27 | KIF26B-001 | 68 | +++ |
| 51 | CNOT1-001 | 57 | +++ |
| 11 | SLC34A2-001 | 51 | +++ |
| 30 | RGS4-001 | 49 | ++ |
| 20 | VCAN-002 | 49 | ++ |
| 67 | CDC6-001 | 48 | ++ |
| 74 | THY1-001 | 65 | +++ |
| 10 | RNF213-001 | 84 | ++++ |
| 61 | RCN1-001 | 75 | ++++ |
| 37 | FZD-001 | 52 | +++ |
| 71 | HMMR-001 | 49 | ++ |
| 60 | C11orf24-001 | 47 | ++ |
| 53 | JUNB-001 | 51 | +++ |
| 25 | ELANE-001 | 62 | +++ |
| 61 | RCC1-001 | 77 | ++++ |
| 62 | MAGEF1-001 | 83 | ++++ |
| 22 | ACACA-001 | 61 | +++ |
| 21 | PLEKHA8-001 | 47 | ++ |
| 57 | EEF2-002 | 31 | ++ |
| 41 | HSP-002 | 47 | ++ |
| 38 | ATP-001 | 19 | + |
| 46 | ORMDL1-002 | 61 | +++ |
| 59 | NET1-001 | 82 | ++++ |
| 63 | NCAPD2-001 | 76 | ++++ |
| 42 | VPS13B-001 | 63 | +++ |
| 64 | C12orf44-001 | 34 | ++ |
| 23 | ITGA11-001 | 53 | +++ |
| 75 | DIO2-001 | 50 | ++ |
| 28 | ANKH-001 | 52 | +++ |
| 65 | HERC4-001 | 61 | +++ |
| 16 | P2RY6-001 | 91 | ++++ |

Candidate peptides that show a high exchange yield (i.e. higher than 40%, preferably higher than 50%, more preferred higher than 70%, and most preferred higher than 80%) are generally preferred for a generation and production of antibodies or fragments thereof, and/or T cell receptors or fragments thereof, as they show sufficient avidity to the MHC molecules and prevent dissociation of the MHC complexes.

Example 7

Binding and Immunogenicity of Selected MHC Class II Peptides

HLA class II proteins are divided into 3 major isotypes HLA-DR, -DP, DQ which are encoded by numerous haplotypes. The combination of various α- and β-chains increases the diversity of the HLA class II proteins found in an arbitrary population. Thus, the selected HLA class II TUMAPs have to bind to several different HLA-DR molecules (i.e. show promiscuous binding ability) in order to be able to contribute to an effective T-cell response in a significant percentage of patients.

The promiscuous binding of POSTN-002 and MMP12-002 to various HLA-DR haplotypes and the stability of the formed complexes was assessed in an in vitro binding assay by an external service provider as follows.

Materials and Methods
List of Peptides

| Sequence No | Peptide ID | Sequence | Origin | Size |
|---|---|---|---|---|
| 76 | MMP12-002 | INNYTPDMNREDVDYAIR | IMA-942 | 18 |
| 77 | POSTN-002 | TNGVIHVVDKLLYPADT | IMA-942 | 17 |

List of Investigated HLA-DR Haplotypes

The 7 investigated HLA-DR haplotypes are selected according to their frequencies in HLA-A*02 and HLA-A*24 positive North Americans population (Table 7.1 and 7.2)

Data are derived from the analysis of 1.35 million HLA-typed volunteers registered in the National Marrow Donor Program (Mori et al., 1997). The analyzed population was subdivided in the following ethnic groups: Caucasian Americans (N=997,193), African Americans (N=110,057), Asian Americans (N=81,139), Latin Americans (N=100,128), and Native Americans (N=19,203).

TABLE 7.1

Haplotype frequencies in HLA-A*02 positive North Americans: The analyzed haplotypes are indicated in the rightmost column.

| Serological haplotype | | Haplotype Frequency [% of HLA-A*02 positive individuals] | | | | | |
|---|---|---|---|---|---|---|---|
| HLA-A | HLA-DR | Caucasian | African | Asian | Latin | Native American | Analyzed |
| 2 | 1 | 8.8 | 7.8 | 3.0 | 6.1 | 6.8 | Yes |
| 2 | 2 | 14.9 | 13.8 | 17.6 | 9.7 | 13.8 | Yes |
| 2 | 3 | 6.1 | 11.1 | 1.8 | 5.3 | 5.5 | Yes |
| 2 | 4 | 21.3 | 9.4 | 15.7 | 23.6 | 24.9 | Yes |
| 2 | 5 | 1.2 | 2.3 | 1.0 | 1.3 | 1.8 | No |
| 2 | 6 | 15.2 | 20.0 | 11.5 | 17.7 | 15.9 | Yes |
| 2 | 7 | 13.0 | 10.5 | 2.5 | 7.8 | 9.0 | Yes |
| 2 | 8 | 4.2 | 5.7 | 10.2 | 16.2 | 8.7 | No |
| 2 | 9 | 1.2 | 2.8 | 16.0 | 1.0 | 2.9 | No |
| 2 | 10 | 1.4 | 2.4 | 1.2 | 1.3 | 0.8 | No |
| 2 | 11 | 8.7 | 10.6 | 5.2 | 6.4 | 4.8 | Yes |
| 2 | 12 | 2.6 | 2.8 | 12.3 | 1.8 | 1.9 | No |
| 2 | 90 | 1.4 | 0.8 | 2.0 | 1.7 | 3.3 | No |
| SUM | | 100.0 | 100.0 | 100.0 | 100.0 | 100.0 | |

TABLE 7.2

Haplotype frequencies in HLA-A*24 positive North Americans: The analyzed haplotypes are indicated in the rightmost column.

| Serological haplotype | | Haplotype Frequency [% of HLA-A*24 positive individuals] | | | | | |
|---|---|---|---|---|---|---|---|
| HLA-A | HLA-DR | Caucasian | African | Asian | Latin | Native American | Analyzed |
| 24 | 1 | 8.2 | 7.9 | 5.4 | 4.1 | 4.6 | Yes |
| 24 | 2 | 15.7 | 18.8 | 24.6 | 10.7 | 14.8 | Yes |
| 24 | 3 | 6.0 | 7.5 | 1.4 | 3.7 | 4.0 | Yes |
| 24 | 4 | 14.9 | 14.4 | 19.8 | 25.8 | 21.6 | Yes |
| 24 | 5 | 2.0 | 1.6 | 1.4 | 2.7 | 1.0 | No |
| 24 | 6 | 17.0 | 18.7 | 9.6 | 20.5 | 20.7 | Yes |
| 24 | 7 | 9.2 | 7.9 | 2.5 | 4.8 | 4.3 | Yes |
| 24 | 8 | 4.0 | 3.8 | 5.7 | 12.4 | 11.3 | No |
| 24 | 9 | 1.4 | 1.7 | 9.9 | 0.7 | 5.8 | No |
| 24 | 10 | 1.6 | 1.2 | 0.8 | 2.0 | 0.6 | No |
| 24 | 11 | 16.5 | 8.0 | 5.2 | 9.0 | 5.4 | Yes |
| 24 | 12 | 1.8 | 7.5 | 11.5 | 2.2 | 2.4 | No |
| 24 | 90 | 1.6 | 1.0 | 2.2 | 1.3 | 3.3 | No |

TABLE 7.2-continued

Haplotype frequencies in HLA-A*24 positive North Americans: The analyzed haplotypes are indicated in the rightmost column.

| Serological haplotype | | Haplotype Frequency [% of HLA-A*24 positive individuals] | | | | |
|---|---|---|---|---|---|---|
| HLA-A | HLA-DR | Caucasian | African | Asian | Latin | Native American | Analyzed |
| SUM | | 100.0 | 100.0 | 100.0 | 100.0 | 100.0 | |

Principle of Test

The ProImmune REVEAL® MHC-peptide binding assay determines the ability of each candidate peptide to bind to the selected HLA class II haplotype and stabilize the HLA-peptide complex. Thereby the candidate peptides are assembled in vitro with a particular HLA class II protein. The level of peptide incorporation into HLA molecules is measured by presence or absence of the native conformation of the assembled HLA-peptide complex at time 0 after completed refolding procedure (so called on-rate).

The binding capacity of candidate peptide to a particular HLA molecule is compared to the one with known very strong binding properties (positive control) resulting in the corresponding REVEAL® MHC-peptide binding score. The positive control peptide is selected and provided by ProImmune based on their experience individually for each HLA haplotype.

Besides the affinity of a peptide to a particular HLA molecule, the enduring stability of the formed HLA-peptide complex is crucial for the occurrence of an immune response. Accordingly presence of the formed HLA-peptide complex is measured after its incubation for 24 h at 37° C. Consequently the stability of the formed MHC-peptide complex is calculated as a ration of the binding scores at 24 h and the binding scores which are received right after the refolding (accordingly at time 0) in percent.

Results

Figure 5:
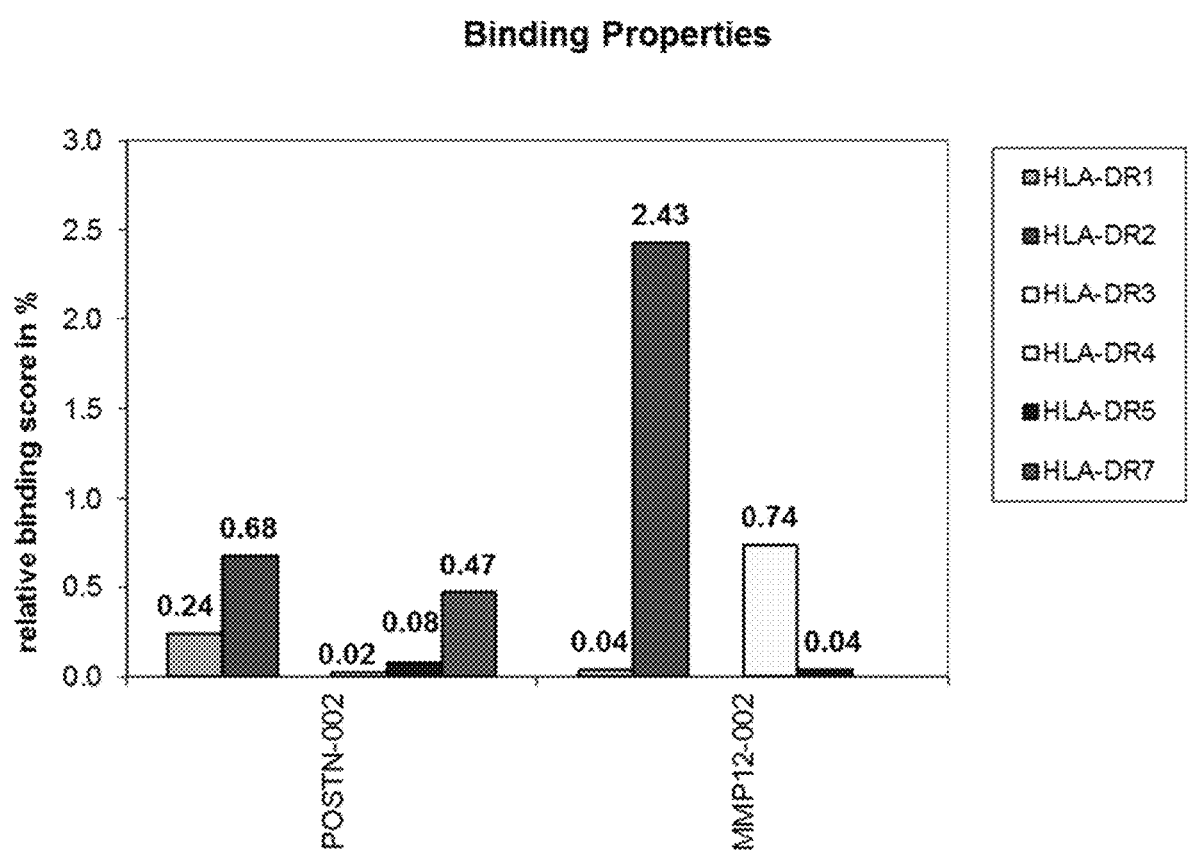
FIG. 5: Binding properties of POSTN-002 and MMP12-002 to the investigated HLA haplotypes: The diagram shows the binding scores of POSTN-002 and MMP12-002 to 5 of the 7 analyzed HLA-DR haplotypes.

The analysis of POSTN-002 and MMP12-002 in REVEAL® MHC-peptide binding assay showed that both peptides bind to various HLA haplotypes. POSTN-002 was shown to form a complex with 5 and MMP12-002 with 4 of 7 investigated HLA haplotypes (FIG. 5). Both peptides did not bind to HLA-DR3 and HLA-DR6. The detected binding scores were within the range of 0.02 to about 2.5% compared to the positive control, and clearly above scores of non-binding peptides.

Figure 6:
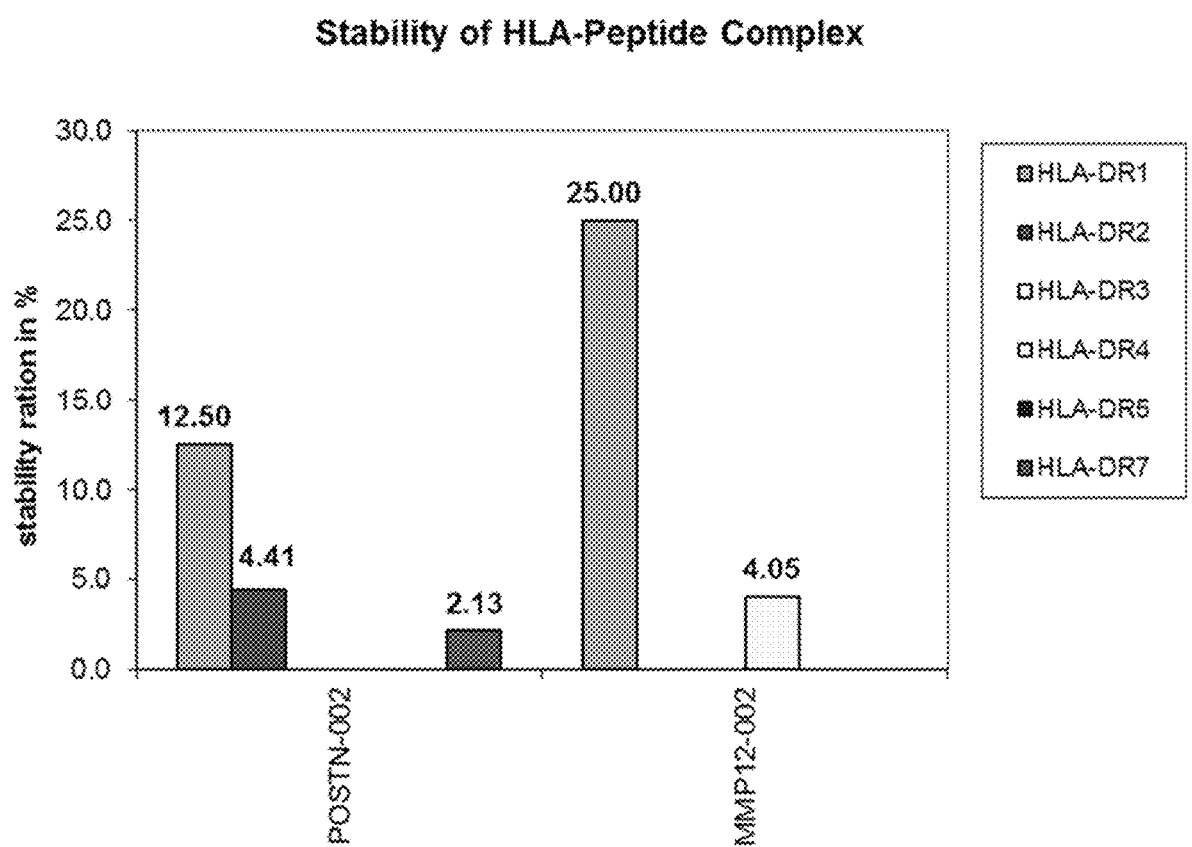
FIG. 6: Stability of HLA-POSTN-002 and MMP12-002 complexes after 24 h at 37° C.: The diagram shows the percentage of intact HLA-POSTN-002 and HLA-MMP12-002 complexes after 24 h at 37° C. with a corresponding HLA molecule.

The stability analysis of the formed HLA-POSTN-002 and HLA-MMP12-002 complexes revealed that 3 and 2 of 6 investigated HLA-peptide complexes were stable after 24 h at 37° C., respectively (FIG. 6).

A conclusion on the immugenicity of a peptide based on its binding capacity to a HLA molecule can be made by comparing the binding score of this peptide to the one with known immunogenicity. Therefore, five well investigated peptides with determined immunogenicity were selected for this comparison. The immunogenicity of these peptides was determined ex vivo in blood samples of vaccinated patients using intracellular cytokine staining (ICS) CD4 T-cells.

Figure 7:
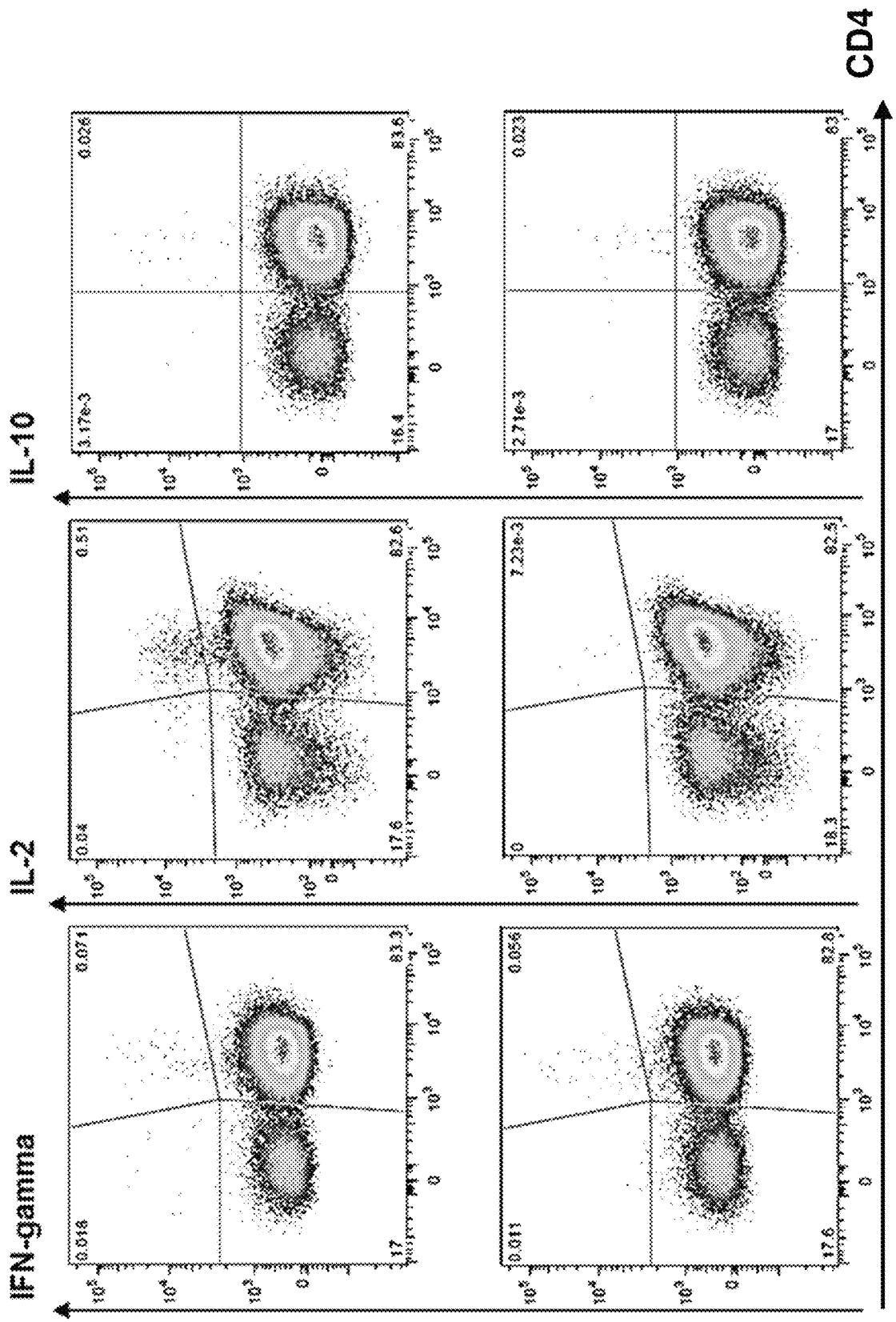
FIG. 7: Exemplary vaccine-induced CD4 T-cell response to CEA-006 in class II ICS assay. Following in vitro sensitization PBMCs of patient 36-031 were analyzed for CD4 T-cell responses to CEA-006 (upper panel) and mock (lower panel) at time point pool V8/EOS. Cells were stimulated with corresponding peptides and stained with viability, anti-CD3, anti-CD8, anti-CD4 and effector markers (from right to left: CD154, TNF-alpha, IFN-gamma, IL-2, IL-10), respectively. Viable CD4 T cells were analyzed for the proportion of cells positive for one or more effector molecules.
Figure 8:
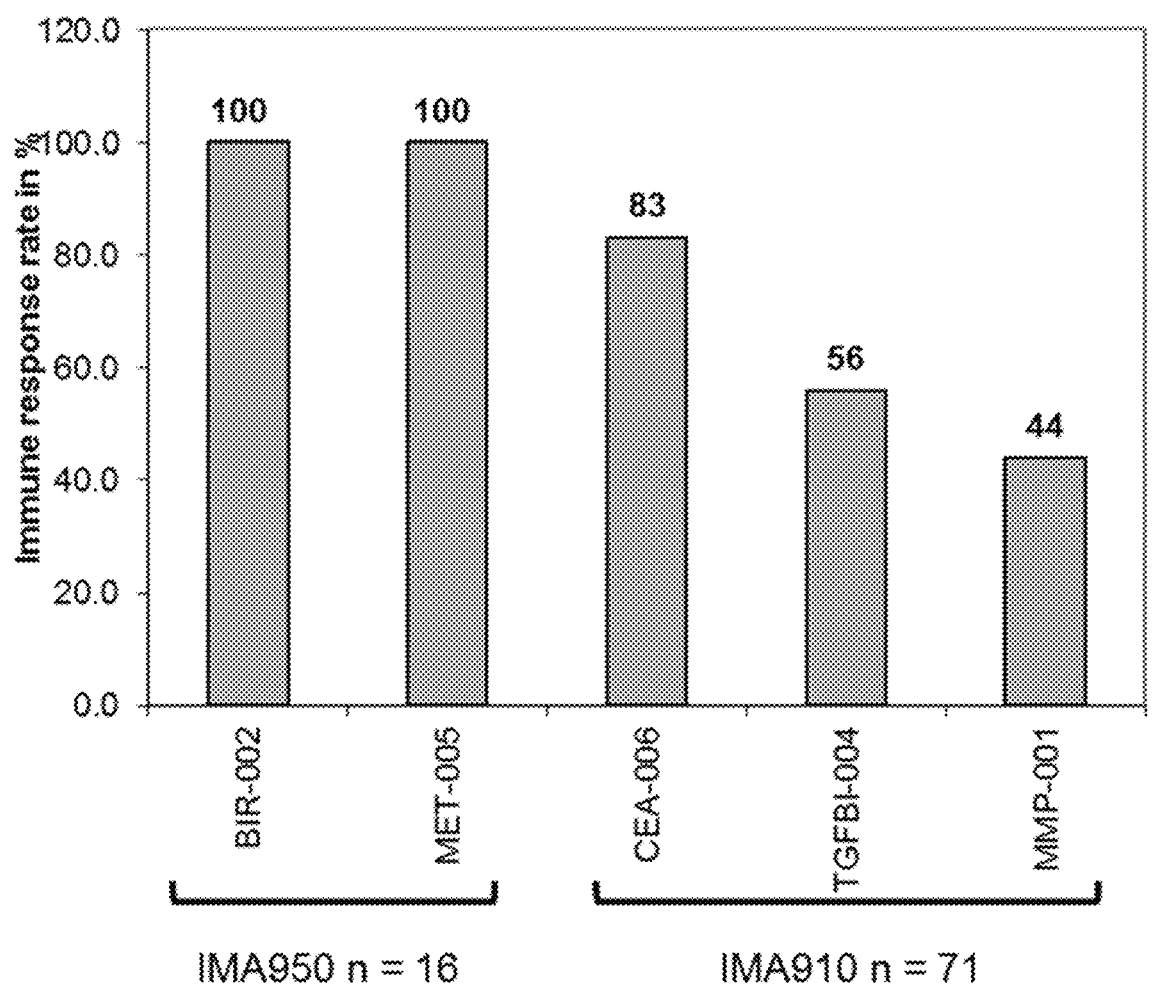
FIG. 8: Immunogenicity of various class II peptides: The diagram shows the immune response rate to 5 various class II peptides detected in 16 patients for IMA950 peptides and in 71 patients for IMA910 peptides using ICS.

In principle, ICS assays analyze the quality of specific T cells in terms of effector functions. Therefore, the peripheral mononuclear cells (PBMCs) were cultivated in vitro and subsequently restimulated by the peptide of interest, a reference peptide and a negative control (here MOCK). Following the restimulated cells were stained for FN-gamma, TNF-alpha, IL-2 and IL-10 production, as well as expression of the co-stimulatory molecule CD154. The counting of affected cells was performed on a flow cytometer (FIG. 7).

The immunogenicity analysis revealed 100% immune response by vaccination with IMA950 peptides (BIR-002 and MET-005) in 16 patients and 44% to 86% immune response by vaccinaton with IMA910 peptides (CEA-006, TGFBI-004 and MMP-001) in 71 patients. To compare the binding scores of POSTN-002 and MMP12-002 to the binding scores of IMA910 and IMA950 peptides, all peptides were arranged in a table for each investigated HLA-DR haplotype according to the detected binding score (Tables 8.1 to 8.5).

TABLE 8.1

Binding scores of POSTN-002 and MMP12-002 to HLA-DR1 compared to the binding scores of class II peptides with known immunogenicity: POSTN-002 and MMP12-002 are ranked 4 and 6, respectively.

| Peptide Rank | Peptide Code | Origin | Relative Binding Score HLA-DR1 |
|---|---|---|---|
| 1 | BIR-002 | IMA950 | 40.06 |
| 2 | CEA-006 | IMA910 | 1.31 |
| 3 | MET-005 | IMA950 | 0.87 |
| 4 | POSTN-002 | IMA-942 | 0.24 |
| 5 | MMP-001 | IMA901 | 0.19 |
| 6 | MMP12-002 | IMA-942 | 0.04 |
| 7 | TGFBI-004 | IMA910 | 0.03 |

TABLE 8.2

Binding scores of POSTN-002 and MMP12-002 to HLA-DR2 compared to the binding scores of class II peptides with known immunogenicity: POSTN-002 and MMP12-002 are ranked 3 and 1, respectively.

| Peptide Rank | Peptide Code | Origin | Relative Binding Score HLA-DR2 |
|---|---|---|---|
| 1 | MMP12-002 | IMA-942 | 2.43 |
| 2 | MMP-001 | IMA901 | 0.7 |
| 3 | POSTN-002 | IMA-942 | 0.68 |
| 4 | MET-005 | IMA950 | 0.28 |
| 5 | TGFBI-004 | IMA910 | 0.28 |
| 6 | BIR-002 | IMA950 | 0.05 |
| 7 | CEA-006 | IMA910 | 0.03 |

TABLE 8.3

Binding scores of POSTN-002 and MMP12-002 to HLA-DR4 compared to the binding scores of class II peptides with known immunogenicity: POSTN-002 and MMP12-002 are ranked 6 and 4, respectively.

| Peptide Rank | Peptide Code | Origin | Relative Binding Score HLA-DR4 |
|---|---|---|---|
| 1 | CEA-006 | IMA910 | 39.65 |
| 2 | BIR-002 | IMA950 | 6.12 |
| 3 | MET-005 | IMA950 | 5.89 |
| 4 | MMP12-002 | IMA-942 | 0.74 |

TABLE 8.3-continued

Binding scores of POSTN-002 and MMP12-002 to HLA-DR4 compared to the binding scores of class II peptides with known immunogenicity: POSTN-002 and MMP12-002 are ranked 6 and 4, respectively.

| Peptide Rank | Peptide Code | Origin | Relative Binding Score HLA-DR4 |
|---|---|---|---|
| 5 | MMP-001 | IMA901 | 0.06 |
| 6 | POSTN-002 | IMA-942 | 0.02 |
| 7 | TGFBI-004 | IMA910 | 0.02 |

TABLE 8.4

Binding scores of POSTN-002 and MMP12-002 to HLA-DR5 compared to the binding scores of class II peptides with known immunogenicity: POSTN-002 and MMP12-002 are ranked 5 and 6, respectively.

| Peptide Rank | Peptide Code | Origin | Relative Binding Score HLA-DR5 |
|---|---|---|---|
| 1 | BIR-002 | IMA950 | 103.9 |
| 2 | MMP-001 | IMA901 | 47.82 |
| 3 | CEA-006 | IMA910 | 24.27 |
| 4 | MET-005 | IMA950 | 0.12 |
| 5 | POSTN-002 | IMA-942 | 0.08 |
| 6 | MMP12-002 | IMA-942 | 0.04 |
| 7 | TGFBI-004 | IMA910 | 0.04 |

TABLE 8.5

Binding scores of POSTN-002 and MMP12-002 to HLA-DR7 compared to the binding scores of class II peptides with known immunogenicity: POSTN-002 and MMP12-002 are ranked 3 and 7, respectively.

| Peptide Rank | Peptide Code | Origin | Relative Binding Score HLA-DR7 |
|---|---|---|---|
| 1 | MET-005 | IMA950 | 3.69 |
| 2 | CEA-006 | IMA910 | 0.63 |
| 3 | POSTN-002 | IMA-942 | 0.47 |
| 4 | BIR-002 | IMA950 | 0.27 |
| 5 | TGFBI-004 | IMA910 | 0.01 |
| 6 | MMP-001 | IMA901 | 0 |
| 7 | MMP12-002 | IMA-942 | 0 |

The comparison of the binding scores of POSTN-002 and MMP12-002 to the binding scores of the other class II peptides with known immunogenicity showed that the binding capacities of both peptides are mostly located in the middle till the lower half of the tables with exception of HLA-DR2. The binding capacities of both peptides to HLA-DR2 are located in the upper half of the table with MMP12-002 being the top candidate. Based on this analysis it must be expected that both peptides, POSTN-002 and MMP12-002, induce an immune response as well.

REFERENCE LIST

Acuff H B, Sinnamon M, Fingleton B, Boone B, Levy S E, Chen X, Pozzi A, Carbone D P, Schwartz D R, Moin K, Sloane B F, Matrisian L M (2006). Analysis of host- and tumor-derived proteinases using a custom dual species microarray reveals a protective role for stromal matrix metalloproteinase-12 in non-small cell lung cancer. Cancer Res 66, 7968-7975.

Adhikary S, Marinoni F, Hock A, Hulleman E, Popov N, Beier R, Bernard S, Quarto M, Capra M, Goettig S, Kogel U, Scheffner M, Helin K, Eilers M (2005). The ubiquitin ligase HectH9 regulates transcriptional activation by Myc and is essential for tumor cell proliferation. Cell 123, 409-421.

Albig A R, Schiemann W P (2005). Identification and characterization of regulator of G protein signaling 4 (RGS4) as a novel inhibitor of tubulogenesis: RGS4 inhibits mitogen-activated protein kinases and vascular endothelial growth factor signaling. Mol. Biol. Cell 16, 609-625.

Allison J P, Krummel M F (1995). The Yin and Yang of T cell costimulation. Science 270, 932-933.

An C H, Kim Y R, Kim H S, Kim S S, Yoo N J, Lee S H (2012). Frameshift mutations of vacuolar protein sorting genes in gastric and colorectal cancers with microsatellite instability. Hum. Pathol. 43, 40-47.

Appay V, Speiser D E, Rufer N, Reynard S, Barbey C, Cerottini J C, Leyvraz S, Pinilla C, Romero P (2006). Decreased specific CD8+ T cell cross-reactivity of antigen recognition following vaccination with Melan-A peptide. Eur. J Immunol. 36, 1805-1814.

Araki W, Takahashi-Sasaki N, Chui D H, Saito S, Takeda K, Shirotani K, Takahashi K, Murayama K S, Kametani F, Shiraishi H, Komano H, Tabira T (2008). A family of membrane proteins associated with presenilin expression and gamma-secretase function. FASEB J 22, 819-827.

Arenberg D A, Polverini P J, Kunkel S L, Shanafelt A, Hesselgesser J, Horuk R, Strieter R M (1997). The role of CXC chemokines in the regulation of angiogenesis in non-small cell lung cancer. J Leukoc. Biol. 62, 554-562.

Asteriti I A, Rensen W M, Lindon C, Lavia P, Guarguaglini G (2010). The Aurora-A/TPX2 complex: a novel oncogenic holoenzyme? Biochim. Biophys. Acta 1806, 230-239.

Aylsworth A, Jiang S X, Desbois A, Hou S T (2009). Characterization of the role of full-length CRMP3 and its calpain-cleaved product in inhibiting microtubule polymerization and neurite outgrowth. Exp. Cell Res. 315, 2856-2868.

Badiglian F L, Oshima C T, De Oliveira L F, De Oliveira C H, De Sousa D R, Gomes T S, Goncalves W J (2009). Canonical and noncanonical Wnt pathway: a comparison among normal ovary, benign ovarian tumor and ovarian cancer. Oncol Rep. 21, 313-320.

Bargo S, Raafat A, McCurdy D, Amirjazil I, Shu Y, Traicoff J, Plant J, Vonderhaar B K, Callahan R (2010). Transforming acidic coiled-coil protein-3 (Tacc3) acts as a negative regulator of Notch signaling through binding to CDC10/Ankyrin repeats. Biochem. Biophys. Res Commun. 400, 606-612.

Beckers A, Organe S, Timmermans L, Scheys K, Peeters A, Brusselmans K, Verhoeven G, Swinnen J V (2007). Chemical inhibition of acetyl-CoA carboxylase induces growth arrest and cytotoxicity selectively in cancer cells. Cancer Res. 67, 8180-8187.

Beckmann R P, Mizzen L E, Welch W J (1990). Interaction of Hsp 70 with newly synthesized proteins: implications for protein folding and assembly. Science 248, 850-854.

Behrens P, Brinkmann U, Fogt F, Wernert N, Wellmann A (2001). Implication of the proliferation and apoptosis associated CSE1L/CAS gene for breast cancer development. Anticancer Res. 21, 2413-2417.

Belaaouaj A, Kim K S, Shapiro S D (2000). Degradation of outer membrane protein A in *Escherichia coli* killing by neutrophil elastase. Science 289, 1185-1188.

Beljan P R, Durdov M G, Capkun V, Ivcevic V, Pavlovic A, Soljic V, Peric M (2012). IMP3 can predict aggressive behaviour of lung adenocarcinoma. Diagn. Pathol. 7, 165.

Benaglio P, McGee T L, Capelli L P, Harper S, Berson E L, Rivolta C (2011). Next generation sequencing of pooled samples reveals new SNRNP200 mutations associated with retinitis pigmentosa. Hum. Mutat. 32, E2246-E2258.

Bennett G, Sadlier D, Doran P P, Macmathuna P, Murray D W (2011). A functional and transcriptomic analysis of NET1 bioactivity in gastric cancer. BMC. Cancer 11, 50.

Bergner A, Kellner J, Tufman A, Huber R M (2009). Endoplasmic reticulum Ca2+-homeostasis is altered in Small and non-small Cell Lung Cancer cell lines. J Exp. Clin Cancer Res. 28, 25.

Bird A W, Hyman A A (2008). Building a spindle of the correct length in human cells requires the interaction between TPX2 and Aurora A. J Cell Biol. 182, 289-300.

Boni R, Wellmann A, Man Y G, Hofbauer G, Brinkmann U (1999). Expression of the proliferation and apoptosis-associated CAS protein in benign and malignant cutaneous melanocytic lesions. Am. J Dermatopathol. 21, 125-128.

Brandt S, Ellwanger K, Beuter-Gunia C, Schuster M, Hausser A, Schmitz I, Beer-Hammer S (2010). SLy2 targets the nuclear SAP30/HDAC1 complex. Int. J Biochem. Cell Biol. 42, 1472-1481.

Brozic P, Turk S, Rizner T L, Gobec S (2011). Inhibitors of aldo-keto reductases AKR1C1-AKR1C4. Curr. Med. Chem. 18, 2554-2565.

Bruckdorfer T, Marder O, Albericio F (2004). From production of peptides in milligram amounts for research to multi-tons quantities for drugs of the future. Curr. Pharm. Biotechnol. 5, 29-43.

Brunsvig P F, Aamdal S, Gjertsen M K, Kvalheim G, Markowski-Grimsrud C J, Sve I, Dyrhaug M, Trachsel S, Moller M, Eriksen J A, Gaudernack G (2006). Telomerase peptide vaccination: a phase I/II study in patients with non-small cell lung cancer. Cancer Immunol. Immunother. 55, 1553-1564.

Brusselmans K, De S E, Verhoeven G, Swinnen J V (2005). RNA interference-mediated silencing of the acetyl-CoA-carboxylase-alpha gene induces growth inhibition and apoptosis of prostate cancer cells. Cancer Res. 65, 6719-6725.

Brustmann H (2004). Expression of cellular apoptosis susceptibility protein in serous ovarian carcinoma: a clinicopathologic and immunohistochemical study. Gynecol. Oncol 92, 268-276.

Bukau B, Horwich A L (1998). The Hsp70 and Hsp60 chaperone machines. Cell 92, 351-366.

Byrns M C, Jin Y, Penning T M (2011). Inhibitors of type 5 17beta-hydroxysteroid dehydrogenase (AKR1C3): overview and structural insights. J Steroid Biochem. Mol. Biol. 125, 95-104.

Calabrese F, Lunardi F, Balestro E, Marulli G, Perissinotto E, Loy M, Nannini N, Valente M, Saetta M, Agostini C, Rea F (2012). Serpin B4 isoform overexpression is associated with aberrant epithelial proliferation and lung cancer in idiopathic pulmonary fibrosis. Pathology 44, 192-198.

Cao X, Coskun U, Rossle M, Buschhorn S B, Grzybek M, Dafforn T R, Lenoir M, Overduin M, Simons K (2009). Golgi protein FAPP2 tubulates membranes. Proc. Natl. Acad. Sci. U.S.A. 106, 21121-21125.

Cataldo D D, Gueders M M, Rocks N, Sounni N E, Evrard B, Bartsch P, Louis R, Noel A, Foidart J M (2003). Pathogenic role of matrix metalloproteases and their inhibitors in asthma and chronic obstructive pulmonary disease and therapeutic relevance of matrix metalloproteases inhibitors. Cell Mol. Biol. (Noisy. -le-grand) 49, 875-884.

Chajes V, Cambot M, Moreau K, Lenoir G M, Joulin V (2006). Acetyl-CoA carboxylase alpha is essential to breast cancer cell survival. Cancer Res. 66, 5287-5294.

Chakraborti S, Mandal M, Das S, Mandal A, Chakraborti T (2003). Regulation of matrix metalloproteinases: an overview. Mol. Cell Biochem. 253, 269-285.

Chami M, Gozuacik D, Saigo K, Capiod T, Falson P, Lecoeur H, Urashima T, Beckmann J, Gougeon M L, Claret M, le M M, Brechot C, Paterlini-Brechot P (2000). Hepatitis B virus-related insertional mutagenesis implicates SERCA1 gene in the control of apoptosis. Oncogene 19, 2877-2886.

Chandler S, Cossins J, Lury J, Wells G (1996). Macrophage metalloelastase degrades matrix and myelin proteins and processes a tumour necrosis factor-alpha fusion protein. Biochem. Biophys. Res Commun. 228, 421-429.

Chang C C, Tai C J, Su T C, Shen K H, Lin S H, Yeh C M, Yeh K T, Lin Y M, Jiang M C (2012). The prognostic significance of nuclear CSE1L in urinary bladder urothelial carcinomas. Ann. Diagn. Pathol. 16, 362-368.

Chanock S J, Foster C B, Miller F W, O'Hanlon T P (2004). HLA-A, -B, -Cw, -DQA1 and -DRB 1 Alleles in a Caucasian Population from Bethesda, USA. Hum. Immunol. 65, 1211-1223.

Chen C Y, Fang H Y, Chiou S H, Yi S E, Huang C Y, Chiang S F, Chang H W, Lin T Y, Chiang I P, Chow K C (2011a). Sumoylation of eukaryotic elongation factor 2 is vital for protein stability and anti-apoptotic activity in lung adenocarcinoma cells. Cancer Sci. 102, 1582-1589.

Chen C Y, Fang H Y, Chiou S H, Yi S E, Huang C Y, Chiang S F, Chang H W, Lin T Y, Chiang I P, Chow K C (2011b). Sumoylation of eukaryotic elongation factor 2 is vital for protein stability and anti-apoptotic activity in lung adenocarcinoma cells. Cancer Sci. 102, 1582-1589.

Chen D, Brooks C L, Gu W (2006). ARF-BP1 as a potential therapeutic target. Br. J Cancer 94, 1555-1558.

Chen D, Kon N, Li M, Zhang W, Qin J, Gu W (2005a). ARF-BP1/Mule is a critical mediator of the ARF tumor suppressor. Cell 121, 1071-1083.

Chen D R, Chien S Y, Kuo S J, Teng Y H, Tsai H T, Kuo J H, Chung J G (2010a). SLC34A2 as a novel marker for diagnosis and targeted therapy of breast cancer. Anticancer Res. 30, 4135-4140.

Chen J, Emara N, Solomides C, Parekh H, Simpkins H (2010b). Resistance to platinum-based chemotherapy in lung cancer cell lines. Cancer Chemother. Pharmacol. 66, 1103-1111.

Chen J F, Zhang L J, Zhao A L, Wang Y, Wu N, Xiong H C, Liang Z, Li J Y, Huang X F, Yang Y (2005b). [Abnormal expression of Thy-1 as a novel tumor marker in lung cancer and its prognostic significance]. Zhonghua Yi. Xue. Za Zhi. 85, 1921-1925.

Chen P, Wang S J, Wang H B, Ren P, Wang X Q, Liu W G, Gu W L, Li D Q, Zhang T G, Zhou C J (2012). The distribution of IGF2 and IMP3 in osteosarcoma and its relationship with angiogenesis. J Mol. Histol. 43, 63-70.

Cho N H, Hong K P, Hong S H, Kang S, Chung K Y, Cho S H (2004). MMP expression profiling in recurred stage I B lung cancer. Oncogene 23, 845-851.

Choi K U, Yun J S, Lee I H, Heo S C, Shin S H, Jeon E S, Choi Y J, Suh D S, Yoon M S, Kim J H (2010). Lysophosphatidic acid-induced expression of periostin in stromal cells: Prognoistic relevance of periostin expression in epithelial ovarian cancer. Int J Cancer.

Chong I W, Chang M Y, Chang H C, Yu Y P, Sheu C C, Tsai J R, Hung J Y, Chou S H, Tsai M S, Hwang J J, Lin S R (2006). Great potential of a panel of multiple hMTH1, SPD, ITGA11 and COL11A1 markers for diagnosis of patients with non-small cell lung cancer. Oncol Rep. 16, 981-988.

Chouchane L, Ahmed S B, Baccouche S, Remadi S (1997). Polymorphism in the tumor necrosis factor-alpha promoter region and in the heat shock protein 70 genes associated with malignant tumors. Cancer 80, 1489-1496.

Chung F Y, Cheng T L, Chang H J, Chiu H H, Huang M Y, Chang M S, Chen C C, Yang M J, Wang J Y, Lin S R (2010). Differential gene expression profile of MAGE family in taiwanese patients with colorectal cancer. J Surg. Oncol 102, 148-153.

Ciocca D R, Calderwood S K (2005). Heat shock proteins in cancer: diagnostic, prognostic, predictive, and treatment implications. Cell Stress. Chaperones. 10, 86-103.

Ciocca D R, Fuqua S A, Lock-Lim S, Toft D O, Welch W J, McGuire W L (1992). Response of human breast cancer cells to heat shock and chemotherapeutic drugs. Cancer Res. 52, 3648-3654.

Claudio J O, Zhu Y X, Benn S J, Shukla A H, McGlade C J, Falcioni N, Stewart A K (2001). HACS1 encodes a novel SH3-SAM adaptor protein differentially expressed in normal and malignant hematopoietic cells. Oncogene 20, 5373-5377.

Coe B P, Henderson L J, Garnis C, Tsao M S, Gazdar A F, Minna J, Lam S, MacAulay C, Lam W L (2005). High-resolution chromosome arm 5p array CGH analysis of small cell lung carcinoma cell lines. Genes Chromosomes. Cancer 42, 308-313.

Colombetti S, Basso V, Mueller D L, Mondino A (2006). Prolonged TCR/CD28 engagement drives IL-2-independent T cell clonal expansion through signaling mediated by the mammalian target of rapamycin. J Immunol. 176, 2730-2738.

Confalonieri S, Quarto M, Goisis G, Nuciforo P, Donzelli M, Jodice G, Pelosi G, Viale G, Pece S, Di Fiore P P (2009). Alterations of ubiquitin ligases in human cancer and their association with the natural history of the tumor. Oncogene 28, 2959-2968.

Cooper C R, Graves B, Pruitt F, Chaib H, Lynch J E, Cox A K, Sequeria L, van Golen K L, Evans A, Czymmek K, Bullard R S, Donald C D, Sol-Church K, Gendernalik J D, Weksler B, Farach-Carson M C, Macoska J A, Sikes R A, Pienta K J (2008). Novel surface expression of reticulocalbin 1 on bone endothelial cells and human prostate cancer cells is regulated by TNF-alpha. J Cell Biochem. 104, 2298-2309.

Cooper W A, Kohonen-Corish M R, McCaughan B, Kennedy C, Sutherland R L, Lee C S (2009). Expression and prognostic significance of cyclin B1 and cyclin A in non-small cell lung cancer. Histopathology 55, 28-36.

Cordes C, Munzel A K, Gorogh T, Leuschner I, Ambrosch P, Gottschlich S, Hoffmann M (2010). Prognostic relevance of the proliferation marker REPP86 for laryngeal cancer. Anticancer Res 30, 3541-3547.

Creighton C J, Bromberg-White J L, Misek D E, Monsma D J, Brichory F, Kuick R, Giordano T J, Gao W, Omenn G S, Webb C P, Hanash S M (2005). Analysis of tumor-host interactions by gene expression profiling of lung adenocarcinoma xenografts identifies genes involved in tumor formation. Mol. Cancer Res 3, 119-129.

D'Angelo G, Rega L R, De Matteis M A (2012). Connecting vesicular transport with lipid synthesis: FAPP2. Biochim. Biophys. Acta 1821, 1089-1095.

Da Forno P D, Pringle J H, Hutchinson P, Osborn J, Huang Q, Potter L, Hancox R A, Fletcher A, Saldanha G S (2008). WNT5A expression increases during melanoma progression and correlates with outcome. Clin Cancer Res 14, 5825-5832.

de Souza Meyer E L, Dora J M, Wagner M S, Maia A L (2005). Decreased type 1 iodothyronine deiodinase expression might be an early and discrete event in thyroid cell dedifferentiation towards papillary carcinoma. Clin Endocrinol. (Oxf) 62, 672-678.

Delpech B, Girard N, Bertrand P, Courel M N, Chauzy C, Delpech A (1997). Hyaluronan: fundamental principles and applications in cancer. J Intern. Med 242, 41-48.

Dengjel J, Nastke M D, Gouttefangeas C, Gitsioudis G, Schoor O, Altenberend F, Muller M, Kramer B, Missiou A, Sauter M, Hennenlotter J, Wernet D, Stenzl A, Rammensee H G, Klingel K, Stevanovic S (2006). Unexpected Abundance of HLA Class II Presented Peptides in Primary Renal Cell Carcinomas. Clin Cancer Res. 12, 4163-4170.

Denli A M, Tops B B, Plasterk R H, Ketting R F, Hannon G J (2004). Processing of primary microRNAs by the Microprocessor complex. Nature 432, 231-235.

Denys H, De W O, Nusgens B, Kong Y, Sciot R, Le A T, Van D K, Jadidizadeh A, Tejpar S, Mareel M, Alman B, Cassiman J J (2004). Invasion and MMP expression profile in desmoid tumours. Br. J Cancer 90, 1443-1449.

Deshpande A, Sicinski P, Hinds P W (2005). Cyclins and cdks in development and cancer: a perspective. Oncogene 24, 2909-2915.

Dharmavaram R M, Huynh A I, Jimenez S A (1998). Characterization of human chondrocyte and fibroblast type XII collagen cDNAs. Matrix Biol. 16, 343-348.

Dobashi Y, Shoji M, Jiang S X, Kobayashi M, Kawakubo Y, Kameya T (1998). Active cyclin A-CDK2 complex, a possible critical factor for cell proliferation in human primary lung carcinomas. Am J Pathol. 153, 963-972.

Dolznig H, Schweifer N, Puri C, Kraut N, Rettig W J, Kerjaschki D, Garin-Chesa P (2005). Characterization of cancer stroma markers: in silico analysis of an mRNA expression database for fibroblast activation protein and endosialin. Cancer Immun. 5, 10.

Dong-Dong L (2007). Small interfering RNA (siRNA) inhibited human liver cancer cell line SMMC7721 proliferation and tumorigenesis. Hepatogastroenterology 54, 1731-1735.

Drucker K L, Kitange G J, Kollmeyer T M, Law M E, Passe S, Rynearson A L, Blair H, Soderberg C L, Morlan B W, Ballman K V, Giannini C, Jenkins R B (2009). Characterization and gene expression profiling in glioma cell lines with deletion of chromosome 19 before and after microcell-mediated restoration of normal human chromosome 19. Genes Chromosomes. Cancer 48, 854-864.

Dudley M E, Wunderlich J R, Robbins P F, Yang J C, Hwu P, Schwartzentruber D J, Topalian S L, Sherry R, Restifo N P, Hubicki A M, Robinson M R, Raffeld M, Duray P, Seipp C A, Rogers-Freezer L, Morton K E, Mavroukakis S A, White D E, Rosenberg S A (2002). Cancer regression and autoimmunity in patients after clonal repopulation with antitumor lymphocytes. Science 298, 850-854.

Dudley M E, Wunderlich J R, Yang J C, Sherry R M, Topalian S L, Restifo N P, Royal R E, Kammula U, White D E, Mavroukakis S A, Rogers L J, Gracia G J, Jones S A, Mangiameli D P, Pelletier M M, Gea-Banacloche J, Robinson M R, Berman D M, Filie A C, Abati A, Rosenberg S A (2005). Adoptive cell transfer therapy following non-myeloablative but lymphodepleting chemotherapy for the treatment of patients with refractory metastatic melanoma. J. Clin. Oncol. 23, 2346-2357.

Ecimovic P, Murray D, Doran P, McDonald J, Lambert D G, Buggy D J (2011). Direct effect of morphine on breast cancer cell function in vitro: role of the NET1 gene. Br. J Anaesth. 107, 916-923.

Ehrmann J, Strakova N, Vrzalikova K, Hezova R, Kolar Z (2008). Expression of STATs and their inhibitors SOCS and PIAS in brain tumors. In vitro and in vivo study. Neoplasma 55, 482-487.

Fang W Y, Liu T F, Xie W B, Yang X Y, Wang S, Ren C P, Deng X, Liu Q Z, Huang Z X, Li X, Ding Y Q, Yao K T (2005). Reexploring the possible roles of some genes associated with nasopharyngeal carcinoma using microarray-based detection. Acta Biochim. Biophys. Sin. (Shanghai) 37, 541-546.

Feng C J, Li H J, Li J N, Lu Y J, Liao G Q (2008). Expression of Mcm7 and Cdc6 in oral squamous cell carcinoma and precancerous lesions. Anticancer Res 28, 3763-3769.

Findeis-Hosey J J, Xu H (2012). Insulin-like growth factor II-messenger RNA-binding protein-3 and lung cancer. Biotech. Histochem. 87, 24-29.

Findeis-Hosey J J, Yang Q, Spaulding B O, Wang H L, Xu H (2010). IMP3 expression is correlated with histologic grade of lung adenocarcinoma. Hum. Pathol. 41, 477-484.

Fong L, Hou Y, Rivas A, Benike C, Yuen A, Fisher G A, Davis M M, Engleman E G (2001). Altered peptide ligand vaccination with Flt3 ligand expanded dendritic cells for tumor immunotherapy. Proc. Natl. Acad. Sci. U.S.A. 98, 8809-8814.

Fukuda T, Oyamada H, Isshiki T, Maeda M, Kusakabe T, Hozumi A, Yamaguchi T, Igarashi T, Hasegawa H, Seidoh T, Suzuki T (2007). Distribution and variable expression of secretory pathway protein reticulocalbin in normal human organs and non-neoplastic pathological conditions. J Histochem. Cytochem. 55, 335-345.

Gamero A M, Young M R, Mentor-Marcel R, Bobe G, Scarzello A J, Wise J, Colburn N H (2010). STAT2 contributes to promotion of colorectal and skin carcinogenesis. Cancer Prev. Res. (Phila) 3, 495-504.

Gares S L, Pilarski L M (2000). Balancing thymocyte adhesion and motility: a functional linkage between beta1 integrins and the motility receptor RHAMM. Dev. Immunol 7, 209-225.

Garg M, Kanojia D, Saini S, Suri S, Gupta A, Surolia A, Suri A (2010a). Germ cell-specific heat shock protein 70-2 is expressed in cervical carcinoma and is involved in the growth, migration, and invasion of cervical cells. Cancer 116, 3785-3796.

Garg M, Kanojia D, Seth A, Kumar R, Gupta A, Surolia A, Suri A (2010b). Heat-shock protein 70-2 (HSP70-2) expression in bladder urothelial carcinoma is associated with tumour progression and promotes migration and invasion. Eur. J Cancer 46, 207-215.

Gattinoni L, Powell D J, Jr., Rosenberg S A, Restifo N P (2006). Adoptive immunotherapy for cancer: building on success. Nat. Rev. Immunol. 6, 383-393. Ghosh S, Albitar L, LeBaron R, Welch W R, Samimi G, Birrer M J, Berkowitz R S, Mok S C (2010). Up-regulation of stromal versican expression in advanced stage serous ovarian cancer. Gynecol. Oncol 119, 114-120.

Gorrin Rivas M J, Arii S, Furutani M, Harada T, Mizumoto M, Nishiyama H, Fujita J, Imamura M (1998). Expression of human macrophage metalloelastase gene in hepatocellular carcinoma: correlation with angiostatin generation and its clinical significance. Hepatology 28, 986-993.

Gorrin-Rivas M J, Arii S, Mori A, Takeda Y, Mizumoto M, Furutani M, Imamura M (2000). Implications of human macrophage metalloelastase and vascular endothelial growth factor gene expression in angiogenesis of hepatocellular carcinoma. Ann Surg 231, 67-73.

Graf F, Mosch B, Koehler L, Bergmann R, Wuest F, Pietzsch J (2010). Cyclin-dependent kinase 4/6 (cdk4/6) inhibitors: perspectives in cancer therapy and imaging. Mini. Rev. Med. Chem. 10, 527-539.

Greenfield J J, High S (1999). The Sec61 complex is located in both the ER and the ER-Golgi intermediate compartment. J Cell Sci. 112 (Pt 10), 1477-1486.

Gregory K E, Keene D R, Tufa S F, Lunstrum G P, Morris N P (2001). Developmental distribution of collagen type XII in cartilage: association with articular cartilage and the growth plate. J Bone Miner. Res. 16, 2005-2016.

Grunda J M, Fiveash J, Palmer C A, Cantor A, Fathallah-Shaykh H M, Nabors L B, Johnson M R (2010). Rationally designed pharmacogenomic treatment using concurrent capecitabine and radiotherapy for glioblastoma; gene expression profiles associated with outcome. Clin Cancer Res. 16, 2890-2898.

Gruter P, Tabernero C, von K C, Schmitt C, Saavedra C, Bachi A, Wilm M, Felber B K, Izaurralde E (1998). TAP, the human homolog of Mex67p, mediates CTE-dependent RNA export from the nucleus. Mol. Cell 1, 649-659.

Gudmundsson J, Sulem P, Gudbjartsson D F, Blondal T, Gylfason A, Agnarsson B A, Benediktsdottir K R, Magnusdottir D N, Orlygsdottir G, Jakobsdottir M, Stacey S N, Sigurdsson A, Wahlfors T, Tammela T, Breyer J P, McReynolds K M, Bradley K M, Saez B, Godino J, Navarrete S, Fuertes F, Murillo L, Polo E, Aben K K, van Oort I M, Suarez B K, Helfand B T, Kan D, Zanon C, Frigge M L, Kristjansson K, Gulcher J R, Einarsson G V, Jonsson E, Catalona W J, Mayordomo J I, Kiemeney L A, Smith J R, Schleutker J, Barkardottir R B, Kong A, Thorsteinsdottir U, Rafnar T, Stefansson K (2009). Genome-wide association and replication studies identify four variants associated with prostate cancer susceptibility. Nat Genet. 41, 1122-1126.

Guo Y, Hsu D K, Feng S L, Richards C M, Winkles J A (2001). Polypeptide growth factors and phorbol ester induce progressive ankylosis (ank) gene expression in murine and human fibroblasts. J Cell Biochem. 84, 27-38.

Hagemann T, Gunawan B, Schulz M, Fuzesi L, Binder C (2001). mRNA expression of matrix metalloproteases and their inhibitors differs in subtypes of renal cell carcinomas. Eur. J Cancer 37, 1839-1846.

Hamamoto R, Silva F P, Tsuge M, Nishidate T, Katagiri T, Nakamura Y, Furukawa Y (2006). Enhanced SMYD3 expression is essential for the growth of breast cancer cells. Cancer Sci. 97, 113-118.

Han J, Lee Y, Yeom K H, Nam J W, Heo I, Rhee J K, Sohn S Y, Cho Y, Zhang B T, Kim V N (2006). Molecular basis for the recognition of primary microRNAs by the Drosha-DGCR8 complex. Cell 125, 887-901.

Han S, Nam J, Li Y, Kim S, Cho S H, Cho Y S, Choi S Y, Choi J, Han K, Kim Y, Na M, Kim H, Bae Y C, Choi S Y, Kim E (2010). Regulation of dendritic spines, spatial memory, and embryonic development by the TANC family of PSD-95-interacting proteins. J Neurosci. 30, 15102-15112.

Hartl F U, Hayer-Hartl M (2002). Molecular chaperones in the cytosol: from nascent chain to folded protein. Science 295, 1852-1858.

Hase M E, Yalamanchili P, Visa N (2006). The *Drosophila* heterogeneous nuclear ribonucleoprotein M protein, HRP59, regulates alternative splicing and controls the production of its own mRNA. J Biol. Chem. 281, 39135-39141.

Hernandez I, Moreno J L, Zandueta C, Montuenga L, Lecanda F (2010). Novel alternatively spliced ADAM8 isoforms contribute to the aggressive bone metastatic phenotype of lung cancer. Oncogene 29, 3758-3769.

Hitakomate E, Hood F E, Sanderson H S, Clarke P R (2010). The methylated N-terminal tail of RCC1 is required for stabilisation of its interaction with chromatin by Ran in live cells. BMC. Cell Biol. 11, 43.

Hjelmqvist L, Tuson M, Marfany G, Herrero E, Balcells S, Gonzalez-Duarte R (2002). ORMDL proteins are a conserved new family of endoplasmic reticulum membrane proteins. Genome Biol. 3, RESEARCH0027.

Ho C Y, Wong C H, Li H Y (2008). Perturbation of the chromosomal binding of RCC1, Mad2 and survivin causes spindle assembly defects and mitotic catastrophe. J Cell Biochem. 105, 835-846.

Hochrainer K, Mayer H, Baranyi U, Binder B, Lipp J, Kroismayr R (2005). The human HERC family of ubiquitin ligases: novel members, genomic organization, expression profiling, and evolutionary aspects. Genomics 85, 153-164.

Hofmann H S, Hansen G, Richter G, Taege C, Simm A, Silber R E, Burdach S (2005). Matrix metalloproteinase-12 expression correlates with local recurrence and metastatic disease in non-small cell lung cancer patients. Clin Cancer Res 11, 1086-1092.

Honda A, Valogne Y, Bou N M, Brechot C, Faivre J (2012). An intron-retaining splice variant of human cyclin A2, expressed in adult differentiated tissues, induces a G1/S cell cycle arrest in vitro. PLoS. ONE. 7, e39249.

Honore B, Baandrup U, Vorum H (2004). Heterogeneous nuclear ribonucleoproteins F and H/H' show differential expression in normal and selected cancer tissues. Exp. Cell Res. 294, 199-209.

Hood F E, Royle S J (2011). Pulling it together: The mitotic function of TACC3. Bioarchitecture. 1, 105-109.

Hosokawa N, Sasaki T, Iemura S, Natsume T, Hara T, Mizushima N (2009). Atg101, a novel mammalian autophagy protein interacting with Atg13. Autophagy. 5, 973-979.

Houghton A M, Grisolano J L, Baumann M L, Kobayashi D K, Hautamaki R D, Nehring L C, Cornelius L A, Shapiro S D (2006). Macrophage elastase (matrix metalloproteinase-12) suppresses growth of lung metastases. Cancer Res 66, 6149-6155.

Houghton A M, Rzymkiewicz D M, Ji H, Gregory A D, Egea E E, Metz H E, Stolz D B, Land S R, Marconcini L A, Kliment C R, Jenkins K M, Beaulieu K A, Mouded M, Frank S J, Wong K K, Shapiro S D (2010). Neutrophil elastase-mediated degradation of IRS-1 accelerates lung tumor growth. Nat Med. 16, 219-223.

Hovhannisyan R H, Carstens R P (2007). Heterogeneous ribonucleoprotein m is a splicing regulatory protein that can enhance or silence splicing of alternatively spliced exons. J Biol. Chem. 282, 36265-36274.

Hua D, Shen L, Xu L, Jiang Z, Zhou Y, Yue A, Zou S, Cheng Z, Wu S (2012). Polypeptide N-acetylgalactosaminyltransferase 2 regulates cellular metastasis-associated behavior in gastric cancer. Int. J Mol. Med. 30, 1267-1274.

Huang C L, Liu D, Nakano J, Ishikawa S, Kontani K, Yokomise H, Ueno M (2005). Wnt5a expression is associated with the tumor proliferation and the stromal vascular endothelial growth factor—an expression in non-small-cell lung cancer. J Clin Oncol 23, 8765-8773.

Huang K H, Chiou S H, Chow K C, Lin T Y, Chang H W, Chiang I P, Lee M C (2010). Overexpression of aldo-keto reductase 1C2 is associated with disease progression in patients with prostatic cancer. Histopathology 57, 384-394.

Huang M Y, Wang H M, Tok T S, Chang H J, Chang M S, Cheng T L, Wang J Y, Lin S R (2012). EVI2B, ATP2A2, S100B, TM4SF3, and OLFM4 as potential prognostic markers for postoperative Taiwanese colorectal cancer patients. DNA Cell Biol. 31, 625-635.

Huo J, Liu Y, Ma J, Xiao S (2010). A novel splice-site mutation of ATP2A2 gene in a Chinese family with Darier disease. Arch. Dermatol. Res. 302, 769-772.

Hwang Y S, Park K K, Cha I H, Kim J, Chung W Y (2012). Role of insulin-like growth factor-II mRNA-binding protein-3 in invadopodia formation and the growth of oral squamous cell carcinoma in athymic nude mice. Head Neck 34, 1329-1339.

Ishikawa N, Daigo Y, Yasui W, Inai K, Nishimura H, Tsuchiya E, Kohno N, Nakamura Y (2004). ADAM8 as a novel serological and histochemical marker for lung cancer. Clin Cancer Res. 10, 8363-8370.

Ishikawa Y, Vranka J, Wirz J, Nagata K, Bachinger H P (2008). The rough endoplasmic reticulum-resident FK506-binding protein FKBP65 is a molecular chaperone that interacts with collagens. J Biol. Chem. 283, 31584-31590.

Ito K, Takahashi A, Morita M, Suzuki T, Yamamoto T (2011). The role of the CNOT1 subunit of the CCR4-NOT complex in mRNA deadenylation and cell viability. Protein Cell 2, 755-763.

Iuchi S, Green H (1999). Basonuclin, a zinc finger protein of keratinocytes and reproductive germ cells, binds to the rRNA gene promoter. Proc. Natl. Acad. Sci. U.S.A. 96, 9628-9632.

Jalbout M, Bouaouina N, Gargouri J, Corbex M, Ben A S, Chouchane L (2003). Polymorphism of the stress protein HSP70-2 gene is associated with the susceptibility to the nasopharyngeal carcinoma. Cancer Lett. 193, 75-81.

Jeng Y M, Wang T H, Lu S H, Yuan R H, Hsu H C (2009). Prognostic significance of insulin-like growth factor II mRNA-binding protein 3 expression in gastric adenocarcinoma. Br. J Surg 96, 66-73.

Jung C K, Jung J H, Park G S, Lee A, Kang C S, Lee K Y (2006). Expression of transforming acidic coiled-coil containing protein 3 is a novel independent prognostic marker in non-small cell lung cancer. Pathol. Int 56, 503-509.

Jung G, Ledbetter J A, Muller-Eberhard H J (1987). Induction of cytotoxicity in resting human T lymphocytes bound to tumor cells by antibody heteroconjugates. Proc Natl Acad Sci USA 84, 4611-4615.

Kabbarah O, Nogueira C, Feng B, Nazarian R M, Bosenberg M, Wu M, Scott K L, Kwong L N, Xiao Y, Cordon-Cardo C, Granter S R, Ramaswamy S, Golub T, Duncan L M, Wagner S N, Brennan C, Chin L (2010). Integrative genome comparison of primary and metastatic melanomas. PLoS. ONE. 5, e10770.

Kadara H, Lacroix L, Behrens C, Solis L, Gu X, Lee J J, Tahara E, Lotan D, Hong W K, Wistuba I I, Lotan R (2009). Identification of gene signatures and molecular markers for human lung cancer prognosis using an in vitro lung carcinogenesis system. Cancer Prev. Res (Phila) 2, 702-711.

Kamlekar R K, Simanshu D K, Gao Y G, Kenoth R, Pike H M, Prendergast F G, Malinina L, Molotkovsky J G, Venyaminov S Y, Patel D J, Brown R E (2013). The glycolipid transfer protein (GLTP) domain of phosphoinositol 4-phosphate adaptor protein-2 (FAPP2): structure drives preference for simple neutral glycosphingolipids. Biochim. Biophys. Acta 1831, 417-427.

Kanno A, Satoh K, Masamune A, Hirota M, Kimura K, Umino J, Hamada S, Satoh A, Egawa S, Motoi F, Unno M, Shimosegawa T (2008). Periostin, secreted from stromal cells, has biphasic effect on cell migration and correlates with the epithelial to mesenchymal transition of human pancreatic cancer cells. Int J Cancer 122, 2707-2718.

Kanno T, Kamba T, Yamasaki T, Shibasaki N, Saito R, Terada N, Toda Y, Mikami Y, Inoue T, Kanematsu A, Nishiyama H, Ogawa O, Nakamura E (2012). JunB promotes cell invasion and angiogenesis in VHL-defective renal cell carcinoma. Oncogene 31, 3098-3110.

Kao R H, Francia G, Poulsom R, Hanby A M, Hart I R (2003). Application of differential display, with in situ hybridization verification, to microscopic samples of breast cancer tissue. Int. J Exp. Pathol. 84, 207-212.

Kars M D, Iseri O D, Gunduz U (2011). A microarray based expression profiling of paclitaxel and vincristine resistant MCF-7 cells. Eur. J Pharmacol. 657, 4-9.

Katagiri C, Iida T, Nakanishi J, Ozawa M, Aiba S, Hibino T (2010). Up-regulation of serpin SCCA1 is associated with epidermal barrier disruption. J Dermatol. Sci. 57, 95-101.

Katoh M (2008). WNT signaling in stem cell biology and regenerative medicine. Curr. Drug Targets. 9, 565-570.

Katoh M, Katoh M (2007). STAT3-induced WNT5A signaling loop in embryonic stem cells, adult normal tissues, chronic persistent inflammation, rheumatoid arthritis and cancer (Review). Int J Mol. Med 19, 273-278.

Kawata H, Shimada N, Kamiakito T, Komatsu K, Morita T, Ota T, Obayashi M, Shitara K, Tanaka A (2012). RhoC and guanine nucleotide exchange factor Net1 in androgen-unresponsive mouse mammary carcinoma SC-4 cells and human prostate cancer after short-term endocrine therapy. Prostate 72, 1071-1079.

Kelly S M, Corbett A H (2009). Messenger RNA export from the nucleus: a series of molecular wardrobe changes. Traffic. 10, 1199-1208.

Kennedy A, Dong H, Chen D, Chen W T (2009). Elevation of seprase expression and promotion of an invasive phenotype by collagenous matrices in ovarian tumor cells. Int J Cancer 124, 27-35.

Kikuchi A, Yamamoto H, Sato A, Matsumoto S (2012). Wnt5a: its signalling, functions and implication in diseases. Acta Physiol (Oxf) 204, 17-33.

Kikuchi Y, Kashima T G, Nishiyama T, Shimazu K, Morishita Y, Shimazaki M, Kii I, Horie H, Nagai H, Kudo A, Fukayama M (2008). Periostin is expressed in pericryptal fibroblasts and cancer-associated fibroblasts in the colon. J Histochem. Cytochem. 56, 753-764.

Kim D H, Park S E, Kim M, Ji Y I, Kang M Y, Jung E H, Ko E, Kim Y, Kim S, Shim Y M, Park J (2011). A functional single nucleotide polymorphism at the promoter region of cyclin A2 is associated with increased risk of colon, liver, and lung cancers. Cancer 117, 4080-4091.

Kim E H, Park A K, Dong S M, Ahn J H, Park W Y (2010a). Global analysis of CpG methylation reveals epigenetic control of the radiosensitivity in lung cancer cell lines. Oncogene 29, 4725-4731.

Kim H S, Kim dH, Kim J Y, Jeoung N H, Lee I K, Bong J G, Jung E D (2010b). Microarray analysis of papillary thyroid cancers in Korean. Korean J Intern. Med. 25, 399-407.

Kim M Y, Oskarsson T, Acharyya S, Nguyen D X, Zhang X H, Norton L, Massague J (2009). Tumor self-seeding by circulating cancer cells. Cell 139, 1315-1326.

Kim S, Park H S, Son H J, Moon W S (2004). [The role of angiostatin, vascular endothelial growth factor, matrix metalloproteinase 9 and 12 in the angiogenesis of hepatocellular carcinoma]. Korean J Hepatol. 10, 62-72.

Kimura J, Kudoh T, Miki Y, Yoshida K (2011). Identification of dihydropyrimidinase-related protein 4 as a novel target of the p53 tumor suppressor in the apoptotic response to DNA damage. Int. J Cancer 128, 1524-1531. Kloth J N, Oosting J, van W T, Szuhai K, Knijnenburg J, Gorter A, Kenter G G, Fleuren G J, Jordanova E S (2007). Combined array-comparative genomic hybridization and single-nucleotide polymorphism-loss of heterozygosity analysis reveals complex genetic alterations in cervical cancer. BMC. Genomics 8, 53.

Knight H M, Pickard B S, Maclean A, Malloy M P, Soares D C, McRae A F, Condie A, White A, Hawkins W, McGhee K, van B M, MacIntyre D J, Starr J M, Deary I J, Visscher P M, Porteous D J, Cannon R E, St C D, Muir W J, Blackwood D H (2009). A cytogenetic abnormality and rare coding variants identify ABCA13 as a candidate gene in schizophrenia, bipolar disorder, and depression. Am J Hum. Genet. 85, 833-846.

Kolehmainen J, Black G C, Saarinen A, Chandler K, Clayton-Smith J, Traskelin A L, Perveen R, Kivitie-Kallio S, Norio R, Warburg M, Fryns J P, de la Chapelle A, Lehesjoki A E (2003). Cohen syndrome is caused by mutations in a novel gene, COH1, encoding a transmembrane protein with a presumed role in vesicle-mediated sorting and intracellular protein transport. Am. J Hum. Genet. 72, 1359-1369.

Konishi N, Shimada K, Nakamura M, Ishida E, Ota I, Tanaka N, Fujimoto K (2008). Function of JunB in transient amplifying cell senescence and progression of human prostate cancer. Clin Cancer Res. 14, 4408-4416.

Kornak U, Brancati F, Le M M, Lichtenbelt K, Hohne W, Tinschert S, Garaci F G, Dallapiccola B, Nurnberg P (2010). Three novel mutations in the ANK membrane protein cause craniometaphyseal dysplasia with variable conductive hearing loss. Am. J Med. Genet. A 152A, 870-874.

Korosec B, Glavac D, Rott T, Ravnik-Glavac M (2006). Alterations in the ATP2A2 gene in correlation with colon and lung cancer. Cancer Genet. Cytogenet. 171, 105-111.

Kramer M W, Escudero D O, Lokeshwar S D, Golshani R, Ekwenna O O, Acosta K, Merseburger A S, Soloway M, Lokeshwar V B (2010). Association of hyaluronic acid family members (HAS1, HAS2, and HYAL-1) with bladder cancer diagnosis and prognosis. Cancer.

Krieg A M (2006). Therapeutic potential of Toll-like receptor 9 activation. Nat. Rev. Drug Discov. 5, 471-484.

Kuang P, Zhou C, Li X, Ren S, Li B, Wang Y, Li J, Tang L, Zhang J, Zhao Y (2012). Proteomics-based identification of secreted protein dihydrodiol dehydrogenase 2 as a potential biomarker for predicting cisplatin efficacy in advanced NSCLC patients. Lung Cancer 77, 427-432.

Kuang S Q, Tong W G, Yang H, Lin W, Lee M K, Fang Z H, Wei Y, Jelinek J, Issa J P, Garcia-Manero G (2008). Genome-wide identification of aberrantly methylated promoter associated CpG islands in acute lymphocytic leukemia. Leukemia 22, 1529-1538.

Kudo Y, Ogawa I, Kitajima S, Kitagawa M, Kawai H, Gaffney P M, Miyauchi M, Takata T (2006). Periostin promotes invasion and anchorage-independent growth in the metastatic process of head and neck cancer. Cancer Res 66, 6928-6935.

Kwon O H, Park J L, Kim M, Kim J H, Lee H C, Kim H J, Noh S M, Song K S, Yoo H S, Paik S G, Kim S Y, Kim Y S (2011). Aberrant up-regulation of LAMB3 and LAMC2 by promoter demethylation in gastric cancer. Biochem. Biophys. Res. Commun. 406, 539-545.

Kwon Y J, Lee S J, Koh J S, Kim S H, Kim Y J, Park J H (2009). Expression patterns of aurora kinase B, heat shock protein 47, and periostin in esophageal squamous cell carcinoma. Oncol Res 18, 141-151.

Labied S, Galant C, Nisolle M, Ravet S, Munaut C, Marbaix E, Foidart J M, Frankenne F (2009). Differential elevation of matrix metalloproteinase expression in women exposed to levonorgestrel-releasing intrauterine system for a short or prolonged period of time. Hum. Reprod. 24, 113-121.

Lau E, Zhu C, Abraham R T, Jiang W (2006). The functional role of Cdc6 in S-G2/M in mammalian cells. EMBO Rep. 7, 425-430.

Lazaris A C, Chatzigianni E B, Panoussopoulos D, Tzimas G N, Davaris P S, Golematis B C (1997). Proliferating cell nuclear antigen and heat shock protein 70 immunolocalization in invasive ductal breast cancer not otherwise specified. Breast Cancer Res. Treat. 43, 43-51.

Le C B, Rynkowski M, Le M M, Bruyere C, Lonez C, Gras T, Haibe-Kains B, Bontempi G, Decaestecker C, Ruysschaert J M, Kiss R, Lefranc F (2010). Long-term in vitro treatment of human glioblastoma cells with temozolomide increases resistance in vivo through up-regulation of GLUT transporter and aldo-keto reductase enzyme AKR1C expression. Neoplasia. 12, 727-739.

Lee K H, Kim J R (2012). Regulation of HGF-mediated cell proliferation and invasion through NF-kappaB, JunB, and MMP-9 cascades in stomach cancer cells. Clin Exp. Metastasis 29, 263-272.

Lee W S, Jain M K, Arkonac B M, Zhang D, Shaw S Y, Kashiki S, Maemura K, Lee S L, Hollenberg N K, Lee M E, Haber E (1998). Thy-1, a novel marker for angiogenesis upregulated by inflammatory cytokines. Circ. Res 82, 845-851.

Lee Y, Ahn C, Han J, Choi H, Kim J, Yim J, Lee J, Provost P, Radmark O, Kim S, Kim V N (2003). The nuclear RNase III Drosha initiates microRNA processing. Nature 425, 415-419.

Lefave C V, Squatrito M, Vorlova S, Rocco G L, Brennan C W, Holland E C, Pan Y X, Cartegni L (2011). Splicing factor hnRNPH drives an oncogenic splicing switch in gliomas. EMBO J 30, 4084-4097.

Leivo I, Jee K J, Heikinheimo K, Laine M, Ollila J, Nagy B, Knuutila S (2005). Characterization of gene expression in major types of salivary gland carcinomas with epithelial differentiation. Cancer Genet. Cytogenet. 156, 104-113.

Lemmel C, Weik S, Eberle U, Dengjel J, Kratt T, Becker H D, Rammensee H G, Stevanovic S (2004). Differential quantitative analysis of MHC ligands by mass spectrometry using stable isotope labeling. Nat. Biotechnol. 22, 450-454.

Li H, Guo L, Li J, Liu N, Liu J (2000a). Alternative splicing of RHAMM gene in chinese gastric cancers and its in vitro regulation. Zhonghua Yi. Xue. Yi. Chuan Xue. Za Zhi. 17, 343-347.

Li H, Guo L, Li J W, Liu N, Qi R, Liu J (2000b). Expression of hyaluronan receptors CD44 and RHAMM in stomach cancers: relevance with tumor progression. Int J Oncol 17, 927-932.

Li H G, Han J J, Huang Z Q, Wang L, Chen W L, Shen X M (2011). IMP3 is a novel biomarker to predict metastasis and prognosis of tongue squamous cell carcinoma. J Craniofac. Surg. 22, 2022-2025.

Li J, Ying J, Fan Y, Wu L, Ying Y, Chan A T, Srivastava G, Tao Q (2010). WNT5A antagonizes WNT/beta-catenin signaling and is frequently silenced by promoter CpG methylation in esophageal squamous cell carcinoma. Cancer Biol. Ther. 10, 617-624.

Li Y, Chu L W, L I Z, Yik P Y, Song Y Q (2009). A study on the association of the chromosome 12p13 locus with sporadic late-onset Alzheimer's disease in Chinese. Dement. Geriatr. Cogn Disord. 27, 508-512.

Liang W J, Qiu F, Hong M H, Guo L, Qin H D, Liu Q C, Zhang X S, Mai H Q, Xiang Y Q, Min H Q, Zeng Y X (2008). [Differentially expressed genes between upward and downward progressing types of nasopharyngeal carcinoma]. Ai. Zheng. 27, 460-465.

Liao B, Hu Y, Brewer G (2011). RNA-binding protein insulin-like growth factor mRNA-binding protein 3 (IMP-3) promotes cell survival via insulin-like growth factor II signaling after ionizing radiation. J Biol. Chem. 286, 31145-31152.

Liao B, Hu Y, Herrick D J, Brewer G (2005). The RNA-binding protein IMP-3 is a translational activator of insulin-like growth factor II leader-3 mRNA during proliferation of human K562 leukemia cells. J Biol. Chem. 280, 18517-18524.

Lin D M, Ma Y, Xiao T, Guo S P, Han N J, Su K, Yi S Z, Fang J, Cheng S J, Gao Y N (2006). [TPX2 expression and its significance in squamous cell carcinoma of lung]. Zhonghua Bing. Li Xue. Za Zhi. 35, 540-544.

Litjens S H, de Pereda J M, Sonnenberg A (2006). Current insights into the formation and breakdown of hemidesmosomes. Trends Cell Biol. 16, 376-383.

Liu J, Yang L, Jin M, Xu L, Wu S (2011a). regulation of the invasion and metastasis of human glioma cells by polypeptide N-acetylgalactosaminyltransferase 2. Mol. Med. Rep. 4, 1299-1305.

Liu T, Jin X, Zhang X, Yuan H, Cheng J, Lee J, Zhang B, Zhang M, Wu J, Wang L, Tian G, Wang W (2012). A novel missense SNRNP200 mutation associated with autosomal dominant retinitis pigmentosa in a Chinese family. PLoS. ONE. 7, e45464.

Liu W, Morito D, Takashima S, Mineharu Y, Kobayashi H, Hitomi T, Hashikata H, Matsuura N, Yamazaki S, Toyoda A, Kikuta K, Takagi Y, Harada K H, Fujiyama A, Herzig R, Krischek B, Zou L, Kim J E, Kitakaze M, Miyamoto S, Nagata K, Hashimoto N, Koizumi A (2011b). Identification of RNF213 as a susceptibility gene for moyamoya disease and its possible role in vascular development. PLoS. ONE. 6, e22542.

Lleres D, Denegri M, Biggiogera M, Ajuh P, Lamond A I (2010). Direct interaction between hnRNP-M and CDC5L/PLRG1 proteins affects alternative splice site choice. EMBO Rep. 11, 445-451.

Lu D, Yang X, Jiang N Y, Woda B A, Liu Q, Dresser K, Mercurio A M, Rock K L, Jiang Z (2011). IMP3, a new biomarker to predict progression of cervical intraepithelial neoplasia into invasive cancer. Am. J Surg. Pathol. 35, 1638-1645.

Lu Z, Zhou L, Killela P, Rasheed A B, Di C, Poe W E, McLendon R E, Bigner D D, Nicchitta C, Yan H (2009). Glioblastoma proto-oncogene SEC61gamma is required for tumor cell survival and response to endoplasmic reticulum stress. Cancer Res. 69, 9105-9111.

Lugassy C, Torres-Munoz J E, Kleinman H K, Ghanem G, Vernon S, Barnhill R L (2009). Overexpression of malignancy-associated laminins and laminin receptors by angiotropic human melanoma cells in a chick chorioallantoic membrane model. J Cutan. Pathol. 36, 1237-1243.

Ma L J, Li W, Zhang X, Huang D H, Zhang H, Xiao J Y, Tian Y Q (2009). Differential gene expression profiling of laryngeal squamous cell carcinoma by laser capture microdissection and complementary DNA microarrays. Arch. Med Res 40, 114-123.

Ma T S, Mann D L, Lee J H, Gallinghouse G J (1999). S R compartment calcium and cell apoptosis in SERCA overexpression. Cell Calcium 26, 25-36.

Ma Y, Lin D, Sun W, Xiao T, Yuan J, Han N, Guo S, Feng X, Su K, Mao Y, Cheng S, Gao Y (2006). Expression of targeting protein for xklp2 associated with both malignant transformation of respiratory epithelium and progression of squamous cell lung cancer. Clin Cancer Res 12, 1121-1127.

MacLennan D H, Rice W J, Green N M (1997). The mechanism of Ca2+ transport by sarco(endo)plasmic reticulum Ca2+-ATPases. J Biol. Chem. 272, 28815-28818.

Maeder C, Kutach A K, Guthrie C (2009). ATP-dependent unwinding of U4/U6 snRNAs by the Brr2 helicase requires the C terminus of Prp8. Nat Struct. Mol. Biol. 16, 42-48.

Manda R, Kohno T, Niki T, Yamada T, Takenoshita S, Kuwano H, Yokota J (2000). Differential expression of the LAMB3 and LAMC2 genes between small cell and non-small cell lung carcinomas. Biochem. Biophys. Res. Commun. 275, 440-445.

Marchand M, Van B N, Weynants P, Brichard V, Dreno B, Tessier M H, Rankin E, Parmiani G, Arienti F, Humblet Y, Bourlond A, Vanwijck R, Lienard D, Beauduin M, Dietrich P Y, Russo V, Kerger J, Masucci G, Jager E, De G J, Atzpodien J, Brasseur F, Coulie P G, van der B P, Boon T (1999). Tumor regressions observed in patients with metastatic melanoma treated with an antigenic peptide encoded by gene MAGE-3 and presented by HLA-A1. Int. J. Cancer 80, 219-230.

Marchand M, Weynants P, Rankin E, Arienti F, Belli F, Parmiani G, Cascinelli N, Bourlond A, Vanwijck R, Humblet Y. (1995). Tumor regression responses in melanoma patients treated with a peptide encoded by gene MAGE-3. Int. J Cancer 63, 883-885.

Masson N M, Currie I S, Terrace J D, Garden O J, Parks R W, Ross J A (2006). Hepatic progenitor cells in human fetal liver express the oval cell marker Thy-1. Am J Physiol Gastrointest. Liver Physiol 291, G45-G54.

McManus K J, Barrett I J, Nouhi Y, Hieter P (2009). Specific synthetic lethal killing of RAD54B-deficient human colorectal cancer cells by FEN1 silencing. Proc. Natl. Acad. Sci. U.S.A. 106, 3276-3281.

Mercer C A, Kaliappan A, Dennis P B (2009). A novel, human Atg13 binding protein, Atg101, interacts with ULK1 and is essential for macroautophagy. Autophagy. 5, 649-662.

Mestiri S, Bouaouina N, Ahmed S B, Khedhaier A, Jrad B B, Remadi S, Chouchane L (2001). Genetic variation in the tumor necrosis factor-alpha promoter region and in the stress protein hsp70-2: susceptibility and prognostic implications in breast carcinoma. Cancer 91, 672-678.

Meyer E L, Goemann I M, Dora J M, Wagner M S, Maia A L (2008). Type 2 iodothyronine deiodinase is highly expressed in medullary thyroid carcinoma. Mol. Cell Endocrinol. 289, 16-22.

Miller N H, Justice C M, Marosy B, Swindle K, Kim Y, Roy-Gagnon M H, Sung H, Behneman D, Doheny K F, Pugh E, Wilson A F (2012). Intra-familial tests of association between familial idiopathic scoliosis and linked regions on 9q31.3-q34.3 and 16p12.3-q22.2. Hum. Hered. 74, 36-44.

Milovanovic T, Planutis K, Nguyen A, Marsh J L, Lin F, Hope C, Holcombe R F (2004). Expression of Wnt genes and frizzled 1 and 2 receptors in normal breast epithelium and infiltrating breast carcinoma. Int. J Oncol 25, 1337-1342.

Mochizuki S, Okada Y (2007). ADAMs in cancer cell proliferation and progression. Cancer Sci. 98, 621-628.

Morgan R A, Dudley M E, Wunderlich J R, Hughes M S, Yang J C, Sherry R M, Royal R E, Topalian S L, Kammula U S, Restifo N P, Zheng Z, Nahvi A, de Vries C R, Rogers-Freezer L J, Mavroukakis S A, Rosenberg S A (2006). Cancer Regression in Patients After Transfer of Genetically Engineered Lymphocytes. Science.

Mori M, Beatty P G, Graves M, Boucher K M, Milford E L (1997). HLA gene and haplotype frequencies in the North American population: the National Marrow Donor Program Donor Registry. Transplantation 64, 1017-1027.

Moroy G, Alix A J, Sapi J, Hornebeck W, Bourguet E (2012). Neutrophil elastase as a target in lung cancer. Anticancer Agents Med. Chem. 12, 565-579.

Morris M R, Ricketts C, Gentle D, Abdulrahman M, Clarke N, Brown M, Kishida T, Yao M, Latif F, Maher E R (2010). Identification of candidate tumour suppressor genes frequently methylated in renal cell carcinoma. Oncogene 29, 2104-2117.

Moss D K, Wilde A, Lane J D (2009). Dynamic release of nuclear RanGTP triggers TPX2-dependent microtubule assembly during the apoptotic execution phase. J Cell Sci. 122, 644-655.

Murakami M, Araki O, Morimura T, Hosoi Y, Mizuma H, Yamada M, Kurihara H, Ishiuchi S, Tamura M, Sasaki T, Mori M (2000). Expression of type II iodothyronine deiodinase in brain tumors. J Clin Endocrinol. Metab 85, 4403-4406.

Nakamura Y, Muguruma Y, Yahata T, Miyatake H, Sakai D, Mochida J, Hotta T, Ando K (2006). Expression of CD90 on keratinocyte stem/progenitor cells. Br. J Dermatol. 154, 1062-1070.

Neidert M C, Schoor O, Trautwein C, Trautwein N, Christ L, Melms A, Honegger J, Rammensee H G, Herold-Mende C, Dietrich P Y, Stevanovic S (2012). Natural HLA class I ligands from glioblastoma: extending the options for immunotherapy. J Neurooncol.

Nestle F O, Alijagic S, Gilliet M, Sun Y, Grabbe S, Dummer R, Burg G, Schadendorf D (1998). Vaccination of melanoma patients with peptide- or tumor lysate-pulsed dendritic cells. Nat Med. 4, 328-332.

Niedergethmann M, Alves F, Neff J K, Heidrich B, Aramin N, Li L, Pilarsky C, Grutzmann R, Allgayer H, Post S, Gretz N (2007). Gene expression profiling of liver metastases and tumour invasion in pancreatic cancer using an orthotopic SCID mouse model. Br. J Cancer 97, 1432-1440.

Nikolova D N, Zembutsu H, Sechanov T, Vidinov K, Kee L S, Ivanova R, Becheva E, Kocova M, Toncheva D, Nakamura Y (2008). Genome-wide gene expression profiles of thyroid carcinoma: Identification of molecular targets for treatment of thyroid carcinoma. Oncol Rep. 20, 105-121.

Nirde P, Derocq D, Maynadier M, Chambon M, Basile I, Gary-Bobo M, Garcia M (2010). Heat shock cognate 70 protein secretion as a new growth arrest signal for cancer cells. Oncogene 29, 117-127.

Nishinakamura R, Uchiyama Y, Sakaguchi M, Fujimura S (2011). Nephron progenitors in the metanephric mesenchyme. Pediatr. Nephrol. 26, 1463-1467.

Odermatt A, Taschner P E, Khanna V K, Busch H F, Karpati G, Jablecki C K, Breuning M H, MacLennan D H (1996). Mutations in the gene-encoding SERCA1, the fast-twitch skeletal muscle sarcoplasmic reticulum Ca2+ ATPase, are associated with Brody disease. Nat Genet. 14, 191-194.

Oh S P, Taylor R W, Gerecke D R, Rochelle J M, Seldin M F, Olsen B R (1992). The mouse alpha 1(XII) and human alpha 1(XII)-like collagen genes are localized on mouse chromosome 9 and human chromosome 6. Genomics 14, 225-231.

Ohta S, Koide M, Tokuyama T, Yokota N, Nishizawa S, Namba H (2001). Cdc6 expression as a marker of proliferative activity in brain tumors. Oncol Rep. 8, 1063-1066.

Ortega P, Moran A, Fernandez-Marcelo T, De J C, Frias C, Lopez-Asenjo J A, Sanchez-Pernaute A, Torres A, Diaz-Rubio E, Iniesta P, Benito M (2010). MMP-7 and SGCE as distinctive molecular factors in sporadic colorectal cancers from the mutator phenotype pathway. Int. J Oncol 36, 1209-1215.

Osborne A R, Rapoport T A, van den Berg B (2005). Protein translocation by the Sec61/SecY channel. Annu. Rev. Cell Dev. Biol. 21, 529-550.

Pascolo S, Ginhoux F, Laham N, Walter S, Schoor O, Probst J, Rohrlich P, Obermayr F, Fisch P, Danos O, Ehrlich R, Lemonnier F A, Rammensee H G (2005). The non-classical HLA class I molecule HFE does not influence the NK-like activity contained in fresh human PBMCs and does not interact with NK cells. Int. Immunol. 17, 117-122.

Pascreau G, Eckerdt F, Lewellyn A L, Prigent C, Maller J L (2009). Phosphorylation of p53 is regulated by TPX2-Aurora A in *xenopus* oocytes. J Biol. Chem. 284, 5497-5505.

Patterson C E, Abrams W R, Wolter N E, Rosenbloom J, Davis E C (2005). Developmental regulation and coordinate reexpression of FKBP65 with extracellular matrix proteins after lung injury suggest a specialized function for this endoplasmic reticulum immunophilin. Cell Stress. Chaperones. 10, 285-295.

Patterson C E, Schaub T, Coleman E J, Davis E C (2000). Developmental regulation of FKBP65. An ER-localized extracellular matrix binding-protein. Mol. Biol. Cell 11, 3925-3935.

Peiro G, Diebold J, Baretton G B, Kimmig R, Lohrs U (2001). Cellular apoptosis susceptibility gene expression in endometrial carcinoma: correlation with Bcl-2, Bax, and caspase-3 expression and outcome. Int. J Gynecol. Pathol. 20, 359-367.

Peng C, Togayachi A, Kwon Y D, Xie C, Wu G, Zou X, Sato T, Ito H, Tachibana K, Kubota T, Noce T, Narimatsu H, Zhang Y (2010). Identification of a novel human UDP-GalNAc transferase with unique catalytic activity and expression profile. Biochem. Biophys. Res. Commun. 402, 680-686.

Penning T M, Burczynski M E, Jez J M, Hung C F, Lin H K, Ma H, Moore M, Palackal N, Ratnam K (2000). Human 3alpha-hydroxysteroid dehydrogenase isoforms (AKR1C1-AKR1C4) of the aldo-keto reductase superfamily: functional plasticity and tissue distribution reveals roles in the inactivation and formation of male and female sex hormones. Biochem. J 351, 67-77.

Perrin-Tricaud C, Rutschmann C, Hennet T (2011). Identification of domains and amino acids essential to the collagen galactosyltransferase activity of GLT25D1. PLoS. ONE. 6, e29390.

Pine S R, Mechanic L E, Enewold L, Chaturvedi A K, Katki H A, Zheng Y L, Bowman E D, Engels E A, Caporaso N E, Harris C C (2011). Increased levels of circulating interleukin 6, interleukin 8, C-reactive protein, and risk of lung cancer. J Natl. Cancer Inst. 103, 1112-1122.

Piskac-Collier A L, Monroy C, Lopez M S, Cortes A, Etzel C J, Greisinger A J, Spitz M R, El-Zein R A (2011). Variants in folate pathway genes as modulators of genetic instability and lung cancer risk. Genes Chromosomes. Cancer 50, 1-12.

Pontisso P, Calabrese F, Benvegnu L, Lise M, Belluco C, Ruvoletto M G, Marino M, Valente M, Nitti D, Gatta A, Fassina G (2004). Overexpression of squamous cell carcinoma antigen variants in hepatocellular carcinoma. Br. J Cancer 90, 833-837.

Prades C, Arnould I, Annilo T, Shulenin S, Chen Z Q, Orosco L, Triunfol M, Devaud C, Maintoux-Larois C, Lafargue C, Lemoine C, Denefle P, Rosier M, Dean M (2002). The human ATP binding cassette gene ABCA13, located on chromosome 7p12.3, encodes a 5058 amino acid protein with an extracellular domain encoded in part by a 4.8-kb conserved exon. Cytogenet. Genome Res 98, 160-168.

Prasad P, Tiwari A K, Kumar K M, Ammini A C, Gupta A, Gupta R, Thelma B K (2010). Association analysis of ADPRT1, AKR1B1, RAGE, GFPT2 and PAI-1 gene polymorphisms with chronic renal insufficiency among Asian Indians with type-2 diabetes. BMC. Med. Genet. 11, 52.

Puppin C, Fabbro D, Dima M, Di L C, Puxeddu E, Filetti S, Russo D, Damante G (2008). High periostin expression correlates with aggressiveness in papillary thyroid carcinomas. J Endocrinol. 197, 401-408.

Purdue M P, Johansson M, Zelenika D, Toro J R, Scelo G, Moore L E, Prokhortchouk E, Wu X, Kiemeney L A, Gaborieau V, Jacobs K B, Chow W H, Zaridze D, Matveev V, Lubinski J, Trubicka J, Szeszenia-Dabrowska N, Lissowska J, Rudnai P, Fabianova E, Bucur A, Bencko V, Foretova L, Janout V, Boffetta P, Colt J S, Davis F G, Schwartz K L, Banks R E, Selby P J, Harnden P, Berg C D, Hsing A W, Grubb R L, III, Boeing H, Vineis P, Clavel-Chapelon F, Palli D, Tumino R, Krogh V, Panico S, Duell E J, Quiros J R, Sanchez M J, Navarro C, Ardanaz E, Dorronsoro M, Khaw K T, Allen N E, Bueno-de-Mesquita H B, Peeters P H, Trichopoulos D, Linseisen J, Ljungberg B, Overvad K, Tjonneland A, Romieu I, Riboli E, Mukeria A, Shangina O, Stevens V L, Thun M J, Diver W R, Gapstur S M, Pharoah P D, Easton D F, Albanes D, Weinstein S J, Virtamo J, Vatten L, Hveem K, Njolstad I, Tell G S, Stoltenberg C, Kumar R, Koppova K, Cussenot O, Benhamou S, Oosterwijk E, Vermeulen S H, Aben K K, van der Marel S L, Ye Y, Wood C G, Pu X, Mazur A M, Boulygina E S, Chekanov N N, Foglio M, Lechner D, Gut I, Heath S, Blanche H, Hutchinson A, Thomas G, Wang Z, Yeager M, Fraumeni J F, Jr., Skryabin K G, McKay J D, Rothman N, Chanock S J, Lathrop M, Brennan P (2011). Genome-wide association study of renal cell carcinoma identifies two susceptibility loci on 2p21 and 11q13.3. Nat Genet. 43, 60-65.

Puyol M, Martin A, Dubus P, Mulero F, Pizcueta P, Khan G, Guerra C, Santamaria D, Barbacid M (2010). A synthetic lethal interaction between K-Ras oncogenes and Cdk4 unveils a therapeutic strategy for non-small cell lung carcinoma. Cancer Cell 18, 63-73.

Qu P, Du H, Wang X, Yan C (2009). Matrix metalloproteinase 12 overexpression in lung epithelial cells plays a key role in emphysema to lung bronchioalveolar adenocarcinoma transition. Cancer Res 69, 7252-7261.

Ramakrishna M, Williams L H, Boyle S E, Bearfoot J L, Sridhar A, Speed T P, Gorringe K L, Campbell I G (2010). Identification of candidate growth promoting genes in ovarian cancer through integrated copy number and expression analysis. PLoS. ONE. 5, e9983.

Rammensee H G, Bachmann J, Emmerich N P, Bachor O A, Stevanovic S (1999). SYFPEITHI: database for MHC ligands and peptide motifs. Immunogenetics 50, 213-219.

Rammensee H G, Bachmann J, Stevanovic S (1997). MHC Ligands and Peptide Motifs. (Heidelberg, Germany: Springer-Verlag).

Rao B, Gao Y, Huang J, Gao X, Fu X, Huang M, Yao J, Wang J, Li W, Zhang J, Liu H, Wang L, Wang J (2011). Mutations of p53 and K-ras correlate TF expression in human colorectal carcinomas: TF downregulation as a marker of poor prognosis. Int. J Colorectal Dis. 26, 593-601.

Rappsilber J, Ryder U, Lamond A I, Mann M (2002). Large-scale proteomic analysis of the human spliceosome. Genome Res. 12, 1231-1245.

Rauch J, O'Neill E, Mack B, Matthias C, Munz M, Kolch W, Gires O (2010). Heterogeneous nuclear ribonucleoprotein H blocks MST2-mediated apoptosis in cancer cells by regulating A-Raf transcription. Cancer Res. 70, 1679-1688.

Rege T A, Hagood J S (2006a). Thy-1 as a regulator of cell-cell and cell-matrix interactions in axon regeneration, apoptosis, adhesion, migration, cancer, and fibrosis. FASEB J 20, 1045-1054.

Rege T A, Hagood J S (2006b). Thy-1, a versatile modulator of signaling affecting cellular adhesion, proliferation, survival, and cytokine/growth factor responses. Biochim. Biophys. Acta 1763, 991-999.

Rettig W J, Garin-Chesa P, Healey J H, Su S L, Ozer H L, Schwab M, Albino A P, Old L J (1993). Regulation and heteromeric structure of the fibroblast activation protein in normal and transformed cells of mesenchymal and neuroectodermal origin. Cancer Res 53, 3327-3335.

Rettig W J, Su S L, Fortunato S R, Scanlan M J, Raj B K, Garin-Chesa P, Healey J H, Old L J (1994). Fibroblast activation protein: purification, epitope mapping and induction by growth factors. Int J Cancer 58, 385-392.

Rini B I, Weinberg V, Fong L, Conry S, Hershberg R M, Small E J (2006). Combination immunotherapy with prostatic acid phosphatase pulsed antigen-presenting cells (provenge) plus bevacizumab in patients with serologic progression of prostate cancer after definitive local therapy. Cancer 107, 67-74.

Ripka S, Konig A, Buchholz M, Wagner M, Sipos B, Kloppel G, Downward J, Gress T, Michl P (2007). WNT5A—target of CUTL1 and potent modulator of tumor cell migration and invasion in pancreatic cancer. Carcinogenesis 28, 1178-1187.

Rivera V T, Boudoukha S, Simon A, Souidi M, Cuvellier S, Pinna G, Polesskaya A (2013). Post-transcriptional regulation of cyclins D1, D3 and G1 and proliferation of human cancer cells depend on IMP-3 nuclear localization. Oncogene.

Rodningen O K, Borresen-Dale A L, Alsner J, Hastie T, Overgaard J (2008). Radiation-induced gene expression in human subcutaneous fibroblasts is predictive of radiation-induced fibrosis. Radiother. Oncol 86, 314-320.

Rodriguez C I, Stewart C L (2007). Disruption of the ubiquitin ligase HERC4 causes defects in spermatozoon maturation and impaired fertility. Dev. Biol. 312, 501-508.

Roemer A, Schwettmann L, Jung M, Roigas J, Kristiansen G, Schnorr D, Loening S A, Jung K, Lichtinghagen R (2004a). Increased mRNA expression of ADAMs in renal cell carcinoma and their association with clinical outcome. Oncol Rep. 11, 529-536.

Roemer A, Schwettmann L, Jung M, Stephan C, Roigas J, Kristiansen G, Loening S A, Lichtinghagen R, Jung K (2004b). The membrane proteases adams and hepsin are differentially expressed in renal cell carcinoma. Are they potential tumor markers? J Urol. 172, 2162-2166.

Rohde M, Daugaard M, Jensen M H, Helin K, Nylandsted J, Jaattela M (2005). Members of the heat-shock protein 70 family promote cancer cell growth by distinct mechanisms. Genes Dev. 19, 570-582.

Romagnoli S, Fasoli E, Vaira V, Falleni M, Pellegrini C, Catania A, Roncalli M, Marchetti A, Santambrogio L, Coggi G, Bosari S (2009). Identification of potential therapeutic targets in malignant mesothelioma using cell-cycle gene expression analysis. Am J Pathol. 174, 762-770.

Romero-Weaver A L, Wang H W, Steen H C, Scarzello A J, Hall V L, Sheikh F, Donnelly R P, Gamero A M (2010). Resistance to IFN-alpha-induced apoptosis is linked to a loss of STAT2. Mol. Cancer Res. 8, 80-92.

Rosenberg S A, Lotze M T, Muul L M, Chang A E, Avis F P, Leitman S, Linehan W M, Robertson C N, Lee R E, Rubin J T. (1987). A progress report on the treatment of 157 patients with advanced cancer using lymphokine-activated killer cells and interleukin-2 or high-dose interleukin-2 alone. N. Engl. J. Med. 316, 889-897.

Rosenberg S A, Packard B S, Aebersold P M, Solomon D, Topalian S L, Toy S T, Simon P, Lotze M T, Yang J C, Seipp C A. (1988). Use of tumor-infiltrating lymphocytes and interleukin-2 in the immunotherapy of patients with metastatic melanoma. A preliminary report. N. Engl. J Med 319, 1676-1680.

Ruan K, Bao S, Ouyang G (2009). The multifaceted role of periostin in tumorigenesis. Cell Mol. Life Sci. 66, 2219-2230.

Ruiz dA, I, Scarselli M, Rosemond E, Gautam D, Jou W, Gavrilova O, Ebert P J, Levitt P, Wess J (2010). RGS4 is a negative regulator of insulin release from pancreatic beta-cells in vitro and in vivo. Proc Natl. Acad. Sci. U.S.A. 107, 7999-8004.

Rusin M, Zientek H, Krzesniak M, Malusecka E, Zborek A, Krzyzowska-Gruca S, Butkiewicz D, Vaitiekunaite R, Lisowska K, Grzybowska E, Krawczyk Z (2004). Intronic polymorphism (1541-1542delGT) of the constitutive heat shock protein 70 gene has functional significance and shows evidence of association with lung cancer risk. Mol. Carcinog. 39, 155-163.

Sagara N, Toda G, Hirai M, Terada M, Katoh M (1998). Molecular cloning, differential expression, and chromosomal localization of human frizzled-1, frizzled-2, and frizzled-7. Biochem. Biophys. Res. Commun. 252, 117-122.

Saiki R K, Gelfand D H, Stoffel S, Scharf S J, Higuchi R, Horn G T, Mullis K B, Erlich H A (1988). Primer-directed enzymatic amplification of DNA with a thermostable DNA polymerase. Science 239, 487-491.

Sakuntabhai A, Ruiz-Perez V, Carter S, Jacobsen N, Burge S, Monk S, Smith M, Munro C S, O'Donovan M, Craddock N, Kucherlapati R, Rees J L, Owen M, Lathrop G M, Monaco A P, Strachan T, Hovnanian A (1999). Mutations in ATP2A2, encoding a Ca2+ pump, cause Darier disease. Nat Genet. 21, 271-277.

Samanta S, Sharma V M, Khan A, Mercurio A M (2012). Regulation of IMP3 by EGFR signaling and repression by ERbeta: implications for triple-negative breast cancer. Oncogene 31, 4689-4697.

Sang Q X (1998). Complex role of matrix metalloproteinases in angiogenesis. Cell Res 8, 171-177.

Sarai N, Kagawa W, Fujikawa N, Saito K, Hikiba J, Tanaka K, Miyagawa K, Kurumizaka H, Yokoyama S (2008). Biochemical analysis of the N-terminal domain of human RAD54B. Nucleic Acids Res. 36, 5441-5450.

Satow R, Shitashige M, Kanai Y, Takeshita F, Ojima H, Jigami T, Honda K, Kosuge T, Ochiya T, Hirohashi S, Yamada T (2010). Combined functional genome survey of therapeutic targets for hepatocellular carcinoma. Clin Cancer Res 16, 2518-2528.

Scanlan M J, Raj B K, Calvo B, Garin-Chesa P, Sanz-Moncasi M P, Healey J H, Old L J, Rettig W J (1994). Molecular cloning of fibroblast activation protein alpha, a member of the serine protease family selectively expressed in stromal fibroblasts of epithelial cancers. Proc Natl. Acad. Sci. U.S.A. 91, 5657-5661.

Schafer R, Sedehizade F, Welte T, Reiser G (2003). ATP- and UTP-activated P2Y receptors differently regulate proliferation of human lung epithelial tumor cells. Am. J Physiol Lung Cell Mol. Physiol 285, L376-L385.

Schegg B, Hulsmeier A J, Rutschmann C, Maag C, Hennet T (2009). Core glycosylation of collagen is initiated by two beta(1-O)galactosyltransferases. Mol. Cell Biol. 29, 943-952.

Schuetz C S, Bonin M, Clare S E, Nieselt K, Sotlar K, Walter M, Fehm T, Solomayer E, Riess O, Wallwiener D, Kurek R, Neubauer H J (2006). Progression-specific genes identified by expression profiling of matched ductal carcinomas in situ and invasive breast tumors, combining laser capture microdissection and oligonucleotide microarray analysis. Cancer Res 66, 5278-5286.

Scieglinska D, Piglowski W, Mazurek A, Malusecka E, Zebracka J, Filipczak P, Krawczyk Z (2008). The HspA2 protein localizes in nucleoli and centrosomes of heat shocked cancer cells. J Cell Biochem. 104, 2193-2206.

Seifert W, Kuhnisch J, Maritzen T, Horn D, Haucke V, Hennies H C (2011). Cohen syndrome-associated protein, COH1, is a novel, giant Golgi matrix protein required for Golgi integrity. J Biol. Chem. 286, 37665-37675.

Shaulian E (2010). AP-1—The Jun proteins: Oncogenes or tumor suppressors in disguise? Cell Signal. 22, 894-899.

Shaulian E, Karin M (2002). AP-1 as a regulator of cell life and death. Nat Cell Biol. 4, E131-E136.

Sherman-Baust C A, Weeraratna A T, Rangel L B, Pizer E S, Cho K R, Schwartz D R, Shock T, Morin P J (2003). Remodeling of the extracellular matrix through overexpression of collagen V I contributes to cisplatin resistance in ovarian cancer cells. Cancer Cell 3, 377-386.

Shigeishi H, Fujimoto S, Hiraoka M, Ono S, Taki M, Ohta K, Higashikawa K, Kamata N (2009). Overexpression of the receptor for hyaluronan-mediated motility, correlates with expression of microtubule-associated protein in human oral squamous cell carcinomas. Int J Oncol 34, 1565-1571.

Shimbo T, Tanemura A, Yamazaki T, Tamai K, Katayama I, Kaneda Y (2010). Serum anti-BPAG1 auto-antibody is a novel marker for human melanoma. PLoS. ONE. 5, e10566.

Shyian M, Gryshkova V, Kostianets O, Gorshkov V, Gogolev Y, Goncharuk I, Nespryadko S, Vorobjova L, Filonenko V, Kiyamova R (2011). Quantitative analysis of SLC34A2 expression in different types of ovarian tumors. Exp. Oncol 33, 94-98.

Siddiqui N, Borden K L (2012). mRNA export and cancer. Wiley. Interdiscip. Rev. RNA. 3, 13-25.

Simpson N E, Tryndyak V P, Beland F A, Pogribny I P (2012). An in vitro investigation of metabolically sensitive biomarkers in breast cancer progression. Breast Cancer Res. Treat. 133, 959-968.

Singh-Jasuja H, Emmerich N P, Rammensee H G (2004). The Tubingen approach: identification, selection, and validation of tumor-associated HLA peptides for cancer therapy. Cancer Immunol. Immunother. 53, 187-195.

Siow D L, Wattenberg B W (2012). Mammalian ORMDL proteins mediate the feedback response in ceramide biosynthesis. J Biol. Chem. 287, 40198-40204.

Slack F J, Weidhaas J B (2008). MicroRNA in cancer prognosis. N. Engl. J Med. 359, 2720-2722.

Small E J, Schellhammer P F, Higano C S, Redfern C H, Nemunaitis J J, Valone F H, Verjee S S, Jones L A, Hershberg R M (2006). Placebo-controlled phase III trial of immunologic therapy with sipuleucel-T (APC8015) in patients with metastatic, asymptomatic hormone refractory prostate cancer. J Clin Oncol. 24, 3089-3094.

Smith M J, Culhane A C, Donovan M, Coffey J C, Barry B D, Kelly M A, Higgins D G, Wang J H, Kirwan W O, Cotter T G, Redmond H P (2009a). Analysis of differential gene expression in colorectal cancer and stroma using fluorescence-activated cell sorting purification. Br. J Cancer 100, 1452-1464.

Smith S C, Nicholson B, Nitz M, Frierson H F, Jr., Smolkin M, Hampton G, El-Rifai W, Theodorescu D (2009b). Profiling bladder cancer organ site-specific metastasis identifies LAMC2 as a novel biomarker of hematogenous dissemination. Am J Pathol. 174, 371-379.

Sohr S, Engeland K (2008). RHAMM is differentially expressed in the cell cycle and downregulated by the tumor suppressor p53. Cell Cycle 7, 3448-3460.

Somers G R, Bradbury R, Trute L, Conigrave A, Venter D J (1999). Expression of the human P2Y6 nucleotide receptor in normal placenta and gestational trophoblastic disease. Lab Invest 79, 131-139.

Srougi M C, Burridge K (2011). The nuclear guanine nucleotide exchange factors Ect2 and Net1 regulate RhoB-mediated cell death after DNA damage. PLoS. ONE. 6, e17108.

Staehler M, Stenzl A, Dietrich P Y, Eisen T, Haferkamp A, Beck J, Mayer A, Walter S, Singh-Jasuja H, Stief C (2007). A phase I study to evaluate safety, immunogenicity and anti-tumor activity of the multi-peptide vaccine IMA901 in renal cell carcinoma patients (RCC). Journal of Clinical Oncology, 2007 ASCO Annual Meeting Proceedings Part I, Vol 25, No. 18S (June 20 Supplement), 2007: 5098 (Abstract).

Starzyk R M, Rosenow C, Frye J, Leismann M, Rodzinski E, Putney S, Tuomanen E I (2000). Cerebral cell adhesion molecule: a novel leukocyte adhesion determinant on blood-brain barrier capillary endothelium. J Infect. Dis. 181, 181-187.

Steckelbroeck S, Jin Y, Gopishetty S, Oyesanmi B, Penning T M (2004). Human cytosolic 3alpha-hydroxysteroid dehydrogenases of the aldo-keto reductase superfamily display significant 3beta-hydroxysteroid dehydrogenase activity: implications for steroid hormone metabolism and action. J Biol. Chem. 279, 10784-10795.

Stewart D J (2010). Tumor and host factors that may limit efficacy of chemotherapy in non-small cell and small cell lung cancer. Crit Rev. Oncol Hematol. 75, 173-234.

Stuart J E, Lusis E A, Scheck A C, Coons S W, Lal A, Perry A, Gutmann D H (2010). Identification of Gene Markers Associated With Aggressive Meningioma by Filtering Across Multiple Sets of Gene Expression Arrays. J Neuropathol. Exp. Neurol.

Suminami Y, Kishi F, Sekiguchi K, Kato H (1991). Squamous cell carcinoma antigen is a new member of the serine protease inhibitors. Biochem. Biophys. Res. Commun. 181, 51-58.

Sunaga N, Imai H, Shimizu K, Shames D S, Kakegawa S, Girard L, Sato M, Kaira K, Ishizuka T, Gazdar A F, Minna J D, Mori M (2012). Oncogenic KRAS-induced interleukin-8 overexpression promotes cell growth and migration and contributes to aggressive phenotypes of non-small cell lung cancer. Int. J Cancer 130, 1733-1744.

Sutherlin M E, Nishimori I, Caffrey T, Bennett E P, Hassan H, Mandel U, Mack D, Iwamura T, Clausen H, Hollingsworth M A (1997). Expression of three UDP-N-acetyl-alpha-D-galactosamine:polypeptide GalNAc N-acetylgalactosaminyltransferases in adenocarcinoma cell lines. Cancer Res. 57, 4744-4748.

Suvasini R, Shruti B, Thota B, Shinde S V, Friedmann-Morvinski D, Nawaz Z, Prasanna K V, Thennarasu K, Hegde A S, Arivazhagan A, Chandramouli B A, Santosh V, Somasundaram K (2011). Insulin growth factor-2 binding protein 3 (IGF2BP3) is a glioblastoma-specific marker that activates phosphatidylinositol 3-kinase/mitogen-activated protein kinase (PI3K/MAPK) pathways by modulating IGF-2. J Biol. Chem. 286, 25882-25890.

Tai C J, Shen S C, Lee W R, Liao C F, Deng W P, Chiou H Y, Hsieh C I, Tung J N, Chen C S, Chiou J F, Li L T, Lin C Y, Hsu C H, Jiang M C (2010). Increased cellular apoptosis susceptibility (CSE1L/CAS) protein expression promotes protrusion extension and enhances migration of MCF-7 breast cancer cells. Exp. Cell Res. 316, 2969-2981.

Takanami I, Abiko T, Koizumi S (2008). Expression of periostin in patients with non-small cell lung cancer: correlation with angiogenesis and lymphangiogenesis. Int J Biol. Markers 23, 182-186.

Tanaka S, Akiyoshi T, Mori M, Wands J R, Sugimachi K (1998). A novel frizzled gene identified in human esophageal carcinoma mediates APC/beta-catenin signals. Proc. Natl. Acad. Sci. U.S.A. 95, 10164-10169.

Tanaka T, Ohkubo S, Tatsuno I, Prives C (2007). hCAS/CSE1L associates with chromatin and regulates expression of select p53 target genes. Cell 130, 638-650.

Terabayashi T, Sakaguchi M, Shinmyozu K, Ohshima T, Johjima A, Ogura T, Miki H, Nishinakamura R (2012). Phosphorylation of Kif26b promotes its polyubiquitination and subsequent proteasomal degradation during kidney development. PLoS. ONE. 7, e39714.

Terry K L, Vitonis A F, Hernandez D, Lurie G, Song H, Ramus S J, Titus-Ernstoff L, Carney M E, Wilkens L R, Gentry-Maharaj A, Menon U, Gayther S A, Pharaoh P D, Goodman M T, Cramer D W, Birrer M J (2010). A polymorphism in the GALNT2 gene and ovarian cancer risk in four population based case-control studies. Int. J Mol. Epidemiol. Genet. 1, 272-277.

Thierry L, Geiser A S, Hansen A, Tesche F, Herken R, Miosge N (2004). Collagen types XII and XIV are present in basement membrane zones during human embryonic development. J Mol. Histol. 35, 803-810.

Thorsen K, Sorensen K D, Brems-Eskildsen A S, Modin C, Gaustadnes M, Hein A M, Kruhoffer M, Laurberg S, Borre M, Wang K, Brunak S, Krainer A R, Torring N, Dyrskjot L, Andersen C L, ORntoft T F (2008). Alternative splicing in colon, bladder, and prostate cancer identified by exon array analysis. Mol. Cell Proteomics. 7, 1214-1224.

Thurner B, Haendle I, Roder C, Dieckmann D, Keikavoussi P, Jonuleit H, Bender A, Maczek C, Schreiner D, von den D P, Brocker E B, Steinman R M, Enk A, Kampgen E, Schuler G (1999). Vaccination with mage-3A1 peptide-pulsed mature, monocyte-derived dendritic cells expands specific cytotoxic T cells and induces regression of some metastases in advanced stage I V melanoma. J Exp. Med 190, 1669-1678.

Timar J, Kasler M, Katai J, Soos M, Mathiasz D, Romany A, Patthy L, Kovacs G, Jozsa A, Szilak L, Forrai T (2006). [Developments in cancer management by innovative genomics. 2006 report of the National Cancer Consortium]. Magy. Onkol. 50, 349-359.

Tischler V, Fritzsche F R, Wild P J, Stefan C, Seifert H H, Riener M O, Hermanns T, Mortezavi A, Gerhardt J, Schraml P, Jung K, Moch H, Soltermann A, Kristiansen G (2010). Periostin is up-regulated in high grade and high stage prostate cancer. BMC. Cancer 10, 273.

Tompkins D H, Besnard V, Lange A W, Keiser A R, Wert S E, Bruno M D, Whitsett J A (2011). Sox2 activates cell proliferation and differentiation in the respiratory epithelium. Am J Respir. Cell Mol. Biol. 45, 101-110.

Tondreau T, Dejeneffe M, Meuleman N, Stamatopoulos B, Delforge A, Martiat P, Bron D, Lagneaux L (2008). Gene expression pattern of functional neuronal cells derived from human bone marrow mesenchymal stromal cells. BMC. Genomics 9, 166.

Tong L, Harwood H J, Jr. (2006). Acetyl-coenzyme A carboxylases: versatile targets for drug discovery. J Cell Biochem. 99, 1476-1488.

Tong W G, Wierda W G, Lin E, Kuang S Q, Bekele B N, Estrov Z, Wei Y, Yang H, Keating M J, Garcia-Manero G (2010). Genome-wide DNA methylation profiling of chronic lymphocytic leukemia allows identification of epigenetically repressed molecular pathways with clinical impact. Epigenetics. 5, 499-508.

Torre G C (1998). SCC antigen in malignant and nonmalignant squamous lesions. Tumour. Biol. 19, 517-526.

Tritz R, Hickey M J, Lin A H, Hadwiger P, Sah D W, Neuwelt E A, Mueller B M, Kruse C A (2009). FAPP2 gene downregulation increases tumor cell sensitivity to Fas-induced apoptosis. Biochem. Biophys. Res. Commun. 383, 167-171.

Tsai J R, Chong I W, Chen Y H, Yang M J, Sheu C C, Chang H C, Hwang J J, Hung J Y, Lin S R (2007). Differential expression profile of MAGE family in non-small-cell lung cancer. Lung Cancer 56, 185-192.

Tseng H (1998). Basonuclin, a zinc finger protein associated with epithelial expansion and proliferation. Front Biosci. 3, D985-D988.

Tseng H, Biegel J A, Brown R S (1999). Basonuclin is associated with the ribosomal RNA genes on human keratinocyte mitotic chromosomes. J Cell Sci. 112 Pt 18, 3039-3047.

Tseng H, Green H (1994). Association of basonuclin with ability of keratinocytes to multiply and with absence of terminal differentiation. J Cell Biol. 126, 495-506.

Tsuji A, Kikuchi Y, Sato Y, Koide S, Yuasa K, Nagahama M, Matsuda Y (2006). A proteomic approach reveals transient association of reticulocalbin-3, a novel member of the CREC family, with the precursor of subtilisin-like proprotein convertase, PACE4. Biochem. J 396, 51-59.

Tsukamoto Y, Uchida T, Karnan S, Noguchi T, Nguyen L T, Tanigawa M, Takeuchi I, Matsuura K, Hijiya N, Nakada C, Kishida T, Kawahara K, Ito H, Murakami K, Fujioka T, Seto M, Moriyama M (2008). Genome-wide analysis of DNA copy number alterations and gene expression in gastric cancer. J Pathol. 216, 471-482.

Twarock S, Tammi M I, Savani R C, Fischer J W (2010). Hyaluronan stabilizes focal adhesions, filopodia, and the proliferative phenotype in esophageal squamous carcinoma cells. J Biol. Chem. 285, 23276-23284.

Twells R C, Metzker M L, Brown S D, Cox R, Garey C, Hammond H, Hey P J, Levy E, Nakagawa Y, Philips M S, Todd J A, Hess J F (2001). The sequence and gene characterization of a 400-kb candidate region for IDDM4 on chromosome 11q13. Genomics 72, 231-242.

Tzankov A, Strasser U, Dirnhofer S, Menter T, Arber C, Jotterand M, Rovo A, Tichelli A, Stauder R, Gunthert U (2011). In situ RHAMM protein expression in acute myeloid leukemia blasts suggests poor overall survival. Ann Hematol.

Uchiyama Y, Sakaguchi M, Terabayashi T, Inenaga T, Inoue S, Kobayashi C, Oshima N, Kiyonari H, Nakagata N, Sato Y, Sekiguchi K, Miki H, Araki E, Fujimura S, Tanaka S, Nishinakamura R (2010). Kif26b, a kinesin family gene, regulates adhesion of the embryonic kidney mesenchyme. Proc. Natl. Acad. Sci. U.S.A. 107, 9240-9245.

Ullman E, Pan J A, Zong W X (2011). Squamous cell carcinoma antigen 1 promotes caspase-8-mediated apoptosis in response to endoplasmic reticulum stress while inhibiting necrosis induced by lysosomal injury. Mol. Cell Biol. 31, 2902-2919.

Utispan K, Thuwajit P, Abiko Y, Charngkaew K, Paupairoj A, Chau-in S, Thuwajit C (2010). Gene expression profiling of cholangiocarcinoma-derived fibroblast reveals alterations related to tumor progression and indicates periostin as a poor prognostic marker. Mol. Cancer 9, 13.

van A M, Schepens M, de B D, Janssen B, Merkx G, Geurts van K A (2000). Construction of a 350-kb sequence-ready 11q13 cosmid contig encompassing the markers D11S4933 and D11S546: mapping of 11 genes and 3 tumor-associated translocation breakpoints. Genomics 66, 35-42.

Vargas-Roig L M, Gago F E, Tello O, Aznar J C, Ciocca D R (1998). Heat shock protein expression and drug resistance in breast cancer patients treated with induction chemotherapy. Int. J Cancer 79, 468-475.

Vazquez-Ortiz G, Pina-Sanchez P, Vazquez K, Duenas A, Taja L, Mendoza P, Garcia J A, Salcedo M (2005). Overexpression of cathepsin F, matrix metalloproteinases 11 and 12 in cervical cancer. BMC. Cancer 5, 68.

Wahl M C, Will C L, Luhrmann R (2009). The spliceosome: design principles of a dynamic RNP machine. Cell 136, 701-718.

Walchli C, Koch M, Chiquet M, Odermatt B F, Trueb B (1994). Tissue-specific expression of the fibril-associated collagens XII and XIV. J Cell Sci. 107 (Pt 2), 669-681.

Wallace A M, Sandford A J, English J C, Burkett K M, Li H, Finley R J, Muller N L, Coxson H O, Pare P D, Abboud R T (2008). Matrix metalloproteinase expression by human alveolar macrophages in relation to emphysema. COPD. 5, 13-23.

Walter S, Herrgen L, Schoor O, Jung G, Wernet D, Buhring H J, Rammensee H G, Stevanovic S (2003). Cutting edge: predetermined avidity of human CD8 T cells expanded on calibrated MHC/anti-CD28-coated microspheres. J. Immunol. 171, 4974-4978.

Wang C, Rajput S, Watabe K, Liao D F, Cao D (2010a). Acetyl-CoA carboxylase-a as a novel target for cancer therapy. Front Biosci. (Schol. Ed) 2, 515-526.

Wang C, Xu C, Sun M, Luo D, Liao D F, Cao D (2009a). Acetyl-CoA carboxylase-alpha inhibitor TOFA induces human cancer cell apoptosis. Biochem. Biophys. Res. Commun. 385, 302-306.

Wang H W, Lin C P, Chiu J H, Chow K C, Kuo K T, Lin C S, Wang L S (2007). Reversal of inflammation-associated dihydrodiol dehydrogenases (AKR1C1 and AKR1C2) overexpression and drug resistance in nonsmall cell lung cancer cells by wogonin and chrysin. Int. J Cancer 120, 2019-2027.

Wang J, Tsui H W, Beier F, Pritzker K P, Inman R D, Tsui F W (2008a). The ANKH DeltaE490Mutation in Calcium Pyrophosphate Dihydrate Crystal Deposition Disease (CPPDD) affects tissue non-specific Alkaline Phosphatase (TNAP) activities. Open Rheumatol. J 2, 23-30.

Wang K K, Liu N, Radulovich N, Wigle D A, Johnston M R, Shepherd F A, Minden M D, Tsao M S (2002). Novel candidate tumor marker genes for lung adenocarcinoma. Oncogene 21, 7598-7604.

Wang Q, Traynor J R (2011). Opioid-induced down-regulation of RGS4: role of ubiquitination and implications for receptor cross-talk. J Biol. Chem. 286, 7854-7864.

Wang S Z, Luo X G, Shen J, Zou J N, Lu Y H, Xi T (2008b). Knockdown of SMYD3 by RNA interference inhibits cervical carcinoma cell growth and invasion in vitro. BMB. Rep. 41, 294-299.

Wang W X, Zhang W J, Peng Z L, Yang K X (2009b). [Expression and clinical significance of CDC6 and hMSH2 in cervical carcinoma]. Sichuan. Da. Xue. Xue. Bao. Yi. Xue. Ban. 40, 857-860.

Wang Y, Zhou F, Wu Y, Xu D, Li W, Liang S (2010b). The relationship between three heat shock protein 70 gene polymorphisms and susceptibility to lung cancer. Clin Chem. Lab Med. 48, 1657-1663.

Warner S L, Stephens B J, Nwokenkwo S, Hostetter G, Sugeng A, Hidalgo M, Trent J M, Han H, Von Hoff D D (2009). Validation of TPX2 as a potential therapeutic target in pancreatic cancer cells. Clin Cancer Res 15, 6519-6528.

Watanabe M, Takemasa I, Kawaguchi N, Miyake M, Nishimura N, Matsubara T, Matsuo E, Sekimoto M, Nagai K, Matsuura N, Monden M, Nishimura O (2008). An application of the 2-nitrobenzenesulfenyl method to proteomic profiling of human colorectal carcinoma: A novel approach for biomarker discovery. Proteomics. Clin Appl. 2, 925-935.

Watanabe T, Kobunai T, Yamamoto Y, Ikeuchi H, Matsuda K, Ishihara S, Nozawa K, Iinuma H, Kanazawa T, Tanaka T, Yokoyama T, Konishi T, Eshima K, Ajioka Y, Hibi T, Watanabe M, Muto T, Nagawa H (2011). Predicting ulcerative colitis-associated colorectal cancer using reverse-transcription polymerase chain reaction analysis. Clin Colorectal Cancer 10, 134-141.

Watrin E, Legagneux V (2005). Contribution of hCAP-D2, a non-SMC subunit of condensin I, to chromosome and chromosomal protein dynamics during mitosis. Mol. Cell Biol. 25, 740-750.

Watt S L, Lunstrum G P, McDonough A M, Keene D R, Burgeson R E, Morris N P (1992). Characterization of collagen types XII and XIV from fetal bovine cartilage. J Biol. Chem. 267, 20093-20099.

Wawrzynska L, Sakowicz A, Rudzinski P, Langfort R, Kurzyna M (2003). The conversion of thyroxine to triiodothyronine in the lung: comparison of activity of type I iodothyronine 5' deiodinase in lung cancer with peripheral lung tissues. Monaldi Arch. Chest Dis. 59, 140-145.

Weeraratna A T, Jiang Y, Hostetter G, Rosenblatt K, Duray P, Bittner M, Trent J M (2002). Wnt5a signaling directly affects cell motility and invasion of metastatic melanoma. Cancer Cell 1, 279-288.

Weiner L, Green H (1998). Basonuclin as a cell marker in the formation and cycling of the murine hair follicle. Differentiation 63, 263-272.

Weinschenk T, Gouttefangeas C, Schirle M, Obermayr F, Walter S, Schoor O, Kurek R, Loeser W, Bichler K H, Wernet D, Stevanovic S, Rammensee H G (2002). Integrated functional genomics approach for the design of patient-individual antitumor vaccines. Cancer Res. 62, 5818-5827.

Wickramasinghe V O, Stewart M, Laskey R A (2010). GANP enhances the efficiency of mRNA nuclear export in mammalian cells. Nucleus. 1, 393-396.

Wildeboer D, Naus S, my Sang Q X, Bartsch J W, Pagenstecher A (2006). Metalloproteinase disintegrins ADAM8 and ADAM19 are highly regulated in human primary brain tumors and their expression levels and activities are associated with invasiveness. J Neuropathol. Exp. Neurol. 65, 516-527.

Willer C J, Sanna S, Jackson A U, Scuteri A, Bonnycastle L L, Clarke R, Heath S C, Timpson N J, Najjar S S, Stringham H M, Strait J, Duren W L, Maschio A, Busonero F, Mulas A, Albai G, Swift A J, Morken M A, Narisu N, Bennett D, Parish S, Shen H, Galan P, Meneton P, Hercberg S, Zelenika D, Chen W M, Li Y, Scott L J, Scheet P A, Sundvall J, Watanabe R M, Nagaraj a R, Ebrahim S, Lawlor D A, Ben-Shlomo Y, Davey-Smith G, Shuldiner A R, Collins R, Bergman R N, Uda M, Tuomilehto J, Cao A, Collins F S, Lakatta E, Lathrop G M, Boehnke M, Schlessinger D, Mohlke K L, Abecasis G R (2008). Newly identified loci that influence lipid concentrations and risk of coronary artery disease. Nat Genet. 40, 161-169.

Winkler G S, Mulder K W, Bardwell V J, Kalkhoven E, Timmers H T (2006). Human Ccr4-Not complex is a ligand-dependent repressor of nuclear receptor-mediated transcription. EMBO J 25, 3089-3099.

Wong C H, Chan H, Ho C Y, Lai S K, Chan K S, Koh C G, Li H Y (2009). Apoptotic histone modification inhibits nuclear transport by regulating RCC1. Nat Cell Biol. 11, 36-45.

Wu A, Wu B, Guo J, Luo W, Wu D, Yang H, Zhen Y, Yu X, Wang H, Zhou Y, Liu Z, Fang W, Yang Z (2011a). Elevated expression of CDK4 in lung cancer. J Transl. Med. 9, 38.

Wu G C, Hu H C, Shi M H (2008). [Expression and clinical significance of a disintegrin and metalloprotease 8 (ADAM8) and epidermal growth factor receptor (EGFR) in non-small cell lung cancer]. Ai. Zheng. 27, 874-878.

Wu H, Xu H, Miraglia L J, Crooke S T (2000). Human RNase III is a 160-kDa protein involved in preribosomal RNA processing. J Biol. Chem. 275, 36957-36965.

Wu K D, Lee W S, Wey J, Bungard D, Lytton J (1995). Localization and quantification of endoplasmic reticulum Ca(2+)-ATPase isoform transcripts. Am. J Physiol 269, C775-C784.

Wu S Q, Lv Y E, Lin B H, Luo L M, Lv S L, Bi A H, Jia Y S (2013). Silencing of periostin inhibits nicotine-mediated tumor cell growth and epithelial-mesenchymal transition in lung cancer cells. Mol. Med. Rep. 7, 875-880.

Wu Y M, Liu C H, Hu R H, Huang M J, Lee J J, Chen C H, Huang J, Lai H S, Lee P H, Hsu W M, Huang H C, Huang M C (201 b). Mucin glycosylating enzyme GALNT2 regulates the malignant character of hepatocellular carcinoma by modifying the EGF receptor. Cancer Res. 71, 7270-7279.

Wu Z, Jiang H, Zhang L, Xu X, Zhang X, Kang Z, Song D, Zhang J, Guan M, Gu Y (2012). Molecular analysis of RNF213 gene for moyamoya disease in the Chinese Han population. PLoS. ONE. 7, e48179.

Wullner U, Neef I, Eller A, Kleines M, Tur M K, Barth S (2008). Cell-specific induction of apoptosis by rationally designed bivalent aptamer-siRNA transcripts silencing eukaryotic elongation factor 2. Curr. Cancer Drug Targets. 8, 554-565.

Xia L M, Tian D A, Zhang Q, Yan W, Wang B, Liu M, Li P Y, Chen B (2008). [Inhibition of HSP70-2 expression by RNA interference induces apoptosis of human hepatocellular carcinoma cells]. Zhonghua Gan Zang. Bing. Za Zhi. 16, 678-682.

Xiao L, Rao J N, Zou T, Liu L, Marasa B S, Chen J, Turner D J, Passaniti A, Wang J Y (2007). Induced JunD in intestinal epithelial cells represses CDK4 transcription through its proximal promoter region following polyamine depletion. Biochem. J 403, 573-581.

Xie Y, Wolff D W, Wei T, Wang B, Deng C, Kirui J K, Jiang H, Qin J, Abel P W, Tu Y (2009). Breast cancer migration and invasion depend on proteasome degradation of regulator of G-protein signaling 4. Cancer Res 69, 5743-5751.

Xiong D, Li G, Li K, Xu Q, Pan Z, Ding F, Vedell P, Liu P, Cui P, Hua X, Jiang H, Yin Y, Zhu Z, Li X, Zhang B, Ma D, Wang Y, You M (2012). Exome sequencing identifies MXRA5 as a novel cancer gene frequently mutated in non-small cell lung carcinoma from Chinese patients. Carcinogenesis 33, 1797-1805.

Yamada H, Yanagisawa K, Tokumaru S, Taguchi A, Nimura Y, Osada H, Nagino M, Takahashi T (2008). Detailed characterization of a homozygously deleted region corresponding to a candidate tumor suppressor locus at 21q11-21 in human lung cancer. Genes Chromosomes. Cancer 47, 810-818.

Yamamoto H, Oue N, Sato A, Hasegawa Y, Yamamoto H, Matsubara A, Yasui W, Kikuchi A (2010). Wnt5a signaling is involved in the aggressiveness of prostate cancer and expression of metalloproteinase. Oncogene 29, 2036-2046.

Yamazaki H, Nishida H, Iwata S, Dang N H, Morimoto C (2009). CD90 and CD110 correlate with cancer stem cell potentials in human T-acute lymphoblastic leukemia cells. Biochem. Biophys. Res Commun. 383, 172-177.

Yang S, Shin J, Park K H, Jeung H C, Rha S Y, Noh S H, Yang W I, Chung H C (2007). Molecular basis of the differences between normal and tumor tissues of gastric cancer. Biochim. Biophys. Acta 1772, 1033-1040.

Yasmeen A, Berdel W E, Serve H, Muller-Tidow C (2003). E- and A-type cyclins as markers for cancer diagnosis and prognosis. Expert. Rev. Mol. Diagn. 3, 617-633.

Yasukawa M, Ishida K, Yuge Y, Hanaoka M, Minami Y, Ogawa M, Sasaki T, Saito M, Tsuji T (2013). Dpysl4 is involved in tooth germ morphogenesis through growth regulation, polarization and differentiation of dental epithelial cells. Int. J Biol. Sci. 9, 382-390.

Ye H, Yu T, Temam S, Ziober B L, Wang J, Schwartz J L, Mao L, Wong D T, Zhou X (2008). Transcriptomic dissection of tongue squamous cell carcinoma. BMC. Genomics 9, 69.

Yee C, Thompson J A, Byrd D, Riddell S R, Roche P, Celis E, Greenberg P D (2002). Adoptive T cell therapy using antigen-specific CD8+ T cell clones for the treatment of patients with metastatic melanoma: in vivo persistence, migration, and antitumor effect of transferred T cells. Proc. Natl. Acad. Sci. U.S.A. 99, 16168-16173.

Yoon H, Liyanarachchi S, Wright F A, Davuluri R, Lockman J C, de la C A, Pellegata N S (2002). Gene expression profiling of isogenic cells with different TP53 gene dosage reveals numerous genes that are affected by TP53 dosage and identifies CSPG2 as a direct target of p53. Proc Natl. Acad. Sci. U.S.A. 99, 15632-15637.

Yoshida K, Sugimoto N, Iwahori S, Yugawa T, Narisawa-Saito M, Kiyono T, Fujita M (2010). CDC6 interaction with ATR regulates activation of a replication checkpoint in higher eukaryotic cells. J Cell Sci. 123, 225-235.

Yu J M, Jun E S, Jung J S, Suh S Y, Han J Y, Kim J Y, Kim K W, Jung J S (2007). Role of Wnt5a in the proliferation of human glioblastoma cells. Cancer Lett. 257, 172-181.

Yuzugullu H, Benhaj K, Ozturk N, Senturk S, Celik E, Toylu A, Tasdemir N, Yilmaz M, Erdal E, Akcali K C, Atabey N, Ozturk M (2009). Canonical Wnt signaling is antagonized by noncanonical Wnt5a in hepatocellular carcinoma cells. Mol. Cancer 8, 90.

Zaka R, Dion A S, Kusnierz A, Bohensky J, Srinivas V, Freeman T, Williams C J (2009). Oxygen tension regulates the expression of ANK (progressive ankylosis) in an HIF-1-dependent manner in growth plate chondrocytes. J Bone Miner. Res. 24, 1869-1878.

Zaremba S, Barzaga E, Zhu M, Soares N, Tsang K Y, Schlom J (1997). Identification of an enhancer agonist cytotoxic T lymphocyte peptide from human carcinoembryonic antigen. Cancer Res. 57, 4570-4577.

Zhang H, Jia Y, Cooper J J, Hale T, Zhang Z, Elbein S C (2004). Common variants in glutamine:fructose-6-phosphate amidotransferase 2 (GFPT2) gene are associated with type 2 diabetes, diabetic nephropathy, and increased GFPT2 mRNA levels. J Clin Endocrinol. Metab 89, 748-755.

Zhang J, Valianou M, Cheng J D (2010a). Identification and characterization of the promoter of fibroblast activation protein. Front Biosci. (Elite. Ed) 2, 1154-1163.

Zhang X, Berger F G, Yang J, Lu X (2011a). USP4 inhibits p53 through deubiquitinating and stabilizing ARF-BP1. EMBO J 30, 2177-2189.

Zhang Y, Zhang G, Li J, Tao Q, Tang W (2010b). The expression analysis of periostin in human breast cancer. J Surg Res 160, 102-106.

Zhang Z C, Satterly N, Fontoura B M, Chook Y M (2011b). Evolutionary development of redundant nuclear localization signals in the mRNA export factor NXF1. Mol. Biol. Cell 22, 4657-4668.

Zhao C, Bellur D L, Lu S, Zhao F, Grassi M A, Bowne S J, Sullivan L S, Daiger S P, Chen L J, Pang C P, Zhao K, Staley J P, Larsson C (2009). Autosomal-dominant retinitis pigmentosa caused by a mutation in SNRNP200, a gene required for unwinding of U4/U6 snRNAs. Am. J Hum. Genet. 85, 617-627.

Zhao Z, Lee C C, Baldini A, Caskey C T (1995). A human homologue of the Drosophila polarity gene frizzled has been identified and mapped to 17q21.1. Genomics 27, 370-373.

Zheng P S, Wen J, Ang L C, Sheng W, Viloria-Petit A, Wang Y, Wu Y, Kerbel R S, Yang B B (2004). Versican/PG-M G3 domain promotes tumor growth and angiogenesis. FASEB J 18, 754-756.

Zhu C Q, Popova S N, Brown E R, Barsyte-Lovejoy D, Navab R, Shih W, Li M, Lu M, Jurisica I, Penn L Z, Gullberg D, Tsao M S (2007). Integrin alpha 11 regulates IGF2 expression in fibroblasts to enhance tumorigenicity of human non-small-cell lung cancer cells. Proc. Natl. Acad. Sci. U.S.A. 104, 11754-11759.

Zhu J H, Hong D F, Song Y M, Sun L F, Wang Z F, Wang J W (2013). Suppression of Cellular Apoptosis Susceptibility (CSE1L) Inhibits Proliferation and Induces Apoptosis in Colorectal Cancer Cells. Asian Pac. J Cancer Prev. 14, 1017-1021.

Zlobec I, Terracciano L, Tornillo L, Gunthert U, Vuong T, Jass J R, Lugli A (2008). Role of RHAMM within the hierarchy of well-established prognostic factors in colorectal cancer. Gut 57, 1413-1419.

Zou J N, Wang S Z, Yang J S, Luo X G, Xie J H, Xi T (2009). Knockdown of SMYD3 by RNA interference down-regulates c-Met expression and inhibits cells migration and invasion induced by HGF. Cancer Lett. 280, 78-85.

Zou T T, Selaru F M, Xu Y, Shustova V, Yin J, Mori Y, Shibata D, Sato F, Wang S, Olaru A, Deacu E, Liu T C, Abraham J M, Meltzer S J (2002). Application of cDNA microarrays to generate a molecular taxonomy capable of distinguishing between colon cancer and normal colon. Oncogene 21, 4855-4862.

Allander S V, Illei P B, Chen Y, Antonescu C R, Bittner M, Ladanyi M, Meltzer P S (2002). Expression profiling of synovial sarcoma by cDNA microarrays: association of ERBB2, IGFBP2, and ELF3 with epithelial differentiation. Am. J Pathol. 161, 1587-1595.

Baker D J, Jeganathan K B, Cameron J D, Thompson M, Juneja S, Kopecka A, Kumar R, Jenkins R B, de Groen P C, Roche P, van Deursen J M (2004). BubR1 insufficiency causes early onset of aging-associated phenotypes and infertility in mice. Nat Genet. 36, 744-749.

Balla A, Kim Y J, Varnai P, Szentpetery Z, Knight Z, Shokat K M, Balla T (2008). Maintenance of hormone-sensitive phosphoinositide pools in the plasma membrane requires phosphatidylinositol 4-kinase IIIalpha. Mol. Biol. Cell 19, 711-721.

Barembaum M, Moreno T A, LaBonne C, Sechrist J, Bronner-Fraser M (2000). Noelin-1 is a secreted glycoprotein involved in generation of the neural crest. Nat Cell Biol. 2, 219-225.

Bhogaraju S, Cajanek L, Fort C, Blisnick T, Weber K, Taschner M, Mizuno N, Lamla S, Bastin P, Nigg E A, Lorentzen E (2013). Molecular basis of tubulin transport within the cilium by IFT74 and IFT81. Science 341, 1009-1012.

Blumental-Perry A, Haney C J, Weixel K M, Watkins S C, Weisz O A, Aridor M (2006). Phosphatidylinositol 4-phosphate formation at ER exit sites regulates ER export. Dev. Cell 11, 671-682.

Cantor J M, Ginsberg M H (2012). CD98 at the crossroads of adaptive immunity and cancer. J Cell Sci. 125, 1373-1382.

Cave H, Suciu S, Preudhomme C, Poppe B, Robert A, Uyttebroeck A, Malet M, Boutard P, Benoit Y, Mauvieux L, Lutz P, Mechinaud F, Grardel N, Mazingue F, Dupont M, Margueritte G, Pages M P, Bertrand Y, Plouvier E, Brunie G, Bastard C, Plantaz D, Vande V, I, Hagemeij er A, Speleman F, Lessard M, Otten J, Vilmer E, Dastugue N (2004). Clinical significance of HOX11L2 expression linked to t(5;14)(q35;q32), of HOX11 expression, and of SIL-TAL fusion in childhood T-cell malignancies: results of EORTC studies 58881 and 58951. Blood 103, 442-450.

Chadwick B P, Obermayr F, Frischauf A M (1996). Nuclear cap binding protein maps close to the xeroderma pigmentosum complementation group A (XPA) locus in human and mouse. Genomics 35, 632-633.

Cornen S, Guille A, Adelaide J, Addou-Klouche L, Finetti P, Saade M R, Manai M, Carbuccia N, Bekhouche I, Letessier A, Raynaud S, Charafe-Jauffret E, Jacquemier J, Spicuglia S, de T H, Viens P, Bertucci F, Birnbaum D, Chaffanet M (2014). Candidate luminal B breast cancer genes identified by genome, gene expression and DNA methylation profiling. PLoS. ONE. 9, e81843.

Dear T N, Sanchez-Garcia I, Rabbitts T H (1993). The HOX11 gene encodes a DNA-binding nuclear transcription factor belonging to a distinct family of homeobox genes. Proc. Natl. Acad. Sci. U.S.A. 90, 4431-4435.

Deves R, Boyd C A (2000). Surface antigen CD98(4F2): not a single membrane protein, but a family of proteins with multiple functions. J Membr. Biol. 173, 165-177.

Ferrando A A, Herblot S, Palomero T, Hansen M, Hoang T, Fox E A, Look A T (2004). Biallelic transcriptional activation of oncogenic transcription factors in T-cell acute lymphoblastic leukemia. Blood 103, 1909-1911.

Fry A M, Mayor T, Meraldi P, Stierhof Y D, Tanaka K, Nigg E A (1998). C-Nap1, a novel centrosomal coiled-coil protein and candidate substrate of the cell cycle-regulated protein kinase Nek2. J Cell Biol. 141, 1563-1574.

Fu J, Bian M, Jiang Q, Zhang C (2007). Roles of Aurora kinases in mitosis and tumorigenesis. Mol. Cancer Res. 5, 1-10.

Garbarino J E, Gibbons I R (2002). Expression and genomic analysis of midasin, a novel and highly conserved AAA protein distantly related to dynein. BMC. Genomics 3, 18.

Gomez-Ferreria M A, Bashkurov M, Mullin M, Gingras A C, Pelletier L (2012). CEP192 interacts physically and functionally with the K63-deubiquitinase CYLD to promote mitotic spindle assembly. Cell Cycle 11, 3555-3558.

Gomez-Ferreria M A, Rath U, Buster D W, Chanda S K, Caldwell J S, Rines D R, Sharp D J (2007). Human Cep192 is required for mitotic centrosome and spindle assembly. Curr. Biol. 17, 1960-1966.

Hinck L (2004). The versatile roles of "axon guidance" cues in tissue morphogenesis. Dev. Cell 7, 783-793.

Ilboudo A, Nault J C, Dubois-Pot-Schneider H, Corlu A, Zucman-Rossi J, Samson M, Le S J (2014). Overexpression of phosphatidylinositol 4-kinase type IIIalpha is associated with undifferentiated status and poor prognosis of human hepatocellular carcinoma. BMC. Cancer 14, 7.

Kaira K, Oriuchi N, Imai H, Shimizu K, Yanagitani N, Sunaga N, Hisada T, Ishizuka T, Kanai Y, Nakajima T, Mori M (2009). Prognostic significance of L-type amino acid transporter 1 (LAT1) and 4F2 heavy chain (CD98) expression in stage I pulmonary adenocarcinoma. Lung Cancer 66, 120-126.

Kataoka N, Ohno M, Kangawa K, Tokoro Y, Shimura Y (1994). Cloning of a complementary DNA encoding an 80 kilodalton nuclear cap binding protein. Nucleic Acids Res. 22, 3861-3865.

Khan J, Wei J S, Ringner M, Saal L H, Ladanyi M, Westermann F, Berthold F, Schwab M, Antonescu C R, Peterson C, Meltzer P S (2001). Classification and diagnostic prediction of cancers using gene expression profiling and artificial neural networks. Nat Med. 7, 673-679.

Kim H J, Cho J H, Quan H, Kim J R (2011). Down-regulation of Aurora B kinase induces cellular senescence in human fibroblasts and endothelial cells through a p53-dependent pathway. FEBS Lett. 585, 3569-3576.

Kulkarni N H, Karavanich C A, Atchley W R, Anholt R R (2000). Characterization and differential expression of a human gene family of olfactomedin-related proteins. Genet. Res. 76, 41-50.

Kunitoku N, Sasayama T, Marumoto T, Zhang D, Honda S, Kobayashi O, Hatakeyama K, Ushio Y, Saya H, Hirota T (2003). CENP-A phosphorylation by Aurora-A in prophase is required for enrichment of Aurora-B at inner centromeres and for kinetochore function. Dev. Cell 5, 853-864.

Lampson M A, Kapoor T M (2005). The human mitotic checkpoint protein BubR1 regulates chromosome-spindle attachments. Nat Cell Biol. 7, 93-98.

Latil A, Chene L, Cochant-Priollet B, Mangin P, Fournier G, Berthon P, Cussenot O (2003). Quantification of expression of netrins, slits and their receptors in human prostate tumors. Int. J Cancer 103, 306-315.

Lee Y, Yoon K A, Joo J, Lee D, Bae K, Han J Y, Lee J S (2013). Prognostic implications of genetic variants in advanced non-small cell lung cancer: a genome-wide association study. Carcinogenesis 34, 307-313.

Lemaitre G, Gonnet F, Vaigot P, Gidrol X, Martin M T, Tortajada J, Waksman G (2005). CD98, a novel marker of transient amplifying human keratinocytes. Proteomics. 5, 3637-3645.

Lucker B F, Behal R H, Qin H, Siron L C, Taggart W D, Rosenbaum J L, Cole D G (2005). Characterization of the intraflagellar transport complex B core: direct interaction of the IFT81 and IFT74/72 subunits. J Biol. Chem. 280, 27688-27696.

Malureanu L A, Jeganathan K B, Hamada M, Wasilewski L, Davenport J, van Deursen J M (2009). BubR1 N terminus acts as a soluble inhibitor of cyclin B degradation by APC/C(Cdc20) in interphase. Dev. Cell 16, 118-131.

Matsuura S, Matsumoto Y, Morishima K, Izumi H, Matsumoto H, Ito E, Tsutsui K, Kobayashi J, Tauchi H, Kajiwara Y, Hama S, Kurisu K, Tahara H, Oshimura M, Komatsu K, Ikeuchi T, Kajii T (2006). Monoallelic BUB1B mutations and defective mitotic-spindle checkpoint in seven families with premature chromatid separation (PCS) syndrome. Am. J Med. Genet. A 140, 358-367.

Mayor T, Hacker U, Stierhof Y D, Nigg E A (2002). The mechanism regulating the dissociation of the centrosomal protein C-Nap1 from mitotic spindle poles. J Cell Sci. 115, 3275-3284.

Minogue S, Waugh M G (2012). The Phosphatidylinositol 4-Kinases: Don't Call it a Comeback. Subcell. Biochem. 58, 1-24.

Nagase T, Seki N, Ishikawa K, Ohira M, Kawarabayasi Y, Ohara O, Tanaka A, Kotani H, Miyajima N, Nomura N (1996). Prediction of the coding sequences of unidentified human genes. VI. The coding sequences of 80 new genes (KIAA0201-KIAA0280) deduced by analysis of cDNA clones from cell line KG-1 and brain. DNA Res. 3, 321-354.

Narayan G, Goparaju C, Arias-Pulido H, Kaufmann A M, Schneider A, Durst M, Mansukhani M, Pothuri B, Murty V V (2006). Promoter hypermethylation-mediated inactivation of multiple Slit-Robo pathway genes in cervical cancer progression. Mol. Cancer 5, 16.

Pandey A, Blagoev B, Kratchmarova I, Fernandez M, Nielsen M, Kristiansen T Z, Ohara O, Podtelejnikov A V, Roche S, Lodish H F, Mann M (2002). Cloning of a novel phosphotyrosine binding domain containing molecule, Odin, involved in signaling by receptor tyrosine kinases. Oncogene 21, 8029-8036.

Perumal D, Singh S, Yoder S J, Bloom G C, Chellappan S P (2012). A novel five gene signature derived from stem-like side population cells predicts overall and recurrence-free survival in NSCLC. PLoS. ONE. 7, e43589.

Pokrovskaya I D, Willett R, Smith R D, Morelle W, Kudlyk T, Lupashin V V (2011). Conserved oligomeric Golgi complex specifically regulates the maintenance of Golgi glycosylation machinery. Glycobiology 21, 1554-1569.

Qian Y, Fritzsch B, Shirasawa S, Chen C L, Choi Y, Ma Q (2001). Formation of brainstem (nor)adrenergic centers and first-order relay visceral sensory neurons is dependent on homeodomain protein Rnx/Tlx3. Genes Dev. 15, 2533-2545.

Reynders E, Foulquier F, Leao T E, Quelhas D, Morelle W, Rabouille C, Annaert W, Matthijs G (2009). Golgi function and dysfunction in the first COG4-deficient CDG type II patient. Hum. Mol. Genet. 18, 3244-3256.

Schmid B C, Rezniczek G A, Fabjani G, Yoneda T, Leodolter S, Zeillinger R (2007). The neuronal guidance cue Slit2 induces targeted migration and may play a role in brain metastasis of breast cancer cells. Breast Cancer Res. Treat. 106, 333-342.

Sharma G, Mirza S, Prasad C P, Srivastava A, Gupta S D, Ralhan R (2007). Promoter hypermethylation of p16INK4A, p14ARF, CyclinD2 and Slit2 in serum and tumor DNA from breast cancer patients. Life Sci. 80, 1873-1881.

Shin J, Gu C, Park E, Park S (2007). Identification of phosphotyrosine binding domain-containing proteins as novel downstream targets of the EphA8 signaling function. Mol. Cell Biol. 27, 8113-8126.

Suzuki M, Shiraishi K, Eguchi A, Ikeda K, Mori T, Yoshimoto K, Ohba Y, Yamada T, Ito T, Baba Y, Baba H (2013). Aberrant methylation of LINE-1, SLIT2, MAL and IGFBP7 in non-small cell lung cancer. Oncol Rep. 29, 1308-1314.

Ungar D, Oka T, Brittle E E, Vasile E, Lupashin V V, Chatterton J E, Heuser J E, Krieger M, Waters M G (2002). Characterization of a mammalian Golgi-localized protein complex, COG, that is required for normal Golgi morphology and function. J Cell Biol. 157, 405-415.

Ungar D, Oka T, Vasile E, Krieger M, Hughson F M (2005). Subunit architecture of the conserved oligomeric Golgi complex. J Biol. Chem. 280, 32729-32735.

Whyte J R, Munro S (2001). The Sec34/35 Golgi transport complex is related to the exocyst, defining a family of complexes involved in multiple steps of membrane traffic. Dev. Cell 1, 527-537.

Wong Y F, Cheung T H, Lo K W, Yim S F, Siu N S, Chan S C, Ho T W, Wong K W, Yu M Y, Wang V W, Li C, Gardner G J, Bonome T, Johnson W B, Smith D I, Chung T K, Birrer M J (2007). Identification of molecular markers and signaling pathway in endometrial cancer in Hong Kong Chinese women by genome-wide gene expression profiling. Oncogene 26, 1971-1982.

Wu L, Chang W, Zhao J, Yu Y, Tan X, Su T, Zhao L, Huang S, Liu S, Cao G (2010). Development of autoantibody signatures as novel diagnostic biomarkers of non-small cell lung cancer. Clin Cancer Res. 16, 3760-3768.

Bobos M, Hytiroglou P, Kostopoulos I, Karkavelas G, Papadimitriou C S (2006). Immunohistochemical distinction between merkel cell carcinoma and small cell carcinoma of the lung. Am. J Dermatopathol. 28, 99-104.

Mena H, Morrison A L, Jones R V, Gyure K A (2001). Central neurocytomas express photoreceptor differentiation. Cancer 91, 136-143.

Schleicher R L, Hunter S B, Zhang M, Zheng M, Tan W, Bandea C I, Fallon M T, Bostwick D G, Varma V A (1997). Neurofilament heavy chain-like messenger RNA and protein are present in benign prostate and down-regulated in prostatic carcinoma. Cancer Res. 57, 3532-3536.

Segal A, Carello S, Caterina P, Papadimitriou J M, Spagnolo D V (1994). Gastrointestinal autonomic nerve tumors: a clinicopathological, immunohistochemical and ultrastructural study of cases. Pathology 26, 439-447.

Szebenyi G, Smith G M, Li P, Brady S T (2002). Overexpression of neurofilament H disrupts normal cell structure and function. J Neurosci. Res. 68, 185-198.

Tanaka Y, Ijiri R, Kato K, Kato Y, Misugi K, Nakatani Y, Hara M (2000). HMB-45/melan-A and smooth muscle actin-positive clear-cell epithelioid tumor arising in the ligamentum teres hepatis: additional example of clear cell 'sugar' tumors. Am. J Surg. Pathol. 24, 1295-1299.

The invention claimed is:

1. A peptide consisting of the amino acid sequence of HLLEDIAHV (SEQ ID NO: 92) in the form of a pharmaceutically acceptable salt.

2. The peptide according to claim 1, wherein the pharmaceutically acceptable salt is a chloride salt, acetate salt, or trifluoro-acetate salt.

3. A pharmaceutical composition comprising the peptide according to claim 1 and a pharmaceutically acceptable carrier.

4. The pharmaceutical composition according to claim 3, wherein the pharmaceutically acceptable carrier is selected from the group consisting of saline, Ringer's solution and dextrose solution.

5. The pharmaceutical composition according to claim 3, further comprising pharmaceutically acceptable excipients.

6. The pharmaceutical composition according to claim 5, wherein said pharmaceutically acceptable excipients are selected from the group consisting of buffers, binding agents, diluents, flavors, and lubricants.

7. A pharmaceutical composition comprising the peptide of claim 1 and an immune enhancing amount of an adjuvant.

8. The pharmaceutical composition of claim 7, wherein the adjuvant is at least one selected from the group consisting of anti-CD40 antibody, imiquimod, resiquimod, GM-CSF, cyclophosphamide, sunitinib, bevacizumab, interferon-alpha, interferon-beta, CpG oligonucleotides and derivatives, poly-(I:C) and derivatives, RNA, sildenafil, particulate formulations with poly(lactide co-glycolide) (PLG), virosomes, interleukin (IL)-1, IL-2, IL-4, IL-7, IL-12, IL-13, IL-15, IL-21, and IL-23.

9. The peptide in the form of a pharmaceutically acceptable salt of claim 1, wherein said peptide is produced by solid phase peptide synthesis or produced by a yeast cell or bacterial cell expression system.

10. A composition comprising the peptide of claim 1, wherein the composition is a pharmaceutical composition and comprises water and a buffer.

* * * * *